United States Patent
Bergmann et al.

(10) Patent No.: US 11,492,344 B2
(45) Date of Patent: *Nov. 8, 2022

(54) ORGANIC MOLECULES FOR USE IN ORGANIC OPTOELECTRONIC DEVICES

(71) Applicant: SAMSUNG DISPLAY CO., LTD., Yongin-si (KR)

(72) Inventors: Larissa Bergmann, Karlsruhe (DE); Daniel Zink, Bruchsal (DE); Stefan Seifermann, Bühl (DE)

(73) Assignee: Samsung Display Co., Ltd., Yongin-si (KR)

(*) Notice: Subject to any disclaimer, the term of this patent is extended or adjusted under 35 U.S.C. 154(b) by 558 days.

This patent is subject to a terminal disclaimer.

(21) Appl. No.: 16/329,052

(22) PCT Filed: Aug. 31, 2017

(86) PCT No.: PCT/EP2017/071832
§ 371 (c)(1),
(2) Date: Feb. 27, 2019

(87) PCT Pub. No.: WO2018/041933
PCT Pub. Date: Mar. 8, 2018

(65) Prior Publication Data
US 2019/0194171 A1  Jun. 27, 2019

(30) Foreign Application Priority Data

Sep. 1, 2016 (EP) .................................. 16186775
Nov. 30, 2016 (DE) ......................... 102016123105.3
Mar. 16, 2017 (DE) ......................... 102017105692.0

(51) Int. Cl.
*C07D 403/14* (2006.01)
*H01L 51/00* (2006.01)
*H01L 51/50* (2006.01)

(52) U.S. Cl.
CPC ........ *C07D 403/14* (2013.01); *H01L 51/0067* (2013.01); *H01L 51/0072* (2013.01); *H01L 51/5012* (2013.01)

(58) Field of Classification Search
CPC .............. C07D 403/14; H01L 51/0067; H01L 51/0072; H01L 51/5012; Y02E 10/549
USPC ....................................................... 428/690
See application file for complete search history.

(56) References Cited

U.S. PATENT DOCUMENTS

| | | | |
|---|---|---|---|
| 9,963,429 B2* | 5/2018 | Mizuki | C07D 209/86 |
| 9,997,717 B2* | 6/2018 | Kawamura | H01L 51/0072 |
| 10,421,746 B2* | 9/2019 | Bergmann | H01L 51/50 |
| 10,981,930 B2* | 4/2021 | Danz | H01L 51/001 |
| 2015/0318488 A1 | 11/2015 | Ito et al. | |
| 2015/0325801 A1 | 11/2015 | Ito et al. | |
| 2016/0028025 A1 | 1/2016 | Ogiwara et al. | |
| 2016/0172601 A1* | 6/2016 | Kawamura | C09K 11/025 257/40 |
| 2016/0204361 A1* | 7/2016 | Mizuki | C07D 209/86 257/40 |
| 2019/0284174 A1* | 9/2019 | Bergmann | C07D 403/14 |
| 2020/0385399 A1* | 12/2020 | Danz | C07D 519/00 |
| 2021/0155849 A1* | 5/2021 | Stubbs | H01L 51/0072 |

FOREIGN PATENT DOCUMENTS

| | | | | |
|---|---|---|---|---|
| WO | 20140148493 A1 | 9/2014 | | |
| WO | WO-2015033894 A1 * | 3/2015 | ......... | H01L 51/0067 |
| WO | PCT/EP2017/071832 | 8/2017 | | |

\* cited by examiner

*Primary Examiner* — Douglas J McGinty
(74) *Attorney, Agent, or Firm* — Lewis Roca Rothgerber Christie LLP

(57) ABSTRACT

An organic molecule is disclosed having:
a first chemical unit according to Formula I

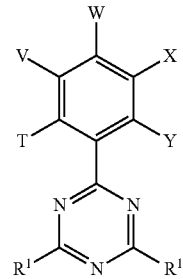

Formula I and
two second chemical units D, which are respectively the same or different in each occurrence, according to Formula II,

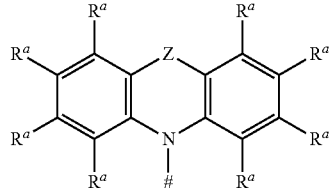

Formula II wherein, in each case, the first chemical unit is connected to the two second chemical units D via a single bond.

19 Claims, 4 Drawing Sheets

ORGANIC MOLECULES FOR USE IN ORGANIC OPTOELECTRONIC DEVICES

CROSS-REFERENCE TO RELATED APPLICATIONS

This application claims priority under 35 U.S.C. § 371 to International Application No. PCT/EP2017/071832, filed Aug. 31, 2017, which claims priority to European Patent Application No. 16186775.9 filed Sep. 1, 2016 and German Patent Application No. 10 2016 123 105.3 filed Nov. 30, 2016, and German Patent Application No. 10 2017 105 692.0 filed Mar. 16, 2017, the disclosures of which are incorporated by reference herein in their entireties.

FIELD OF INVENTION

The invention relates to purely organic molecules and the use thereof in organic light-emitting diodes (OLEDs) and in other organic optoelectronic devices.

BRIEF DESCRIPTION OF THE DRAWINGS

Exemplary embodiments of the present invention will be described below in more detail, with reference to the accompanying drawings, of which.

DETAILED DESCRIPTION OF EXEMPLARY EMBODIMENTS OF THE INVENTION

Figure 1:
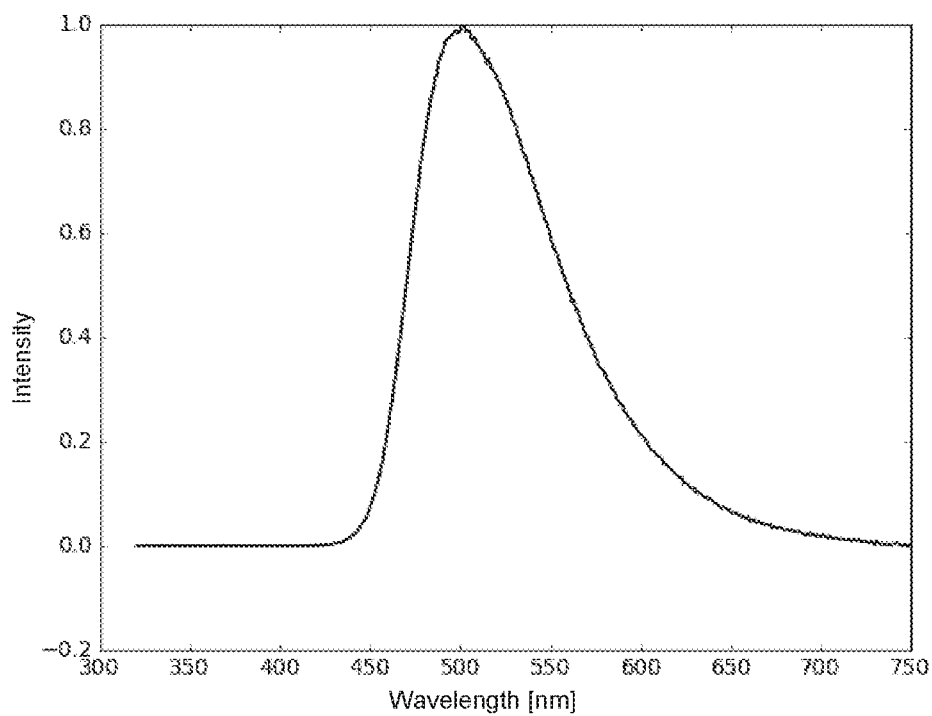
FIG. 1 is an emission spectrum of Example 1 (10% in PMMA).

Exemplary embodiments of the invention will now be discussed in further detail. This invention may, however, be embodied in many different forms and should not be construed as limited to the embodiments set forth herein.

The underlying task of the present invention was to provide molecules which are suitable for use in optoelectronic devices.

This task is solved by the novel class of organic molecules described here.

The organic molecules according to the invention are purely organic molecules; i.e. they do not have any metal ions, and thus differ from the metal complex compounds known for use in organic optoelectronic devices.

The organic molecules according to the invention are characterized by emissions in the blue, sky blue, or green spectral range. The photoluminescence quantum yields of the organic molecules according to the invention are in particular 20% and more. The molecules according to the invention in particular exhibit thermally activated delayed fluorescence (TADF). The use of the molecules according to the invention in an optoelectronic device, for example an organic light-emitting diode (OLED), results in higher efficiencies of the device. Corresponding OLEDs have a higher stability than OLEDs having known emitter materials and comparable color.

The blue spectral range here is understood to be the visible range from 430 nm to 470 nm. The sky blue spectral range here is understood to be the range between 470 nm and 499 nm. The green spectral range here is understood to be the range between 500 nm and 599 nm. The emission maximum is in the respective range.

The organic molecules contain a first chemical unit comprising or consisting of a structure according to Formula I:

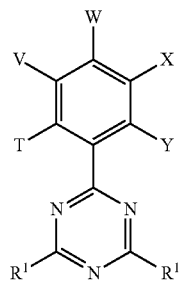

Formula I and
two second chemical units D, which are respectively the same or different in each occurrence, comprising a or consisting of a structure according to Formula II.

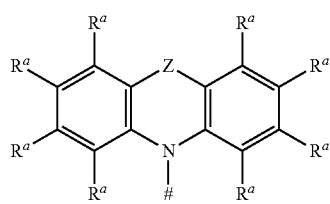

Formula II

The first chemical unit is thereby respectively connected to the two second chemical units D via a single bond.

T is the point of attachment of the single bond between the first chemical unit as per Formula I and a second chemical unit D or H.

V is the point of attachment of the single bond between the first chemical unit and a second chemical unit D or H.

W is the point of attachment of the single bond between the first chemical unit and a second chemical unit D or is selected from the group consisting of H, CN and $CF_3$.

X is the point of attachment of the single bond between the first chemical unit as per Formula I and a second chemical unit D or is selected from the group consisting of H, CN and $CF_3$.

Y is the point of attachment of the single bond between the first chemical unit as per Formula I and a second chemical unit D or is selected from the group consisting of H, CN and $CF_3$;

# is the point of attachment of the single bond between the respective second chemical unit D and the first chemical unit as per Formula I.

In each occurrence Z is the same or different, is a direct bond or is selected from the group consisting of $CR^3R^4$, $C=CR^3R^4$, $C=O$, $C=NR^3$, $NR^3$, O, $SiR^3R^4$, S, S(O) and $S(O)_2$.

In each occurrence $R^1$ is the same or different, is a linear alkyl group having 1 to 5 C atoms, a linear alkenyl or alkinyl group having 2 to 8 C atoms, a branched or cyclic alkyl, alkenyl or alkinyl group having 3 to 10 C atoms, wherein one or more H atoms can be replaced by deuterium, or an aromatic or heteroaromatic ring system having 5 to 15 aromatic ring atoms, which can in each case be substituted with one or more radicals $R^6$.

In each occurrence $R^a$, $R^3$ and $R^4$ is the same or different, is H, deuterium, $N(R^5)_2$, OH, $Si(R^5)_3$, $B(OR^5)_2$, $OSO_2R^5$, $CF_3$, CN, F, Br, I, a linear alkyl, alkoxy or thioalkoxy group having 1 to 40 C atoms or a linear alkenyl or alkinyl group having 2 to 40 C atoms or a branched or cyclic alkyl, alkenyl, alkinyl, alkoxy or thioalkoxy group having 3 to 40 C atoms, which can in each case be substituted with one or more radicals $R^5$, wherein one or more non-adjacent $CH_2$ groups can be replaced by $R^5C=CR^5$, C≡C, $Si(R^5)_2$, $Ge(R^5)_2$, $Sn(R^5)_2$, C=O, C=S, C=Se, $C=NR^5$, $P(=O)(R^5)$, SO, $SO_2$, $NR^5$, O, S or $CONR^5$ and wherein one or more H atoms can be substituted with deuterium, CN, $CF_3$ or $NO_2$; or an aromatic or heteroaromatic ring system having 5 to 60 aromatic ring atoms, which can in each case be substituted with one or more radicals $R^5$, or an aryloxy or heteroaryloxy group having 5 to 60 aromatic ring atoms, which can be can be substituted with one or more radicals $R^5$, or a diarylamino group, diheteroarylamino group or arylheteroarylamino group having 10 to 40 aromatic ring atoms, which can be substituted with one or more radicals $R^5$.

In each occurrence $R^5$ is the same or different, is H, deuterium, $N(R^6)_2$, OH, $Si(R^6)_3$, $B(OR^6)_2$, $OSO_2R^6$, $CF_3$, CN, F, Br, I, a linear alkyl, alkoxy or thioalkoxy group having 1 to 40 C atoms or a linear alkenyl or alkinyl group having 2 to 40 C atoms or a branched or cyclic alkyl, alkenyl, alkinyl, alkoxy or thioalkoxy group having 3 to 40 C atoms, which can respectively be substituted with one or more radicals $R^6$, wherein one or more non-adjacent $CH_2$ groups can be replaced by $R^6C=CR^6$, C≡C, $Si(R^6)_2$, $Ge(R^6)_2$, $Sn(R^6)_2$, C=O, C=S, C=Se, $C=NR^6$, $P(=O)(R^6)$, SO, $SO_2$, $NR^6$, O, S or $CONR^6$ and wherein one or more H atoms can be substituted with deuterium, CN, $CF^3$ or $NO_2$; or an aromatic or heteroaromatic ring system having 5 to 60 aromatic ring atoms, which can respectively be substituted with one or more radicals $R^6$, or an aryloxy or heteroaryloxy group having 5 to 60 aromatic ring atoms, which can be substituted with one or more radicals $R^6$, or a diarylamino group, diheteroarylamino group or arylheteroarylamino group having 10 to 40 aromatic ring atoms, which can be substituted with one or more radicals $R^6$.

In each occurrence $R^6$ is the same or different, is H, deuterium, OH, $CF_3$, CN, F, a linear alkyl, alkoxy or thioalkoxy group having 1 to 5 C atoms or a linear alkenyl or alkinyl group having 2 to 5 C atoms or a branched or cyclic alkyl, alkenyl, alkinyl, alkoxy or thioalkoxy group having 3 to 5 C atoms, wherein one or more H atoms can be replaced by deuterium, CN, $CF_3$ or $NO_2$; or an aromatic or heteroaromatic ring system having 5 to 60 aromatic ring atoms or an aryloxy or heteroaryloxy group having 5 to 60 aromatic ring atoms or a diarylamino group, diheteroarylamino group or arylheteroarylamino group having 10 to 40 aromatic ring atoms.

Each of the radicals $R^a$, $R^3$, $R^4$ or $R^5$ can also form a mono- or polycyclic, aliphatic, aromatic and/or benzoannelated ring system with one or more further radicals $R^a$, $R^3$, $R^4$ or $R^5$.

Exactly one radical selected from the group consisting of W, X and Y is CN or $CF_3$ and exactly two radicals selected from the group consisting of T, V, W, X and Y are a point of attachment of a single bond between the first chemical unit as per Formula I and a second chemical unit D.

In one embodiment, the stipulation applies that X is H if W is the point of attachment of the single bond between the two chemical units and Y is CN, and that W is H if X is the point of attachment of the single bond between the two chemical units and Y is CN.

In one embodiment, $R^1$ is the same or different in each occurrence and is methyl or phenyl.

In one embodiment, W is the point of attachment of the single bond between the first chemical unit and a second chemical unit D or is selected from the group consisting of CN and $CF_3$.

In one embodiment, W is CN.

In a further embodiment of the organic molecules, in each occurrence the second chemical group D is the same or different comprising a structure of Formula IIa or consisting of a structure of Formula IIa:

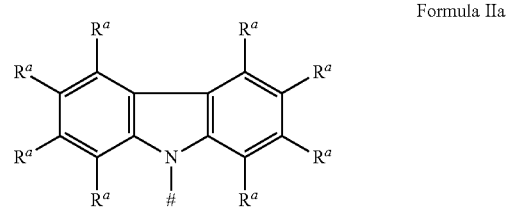

Formula IIa wherein the definitions stated for Formula I and II apply for # and $R^a$.

In a further embodiment of the organic molecules according to the invention, in each occurrence the second chemical unit D is the same or different comprising a structure of Formula IIb, Formula IIb-2, Formula IIb-3 or Formula IIb-4 or consisting thereof:

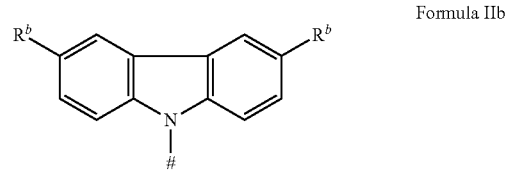

Formula IIb

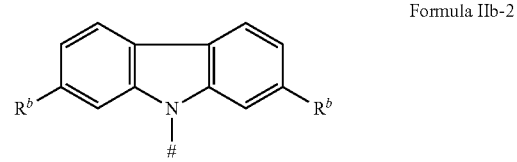

Formula IIb-2

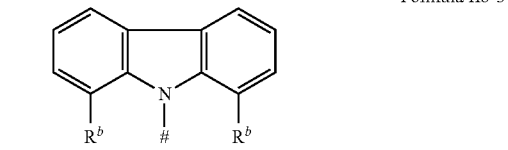

Formula IIb-3

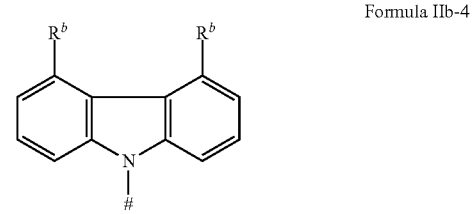

Formula IIb-4 wherein

In each occurrence $R^b$ is the same or different, is $N(R^5)_2$, OH, $Si(R^5)_3$, $B(OR^5)_2$, $OSO_2R^5$, $CF_3$, CN, F, Br, I, a linear alkyl, alkoxy or thioalkoxy group having 1 to 40 C atoms or a linear alkenyl or alkinyl group having 2 to 40 C atoms or a branched or cyclic alkyl, alkenyl, alkinyl, alkoxy or thioalkoxy group having 3 to 40 C atoms, which can in each case be substituted with one or more radicals $R^5$, wherein one or more non-adjacent $CH_2$ groups can be replaced by $R^5C=CR^5$, $C\equiv C$, $Si(R^5)_2$, $Ge(R^5)_2$, $Sn(R^5)_2$, C=O, C=S, C=Se, $C=NR^5$, $P(=O)(R^5)$, SO, $SO_2$, $NR^5$, O, S or $CONR^5$ and wherein one or more H atoms can be substituted with deuterium, CN, $CF_3$ or $NO_2$; or an aromatic or heteroaromatic ring system having 5 to 60 aromatic ring atoms, which can in each case be substituted with one or more radicals $R^5$, or an aryloxy or heteroaryloxy group having 5 to 60 aromatic ring atoms, which can be substituted with one or more radicals $R^5$, or a diarylamino group, diheteroarylamino group or arylheteroarylamino group having 10 to 40 aromatic ring atoms, which can be substituted with one or more radicals $R^5$. Otherwise, the abovementioned definitions apply.

In a further embodiment of the organic molecules according to the invention, in each occurrence the second chemical unit D is the same or different respectively comprising a structure of Formula IIc, Formula IIc-2, Formula IIc-3 or Formula IIc-4 or consisting thereof:

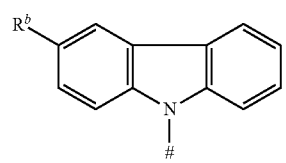

Formula IIc

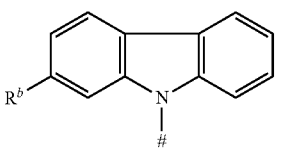

Formula IIc-2

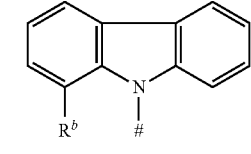

Formula IIc-3

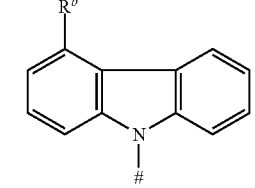

Formula IIc-4 wherein the abovementioned definitions apply.

In a further embodiment of the organic molecules according to the invention, in each occurrence $R^b$ is independently selected from the group consisting of Me, $^iPr$, $^tBu$, CN, $CF_3$, Ph, which can respectively be substituted with one or more radicals selected from Me, $^iPr$, $^tBu$, CN, $CF_3$ and Ph, pyridinyl, which can respectively be substituted with one or more radicals selected from Me, $^iPr$, $^tBu$, CN, $CF_3$ and Ph, pyrimidinyl, which can respectively be substituted with one or more radicals selected from Me, $^iPr$, $^tBu$, CN, $CF_3$ and Ph, carbazolyl, which can respectively be substituted with one or more radicals selected from Me, $^iPr$, $^tBu$, ON, $CF_3$ and Ph, triazinyl, which can respectively be substituted with one or more radicals selected from Me, $^iPr$, $^tBu$, CN, $CF_3$ and Ph, and $N(Ph)_2$.

Examples of the second chemical group D are shown below:

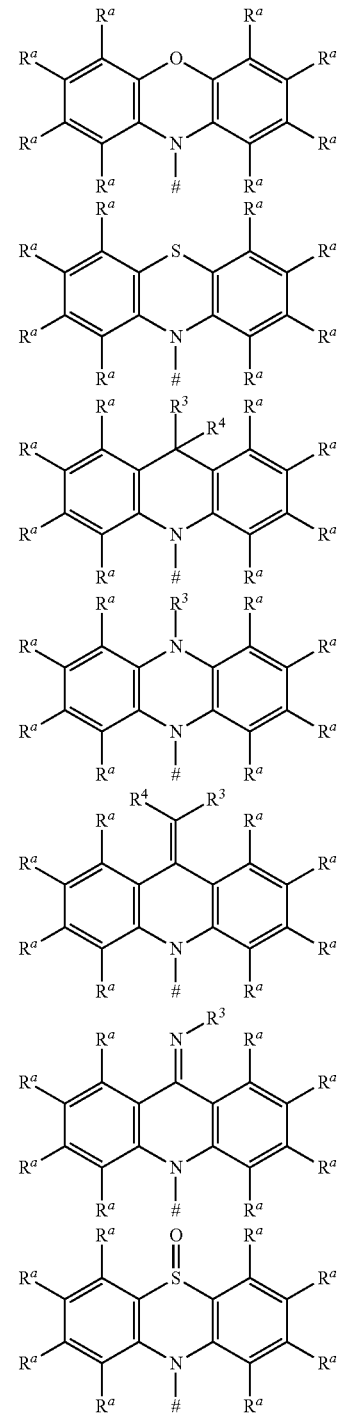

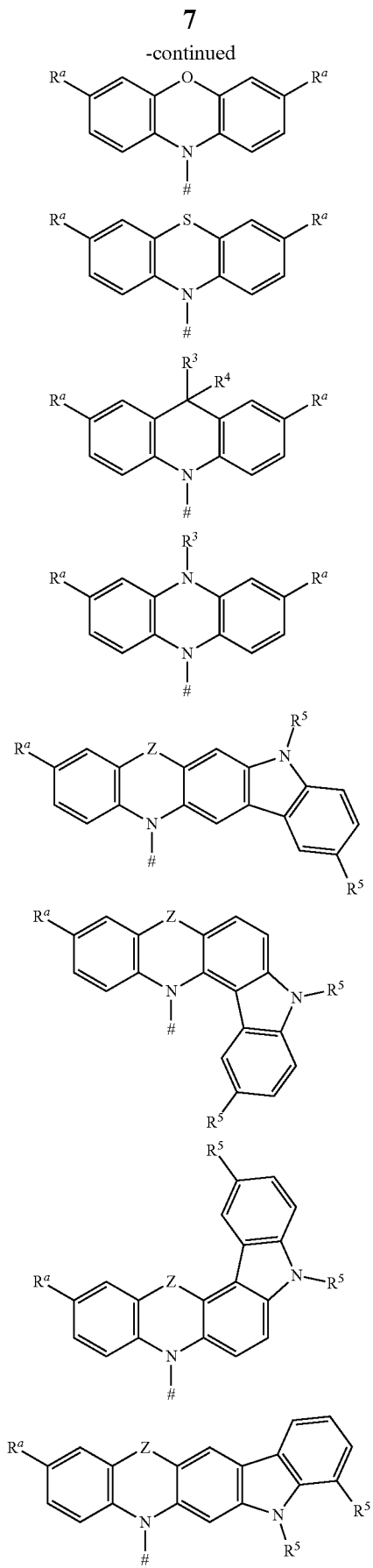
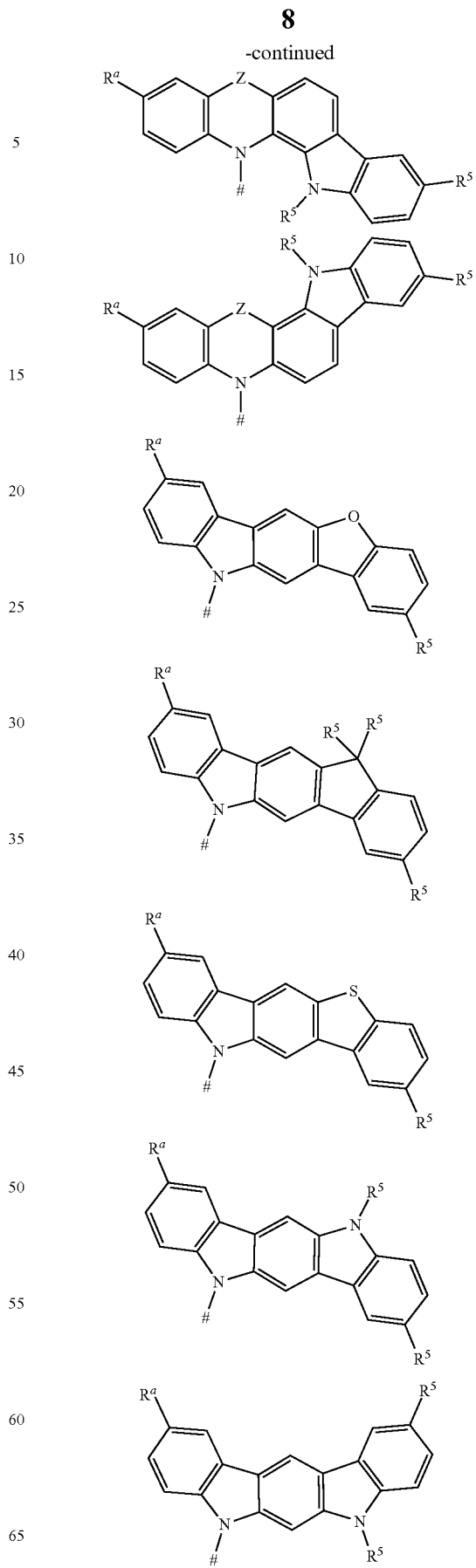

-continued

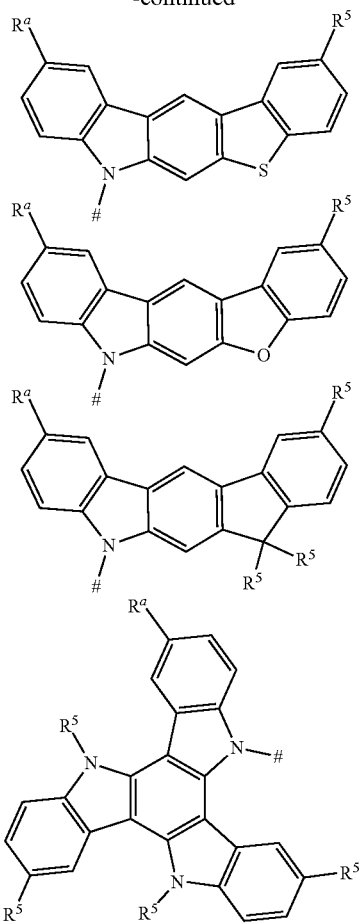

wherein the abovementioned definitions apply for #, Z, $R^a$, $R^3$, $R^4$ and $R^5$. In one embodiment, in each occurrence, the radical $R^5$ is the same or different and is selected from the group consisting of H, methyl, ethyl, phenyl and mesityl. In one embodiment, in each occurrence, the radical $R^a$ is the same or different and is selected from the group consisting of H, methyl (Me), i-propyl ($CH(CH_3)_2$) ($^i$Pr), t-butyl ($^t$Bu), phenyl (Ph), CN, $CF_3$ and diphenylamine ($NPh_2$).

In one embodiment, the organic molecules according to the invention have a structure of Formula III or consist thereof:

Formula III

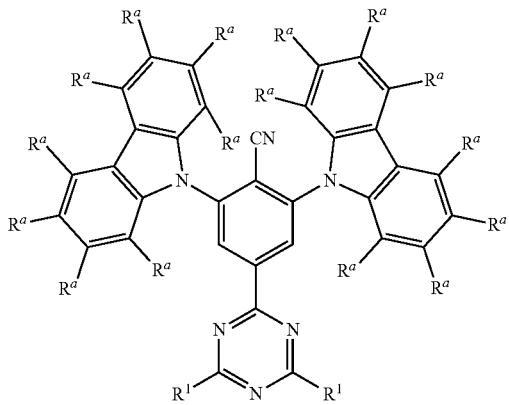

wherein the abovementioned definitions apply.

In a further embodiment, the organic molecules according to the invention have a structure of Formula IIIa:

Formula IIIa wherein

In each occurrence $R^c$ is independently selected from the group consisting of Me, $^i$Pr, $^t$Bu, CN, $CF_3$, Ph, which can respectively be substituted with one or more radicals selected from Me, $^i$Pr, $^t$Bu, CN, $CF_3$ and Ph, pyridinyl, which can respectively be substituted with one or more radicals selected from Me, $^i$Pr, $^t$Bu, CN, CF and Ph, pyrimidinyl, which can respectively be substituted with one or more radicals selected from Me, $^i$Pr, $^t$Bu, CN, $CF_3$ and Ph, carbazolyl, which can respectively be substituted with one or more radicals selected from Me, $^i$Pr, $^t$Bu, CN, $CF_3$ and Ph, triazinyl, which can respectively be substituted with one or more radicals selected from Me, $^i$Pr, $^t$Bu, CN, $CF_3$ and Ph, and $N(Ph)_2$.

In a further embodiment, the organic molecules according to the invention have a structure of Formula IIIb or consist thereof:

Formula IIIb wherein the abovementioned definitions apply.

In a further embodiment, the organic molecules according to the invention have a structure of Formula IIIc or consist thereof:

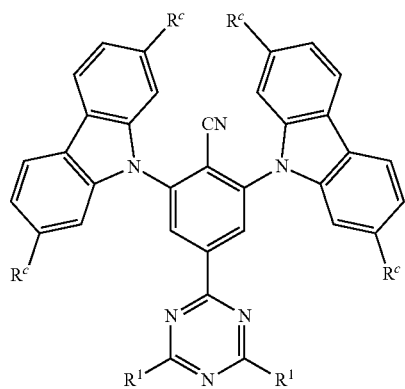

Formula IIIc wherein the abovementioned definitions apply.

In a further embodiment, the organic molecules according to the invention have a structure of Formula IIId or consist thereof:

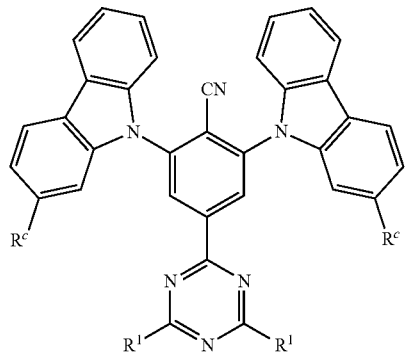

Formula IIId wherein the abovementioned definitions apply.

In a further embodiment, the organic molecules according to the invention have a structure of Formula IIIe or consist thereof:

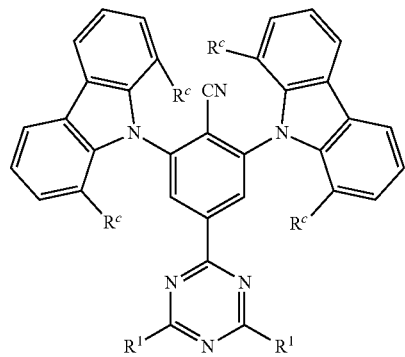

Formula IIIe wherein the abovementioned definitions apply.

In a further embodiment, the organic molecules according to the invention have a structure of Formula IIIf:

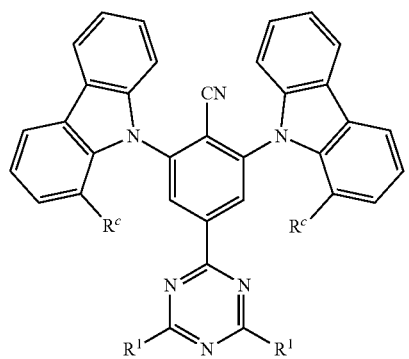

Formula IIIf wherein the abovementioned definitions apply.

In a further embodiment, the organic molecules according to the invention have a structure of Formula IIIg or consist thereof:

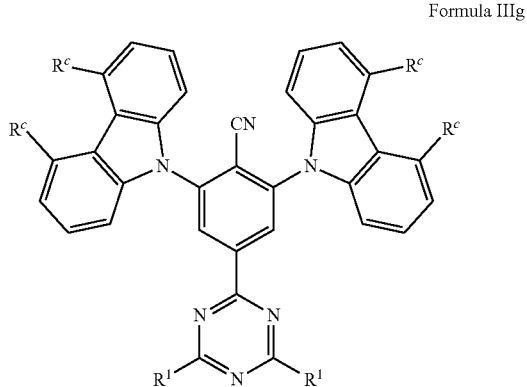

Formula IIIg wherein the abovementioned definitions apply.

In a further embodiment, the organic molecules according to the invention have a structure of Formula IIIh or consist thereof:

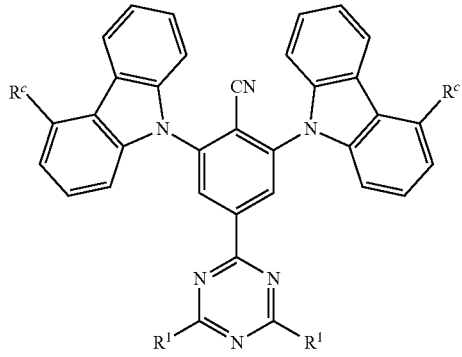

Formula IIIh wherein the abovementioned definitions apply.

In one embodiment, the organic molecules according to the invention have a structure of Formula IV or consist thereof:

Formula IV

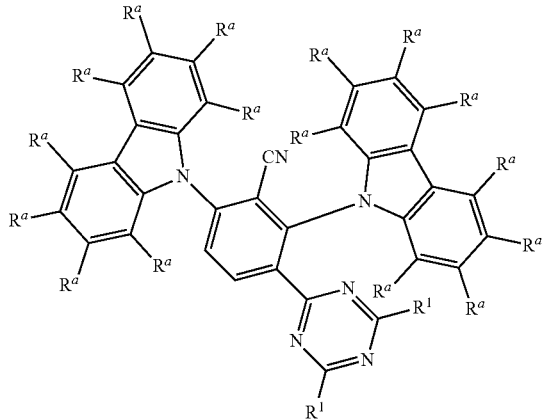

wherein the abovementioned definitions apply.

In a further embodiment, the organic molecules according to the invention have a structure of Formula IVa or consist thereof:

Formula IVa

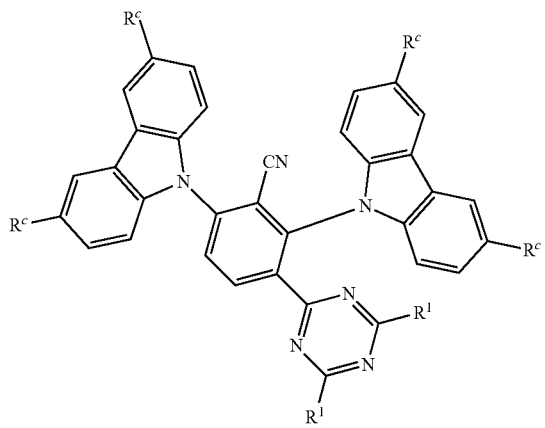

wherein the abovementioned definitions apply.

In a further embodiment, the organic molecules according to the invention have a structure of Formula IVb or consist thereof:

Formula IVb

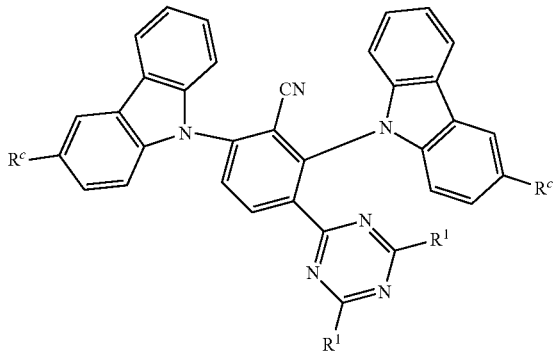

wherein the abovementioned definitions apply.

In a further embodiment, the organic molecules according to the invention have a structure of Formula IVc or consist thereof:

Formula IVc

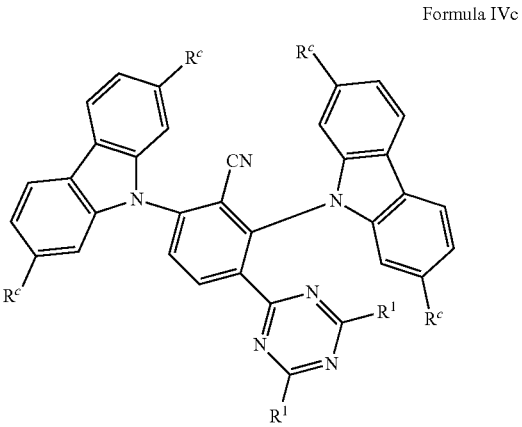

wherein the abovementioned definitions apply.

In a further embodiment, the organic molecules according to the invention have a structure of Formula IVd or consist thereof:

Formula IVd

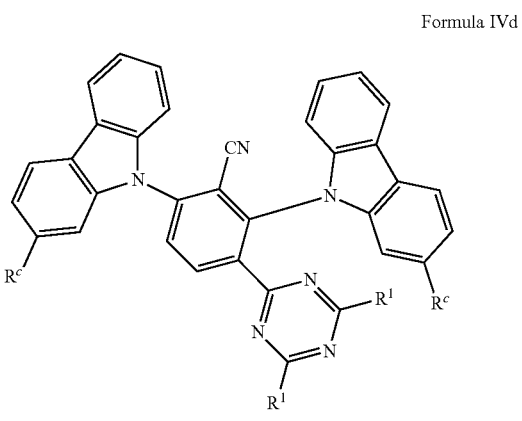

wherein the abovementioned definitions apply.

In a further embodiment, the organic molecules according to the invention have a structure of Formula IVe or consist thereof:

Formula IVe

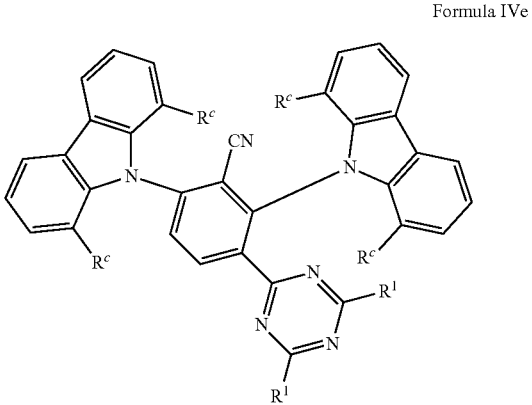

wherein the abovementioned definitions apply.

In a further embodiment, the organic molecules according to the invention have a structure of Formula IVf or consist thereof:

Formula IVf

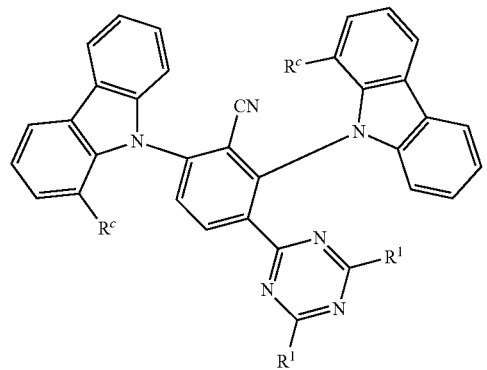

wherein the abovementioned definitions apply.

In a further embodiment, the organic molecules according to the invention have a structure of Formula IVg or consist thereof:

Formula IVg

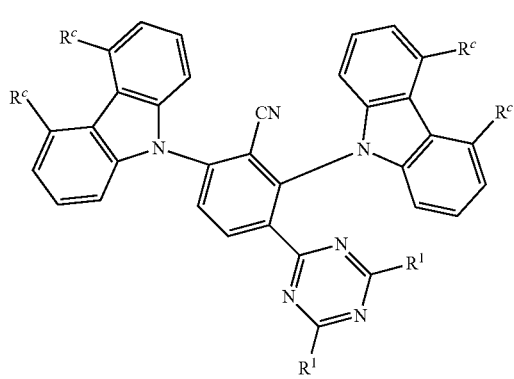

wherein the abovementioned definitions apply.

In a further embodiment, the organic molecules according to the invention have a structure of Formula IVh or consist thereof:

Formula IVh

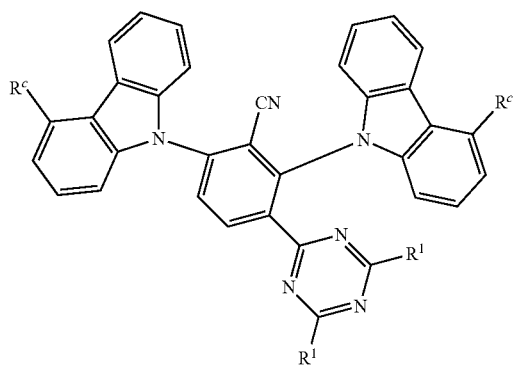

wherein the abovementioned definitions apply.

In one embodiment, the organic molecules according to the invention have a structure of Formula V or consist thereof:

Formula V

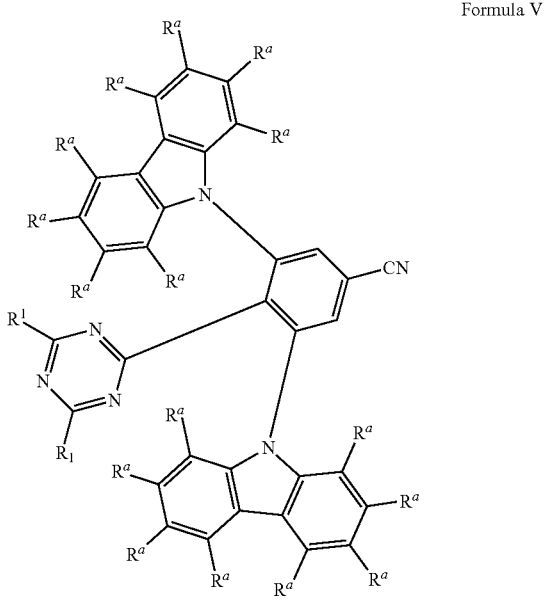

wherein the abovementioned definitions apply.

In a further embodiment, the organic molecules according to the invention have a structure of Formula Va or consist thereof:

Formula Va

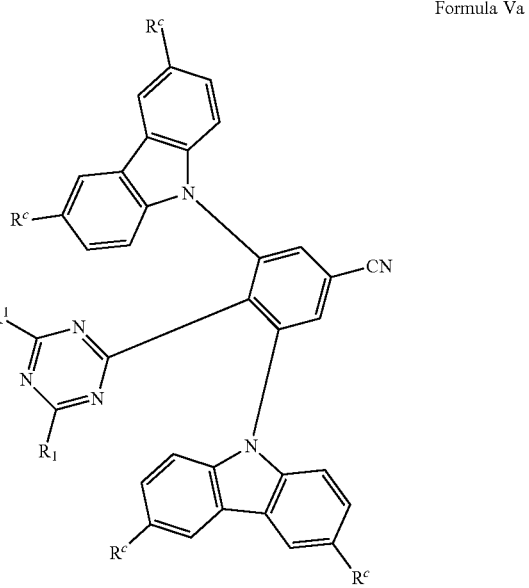

wherein the abovementioned definitions apply.

In a further embodiment, the organic molecules according to the invention have a structure of Formula Vb or consist thereof:

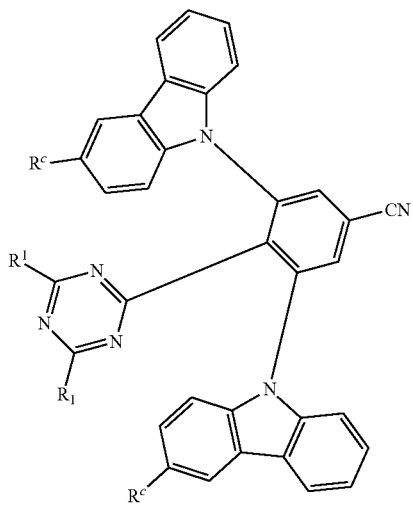

Formula Vb wherein the abovementioned definitions apply.

In a further embodiment, the organic molecules according to the invention have a structure of Formula Vc or consist thereof:

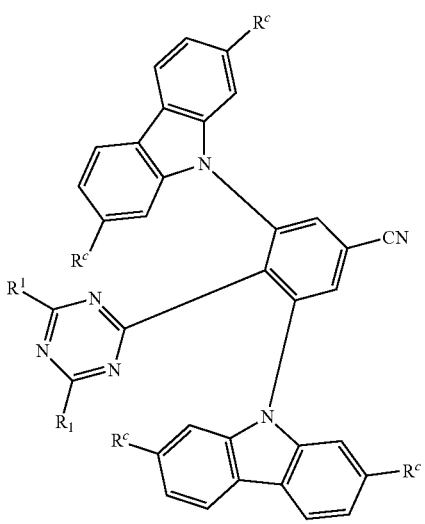

Formula Vc wherein the abovementioned definitions apply.

In a further embodiment, the organic molecules according to the invention have a structure of Formula Vd or consist thereof:

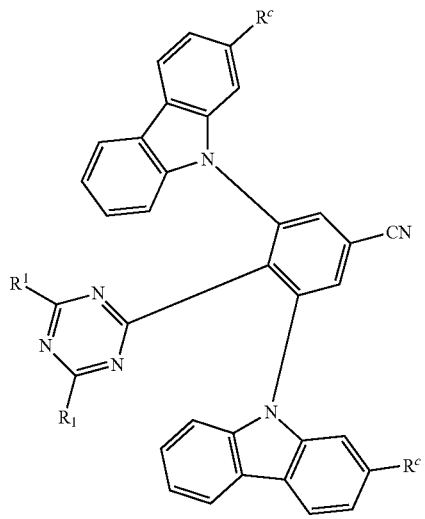

Formula Vd wherein the abovementioned definitions apply.

In a further embodiment, the organic molecules according to the invention have a structure of Formula Ve or consist thereof:

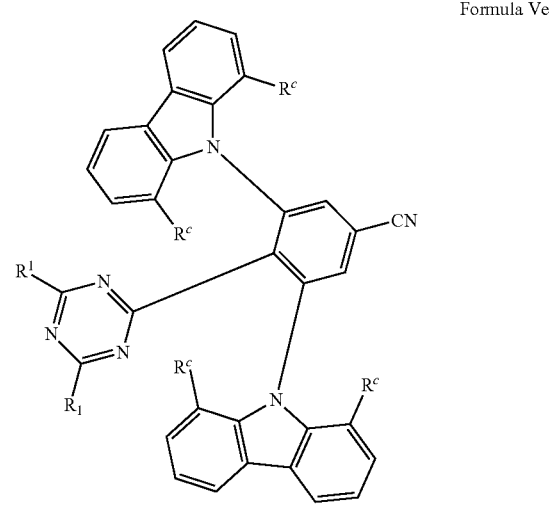

Formula Ve wherein the abovementioned definitions apply.

In a further embodiment, the organic molecules according to the invention have a structure of Formula Vf or consist thereof:

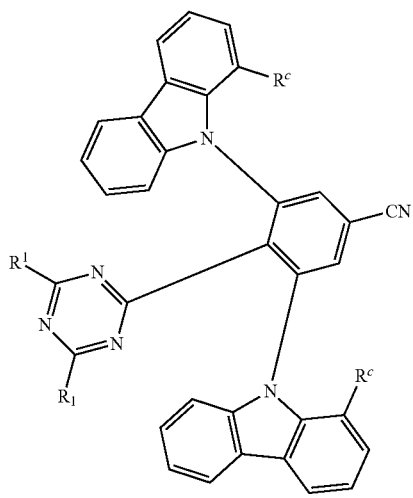

Formula Vf wherein the abovementioned definitions apply.

In a further embodiment, the organic molecules according to the invention have a structure of Formula Vg or consist thereof:

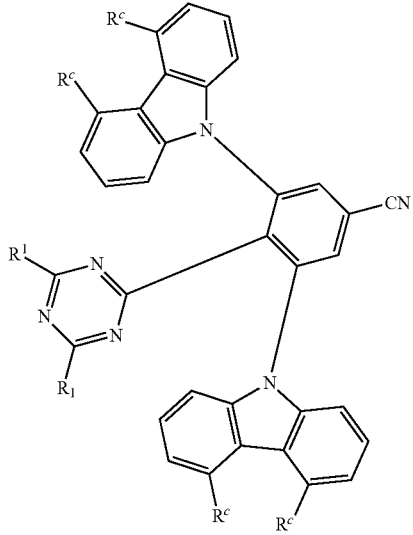

Formula Vg wherein the abovementioned definitions apply.

In a further embodiment, the organic molecules according to the invention have a structure of Formula Vh or consist thereof:

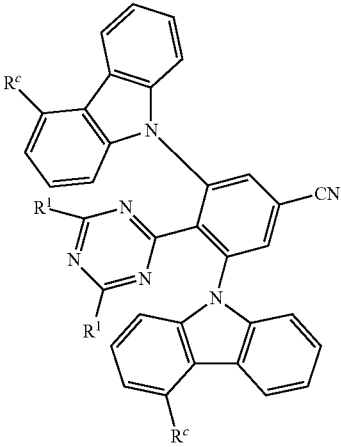

Formula Vh wherein the abovementioned definitions apply.

In one embodiment, the organic molecules according to the invention have a structure of Formula VI or consist thereof:

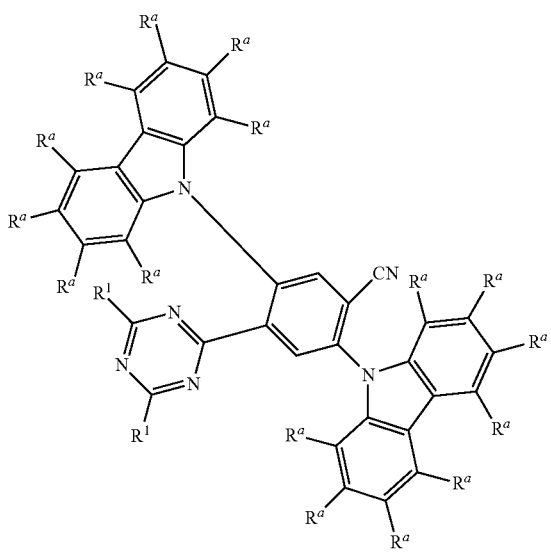

Formula VI wherein the abovementioned definitions apply.

In a further embodiment, the organic molecules according to the invention have a structure of Formula VIa or consist thereof:

Formula VIa

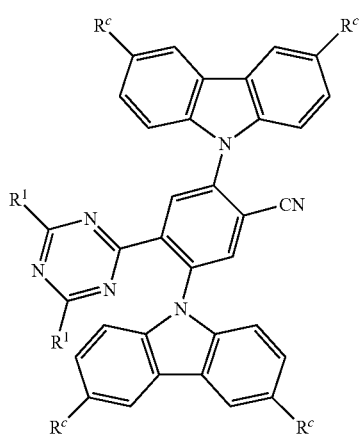

wherein the abovementioned definitions apply.

In a further embodiment, the organic molecules according to the invention have a structure of Formula VIb or consist thereof:

Formula VIb

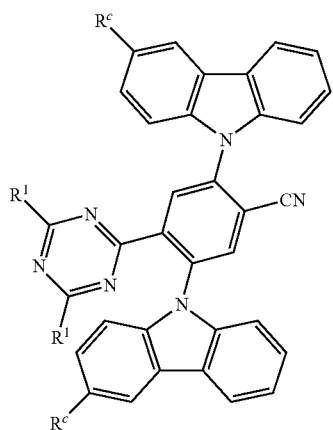

wherein the abovementioned definitions apply.

In a further embodiment, the organic molecules according to the invention have a structure of Formula VIc or consist thereof:

Formula VIc

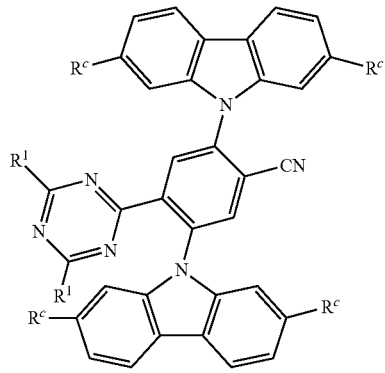

wherein the abovementioned definitions apply.

In a further embodiment, the organic molecules according to the invention have a structure of Formula VId or consist thereof:

Formula VId

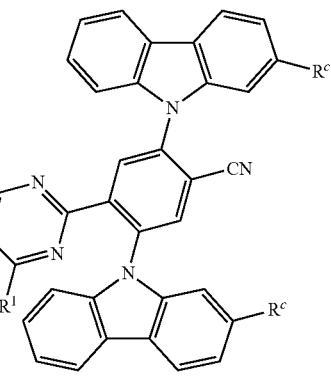

wherein the abovementioned definitions apply.

In a further embodiment, the organic molecules according to the invention have a structure of Formula VIe or consist thereof:

Formula VIe

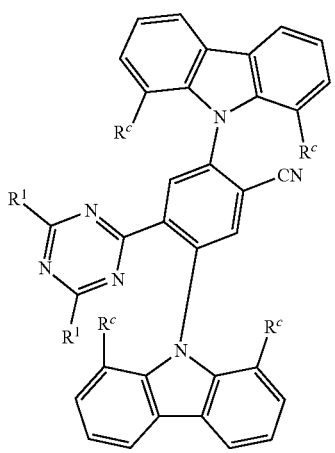

wherein the abovementioned definitions apply.

In a further embodiment, the organic molecules according to the invention have a structure of Formula VIf or consist thereof:

Formula VIf

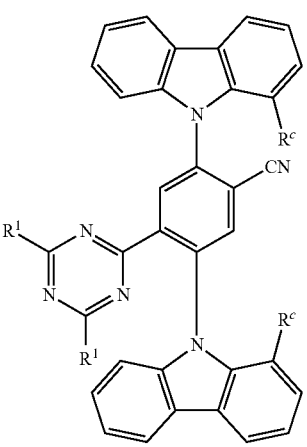

wherein the abovementioned definitions apply.

In a further embodiment, the organic molecules according to the invention have a structure of Formula VIg or consist thereof:

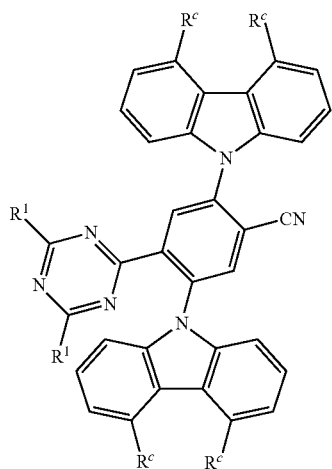

Formula VIg wherein the abovementioned definitions apply.

In a further embodiment, the organic molecules according to the invention have a structure of Formula VIh or consist thereof:

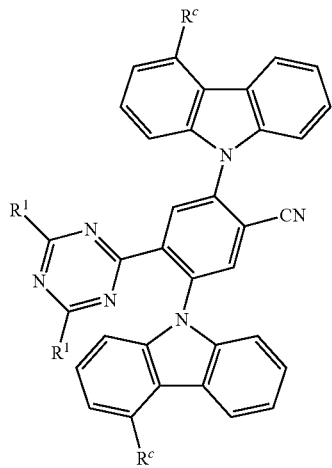

Formula VIh wherein the abovementioned definitions apply.

In one embodiment, the organic molecules according to the invention have a structure of Formula VII or consist thereof:

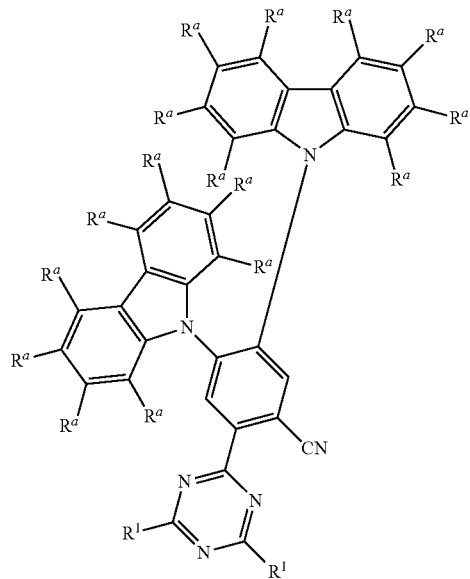

Formula VII wherein the abovementioned definitions apply.

In a further embodiment, the organic molecules according to the invention have a structure of Formula VIIa or consist thereof:

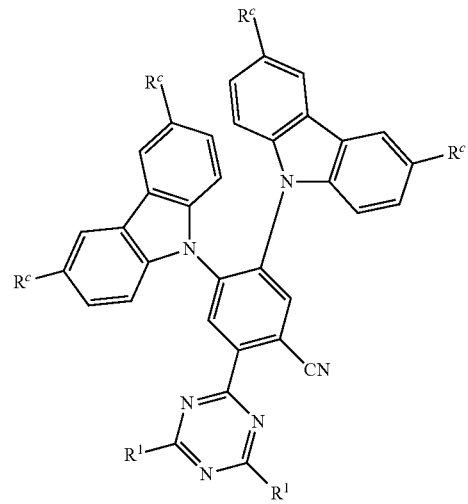

Formula VIIa wherein the abovementioned definitions apply.

In a further embodiment, the organic molecules according to the invention have a structure of Formula VIIb or consist thereof:

Formula VIIb

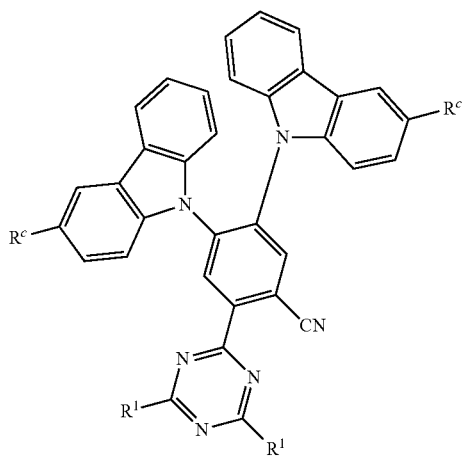

wherein the abovementioned definitions apply.

In a further embodiment, the organic molecules according to the invention have a structure of Formula VIIc or consist thereof:

Formula VIIc

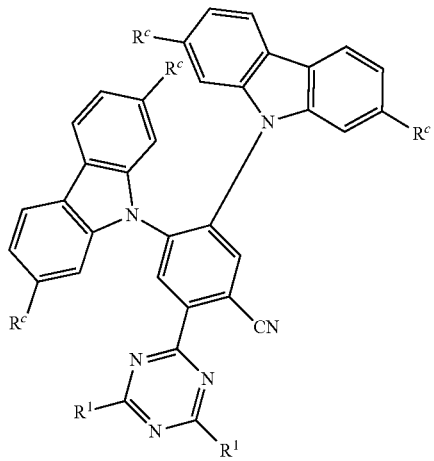

wherein the abovementioned definitions apply.

In a further embodiment, the organic molecules according to the invention have a structure of Formula VIId or consist thereof:

Formula VIId

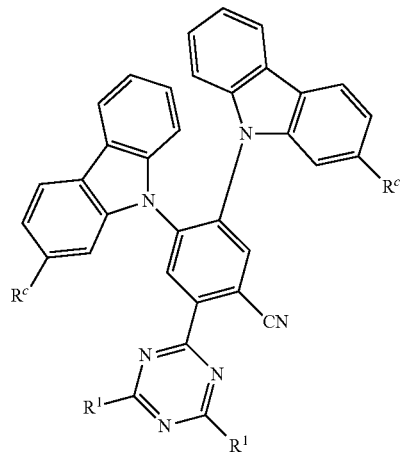

wherein the abovementioned definitions apply.

In a further embodiment, the organic molecules according to the invention have a structure of Formula VIIe or consist thereof:

Formula VIIe

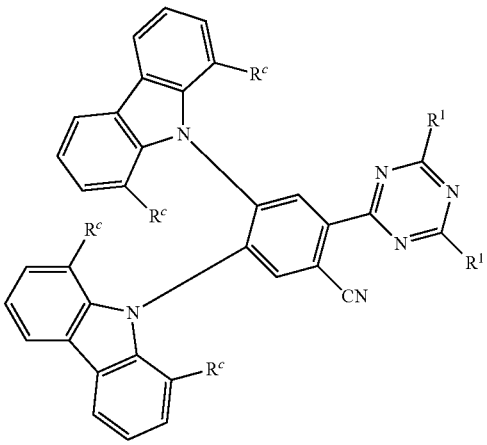

wherein the abovementioned definitions apply.

In a further embodiment, the organic molecules according to the invention have a structure of Formula VIIf or consist thereof:

Formula VIIf

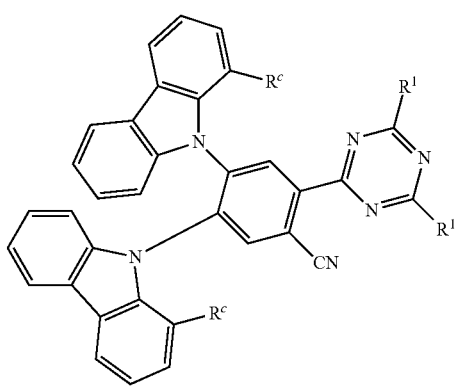

wherein the abovementioned definitions apply.

In a further embodiment, the organic molecules according to the invention have a structure of Formula VIIg or consist thereof:

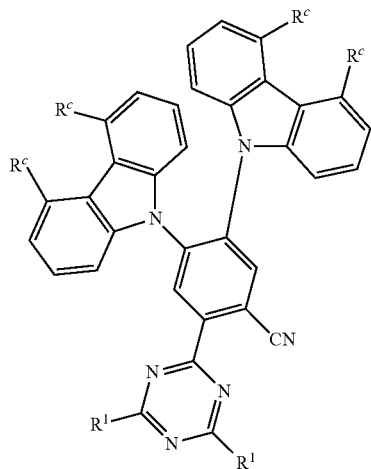

Formula VIIg wherein the abovementioned definitions apply.

In a further embodiment, the organic molecules according to the invention have a structure of Formula VIIh or consist thereof:

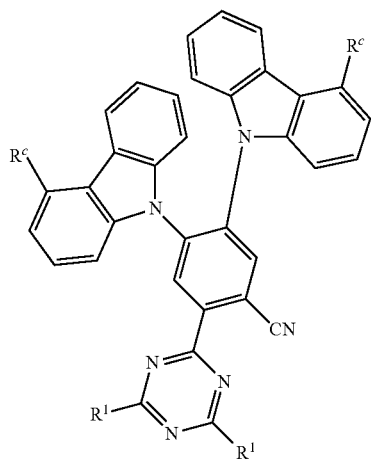

Formula VIIh wherein the abovementioned definitions apply.

In one embodiment, the organic molecules according to the invention have a structure of Formula VIII or consist thereof:

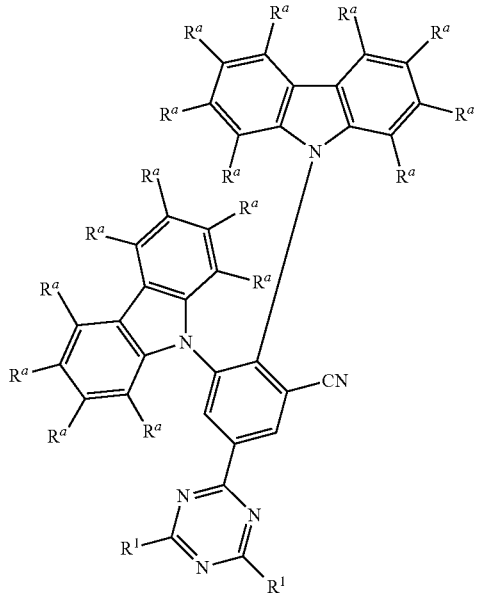

Formula VIII wherein the abovementioned definitions apply.

In one embodiment, in each occurrence $R^c$ is independently selected from the group consisting of CN, $CF_3$, Me, $^i$Pr, $^t$Bu, Ph, which can in each case be substituted with one or more radicals selected from CN, $CF_3$, Me, $^i$Pr, $^t$Bu, CN, $CF_3$ and Ph, and carbazolyl, which can in each case be substituted with one or more radicals selected from CN, $CF_3$, Me, $^i$Pr, $^t$Bu, and Ph.

In the context of this invention, an aryl group contains 6 to 60 aromatic ring atoms; a heteroaryl group contains 5 to 60 aromatic ring atoms, at least one of which represents a heteroatom. The heteroatoms are, in particular, N, O and/or S. In the event that other definitions, which differ from the stated definitions, for example with respect to the number of aromatic ring atoms or the contained heteroatoms, are specified in the description of specific embodiments of the invention, then these definitions apply.

An aryl group or heteroaryl group is understood to be a simple aromatic ring, i.e. benzene, or a simple heteroaromatic ring, for example pyridine, pyrimidine or thiophene, or a heteroaromatic polycyclic compound, for example phenanthrene, quinoline or carbazole. In the context of the present application, a condensed (annelated) aromatic or heteroaromatic polycyclic compound consists of two or more simple aromatic or heteroaromatic rings which are condensed with one another.

An aryl or heteroaryl group, which can in each case be substituted with the abovementioned radicals and which can be linked to the aromatic or heteroaromatic group via any desired positions, are in particular understood to be groups which are derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene; pyrrole, indole, isoindole, carbazole, pyridine, quinoline, isoquinoline, acridine, phenanthridine, benzo-5,6-quinoline, isoquinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, napthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,2,3,4-tetrazine, purine, pteridine, indolizine and benzothiadiazole or combinations of said groups.

A cyclic alkyl, alkoxy or thioalkoxy group is understood here to be a monocyclic, a bicyclic or a polycyclic group.

Within the scope of the present invention, a $C_1$ to $C_{40}$ alkyl group, in which individual H atoms or $CH_2$ groups can also be substituted with the groups mentioned above, are understood to be, for example, the radicals methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2,2,2]octyl, 2-bicyclo[2,2,2]-octyl, 2-(2,6-dimethyl)octyl, 3-(3,7-dimethyl)octyl, adamantyl, trifluoromethyl, pentafluorethyl, 2,2,2-trifluorethyl, 1,1-dimethyl-n-hex-1-yl-, 1,1-dimethyl-n-hept-1-yl-, 1,1-dimethyl-n-oct-1-yl-, 1,1-dimethyl-n-dec-1-yl-, 1,1-dimethyl-n-dodec-1-yl-, 1,1-dimethyl-n-tetradec-1-yl-, 1,1-dimethyl-n-hexadec-1-yl-, 1,1-dimethyl-n-octadec-1-yl-, 1,1-diethyl-n-hex-1-yl-, 1,1-diethyl-n-hept-1-yl-, 1,1-diethyl-n-oct-1-yl-, 1,1-diethyl-n-dec-1-yl-, 1,1-diethyl-n-dodec-1-yl-, 1,1-diethyl-n-tetradec-1-yl-, 1,1-diethyln-n-hexadec-1-yl-, 1,1-diethyl-n-octadec-1-yl-, 1-(n-propyl)-cyclohex-1-yl-, 1-(n-butyl)-cyclohex-1-yl-, 1-(n-hexyl)-cyclohex-1-yl-, 1-(n-octyl)-cyclohex-1-yl- and 1-(n-decyl)-cyclohex-1-yl. An alkenyl group is understood to be ethenyl, propenyl, butenyl, pentenyl, cyclopentenyl, hexenyl, cyclohexenyl, heptenyl, cycloheptenyl, octenyl, cyclooctenyl or cyclooctadienyl, for example. An alkinyl group is understood to be ethinyl, propinyl, butinyl, pentinyl, hexinyl, heptinyl or octinyl, for example. A $C_1$ to $C_{40}$ alkoxy group is understood to be methoxy, trifluoromethoxy, ethoxy, n-propoxy, i-propoxy, n-butoxy, i-butoxy, s-butoxy, t-butoxy or 2-methylbutoxy, for example.

One embodiment of the invention relates to organic molecules, which have an $\Delta E(S_1-T_1)$ value between the lowest excited singlet ($S_1$) state and the triplet ($T_1$) state below it that is no higher than 5000 cm$^{-1}$, in particular no higher than 3000 cm$^{-1}$, or no higher than 1500 cm$^{-1}$ or 1000 cm$^{-1}$ and/or an emission lifetime of at most 150 µs, in particular at most 100 µs, at most 50 µs, or at most 10 µs and/or a main emission band having a full width at half maximum of less than 0.55 eV, in particular less than 0.50 eV, less than 0.48 eV, or less than 0.45 eV.

The organic molecules in particular have an emission maximum between 420 and 500 nm, between 430 and 480 nm or between 450 and 470 nm.

The molecules in particular have a "blue material index" (BMI), the quotient of the PLQY (in %) and the CIE$_y$ color coordinate of the light emitted by the molecule according to the invention, that is greater than 150, in particular greater than 200, greater than 250 or greater than 300.

In a further aspect, the invention relates to a method for producing an organic molecule according to the invention of the type described here (with a possible subsequent reaction), wherein the 4 and 6 position $R^1$-substituted 2-halogen-1,3,5-triazine is used as the educt, 2-halogen-1,3,5-triazines according to the invention are 2-chloro-1,3,5-triazine, 2-bromo-1,3,5-triazine and 2-iodo-1,3,5-triazine.

In one embodiment, 2-chloro-4,6-diphenyl-1,3,5-triazine, 2-bromo-4,6-diphenyl-1,3,5-triazine, 2-iodo-4,6-diphenyl-1,3,5-triazine, 2-chloro-4,6-dimethyl-1,3,5-triazine, 2-bromo-4,6-dimethyl-1,3,5-triazine or 2-iodo-4,6-dimethyl-1,3,5-triazine are used as the educt.

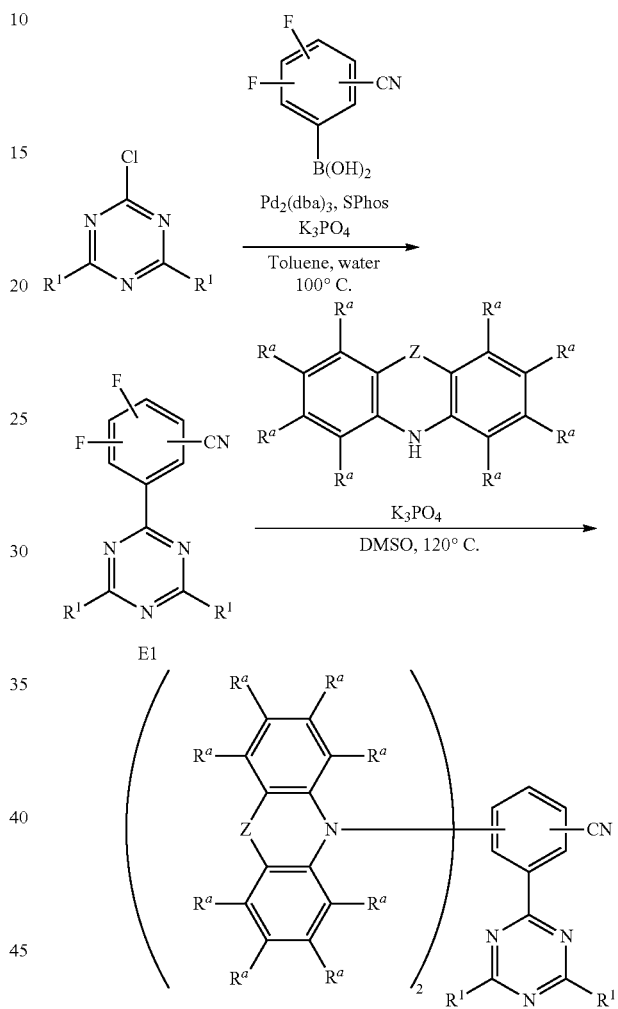

In the above schematic diagram, in one embodiment, the chemical group CN is replaced by $CF_3$.

In one embodiment, in 4 and 6 position $R^1$-substituted 2-halogen-1,3,5-triazine as the educt is reacted with a difluoro cyanophenylboronic acid or a corresponding difluoro cyanophenylboronic acid ester in a palladium-catalyzed cross-coupling reaction. According to the invention, 2,6-difluoro-4-cyanophenylboronic acid, 2,5-difluoro-4-cyanophenylboronic acid, 3,5-difluoro-4-cyanophenylboronic acid, 4,5,-difluoro-3-cyanophenylboronic acid, 2,4-difluoro-3-cyanophenylboronic acid and 4,5-difluoro-2-cyanophenylboronic acid, for example, can be used. The product is obtained by deprotonation of the corresponding amine and subsequent nucleophilic substitution of the two fluorine groups. To do this, two nitrogen heterocyclic compounds are reacted with an educt E1 in the context of a nucleophilic aromatic substitution. Typical conditions include the use of a base, such as potassium phosphate tribasic or sodium hydride, in an aprotic polar solvent, such as dimethyl sulfoxide (DMSO) or N,N-dimethylformamide (DMF).

In a further aspect, the invention relates to the use of the organic molecules as luminescent emitters or as host material in an organic optoelectronic device, in particular wherein the organic optoelectronic device is selected from the group consisting of:
  organic light-emitting diodes (OLEDs),
  light-emitting electrochemical cells,
  OLED sensors, in particular in gas and vapor sensors which are not hermetically shielded to the outside,
  organic diodes,
  organic solar cells,
  organic transistors,
  organic field-effect transistors,
  organic lasers and
  down-conversion elements.

In a further aspect, the invention relates to a composition having or consisting of:
  (a) at least one organic molecule according to the invention, in particular as an emitter and/or host, and
  (b) at least one, i.e. one or more emitter and/or host materials, that is or are different from the organic molecule according to the invention, and
  (c) optionally one or more dyes and/or one or more organic solvents.

In one embodiment, the composition according to the invention consists of an organic molecule according to the invention and one or more host materials. In particular, the host material or materials possess triplet ($T_1$) and singlet ($S_1$) energy levels, which are energetically higher than the triplet ($T_1$) and singlet ($S_1$) energy levels of the organic molecule according to the invention. In one embodiment, in addition to the organic molecule according to the invention, the composition has an electron-dominant and a hole-dominant host material. The highest occupied orbital (HOMO) and the lowest unoccupied orbital (LUMO) of the hole-dominant host material are in particular energetically higher than that of the electron-dominant host material. The HOMO of the hole-dominant host material is energetically below the HOMO of the organic molecule according to the invention, while the LUMO of the electron-dominant host material is energetically above the LUMO of the organic molecule according to the invention. In order to avoid exciplex formation between emitter and host material or host materials, the materials should be selected such that the energy distances between the respective orbitals are small. The distance between the LUMO of the electron-dominant host material and the LUMO of the organic molecule according to the invention is in particular less than 0.5 eV, preferably less than 0.3 eV, even more preferably less than 0.2 eV. The distance between the HOMO of the hole-dominant host material and the HOMO of the organic molecule according to the invention is in particular less than 0.5 eV, preferably less than 0.3 eV, even more preferably less than 0.2 eV.

In a further aspect, the invention relates to an organic optoelectronic device which has an organic molecule according to the invention or a composition according to the invention. The organic optoelectronic device is in particular formed as a device selected from the group consisting of organic light-emitting diode (OLED); light-emitting electrochemical cell; OLED sensor, in particular gas and vapor sensors which are not hermetically shielded to the outside; organic diode; organic solar cell; organic transistor; organic field-effect transistor; organic laser and down-conversion element.

An organic optoelectronic device having
  a substrate,
  an anode and
  a cathode, wherein the anode or the cathode are disposed on the substrate, and
  at least one light-emitting layer, which is disposed between the anode and the cathode and which has an organic molecule according to the invention, represents a further embodiment of the invention.

In one embodiment, the optoelectronic device is an OLED. A typical OLED, for example, has the following layer structure:
  1. Substrate (supporting material)
  2. Anode
  3. Hole injection layer (HIL)
  4. Hole transport layer (HTL)
  5. Electron blocking layer (EBL)
  6. Emitting layer (EML)
  7. Hole blocking layer (HBL)
  8. Electron transport layer (ETL)
  9. Electron injection layer (EIL)
  10. Cathode.

The presence of specific layers is merely optional. Several of these layers can also coincide. Specific layers can also be present more than once in the component.

According to one embodiment, at least one electrode of the organic component is designed to be translucent. In this case, "translucent" describes a layer that is transmissive to visible light. The translucent layer can be clearly translucent, i.e. transparent, or at least partially light-absorbing and/or partially light-diffusing, so that the translucent layer can, for example, also be diffusely or milkily translucent. A layer referred to here as translucent is in particular designed to be as transparent as possible, so that in particular the absorption of light is as low as possible.

According to a further embodiment, the organic component, in particular an OLED, has an inverted structure. The inverted structure is characterized in that the cathode is located on the substrate and the other layers are disposed in a correspondingly inverted manner:
  1. Substrate (supporting material)
  2. Cathode
  3. Electron injection layer (EIL)
  4. Electron transport layer (ETL)
  5. Hole blocking layer (HBL)
  6. Emission layer or emitting layer (EML)
  7. Electron blocking layer (EBL)
  8. Hole transport layer (HTL)
  9. Hole injection layer (HIL)
  10. Anode The presence of specific layers is merely optional. Several of these layers can also coincide. Specific layers can also be present more than once in the component.

In one embodiment, in the inverted OLED, the anode layer of the typical structure e.g. an ITO layer (indium tin oxide), is connected as the cathode.

According to a further embodiment, the organic component, in particular an OLED, has a stacked structure. In this case, the individual OLEDs are arranged one above the other and not next to one another as usual. The production of mixed light can be made possible with the aid of a stacked structure. This structure can be used to produce white light, for example. To produce said white light, the entire visible spectrum is typically imaged by combining the emitted light of blue, green and red emitters. Furthermore, with practically the same efficiency and identical luminance, significantly longer lifetimes can be achieved in comparison to conventional OLEDs. A so-called charge generation layer (CGL) between two OLEDs is optionally used for the stacked structure. Said layer consists of an n-doped and a p-doped layer, wherein the n-doped layer is typically disposed closer to the anode.

In one embodiment—a so-called tandem OLED—two or more emission layers occur between the anode and the cathode. In one embodiment, three emission layers are arranged one above the other, wherein one emission layer emits red light, one emission layer emits green light and one emission layer emits blue light, and additional charge generation, blocking or transport layers are optionally disposed between the individual emission layers. In a further embodiment, the respective emission layers are disposed directly adjacent to one another. In another embodiment, one respective charge generation layer is situated between the emission layers. Emission layers that are directly adjacent to one another and emission layers that are separated by charge generation layers can furthermore be combined in an OLED.

An encapsulation arrangement can furthermore be disposed above the electrodes and the organic layers as well. The encapsulation arrangement can, for example, be designed in the form of a glass cover or in the form of a thin-film encapsulation arrangement.

The supporting material of the optoelectronic device can, for example, be glass, quartz, plastic, metal, a silicon wafer or any other suitable solid or flexible, optionally transparent material. The supporting material can, for example, have one or more materials in the form of a layer, a film, a plate or a laminate.

Transparent conductive metal oxides such as, for example, ITO (indium tin oxide), zinc oxide, tin oxide, cadmium oxide, titanium oxide, indium oxide or aluminum zinc oxide (AZO), $Zn_2Sn_4$, $CdSnO_3$, $ZnSnO_3$, $MgIn_2O_4$, $GaInO_3$, $Zn_2In_2O_5$ or $In_4Sn_3O_{12}$ or mixtures of different transparent conductive oxides, for example, can be used as the anode of the optoelectronic device.

PEDOT:PSS (poly-3,4-ethylenedioxythiophene: polystyrene sulfonic acid), PEDOT (poly-3,4-ethylenedioxythiophene), m-MTDATA (4,4',4"-tris[phenyl(m-tolyl)amino]triphenylamine), Spiro-TAD (2,2',7,7'-tetrakis(N,N-diphenylamino)-9,9-spirobifluorene), DNTPD (4,4'-bis[N-[4-{N,N-bis(3-methyl-phenyl]amino}phenyq-N-phenylamino]biphenyl), NPB (N,N'-bis-(1-naphthalenyl)-N,N'-bis-phenyl-(1,1'-biphenyl)-4,4'-diamine), NPNPB (N,N'-diphenyl-N,N'-di-[4-(N,N-diphenyl-amino)phenyl]benzene), MeO-TPD (N,N,N',N'-tetrakis(4-methoxyphenyl)benzene), HAT-ON (1,4,5,8,9,11-hexaazatriphenylenehexacarbonitrile) or Spiro-NPD (N,N'-diphenyl-N,N'-bis-(1-naphthyl)-9,9'-spirobifluorene-2,7-diamine), for example, are suitable materials for an HIL. The layer thickness is 10-80 nm, for example. Small molecules (e.g. copper phthalocyanine (CuPc e.g. 10 nm thick)) or metal oxides, such as $MoO_3$, $V_2O_5$, can also be used.

Tertiary amines, carbazole derivatives, polyethylenedioxythiophene doped with polystyrene sulfonic acid, polyaniline poly-TPD (poly(4-butylphenyl-diphenyl-amine)) doped with camphorsulfonic acid, [alpha]-NPD (poly(4-butylphenyl-diphenyl-amine)), TAPC (4,4'-cyclohexylidene-bis[N,N-bis(4-methylphenyl)benzenamine]), TCTA (tris(4-carbazoyl-9-ylphenyl)amine), 2-TNATA (4,4',4"-tris [2-naphthyl(phenyl)amino]triphenylamine), Spiro-TAD, DNTPD, NPB, NPNPB, Me0-TPD, HAT-CN or TrisPcz (9,9'-diphenyl-6-(9-phenyl-9H-carbazole-3-yl)-9H,9'H-3,3'-bicarbazole) can be used as materials for an HTL. The layer thickness is 10 nm to 100 nm, for example.

The HTL can have a p-doped layer, which has an inorganic or organic dopant in an organic hole-transporting matrix. Transition metal oxides such as vanadium oxide, molybdenum oxide or tungsten oxide, for example, can be used as the inorganic dopant. Tetrafluorotetracyanoquinodimethane (F4-TCNQ), copper pentafluorobenzoate (Cu(I) pFBz) or transition metal complexes can, for example, be used as the organic dopants. The layer thickness is 10 nm to 100 nm, for example.

mCP (1,3-bis(carbazole-9-yl)benzene), TCTA, 2-TNATA, mCBP (3,3-Di(9H-carbazole-9-yl)biphenyl), tris-Pcz (9,9'-diphenyl-6-(9-phenyl-9H-carbazole-3-yl)-9H,9'H-3,3'-bicarbazole), CzSi (9-(4-tert-butylphenyl)-3,6-bis(triphenylsilyl)-9H-carbazole) or DCB (N,N'-dicarbazolyl-1,4-dimethylbenzene) can, for example, be used as the materials of an electron blocking layer. The layer thickness is 10 nm to 50 nm, for example.

The emitter layer EML or emission layer consists of or contains emitter material or a mixture having at least two emitter materials and optionally one or more host materials. Suitable host materials are, for example, mCP, TCTA, 2-TNATA, mOBP, CBP (4,4'-Bis-(N-carbazolyl)-biphenyl), Sif87 (dibenzo[b,d]thiophene-2-yltriphenylsilane), Sif88 (dibenzo[b,d]thiophene-2-yl)diphenylsilane), 9-[3-(dibenzofuran-2-yl)phenyl]-9H-carbazole, 9-[3-(dibenzofuran-2-yl)phenyl]-9H-carbazole, 9-[3-(dibenzothiophene-2-yl)phenyl]-9H-carbazole, 9-[3,5-bis(2-dibenzofuranyl)phenyl]-9H-carbazole, 9-[3,5-bis(2-dibenzothiophenyl)phenyl]-9H-carbazole, T2T (2,4,6-tris(biphenyl-3-yl)-1,3,5-triazine), T3T (2,4,6-tris(triphenyl-3-yl)-1,3,5-triazine) TST (2,4,6-tris(9,9'-spirobifluorene-2-yl)-1,3,5-triazine) andior DPEPO (Bis[2-((oxo)diphenylphosphino)phenyl]ether). In one embodiment, the EML contains 50-80 wt %, preferably 60-75 wt % of a host material selected from the group consisting of CBP, mCP, mCBP, 9-[3-(dibenzofuran-2-yl) phenyl]-9H-carbazole, 9-[3-(dibenzofuran-2-yl)phenyl]-9H-carbazole, 9-[3-(dibenzothiophene-2-yl)phenyl]-9H-carbazole, 9-[3,5-bis(2-dibenzofuranyl)phenyl]-9H-carbazole and 9-[3,5-bis(2-dibenzothlophenyl)phenyl]-9H-carbazole; 10-45 wt %, preferably 15-30 wt % T2T and 5-40 wt %, preferably 10-30 wt. %, of an organic molecule according to the invention as the emitter. The common matrix materials, such as CBP, are suitable for emitter material emitting in the green or in the red range or for a mixture having at least two emitter materials. UHG matrix materials (ultra-high energy gap materials) (see, for example, M. E. Thompson et al, Chem. Mater. 2004, 16, 4743) or other so-called wide-gap matrix materials can be used for emitter material emitting in the blue range or a mixture having at least two emitter materials. The layer thickness is 10 nm to 250 nm, for example.

The hole blocking layer HBL can, for example, have BCP (2,9-dimethyl-4,7-diphenyl-1,10-phenanthroline=bathocuproine), bis-(2-methyl-8-hydroxyquinolinato)-(4-phenylphenolato)-aluminum(III) (BAlq), Nbphen (2,9-bis(naphthalene-2-yl)-4,7-diphenyl-1,10-phenanthroline), Alq3 (aluminum-tris(8-hydroxyquinoline)), T2T, TSPO1 (diphenyl-4-triphenylsilyl-phenylphosphine oxide) or TCB/TCP (1,3,5-tris(N-carbazolyl)benzene/ 1,3,5-tris(carbazole-9-yl)benzene). The layer thickness is 10 nm to 50 nm, for example.

The electron transport layer ETL can, for example, have materials on the basis of $AlQ_3$. TSPO1, Nbphen, BPyTP2 (2,7-di(2,2'-bipyridine-5-yl)triphenyl)), Sif87, Sif88, BmPy-PhB (1,3-bis[3,5-di(pyridine-3-yl)phenyl]benzene) or BTB (4,4'-bis-[2-(4,6-diphenyl-1,3,5-triazinyl)]-1,1'-biphenyl). The layer thickness is 10 nm to 200 nm, for example.

CsF, LiF, 8-hydroxyquinolinolatolithium (Liq), Li$_2$O, BaF$_2$, MgO or NaF can be used as materials for a thin electron injection layer EIL.

Metals or alloys, for example Al, Al>AlF, Ag, Pt, Au, Mg, Ag:Mg, can be used as materials of the cathode layer. Typical layer thicknesses are 100 nm to 200 nm. In particular, one or more metals are used, which are stable when exposed to air and/or which are self-passivating, for example by forming a thin protective oxide layer.

Aluminum oxide, vanadium oxide, zinc oxide, zirconium oxide, titanium oxide, hafnium oxide, lanthanum oxide, tantalum oxide, for example, are suitable materials for encapsulation.

In one embodiment of the organic optoelectronic device according to the invention, the organic molecule according to the invention is used as the emission material in a light-emitting layer EML, wherein it is used either as a pure layer or in combination with one or more host materials.

One embodiment of the invention relates to organic optoelectronic devices which have an external quantum efficiency (EQE) at 1000 cd/m$^2$ greater than 5%, in particular greater than 8%, in particular greater than 10%, or greater than 13%, or greater than 16% and in particular greater than 20% and/or an emission maximum at a wavelength between 420 nm and 500 nm, in particular between 430 nm and 490 nm, or between 440 nm and 480 nm, and in particular between 450 nm and 470 nm and/or an LT80 value at 500 cd/m' greater than 30 h, in particular greater than 70 h, or greater than 100 h, or greater than 150 h and in particular greater than 200 h.

In another embodiment, the mass fraction of the organic molecule according to the invention in the emitter layer EML of a light-emitting layer in devices emitting optical light, in particular in OLEDs, is between 1% and 80%. In one embodiment of the organic optoelectronic device according to the invention, the light-emitting layer is disposed on a substrate, wherein an anode and a cathode are preferably disposed on the substrate and the light-emitting layer is disposed between the anode and the cathode.

In one embodiment, the light-emitting layer can have only one organic molecule according to the invention in 100% concentration, wherein the anode and the cathode are disposed on the substrate, and the light-emitting layer is disposed between the anode and the cathode.

In one embodiment of the organic optoelectronic device according to the invention, a hole- and electron-injecting layer is disposed between the anode and the cathode, and a hole- and electron-transporting layer is disposed between the hole- and electron-injecting layer, and the light-emitting layer is disposed between the hole- and electron-transporting layer.

In another embodiment of the invention, the organic optoelectronic device has: a substrate, an anode, a cathode and at least one respective hole- and electron-injecting layer, and at least one respective hole- and electron-transporting layer, and at least one light-emitting layer, which has the organic molecule according to the invention and one or more host materials, the triplet (T$_1$) and singlet (S$_1$) energy levels of which are energetically higher than the triplet (T$_1$) and singlet (S$_1$) energy levels of the organic molecule, wherein the anode and the cathode are disposed on the substrate, and the hole- and electron-injecting layer is disposed between the anode and the cathode, and the hole- and electron-transporting layer is disposed between the hole- and electron-injecting layer, and the light-emitting layer is disposed between the hole- and electron-transporting layer.

In a further aspect, the invention relates to a method for producing an optoelectronic component. To do this, an organic molecule according to the invention is used.

In one embodiment, the production method comprises the processing of the organic molecule according to the invention by means of a vacuum evaporation method or from a solution.

The invention also relates to a method for producing an optoelectronic device according to the invention, in which at least one layer of the optoelectronic device is coated using a sublimation process, is coated using an OVPD (organic vapor phase deposition) process, is coated using a carrier-gas sublimation, and/or is produced from solution or using a pressure process.

Known methods are used for the production of the optoelectronic device according to the invention. The layers are generally disposed individually onto a suitable substrate in successive deposition method steps. The common methods, such as thermal evaporation, chemical vapor deposition (CVD), physical vapor deposition (PVD) can be used for the vapor deposition. For active matrix OLED (AMOLED) displays, deposition takes place onto an AMOLED backplane as the substrate.

Layers can alternatively be deposited from solutions or dispersions in suitable solvents. Spin coating, dip coating and jet pressure methods are examples of suitable coating methods. According to the invention, the individual layers can be produced via the same as well as via respective different coating methods.

EXAMPLES

General Synthesis Scheme I

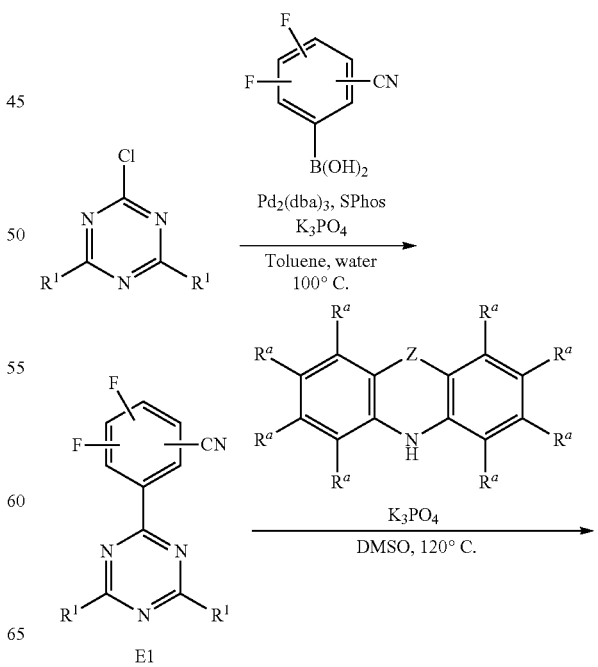

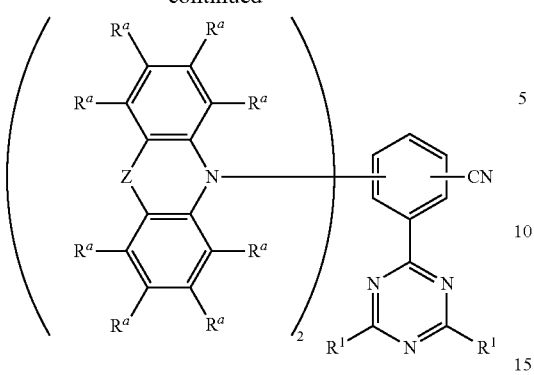

General Synthesis Specification AAV1:

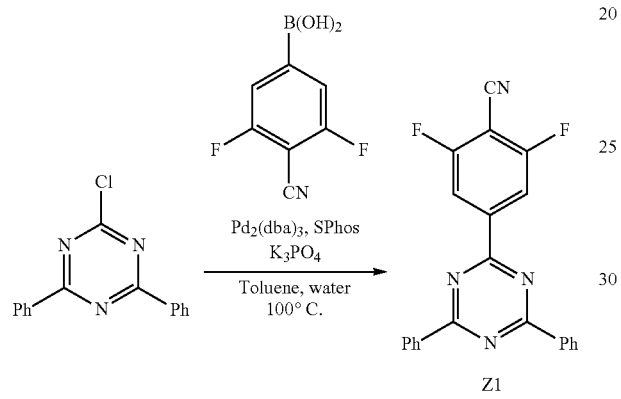

2-chloro-4,6-diphenyl-1,3,5-triazine (1.00 equivalent), 3,5-difluoro-4-cyanophenylboronic acid (1.80 equivalent), Pd$_2$(dba)$_3$ (0.02 equivalent), 2-dicyclohexylphosphino-2',6'-dimethoxybiphenyl 3.00) tribasic phosphate potassium and equivalent) 0.08) SPhos)) t a in nitrogen under stirred are equivalent)oluene/water mixture (ratio 6:1) at 100° C. for 16 hours. The reaction mixture is then added to 600 mL saturated sodium chloride solution and extracted with ethylacetate (2×300 mL). The combined organic phases are washed with saturated sodium chloride solution, dried over MgSO4, and the solvent is removed. The obtained raw product is purified by means of flash chromatography and the product is obtained as a solid.

According to the invention, a corresponding boronic acid ester can be used instead of a boronic acid.

General Synthesis Specification AAV2:

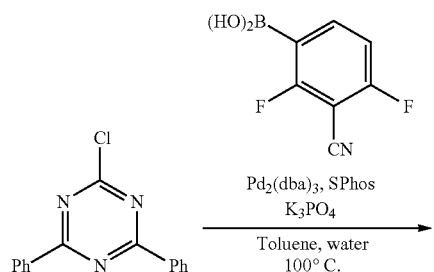

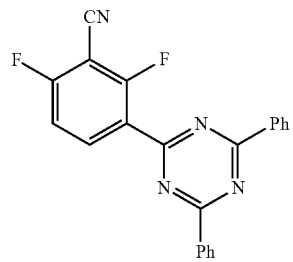

The synthesis of Z2 takes place in an analogous manner to that of AAV1, wherein 2-chloro-4,6-diphenyl-1,3,5-triazine is reacted with 2,4-difluoro-3-cyanophenylboronic acid.

General Synthesis Specification AAV3:

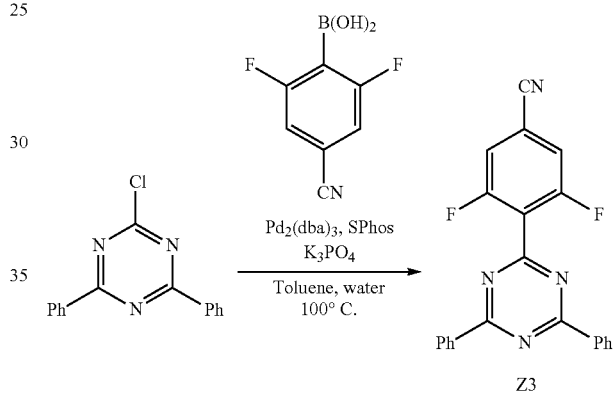

The synthesis of Z3 takes place in an analogous manner to that of AAV1, wherein 2-chloro-4,6-diphenyl-1,3,5-triazine is reacted with 2,6-difluoro-4-cyanophenylboronic acid.

General Synthesis Specification AAV4:

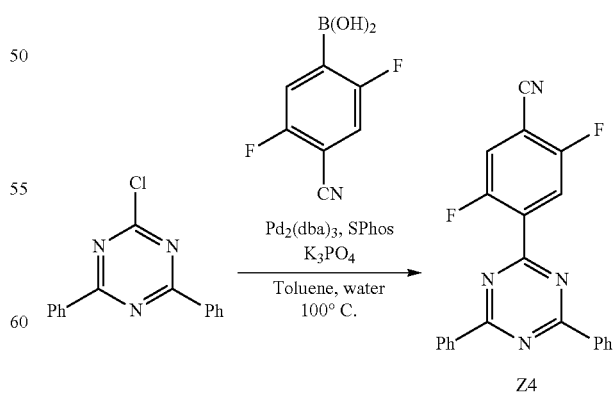

The synthesis of Z4 takes place in an analogous manner to that of AAV1, wherein 2-chloro-4,6-diphenyl-1,3,5-triazine is reacted with 2,5-difluoro-4-cyanophenylboronic acid.

General Synthesis Specification AAV5:

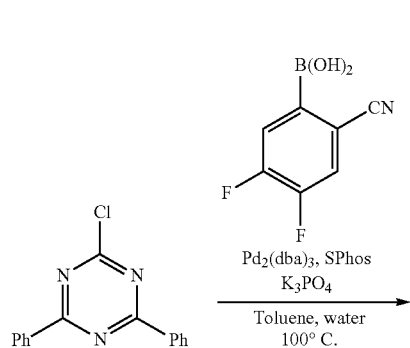

General Synthesis Specification AAV6:

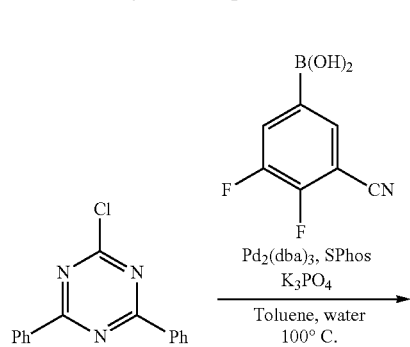

The synthesis of Z5 takes place in an analogous manner to that of AAV1, wherein 2-chloro-4,6-diphenyl-1,3,5-triazine is reacted with 4,5-difluoro-2-cyanophenylboronic acid.

The synthesis of Z6 takes place in an analogous manner to that of AAV1, wherein 2-chloro-4,6-diphenyl-1,3,5-triazine is reacted with 4,5-difluoro-3-cyanophenylboronic acid.

General Synthesis Specification AAV7:

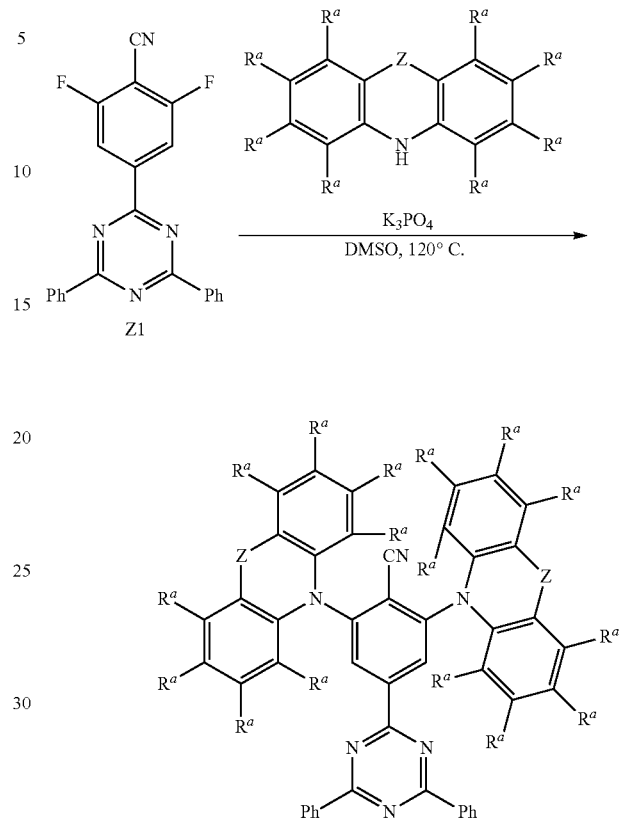

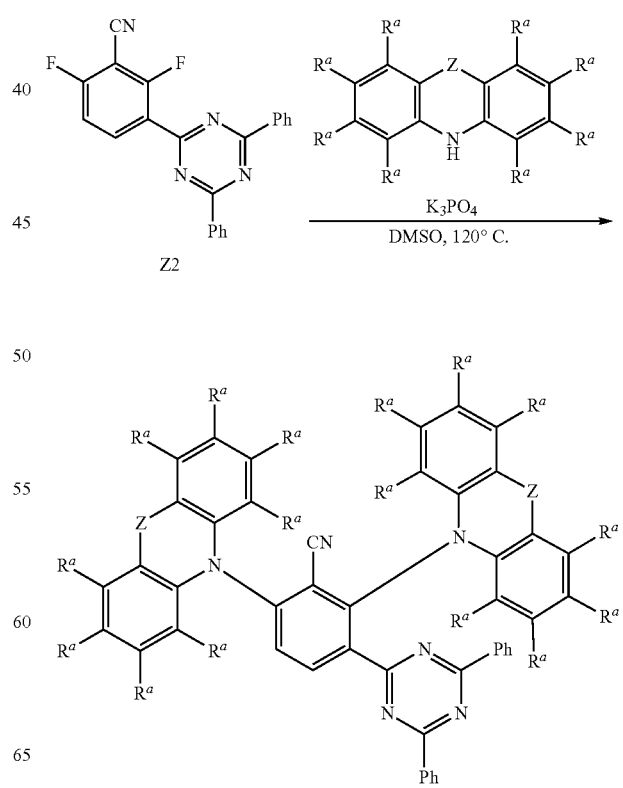

-continued
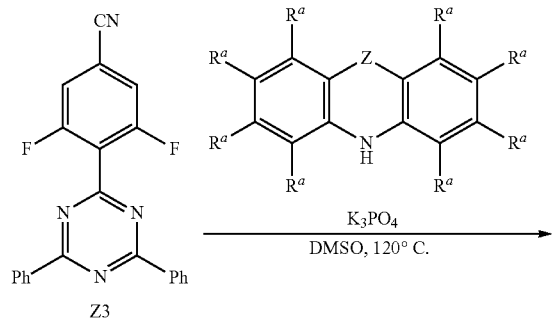
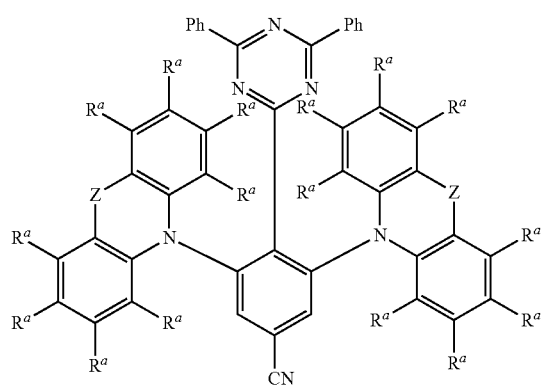
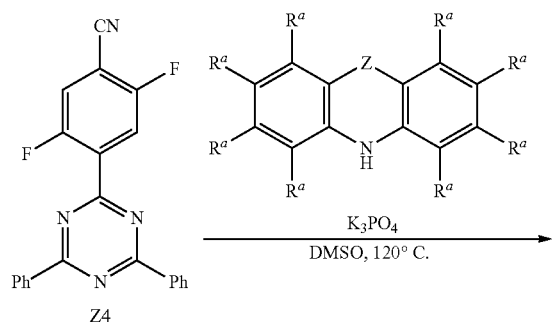
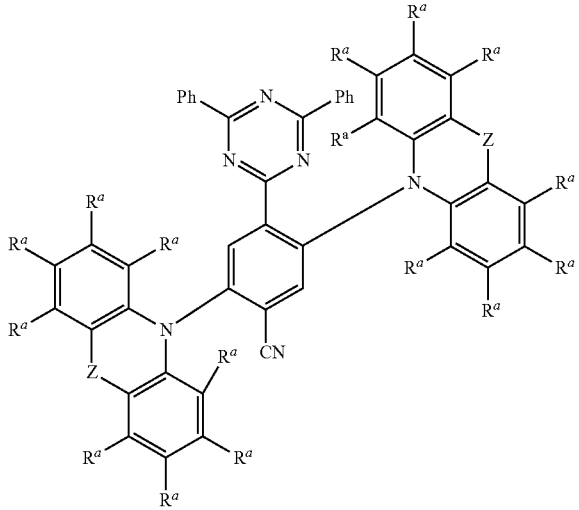
-continued
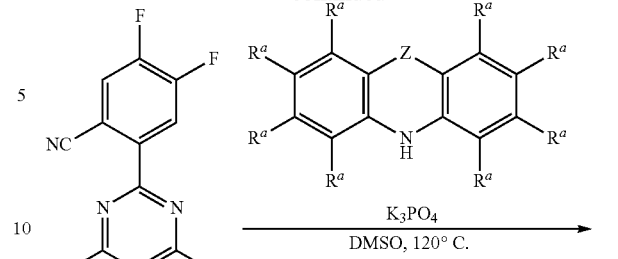
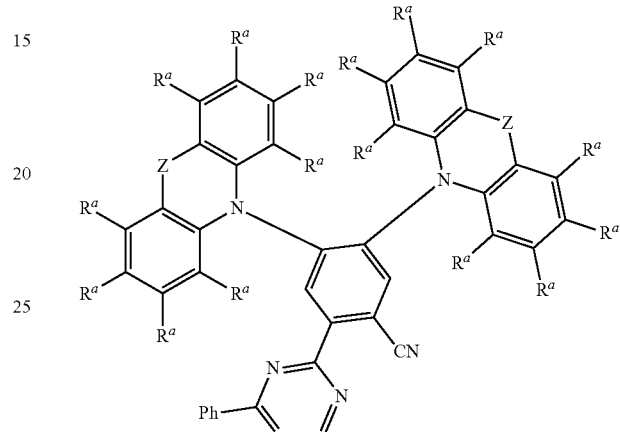
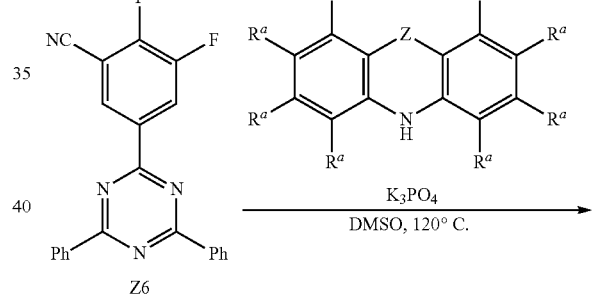
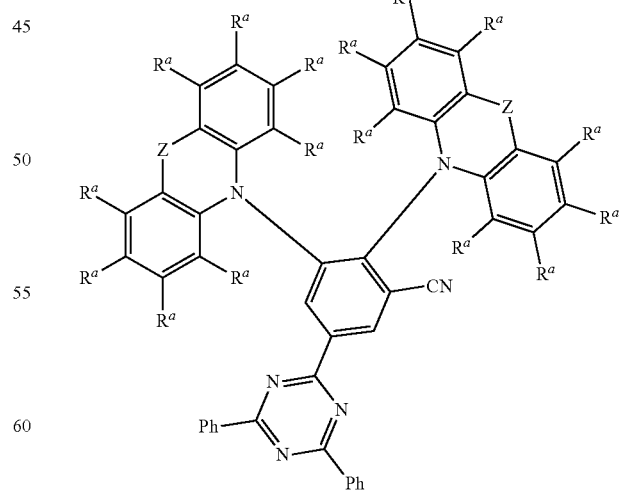
Z1, Z2, Z3, Z4, Z5 or Z6 (respectively 1.00 equivalent), the corresponding donor molecule D-H (2.00 equivalent) and potassium phosphate tribasic (4.00 equivalent) are suspended in DMSO under nitrogen and stirred at 120° C. (16 h). The reaction mixture is then added to saturated sodium chloride solution and extracted three times with dichloromethane. The combined organic phases are washed twice with saturated sodium chloride solution, dried over magnesium sulfate, and the solvent is subsequently removed. Lastly, the raw product was purified by recrystallization from toluene or by means of flash chromatography. The product is obtained as a solid.

In order to obtain the corresponding $R^1$-substituted compounds, the corresponding $R^1$ 2-chloro-1,3,5-triazine in 4 and 6 position is used instead of 2-chloro-4,6-diphenyl-1,3,5-triazine. For example 2-chloro-4,6-methyl-1,3,5-triazine D-H in particular corresponds to a 3,6-substituted carbazole (e.g. 3,6-dimethylcarbazole, 3,6-diphenylcarbazole, 3,6-di-tert-butylcarbazole), a 2,7-substituted carbazole (e.g. 2,7-dimethylcarbazole, 2,7-diphenylcarbazole, 2,7-di-tert-butylcarbazole), an 1,8-substituted carbazole (e.g. 1,8-dimethylcarbazole, 1,8-diphenylcarbazole, 1,8-di-tert-butylcarbazole), a 1-substituted carbazole (e.g. 1-methylcarbazole, 1-phenylcarbazole, 1-tert-butylcarbazole), a 2-substituted carbazole (e.g. 2-methylcarbazole, 2-phenylcarbazole, 2-tert-butylcarbazole) or a 3-substituted carbazole (e.g. 3-methylcarbazole, 3-phenylcarbazole, 3-tert-butylcarbazole).

Photophysical Measurements

Pretreatment of Optical Glasses

All glasses (cuvettes and substrates made of quartz glass, diameter: 1 cm) were cleaned after every use: washed three times in each case with dichloromethane, acetone, ethanol, demineralized water, placed in 5% Hellmanex solution for 24 h, thoroughly rinsed with demineralized water. The optical glasses were dried by blowing nitrogen over them.

Sample preparation, Film: Spin Coating

Device; Spin150, SPS Euro.

The sample concentration was equivalent to 10 mg/ml, prepared in toluene or chlorobenzene.

Program: 1) 3 s at 400 rpm; 2) 20 s at 1000 rpm at 1000 rpm/s. 3) 10 s at 4000 rpm at 1000 rpm/s. After coating, the films were dried on a LHG precision heating plate for 1 min at 76° C. in air.

Photoluminescence Spectroscopy and TCSPC

Steady-state emission spectroscopy was carried out using a fluorescence spectrometer of the Horiba Scientific company, Model Fluoromax-4, equipped with a 150W xenon arc lamp, excitation and emission monochromators, and a Hamamatsu R928 photomultiplier tube, as well as a "Time-Correlated Single Photon Counting" (TCSPC) option. The emission and excitation spectra were corrected by means of standard correction curves.

The emission decay times were likewise measured on this system, using the TCSPC method with the FM-2013 accessories and a TCSPC hub of the Horiba Yvon Jobin company. Excitation sources:

NanoLED 370 (wavelength: 371 nm, pulse duration: 1.1 ns)

NanoLED 290 (wavelength: 294 nm, pulse duration: <1 ns)

SpectraLED 310 (wavelength: 314 nm)

SpectraLED 355 (wavelength: 355 nm).

The analysis (exponential fitting) was performed using the DataStation software package and the DAS6 analysis software. The fit was specified with the aid of the Chi-square method $$c^2 = \sum_{k=1}^{i} \frac{(e_i - o_i)^2}{e_i}$$

with $e_i$: variable predicted by the fit and $o_i$: measured variable.

Quantum Efficiency Determination

The measurement of the photoluminescence quantum yield (PLQY) was carried out by means of an Absolute PL Quantum Yield Measurement C9920-03G system of the company Hamamatsu Photonics. Said system consists of a 150W xenon gas discharge lamp, automatically adjustable Czerny-Turner monochromators (250-950 nm) and an Ulbricht sphere with a high reflectance Spectralon coating (a Teflon derivative), which is connected via a fiber optic cable to a PMA-12 multichannel detector with a BT (back-thinned)-CCD chip having 1024×122 pixels (size 24×24 μm). The analysis of the quantum efficiency and the CIE coordinates was carried out using the software U6039-05 Version 3.6.0.

The emission maximum is measured in nm, the quantum yield Φ is measured in % and the CIE color coordinates are stated as x, y values.

The photoluminescence quantum yield was determined according to the following protocol:

1) Implementation of quality assurance measures: Anthracene in ethanol at a known concentration serves as the reference material.

2) Determination of the excitation wavelength: The absorption maximum of the organic molecule was first determined and excited with said wavelength.

3) Implementation of the sample measurement:

The absolute quantum yield of degassed solutions and films was determined under a nitrogen atmosphere.

The calculation was performed within the system according to the following equation:

$$\Phi_{PL} = \frac{n_{photon}, \text{emitted}}{n_{photon}, \text{absorbed}} = \frac{\int \frac{\lambda}{hc} \left[ \text{Int}_{emitted}^{Sample}(\lambda) - \text{Int}_{absorbed}^{Sample}(\lambda) \right] d\lambda}{\int \frac{\lambda}{hc} \left[ \text{Int}_{emitted}^{Reference}(\lambda) - \text{Int}_{absorbed}^{Reference}(\lambda) \right] d\lambda}$$

with the photon number $n_{photon}$ and the intensity Int.

Production and characterization of organic electroluminescence devices from the gas phase With the organic molecules according to the invention, OLED devices can be produced by means of vacuum sublimation techniques. If a layer contains multiple components, the ratio of said components is stated in percent by weight.

These not yet optimized OLEDs can be characterized in the usual manner. To do this, the electroluminescence spectra, the external quantum efficiency (measured in %) as a function of the brightness and calculated from the light detected by the photodiode, and the current are recorded. The lifetime of the OLEDs can be determined from the time profile of the electroluminescence spectra. The LT50 value corresponds to the time at which the luminance has fallen to 50% of the starting value. The LT70 value analogously corresponds to the time at which the luminance has fallen to 70% of the starting value.

The values are obtained from the average of the various pixels of an OLED.

HPLC-MS:

HPLC-MS spectroscopy was measured using an HPLC system of the company Agilent (1100 series) with a connected MS detector (Thermo LTQ XL). An Agilent Eclipse Plus C18 column with a particle size of 3.5 μm, a length of 150 mm and an inner diameter of 4.6 mm was used for the HPLC. This was carried out without a precolumn and at room temperature using the solvents acetonitrile, water and tetrahydrofuran in the following concentrations:

| Solvent A: | H₂O (90%) | MeCN (10%) |
| Solvent B: | H₂O (10%) | MeCN (90%) |
| Solvent C: | THF (100%) | |

An injection volume of 15 μL and a concentration of 10 μg/ml were used with the following gradient:

| Flow [ml/min] | Time [min] | A [%] | B [%] | C [%] | Pressure [Bar] |
| --- | --- | --- | --- | --- | --- |
| 0.3 | 0 | 80 | 20 | — | 115 |
| 0.3 | 5 | 80 | 20 | — | 115 |
| 0.3 | 14 | 0 | 90 | 10 | 65 |
| 0.3 | 25 | 0 | 90 | 10 | 65 |
| 0.3 | 26 | 80 | 20 | — | 115 |
| 0.3 | 33 | 80 | 20 | — | 115 |

The sample is ionized by means of APCI (Atmospheric Pressure Chemical Ionization).

Example 1

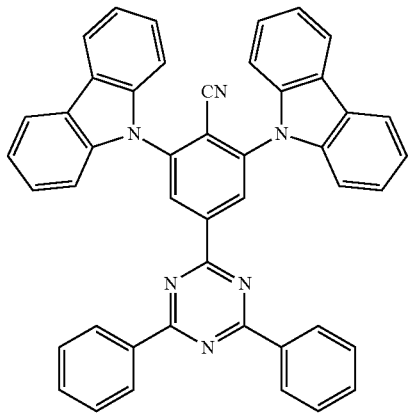 [SMILES: N#Cc1c(-n2c3ccccc3c3ccccc32)cc(-c2nc(-c3ccccc3)nc(-c3ccccc3)n2)cc1-n1c2ccccc2c2ccccc21]

Example 1 was produced in accordance with AAV1 (Yield 77%) and AAV7 (Yield 35%). MS (HPLC-MS), m/z (retention time): 664, (8.42 min)

FIG. 1 shows the emission spectrum of Example 1 (10% in PMMA). The emission maximum is at 502 nm. The photoluminescence quantum yield (PLQY) is 65% and the full width at half maximum is 0.42 eV. The emission lifetime is 9 μs.

Example 2

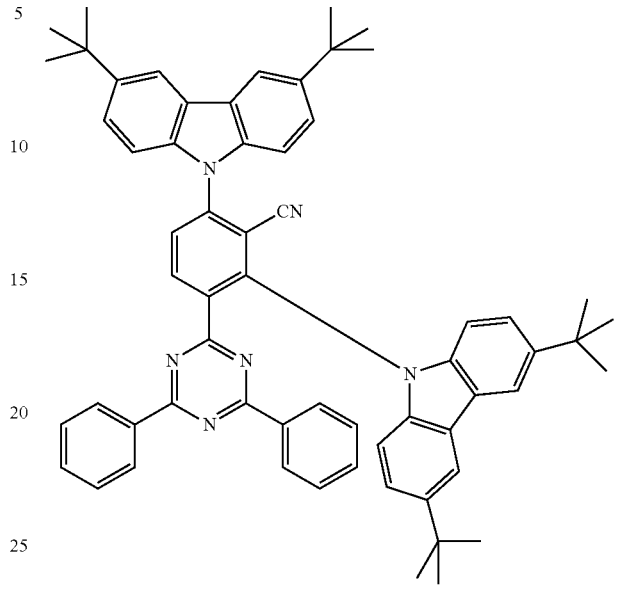

Example 2 was produced in accordance with AAV2 (Yield 41%) and AAV7 (Yield 30%).

Figure 2:
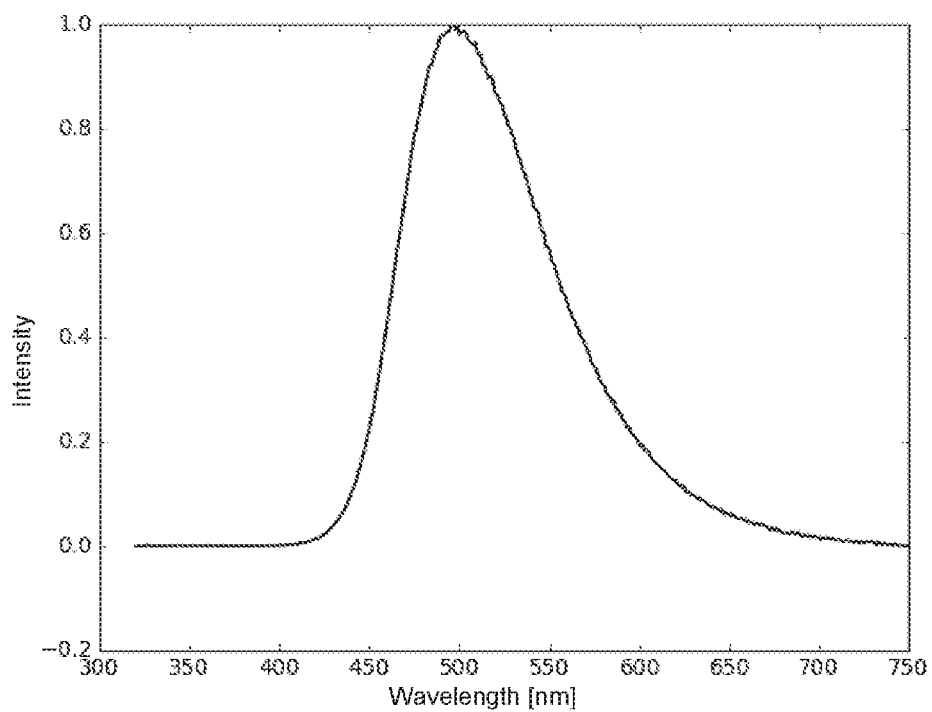
FIG. 2 is an emission spectrum of Example 2 (10% in PMMA).

FIG. 2 shows the emission spectrum of Example 2 (10% in PMMA). The emission maximum is at 497 nm. The photoluminescence quantum yield (PLQY) is 70% and the full width at half maximum is 0.45 eV. The emission lifetime is 14 μs.

Example 3

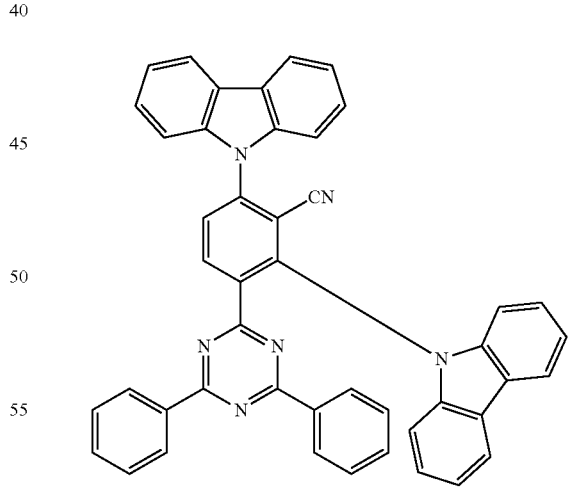

Example 3 was produced in accordance with AAV2 (yield 41%) and AAV7 (yield 84%).

Figure 3:
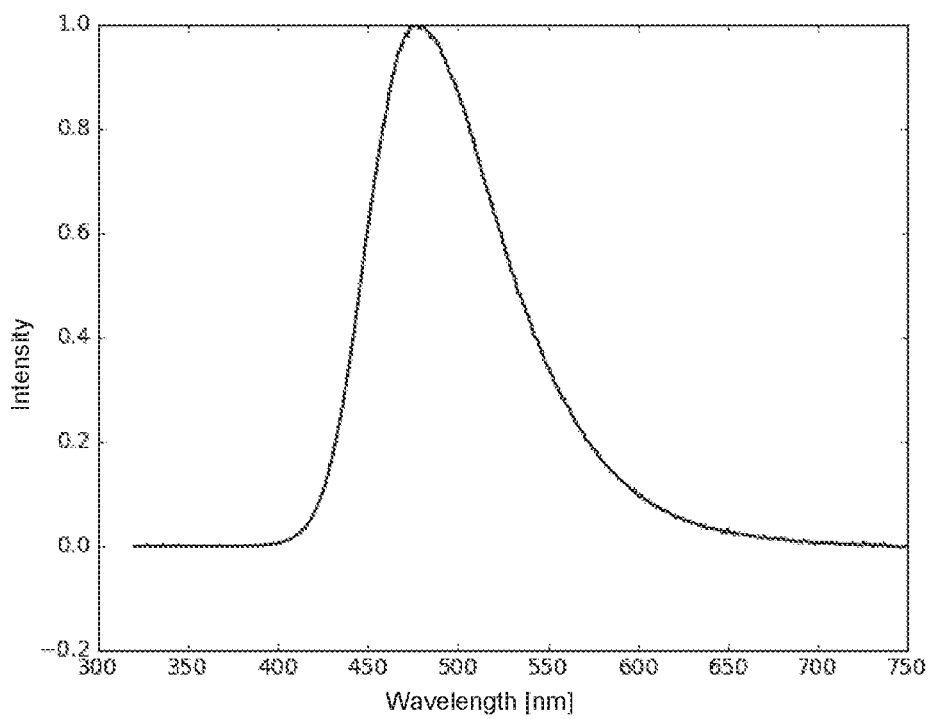
FIG. 3 is an emission spectrum of Example 3 (10% in PMMA).

FIG. 3 shows the emission spectrum of Example 3 (10% in PMMA). The emission maximum is at 477 nm. The photoluminescence quantum yield (PLQY) is 77% and the full width at half maximum is 0.45 eV. The emission lifetime is 70 μs.

Example 4

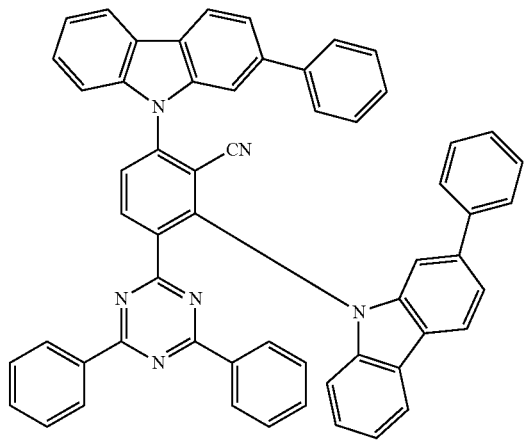 [SMILES: N#Cc1c(-n2c3ccccc3c3ccc(-c4ccccc4)cc32)ccc(-c2nc(-c3ccccc3)nc(-c3ccccc3)n2)c1-n1c2ccccc2c2ccc(-c3ccccc3)cc21]

Example 4 was produced in accordance with AAV2 (Yield 41%) and AAV7 (Yield 70%).

Figure 4:
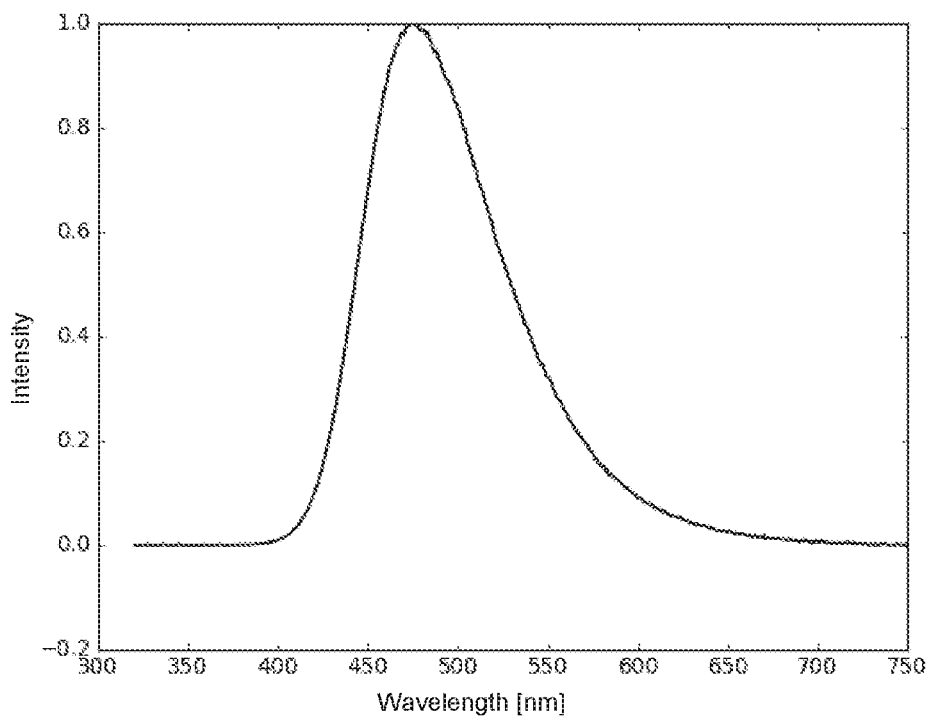
FIG. 4 is an emission spectrum of Example 4 (10% in PMMA).

FIG. 4 shows the emission spectrum of Example 4 (10% in PMMA). The emission maximum is at 475 nm. The photoluminescence quantum yield (PLQY) is 63% and the full width at half maximum is 0.46 eV. The emission lifetime is 47 μs.

Example 5

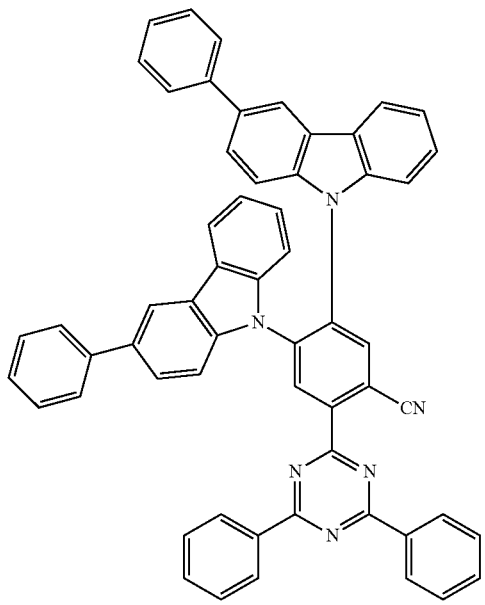 [SMILES: N#Cc1cc(-n2c3ccccc3c3cc(-c4ccccc4)ccc32)c(-n2c3ccccc3c3cc(-c4ccccc4)ccc32)cc1-c1nc(-c2ccccc2)nc(-c2ccccc2)n1]

Example 5 was produced in accordance with AAV5 (Yield 68%) and AAV7 (Yield 91%).

Figure 5:
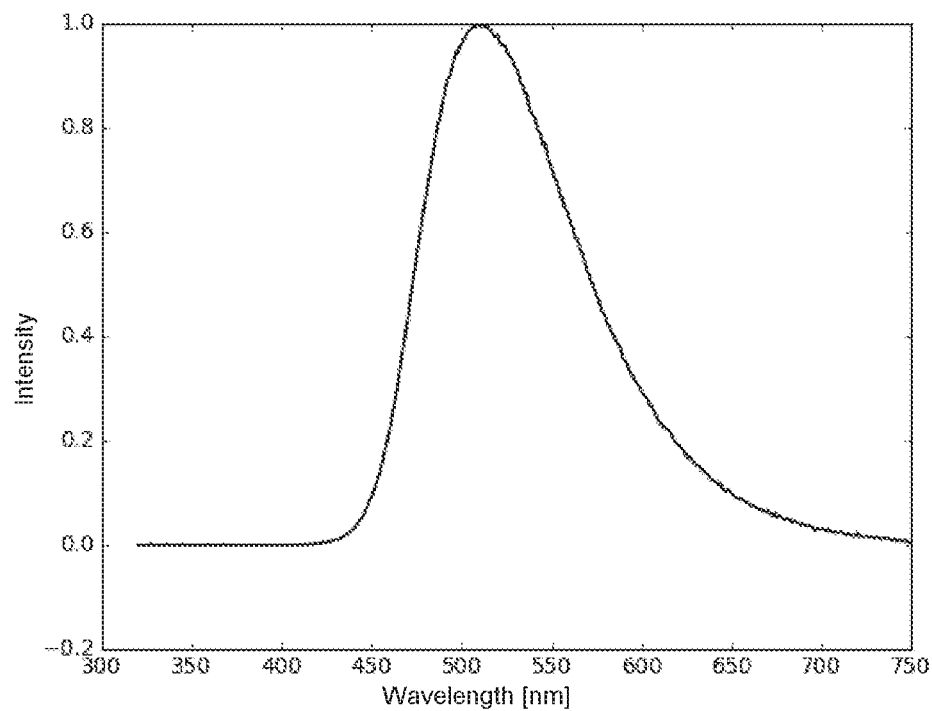
FIG. 5 is an emission spectrum of Example 5 (10% in PMMA).

FIG. 5 shows the emission spectrum of Example 5 (10% in PMMA). The emission maximum is at 510 nm. The photoluminescence quantum yield (PLQY) is 73% and the full width at half maximum is 0.46 eV. The emission lifetime is 95 μs.

Example 6

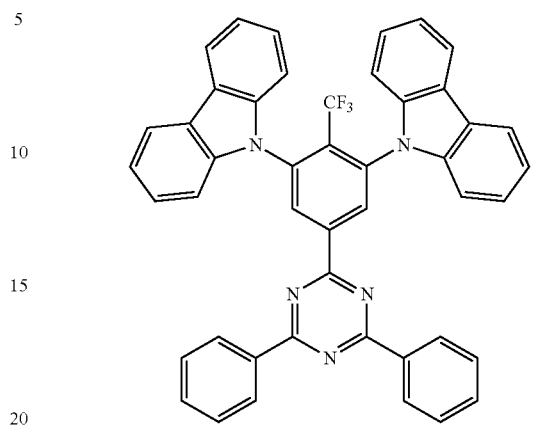

Example 6 was produced in accordance with AAV1, whereby 3,5-difluoro-4-(trifluoromethyl)phenylboronic acid pinacol ester was used instead of 3,5-difluoro-4-cyanophenylboronic acid (Yield 66%), and AAV7 (Yield 35%).

Figure 6:
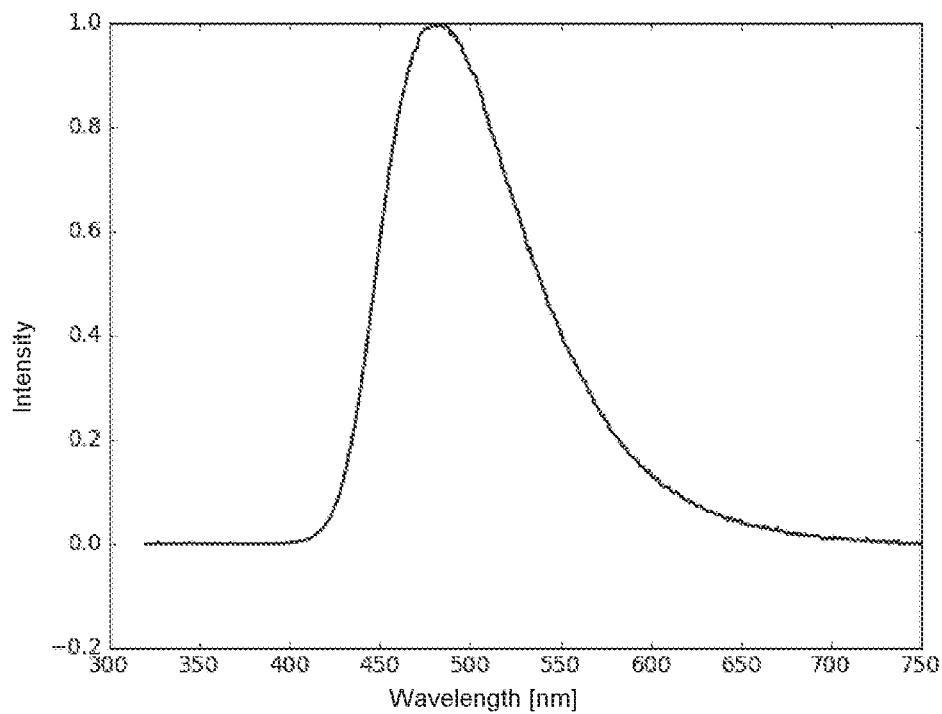
FIG. 6 is an emission spectrum of Example 6 (10% in PMMA).

FIG. 6 shows the emission spectrum of Example 6 (10% in PMMA). The emission maximum is at 479 nm. The photoluminescence quantum yield (PLQY) is 67% and the full width at half maximum is 0.47 eV. The emission lifetime is 14 μs. The identity of the compound (Example 6) was determined via HPLC-MS: m/z=707.30, $t_R$=10.60 min,

Example 7

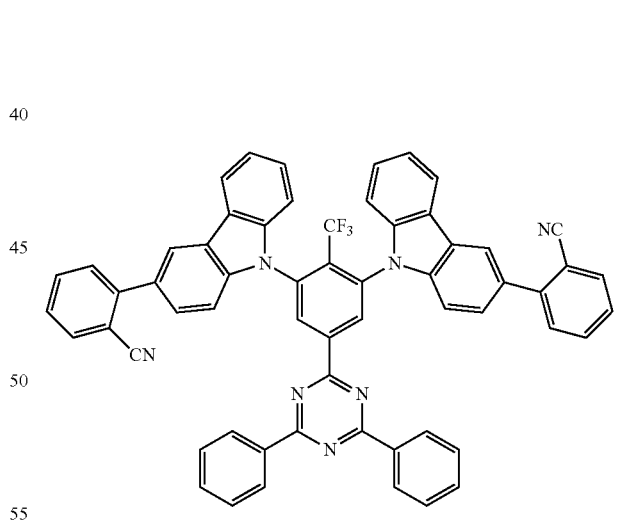

Example 7 was produced in accordance with AAV1, whereby 3,5-difluoro-4-(trifluoromethyl)phenylboronic acid pinacol ester was used instead of 3,5-difluoro-4-cyanophenylboronic acid (Yield 66%), and AAV7 (Yield 45%).

Figure 7:
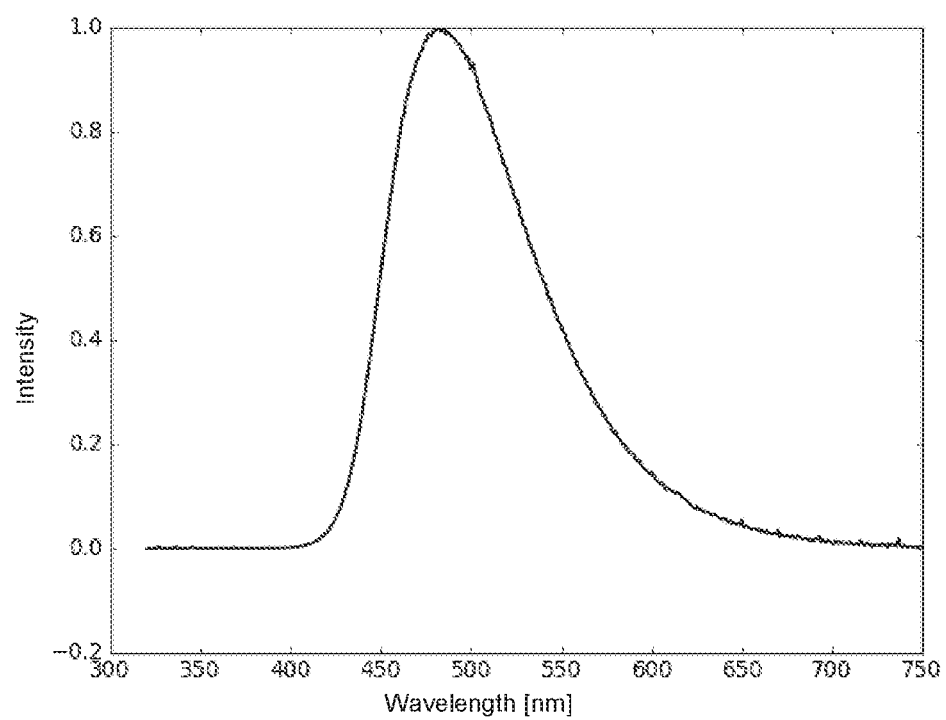
FIG. 7 is an emission spectrum of Example 6 (10% in PMMA).

FIG. 7 shows the emission spectrum of Example 7 (10% in PMMA). The emission maximum is at 482 nm. The photoluminescence quantum yield (PLQY) is 63% and the full width at half maximum is 0.47 eV. The emission lifetime is 7 μs. The identity of the compound (Example 7) was determined via HPLC-MS: m/z=910.16, $t_R$=10.13 min.

Examples of Molecules According to the Invention:
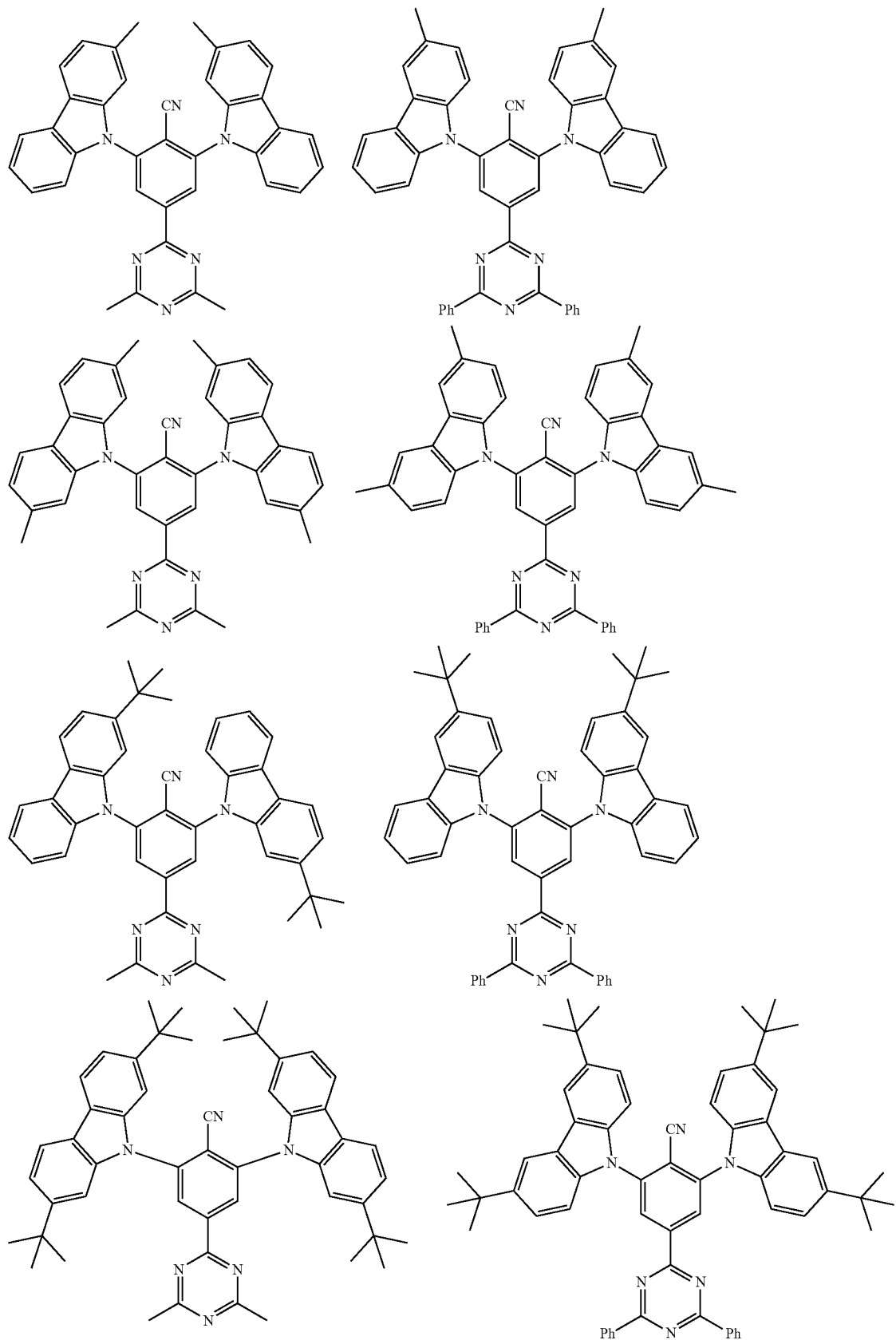

-continued
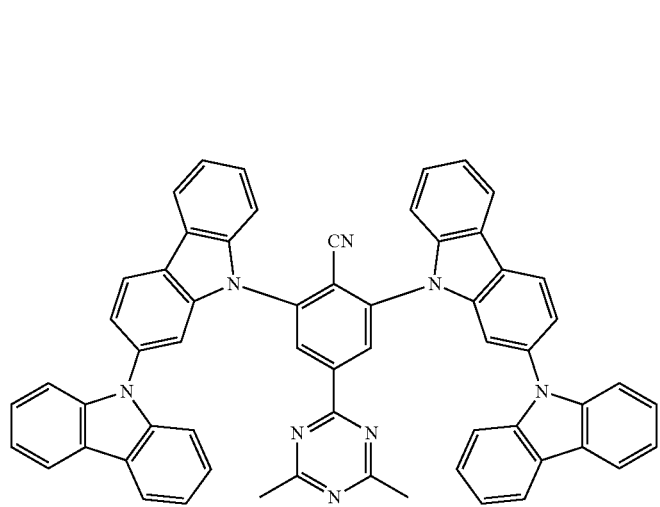
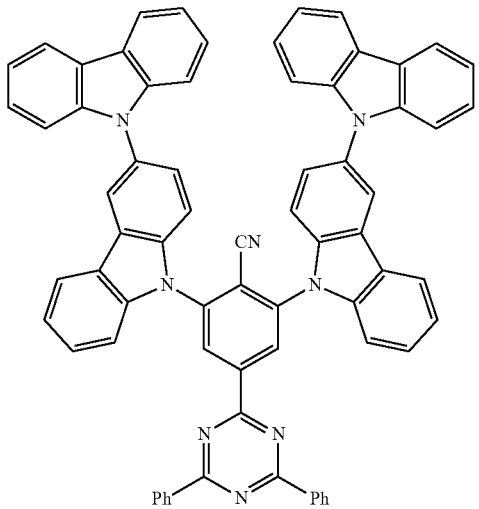
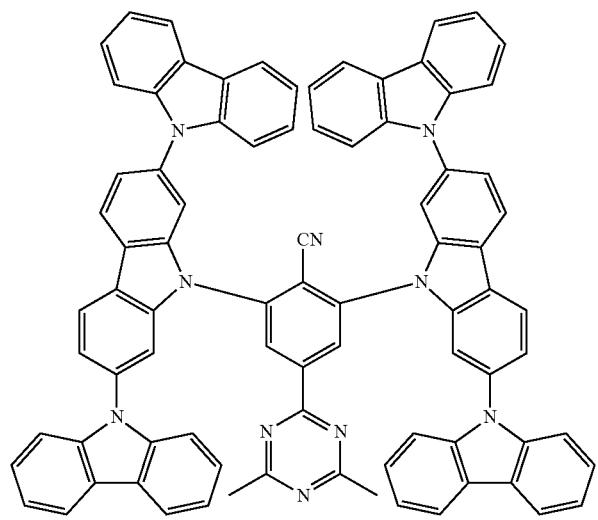
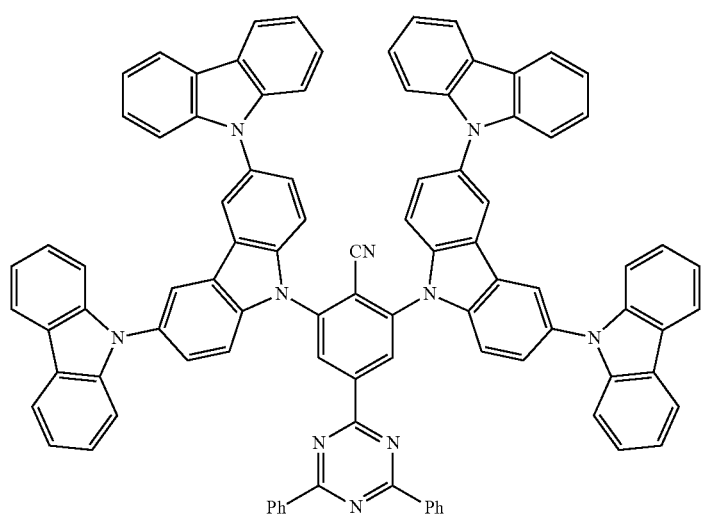
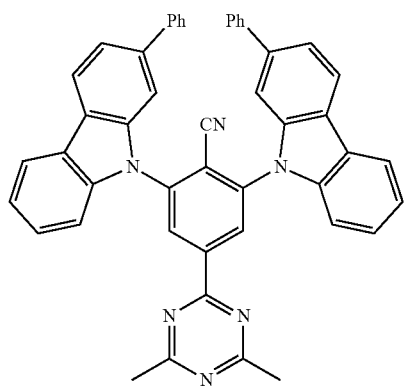

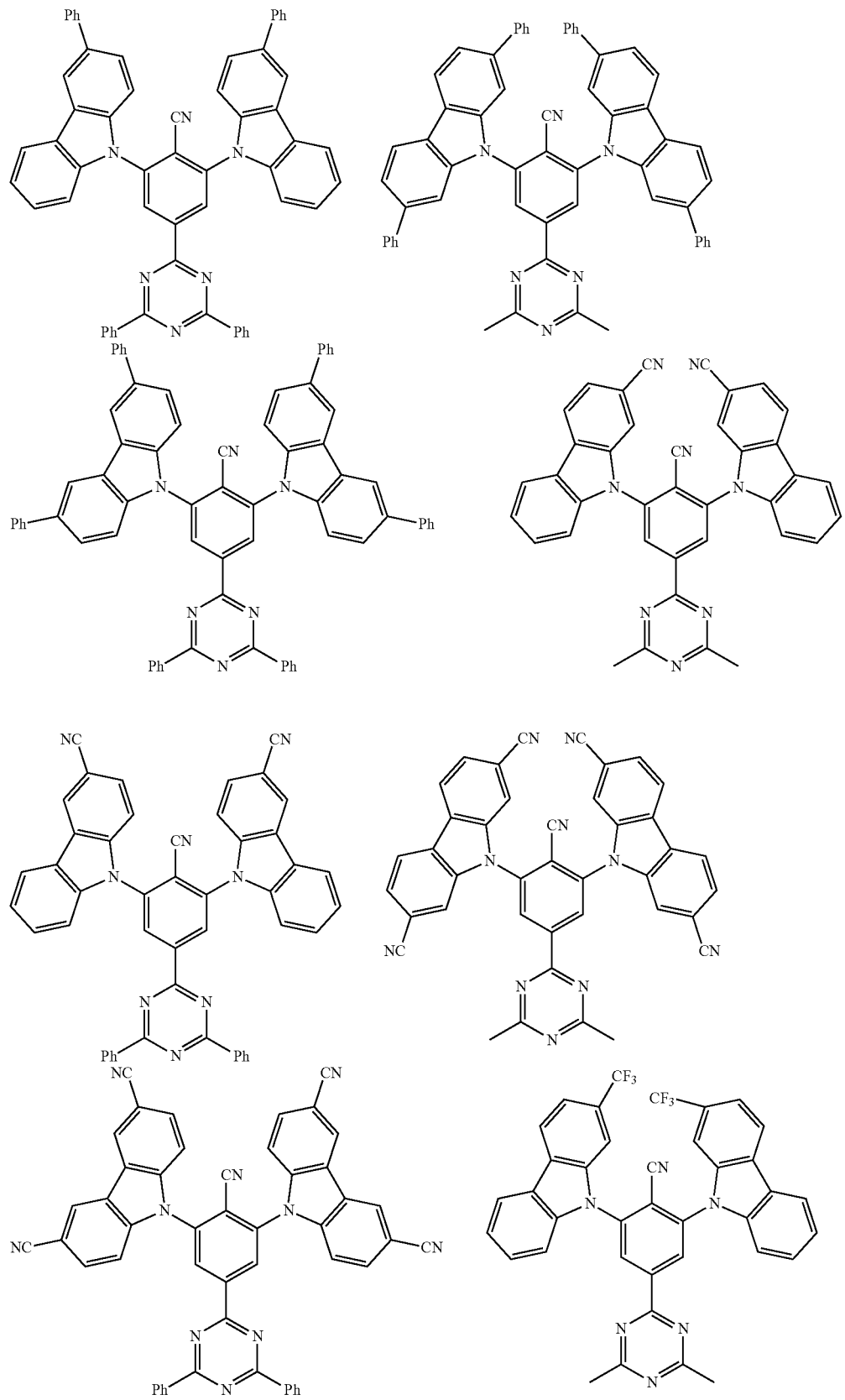

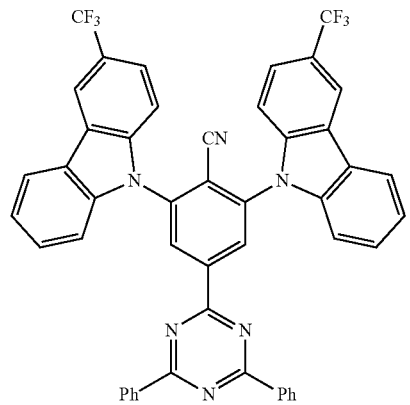
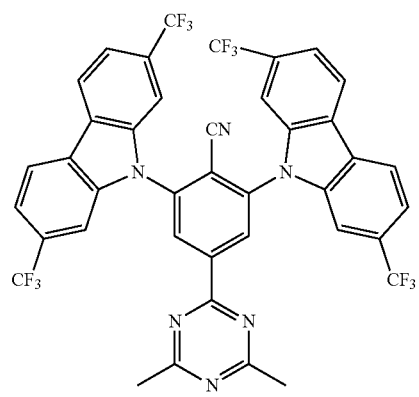
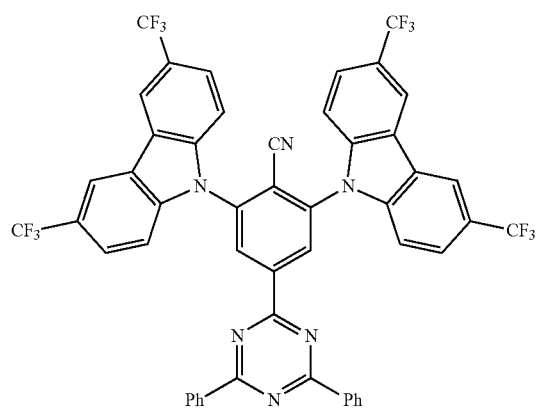
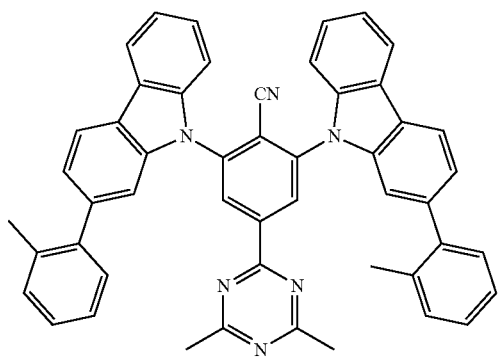
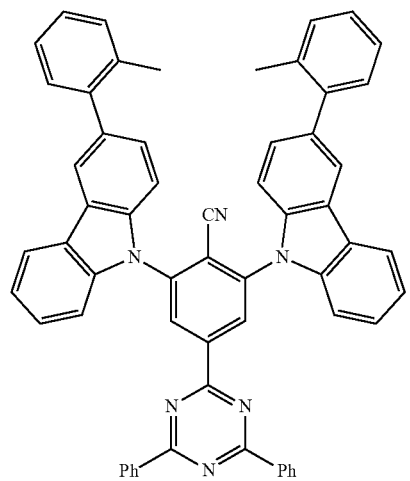
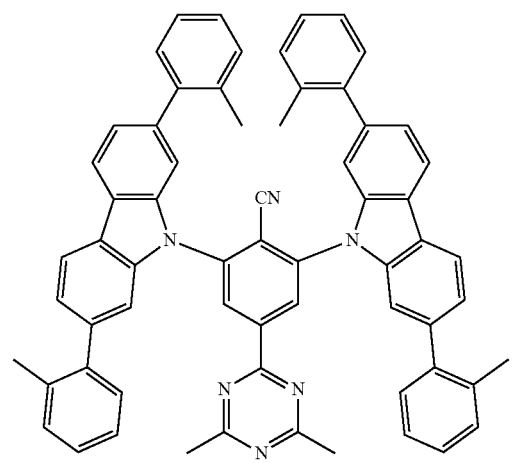

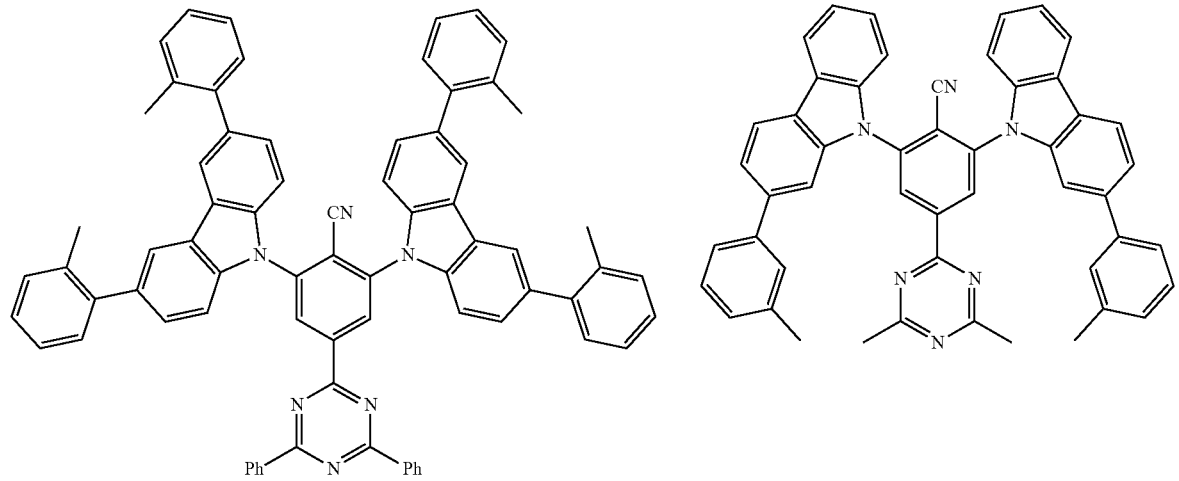
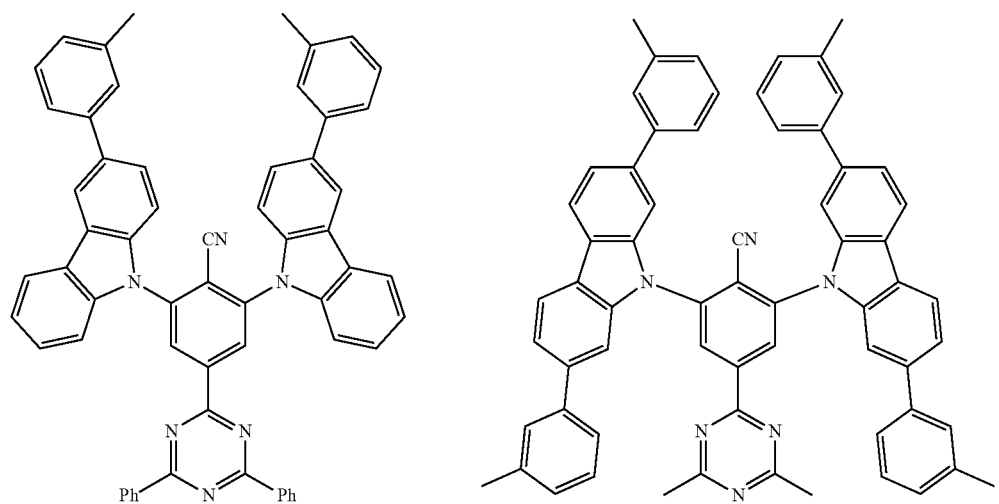
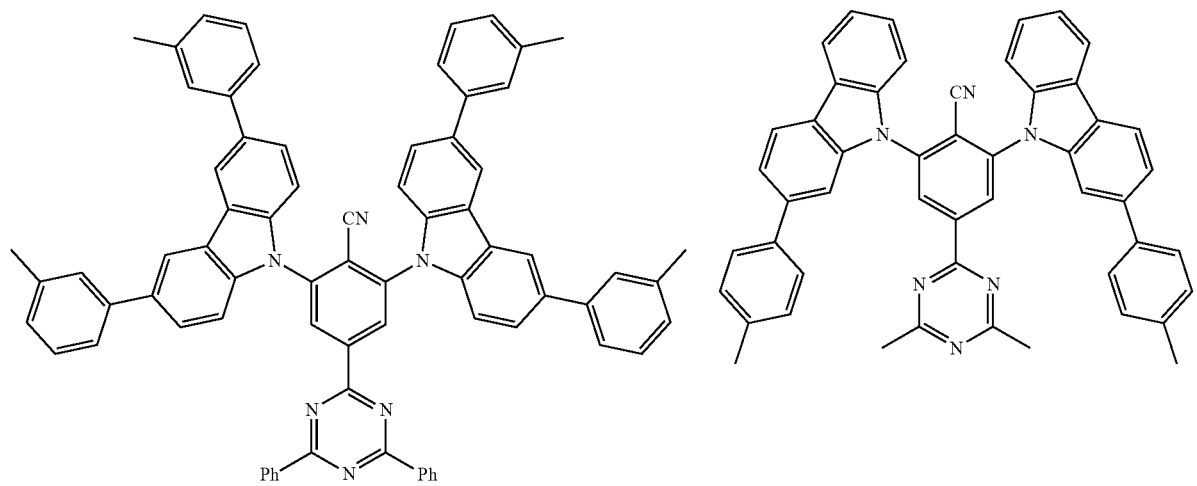

-continued
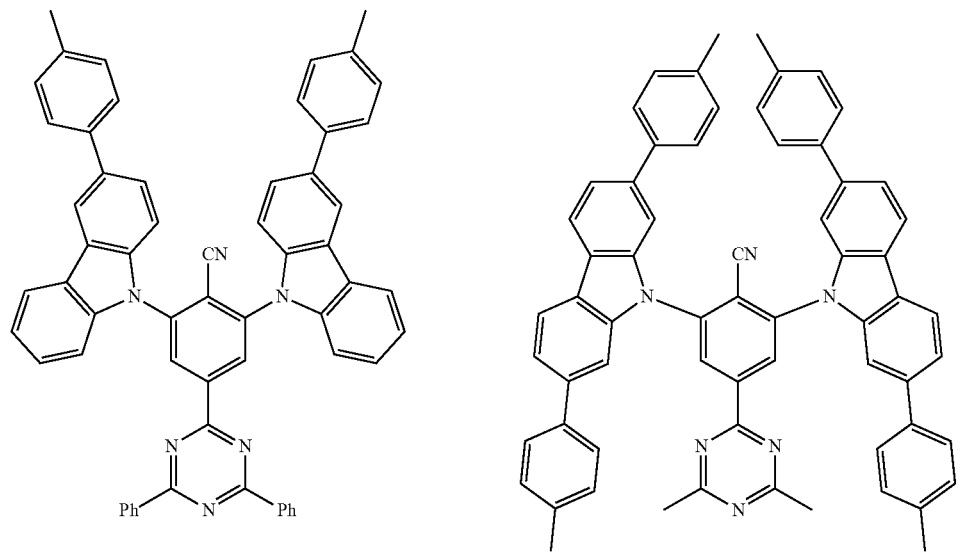
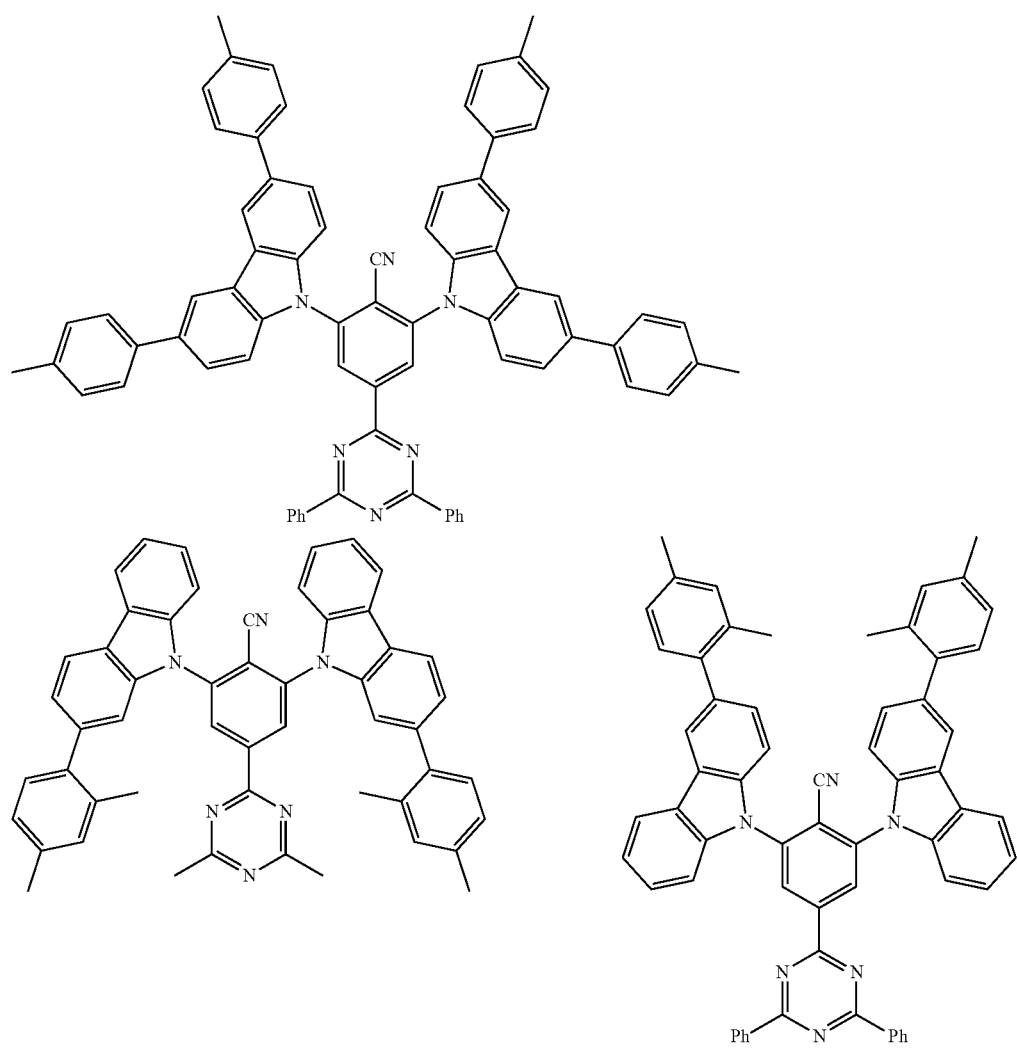

-continued
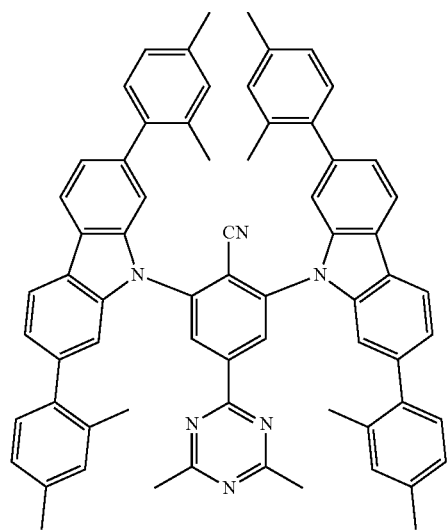
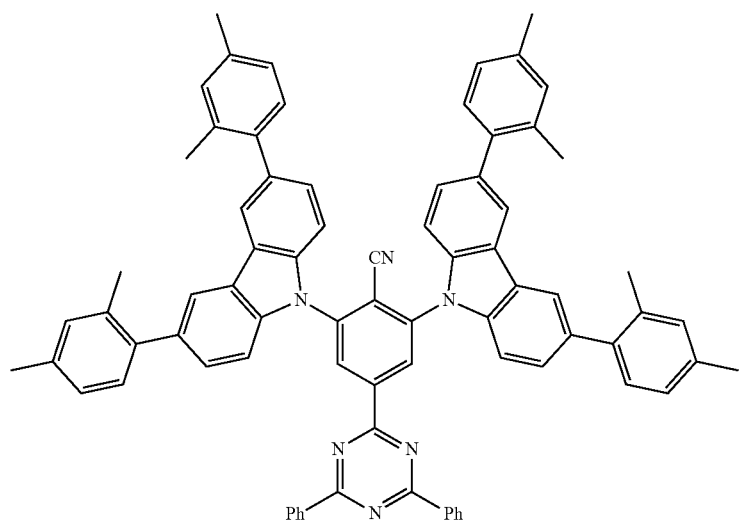
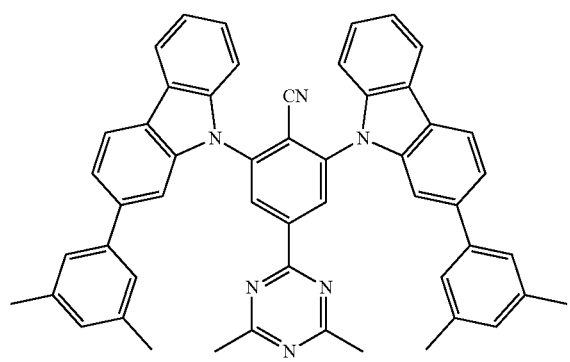
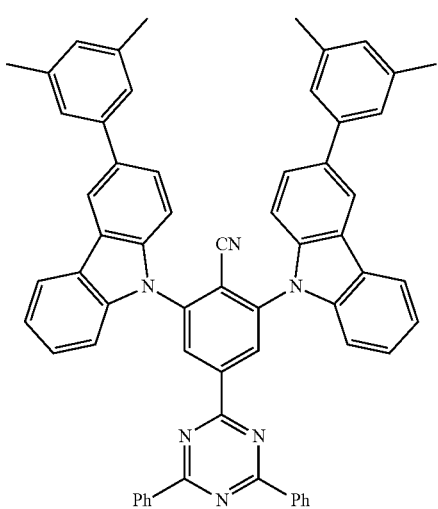

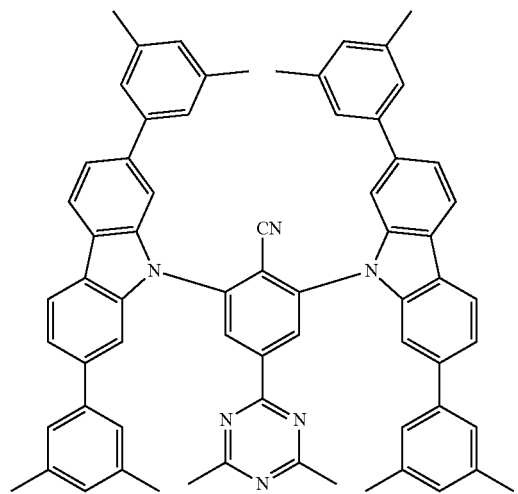
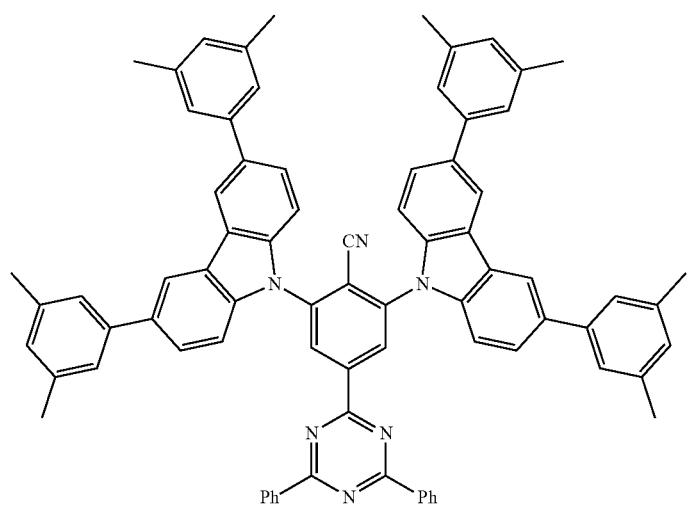
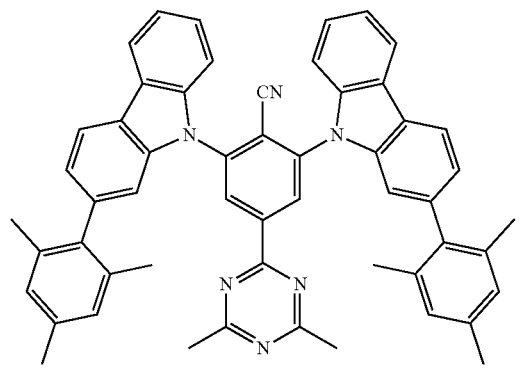
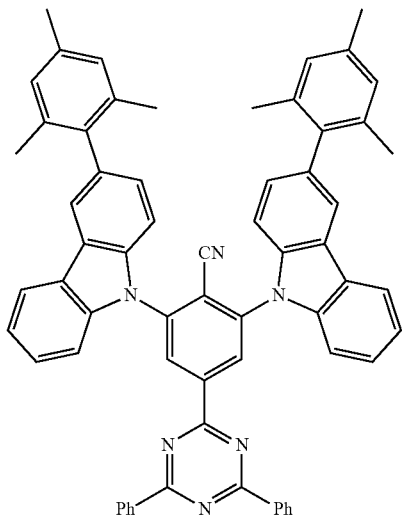

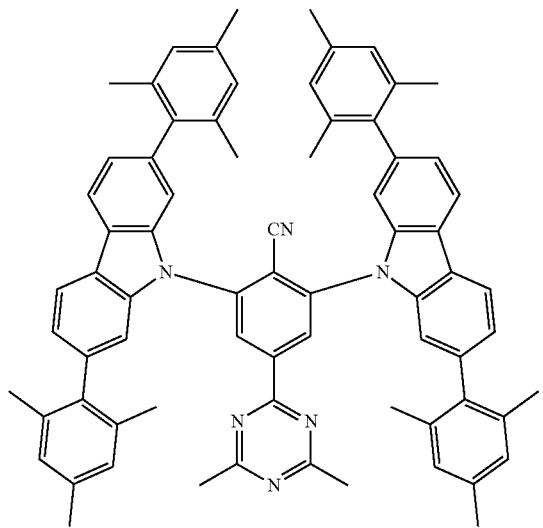
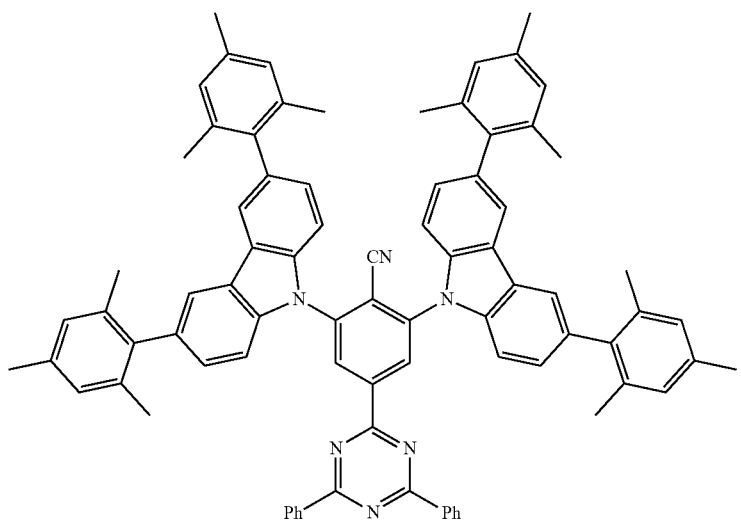
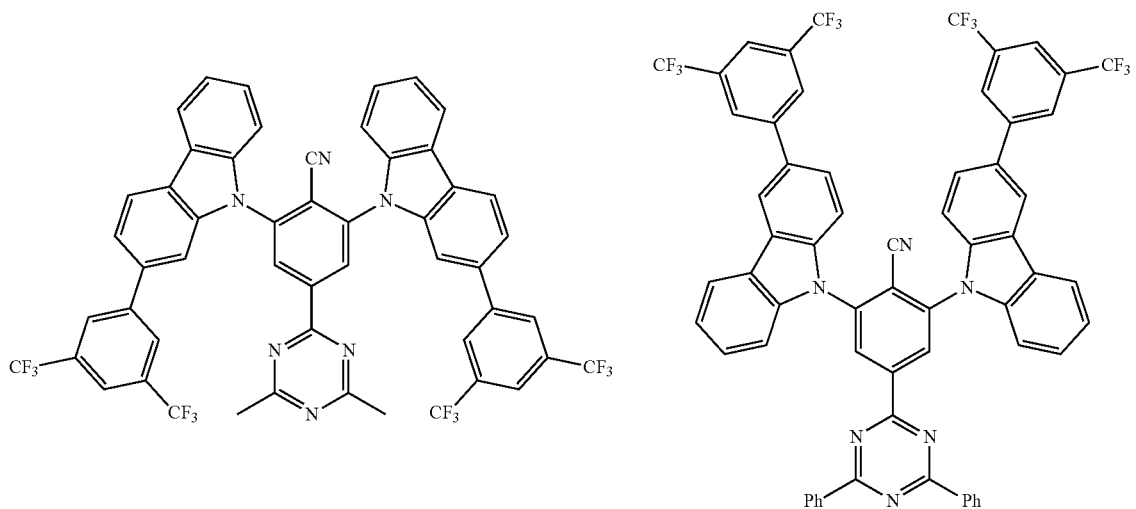

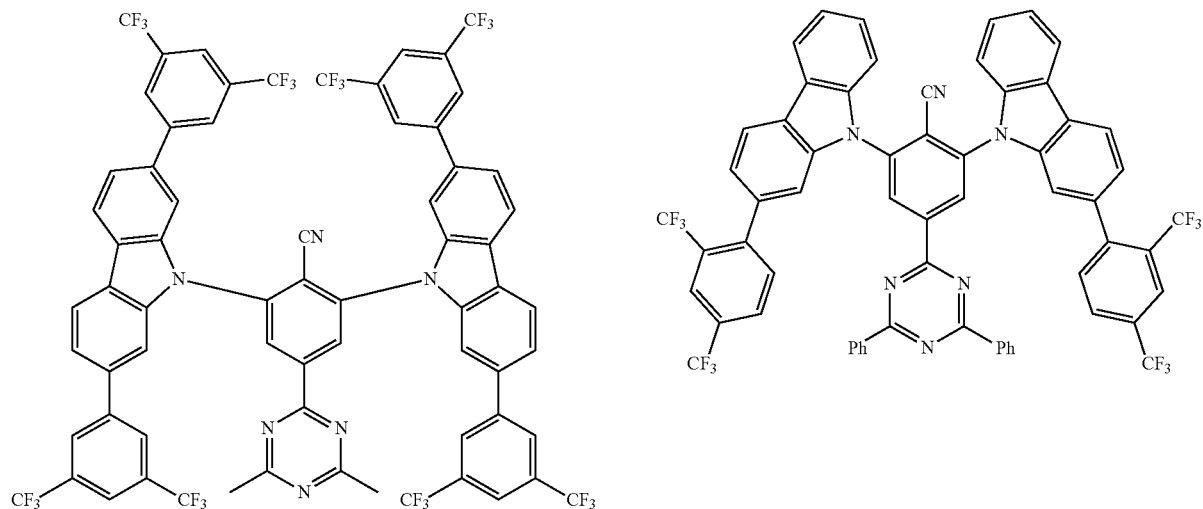
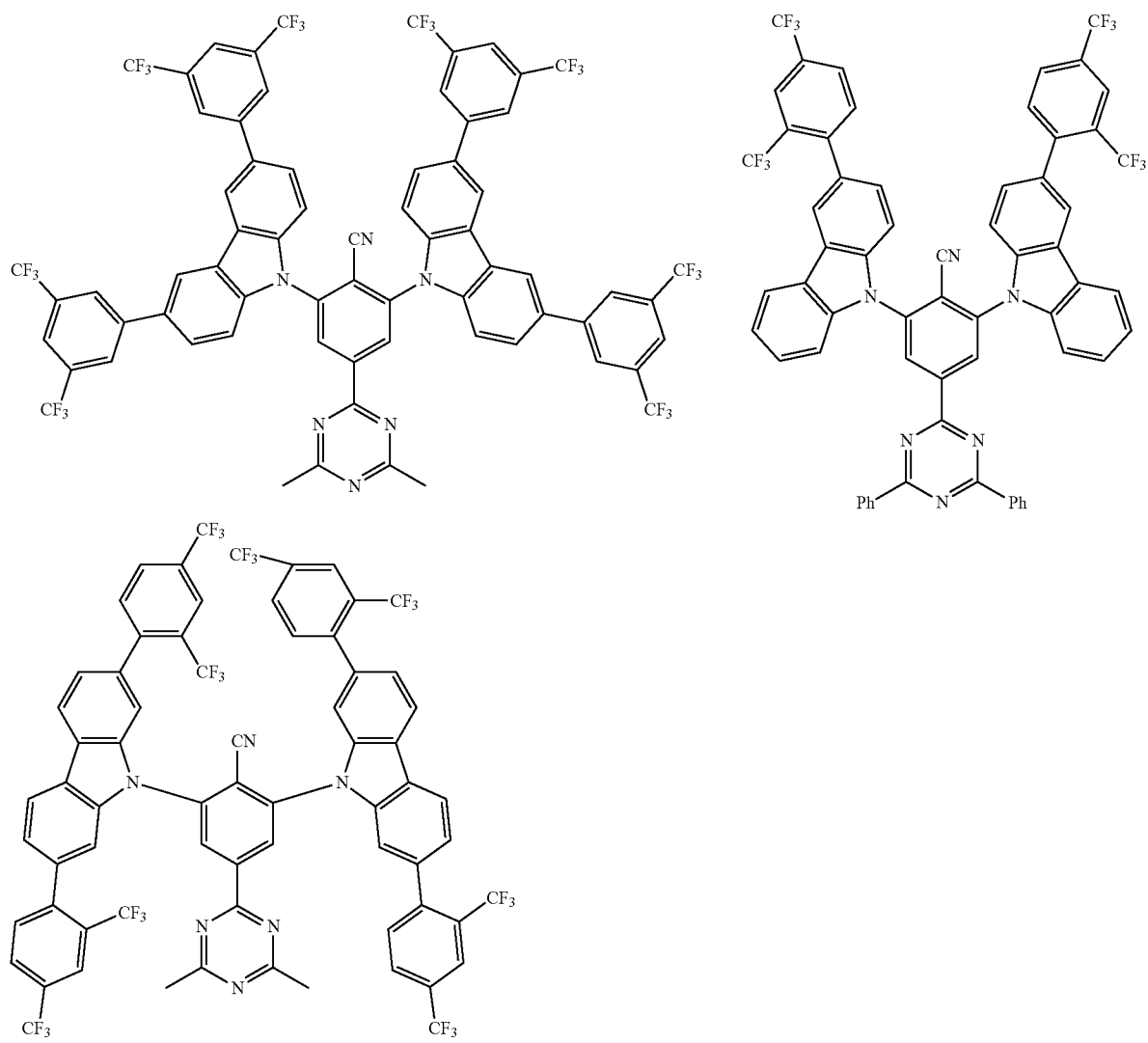

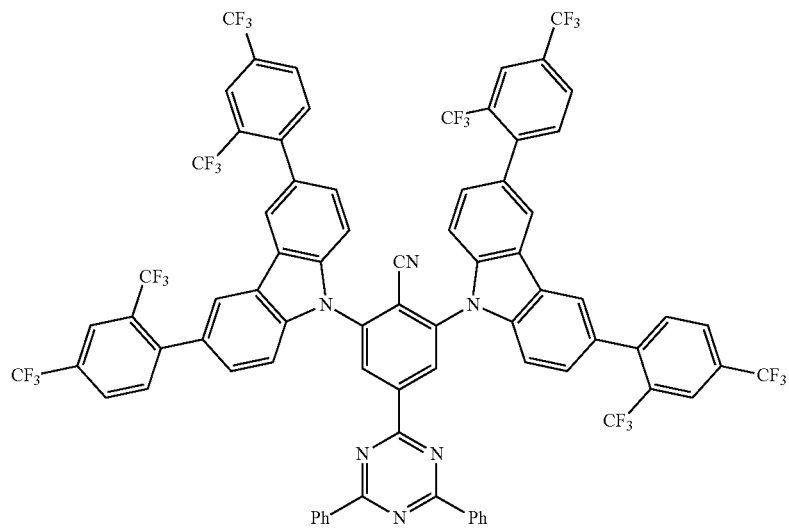
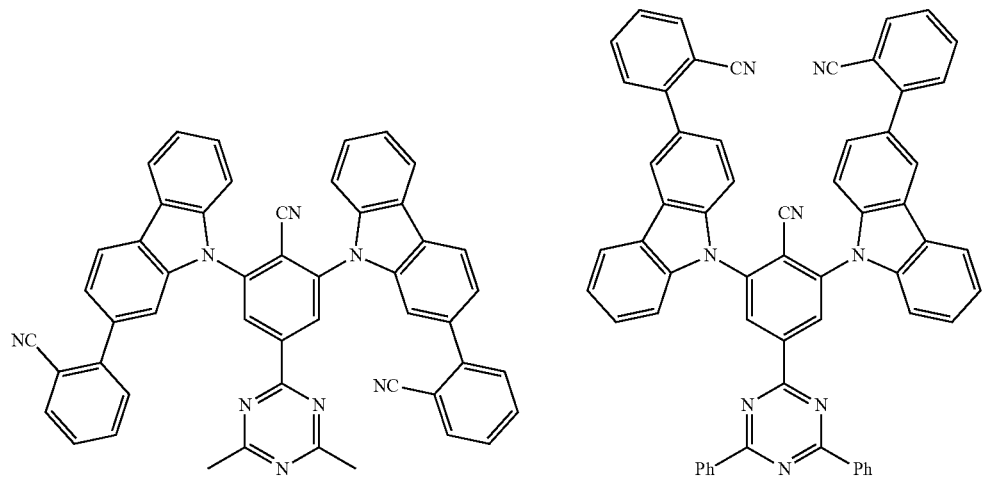
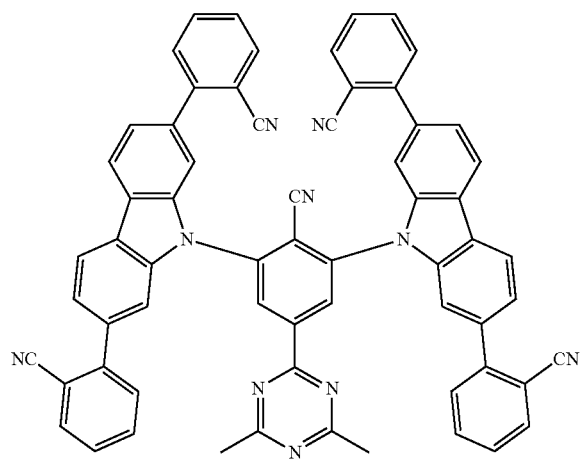

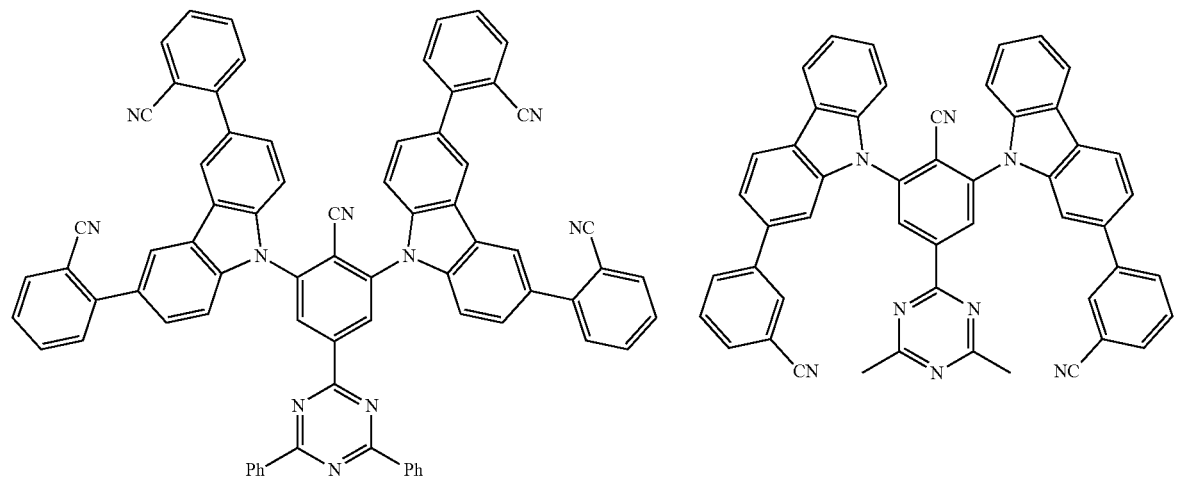
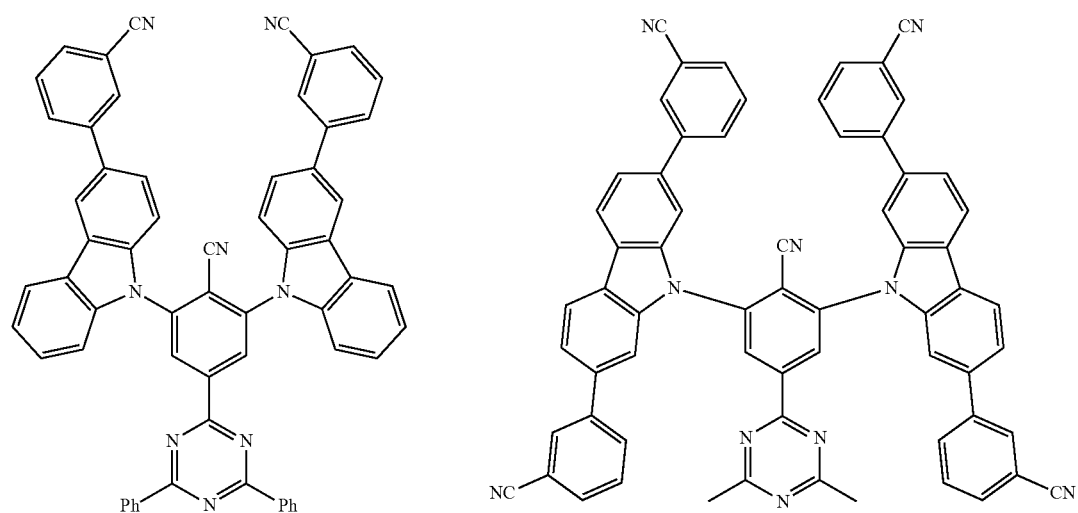
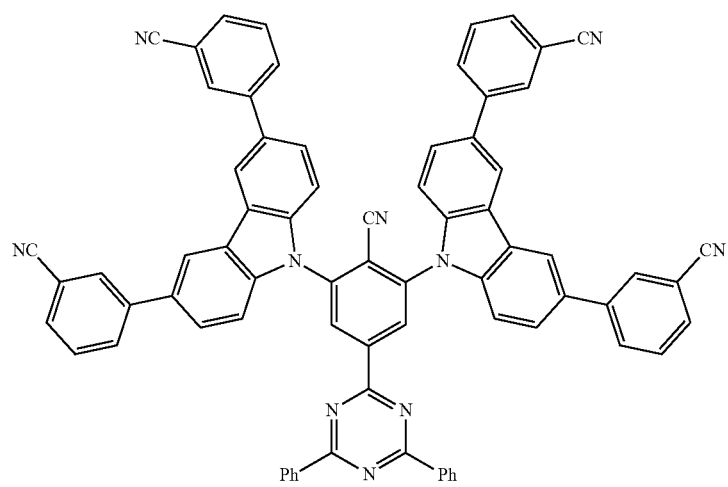

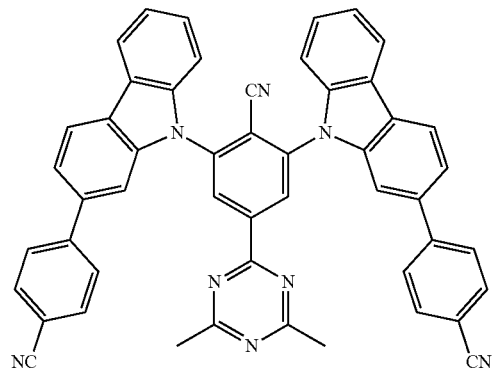
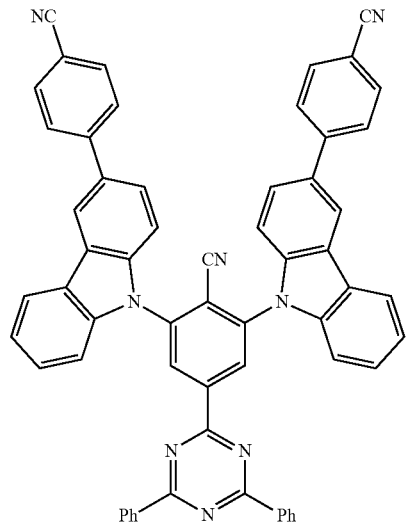
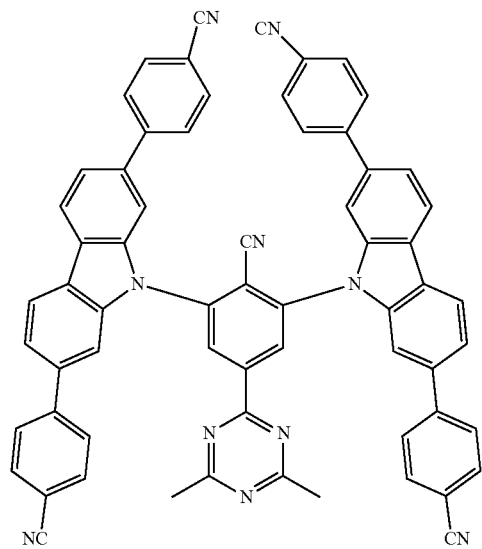
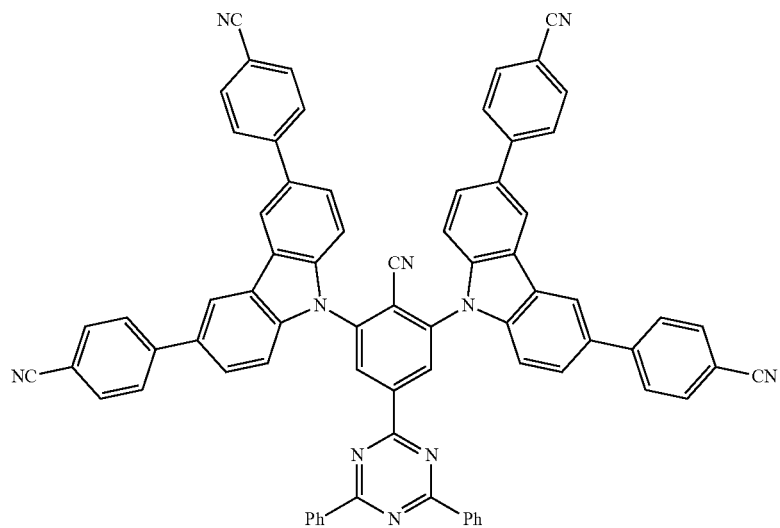

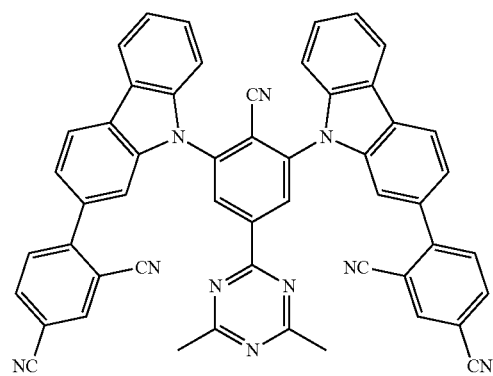
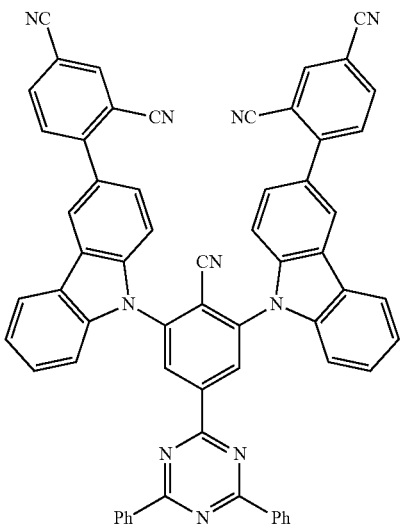
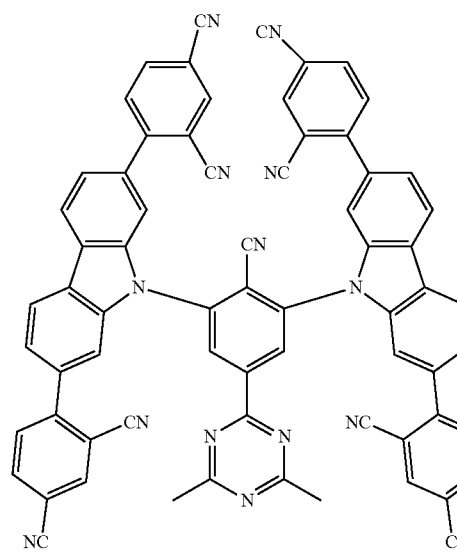
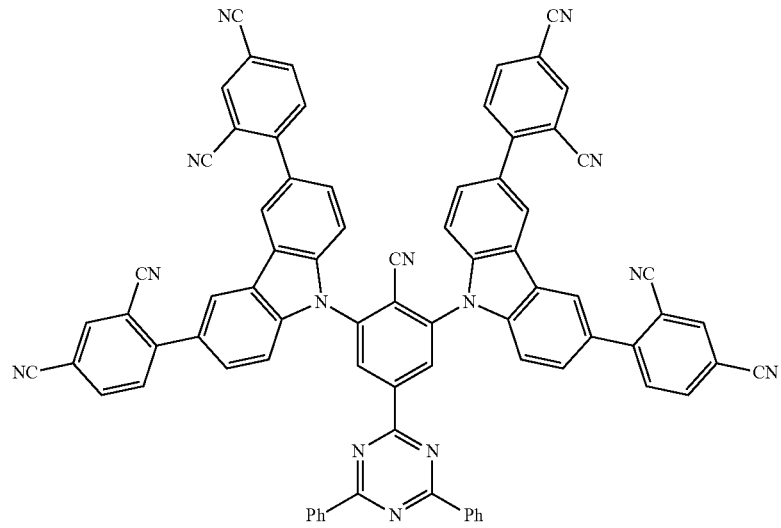

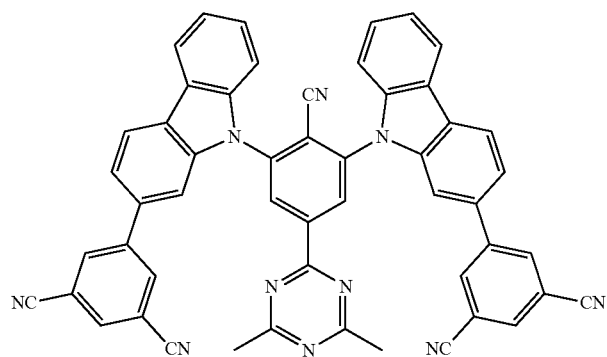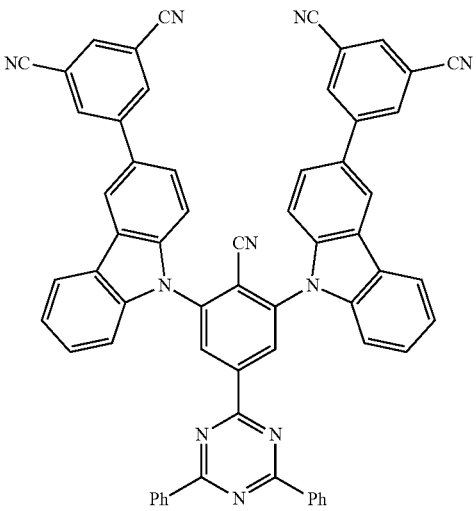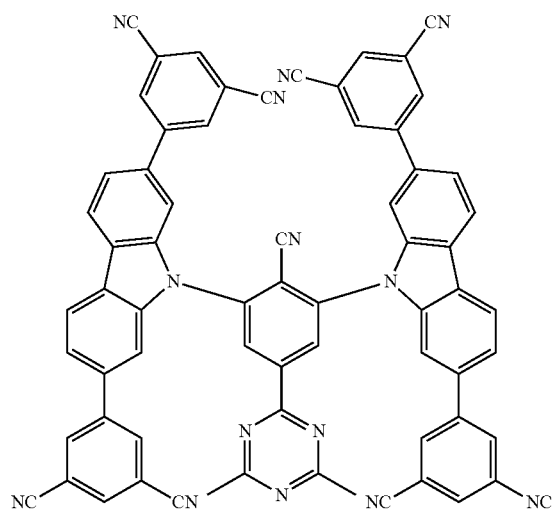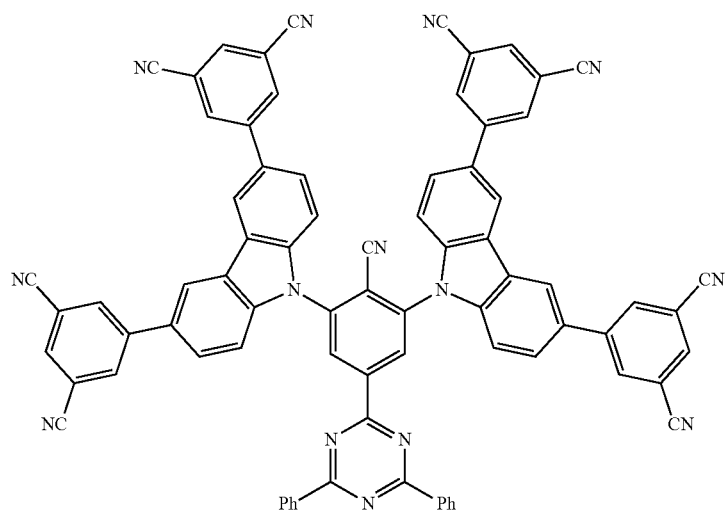

-continued
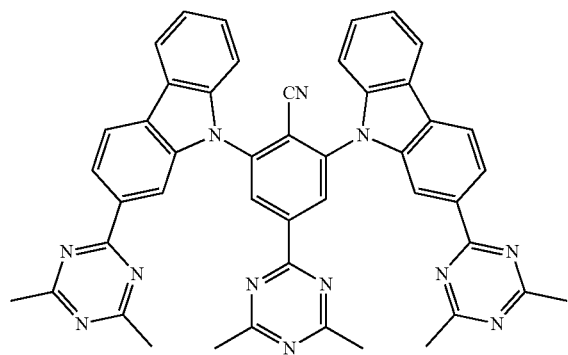 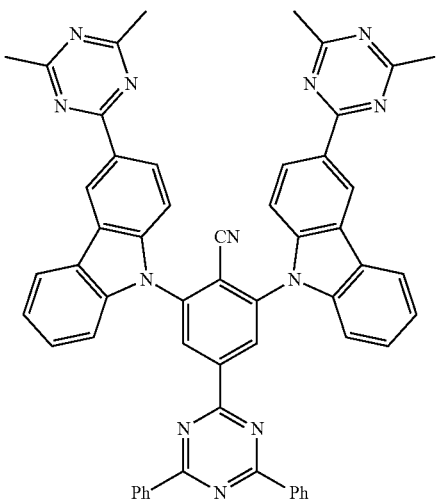
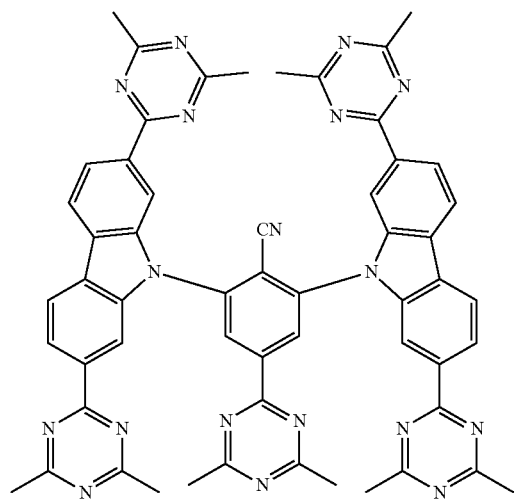
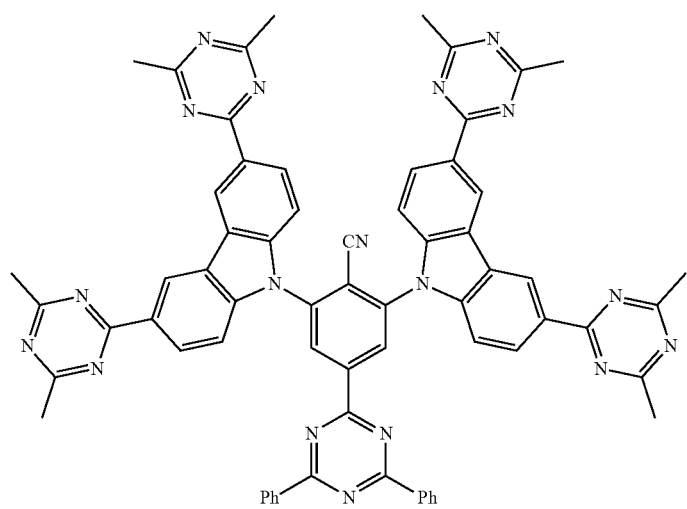

-continued
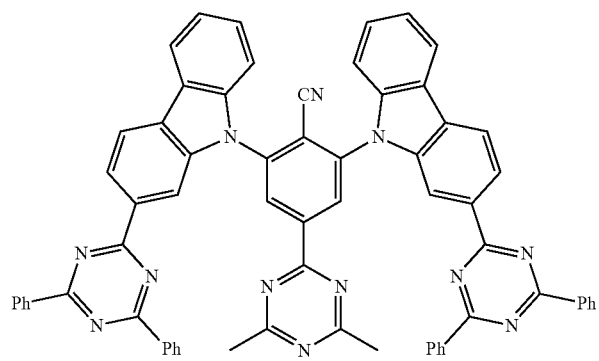
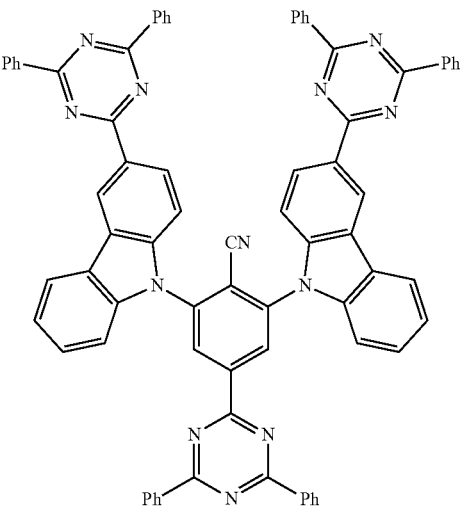
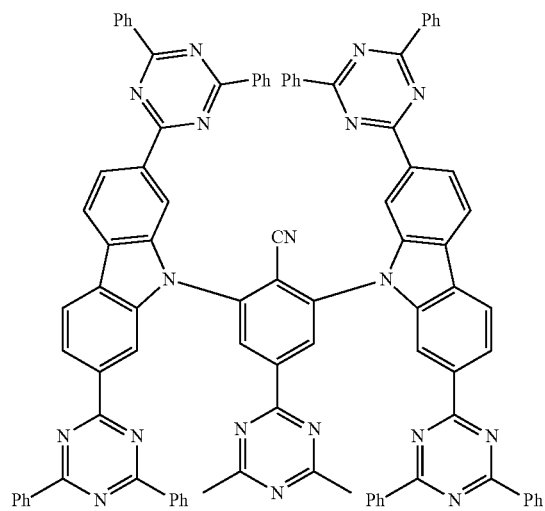
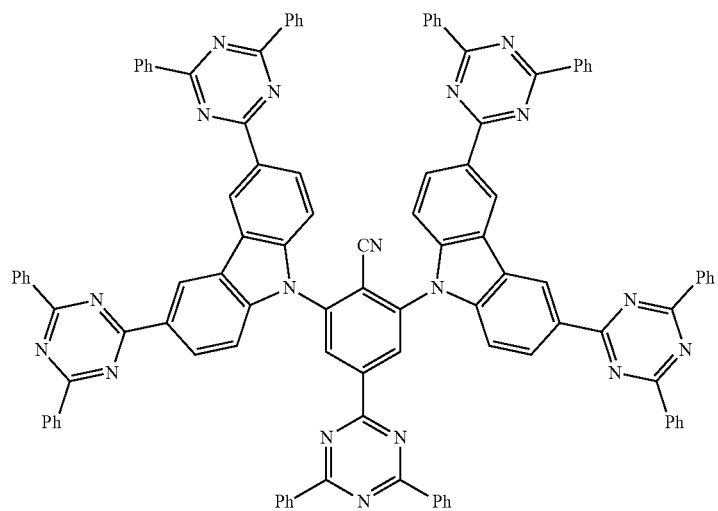

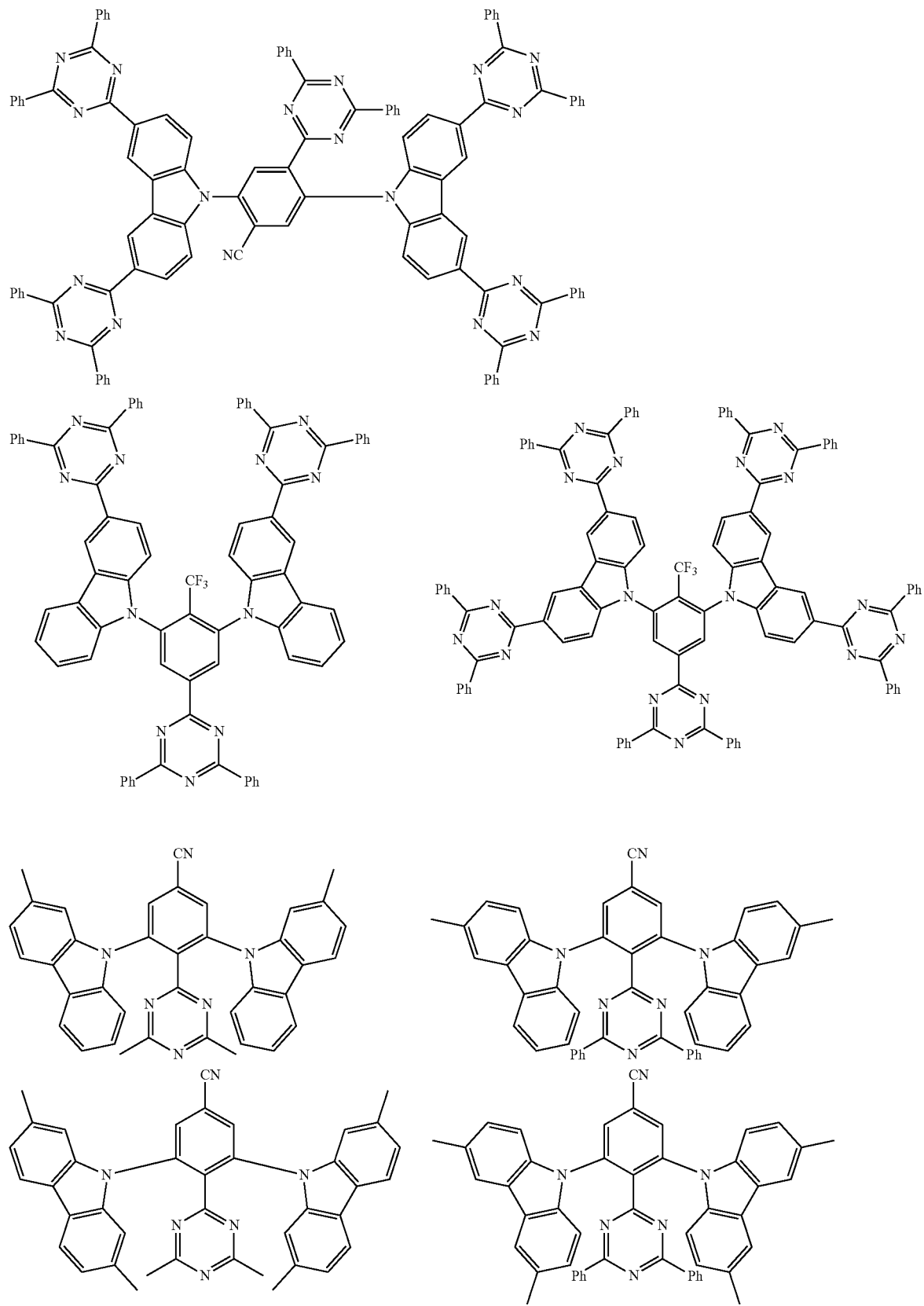

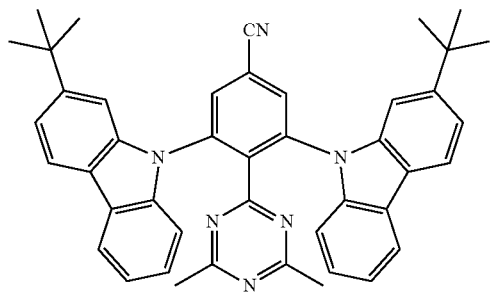
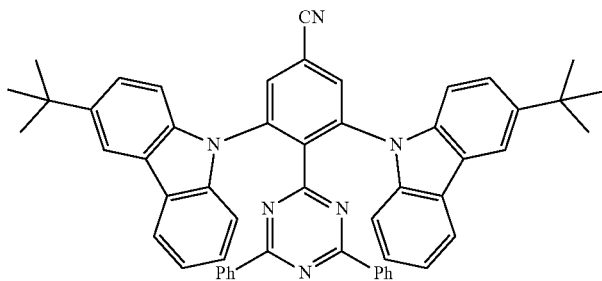
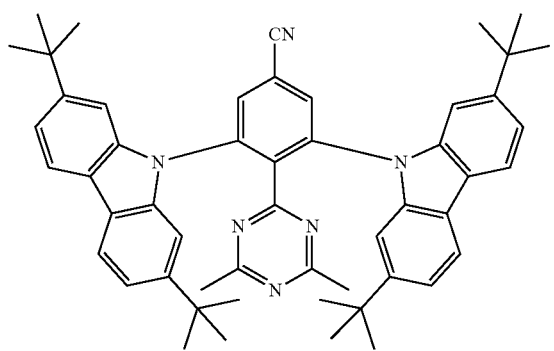
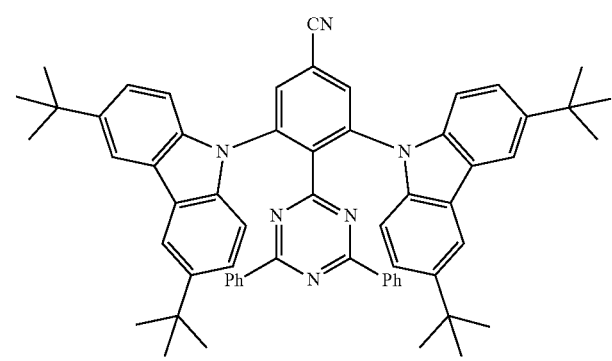
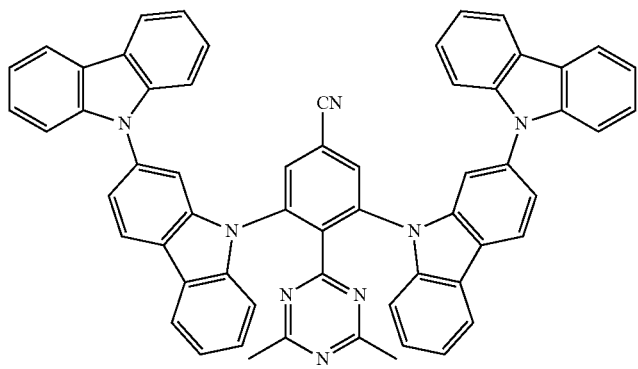
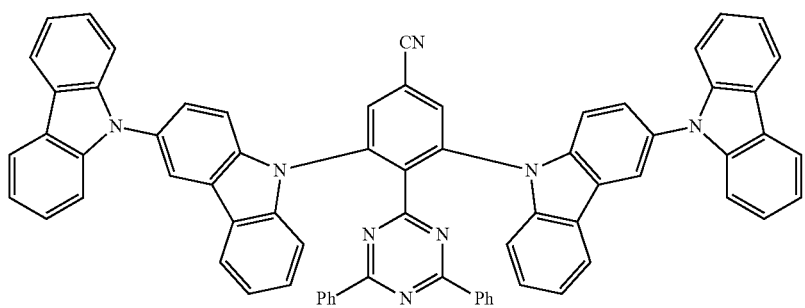

-continued
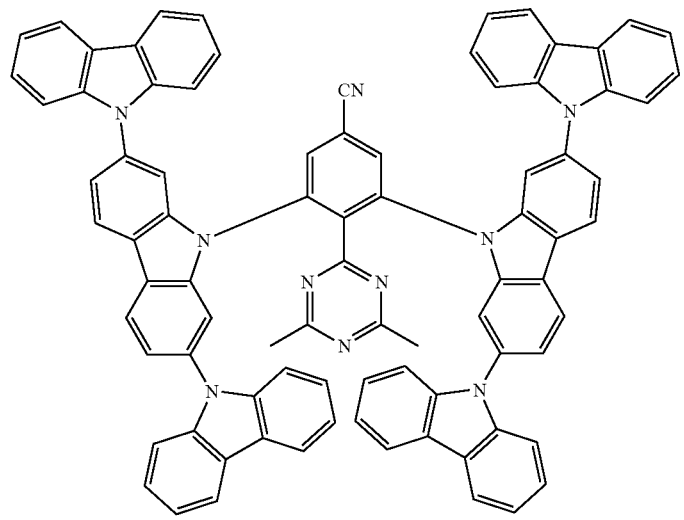
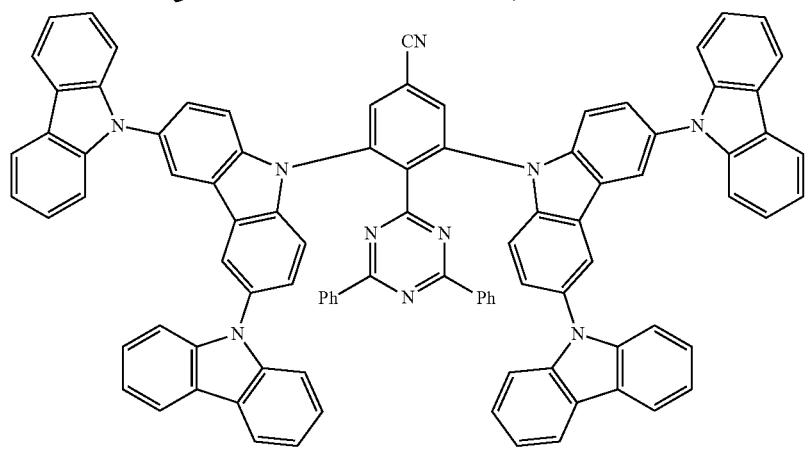
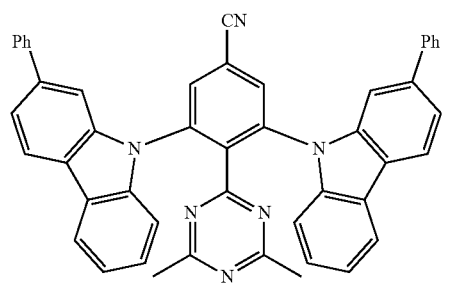
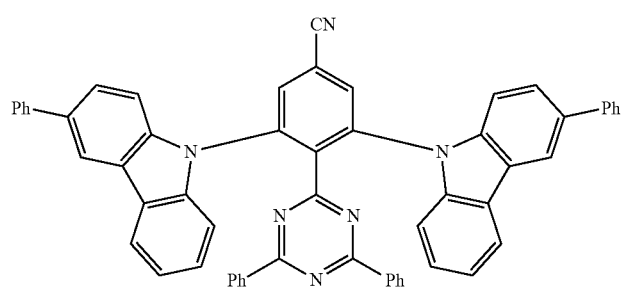
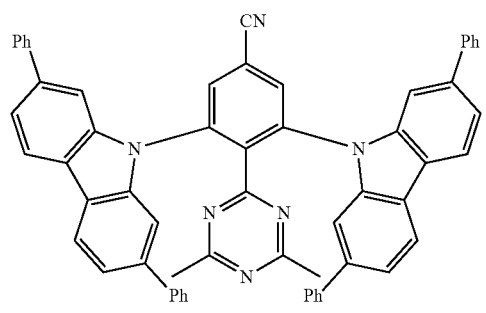
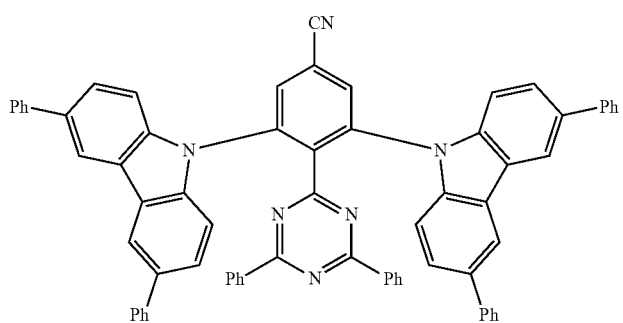

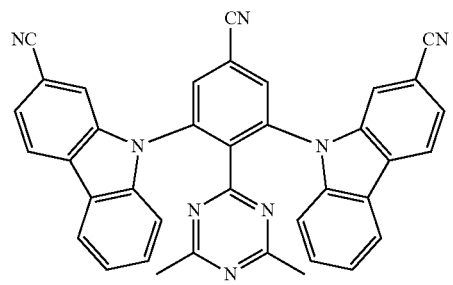
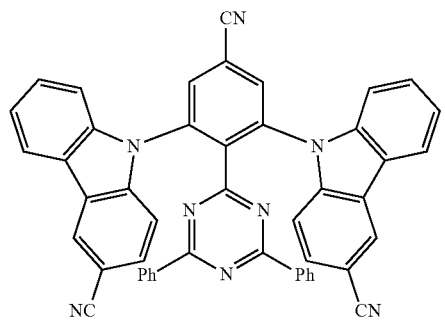
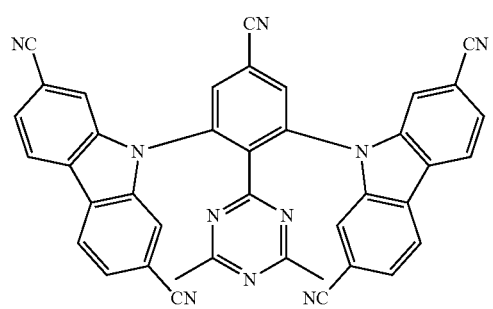
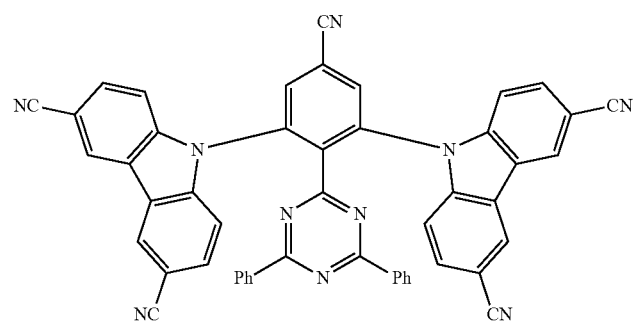
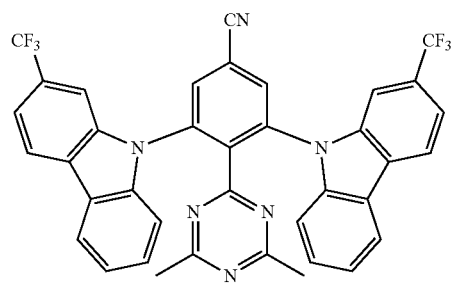
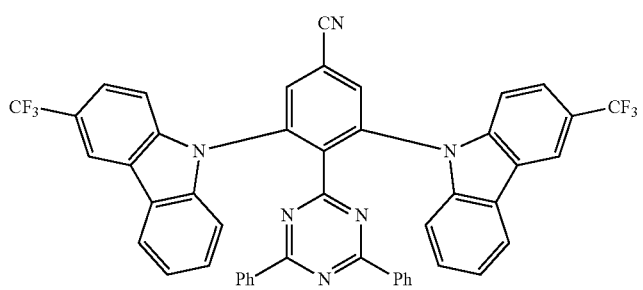
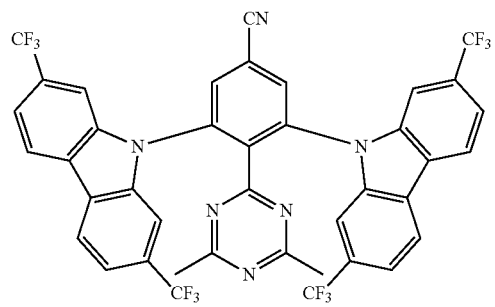
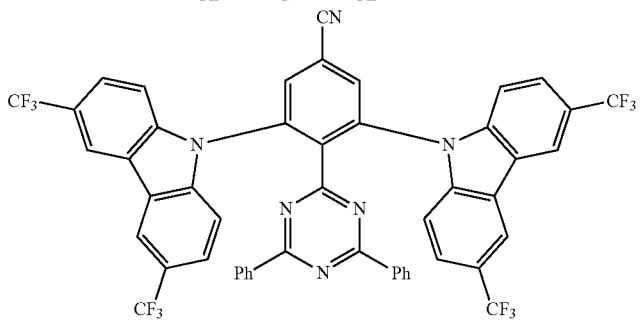
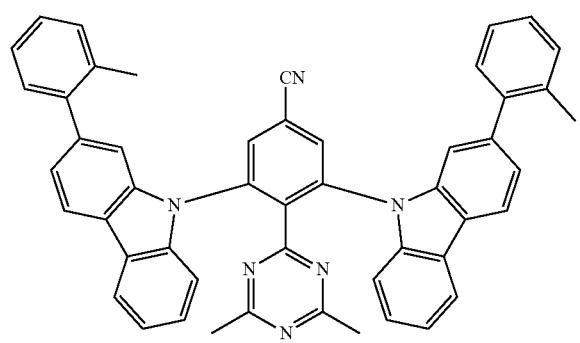

-continued
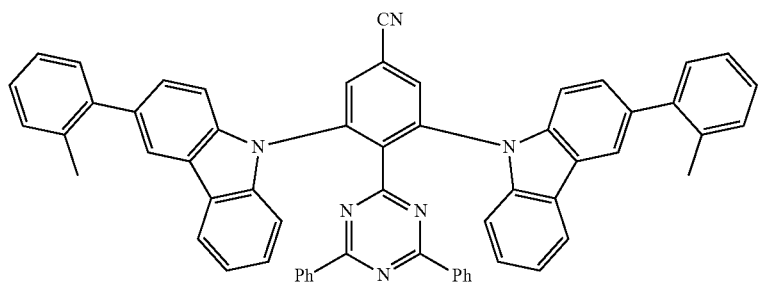
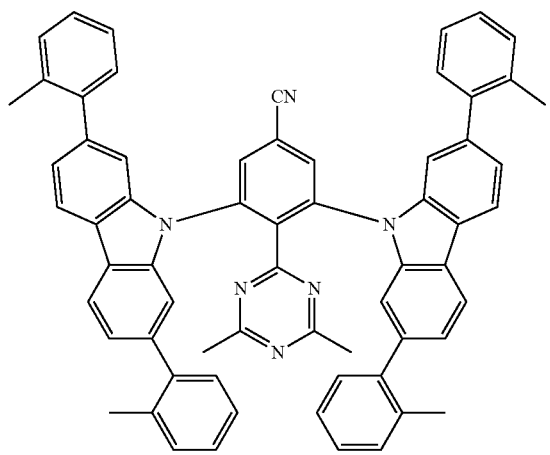
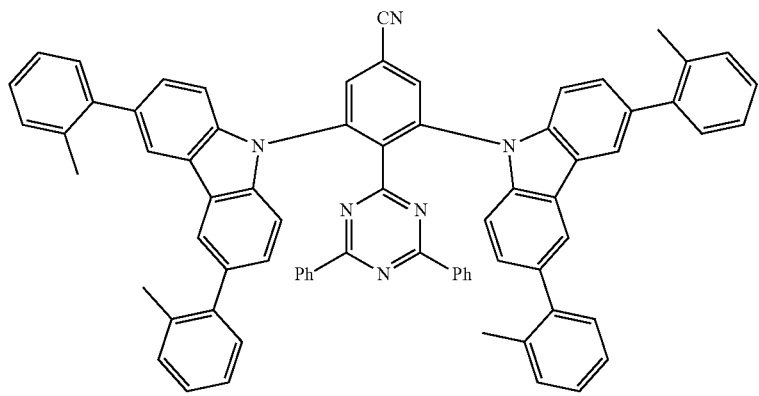
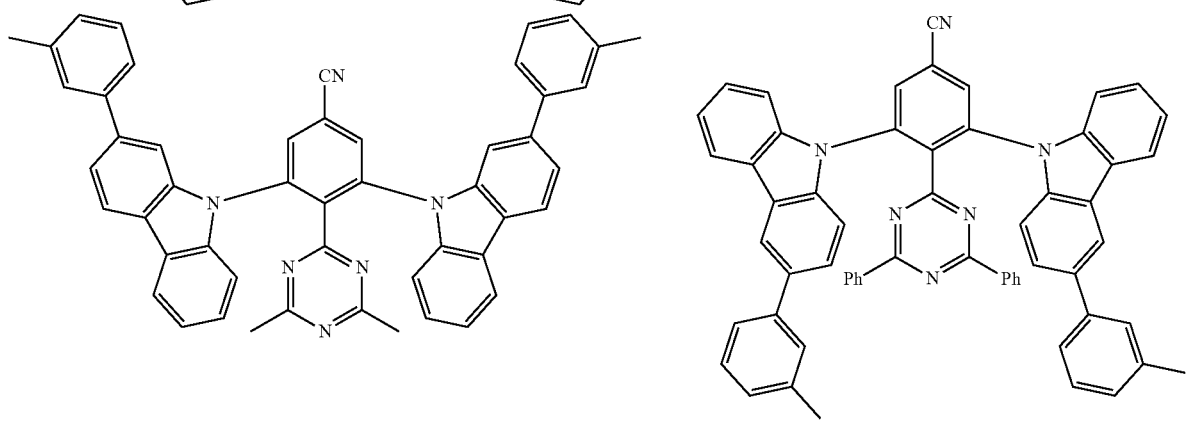

-continued
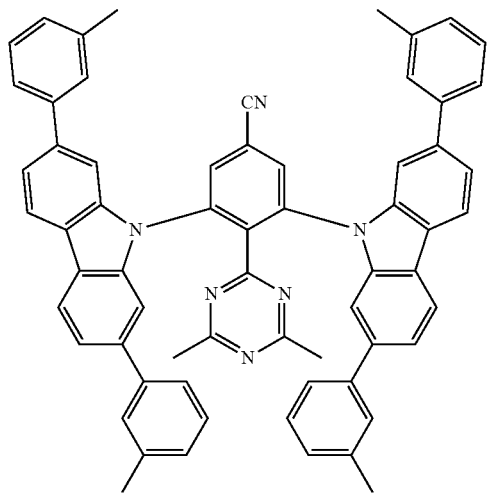
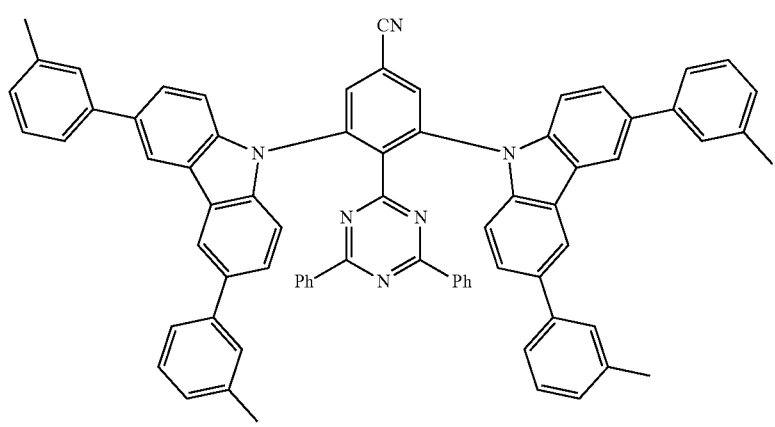
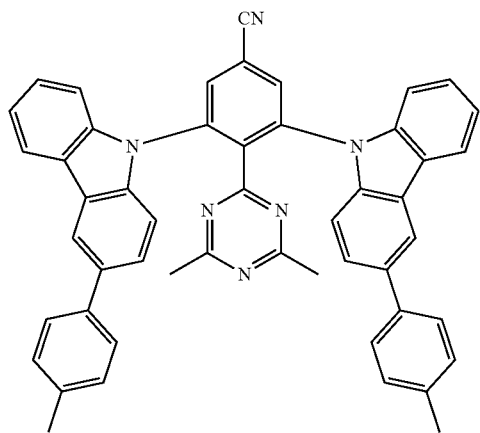
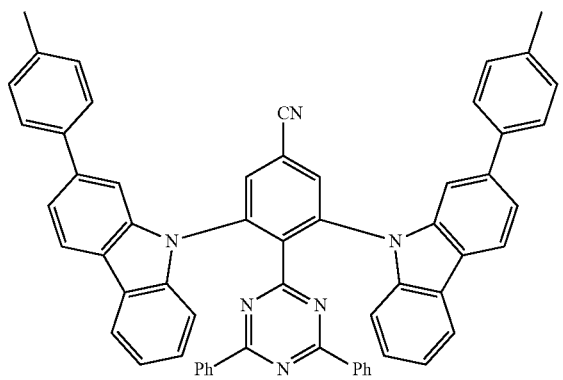

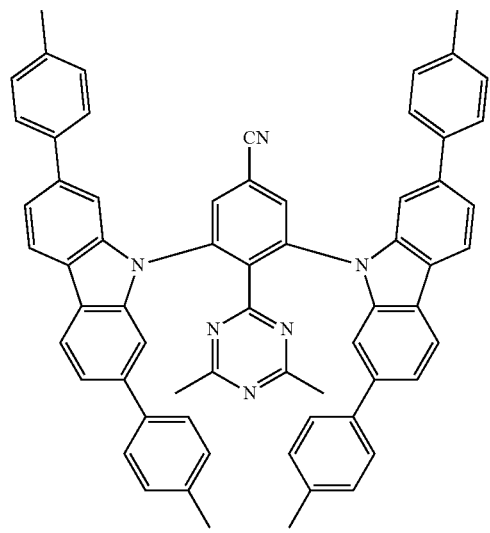
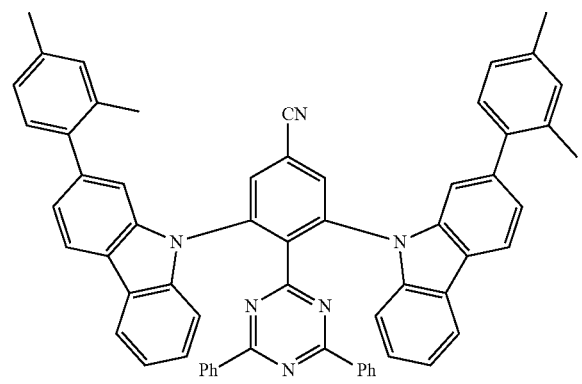
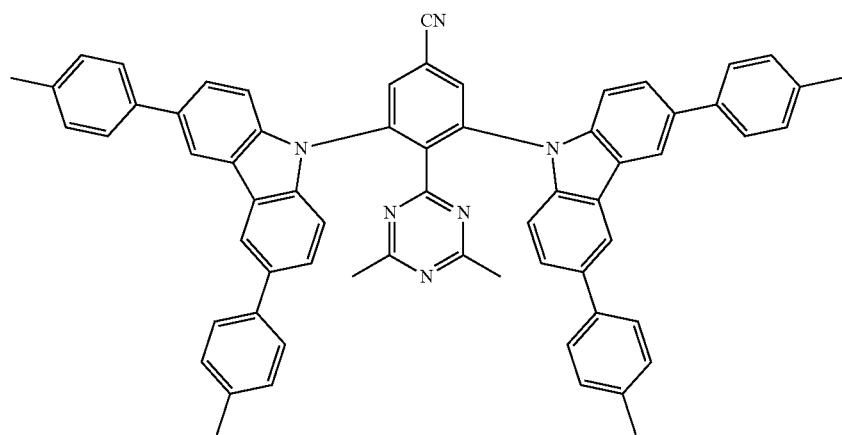
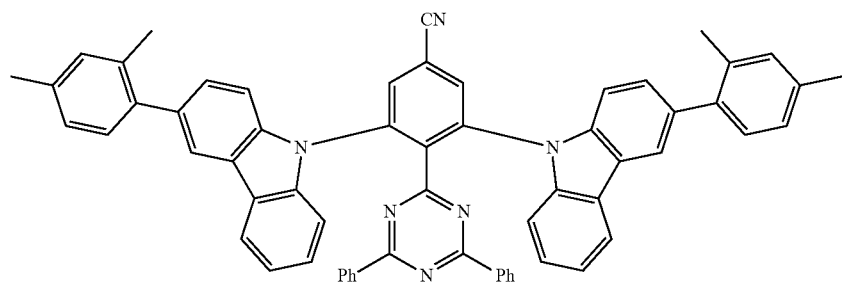

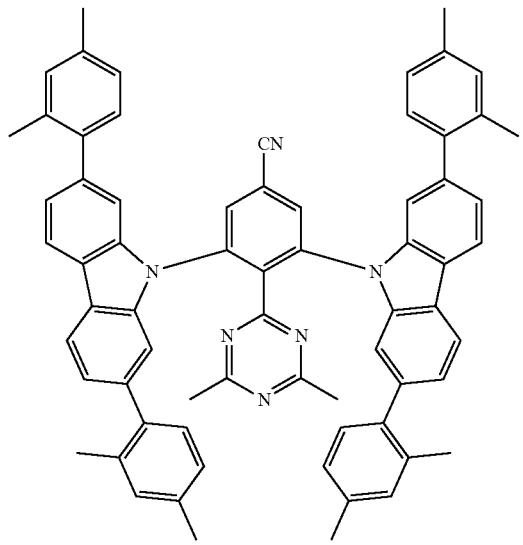
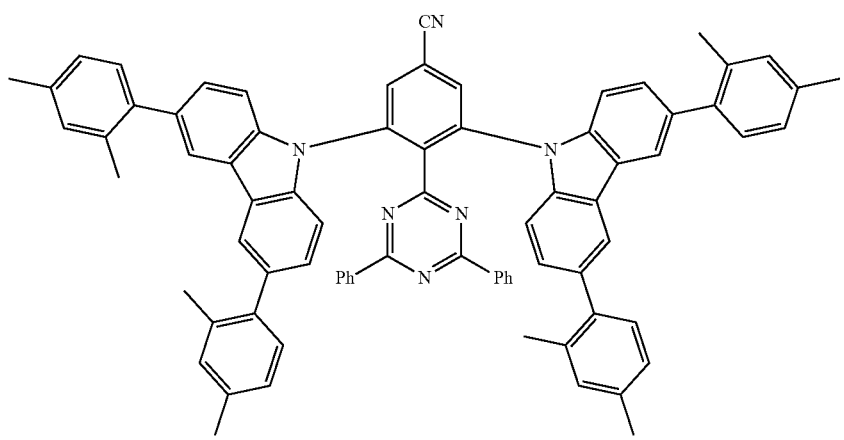
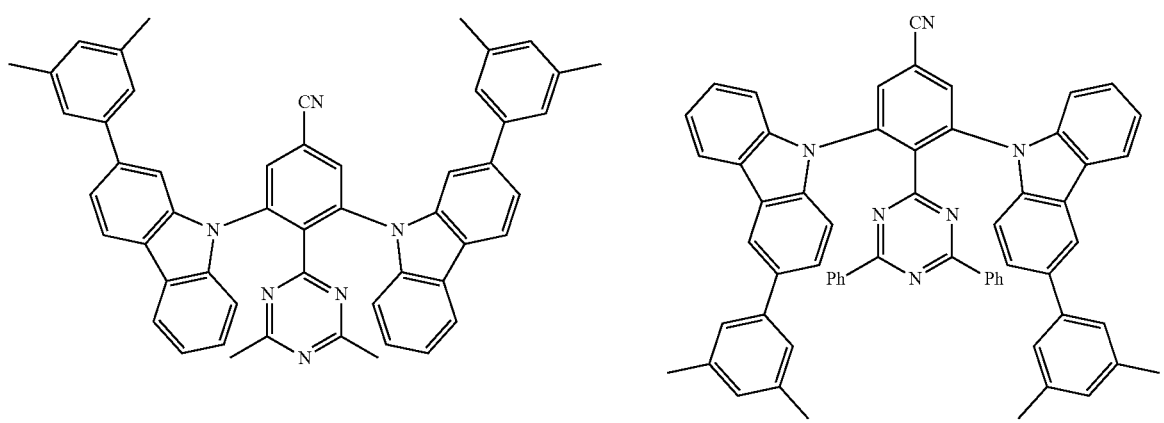

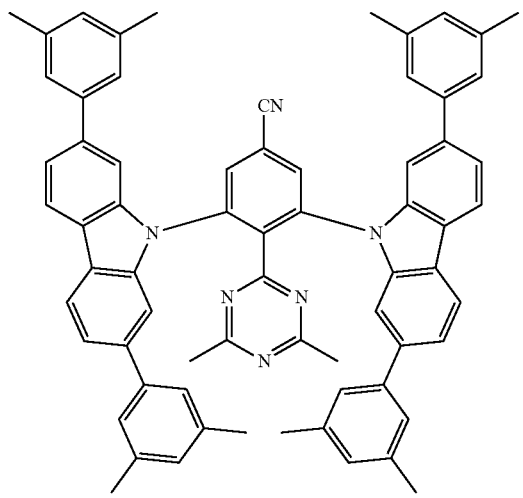
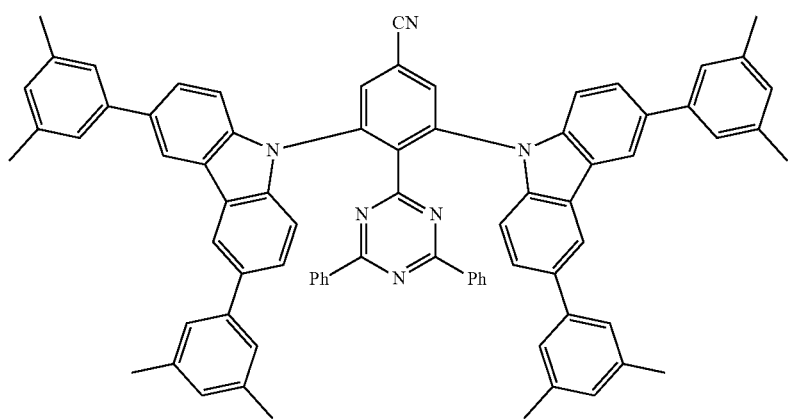
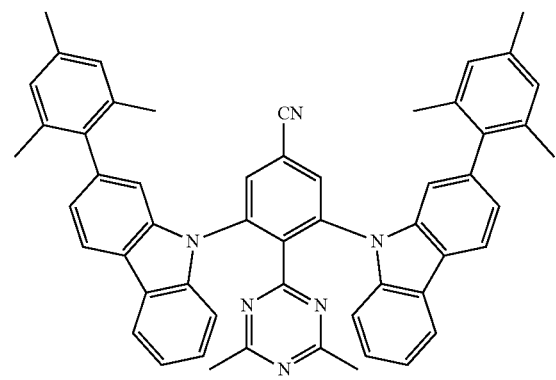
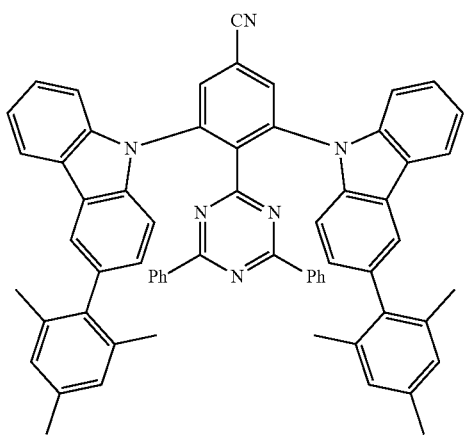

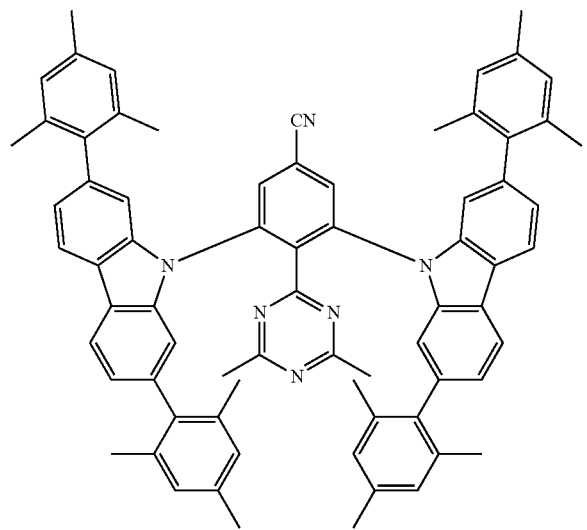
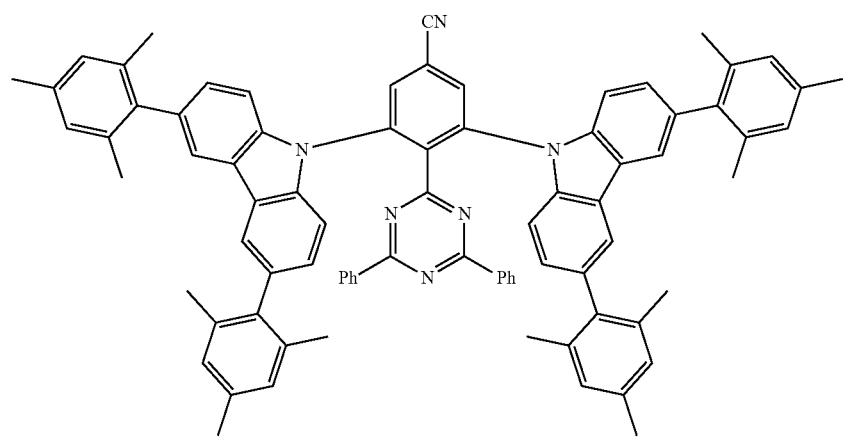
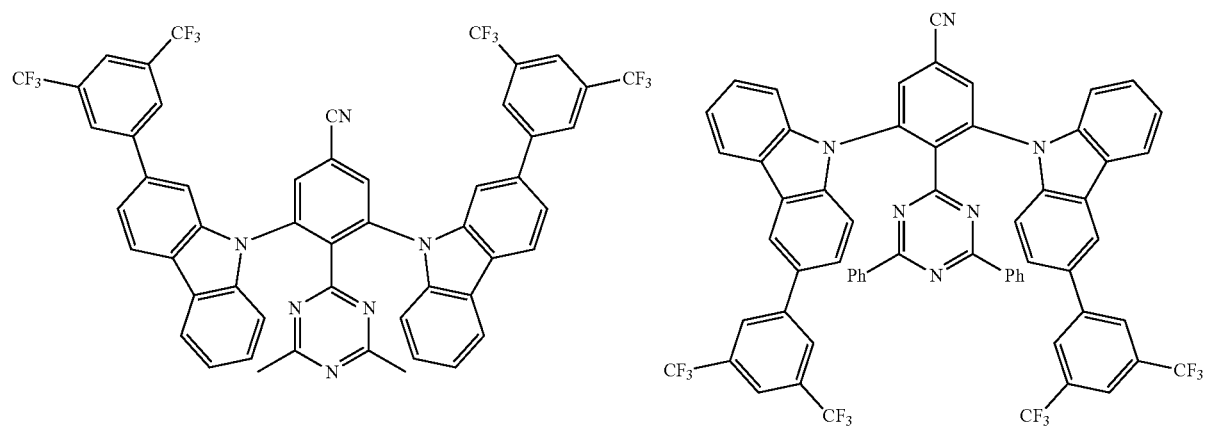

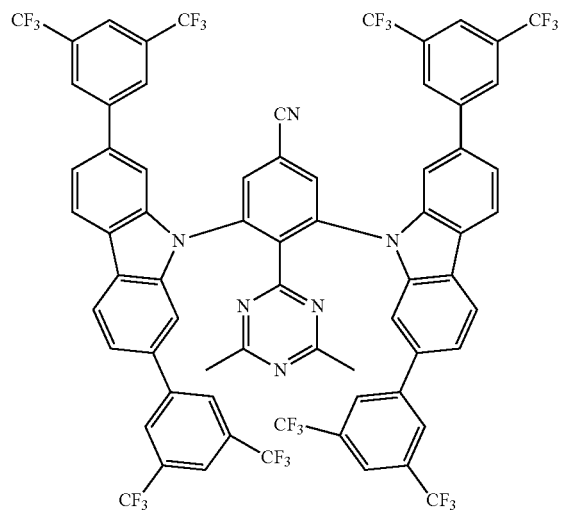
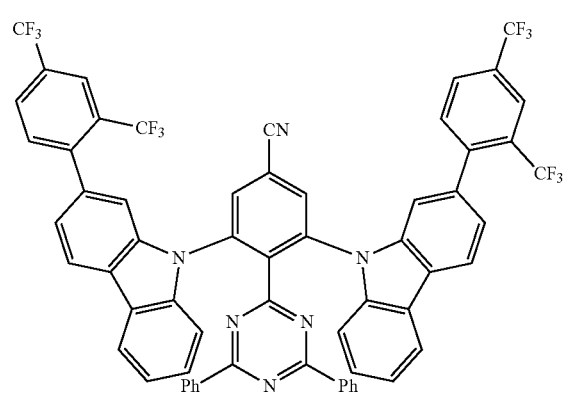
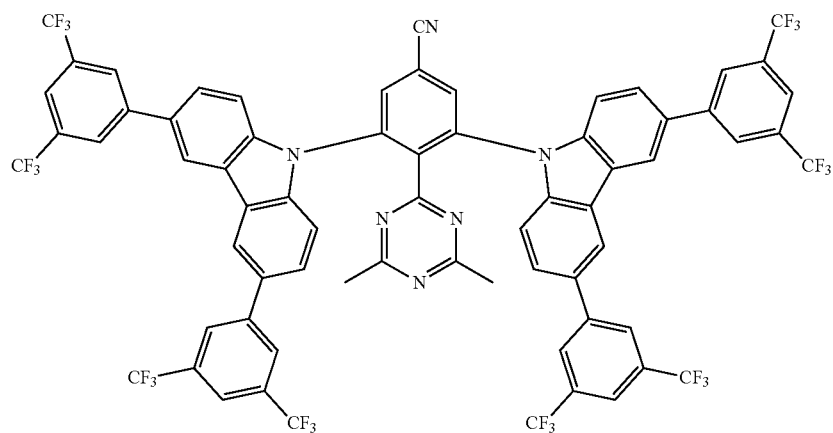
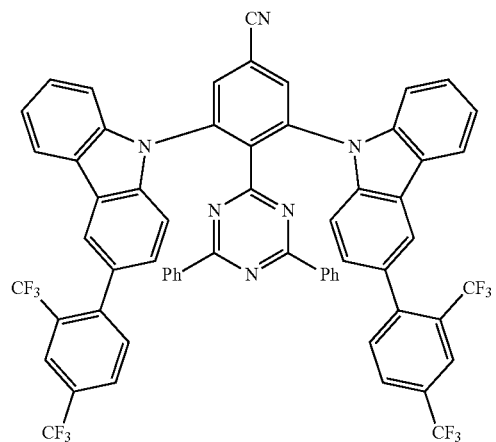
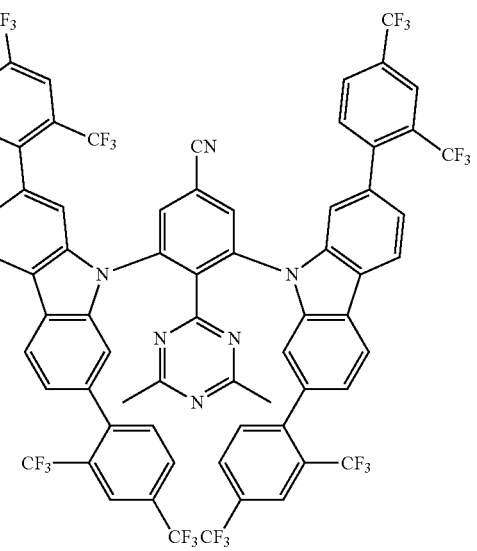

-continued
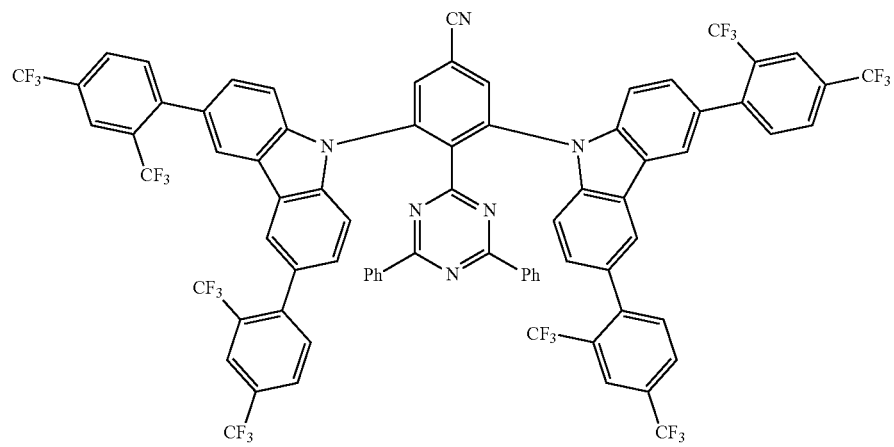
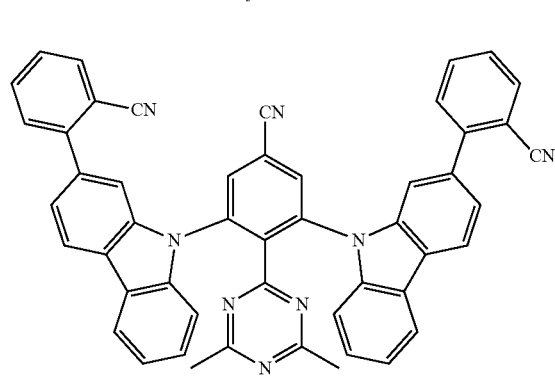
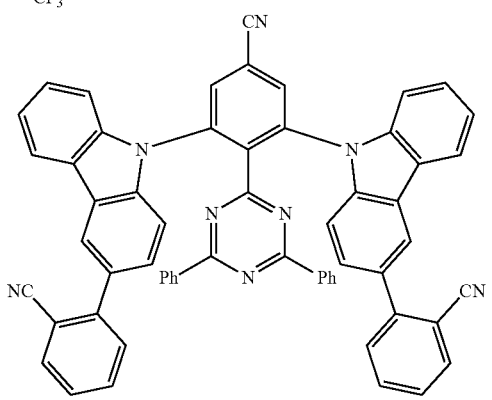
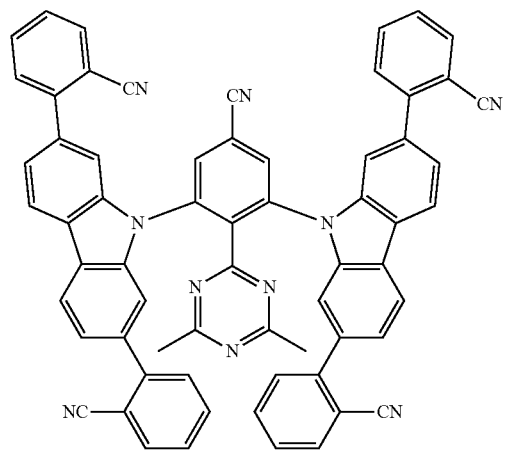
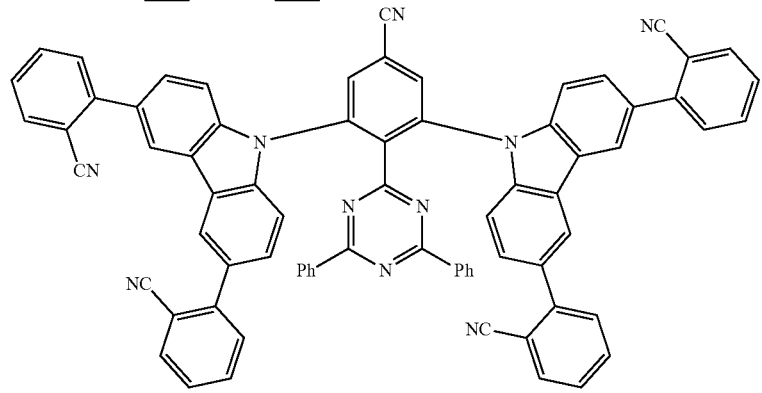

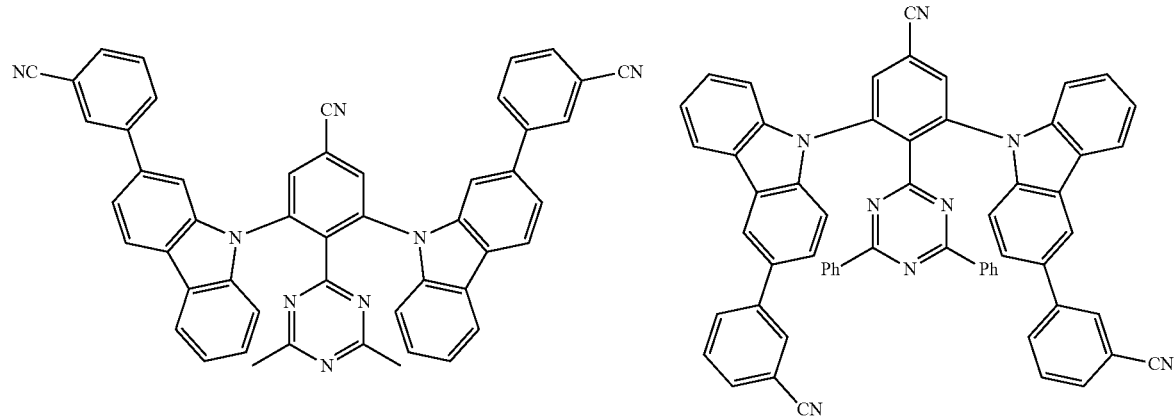
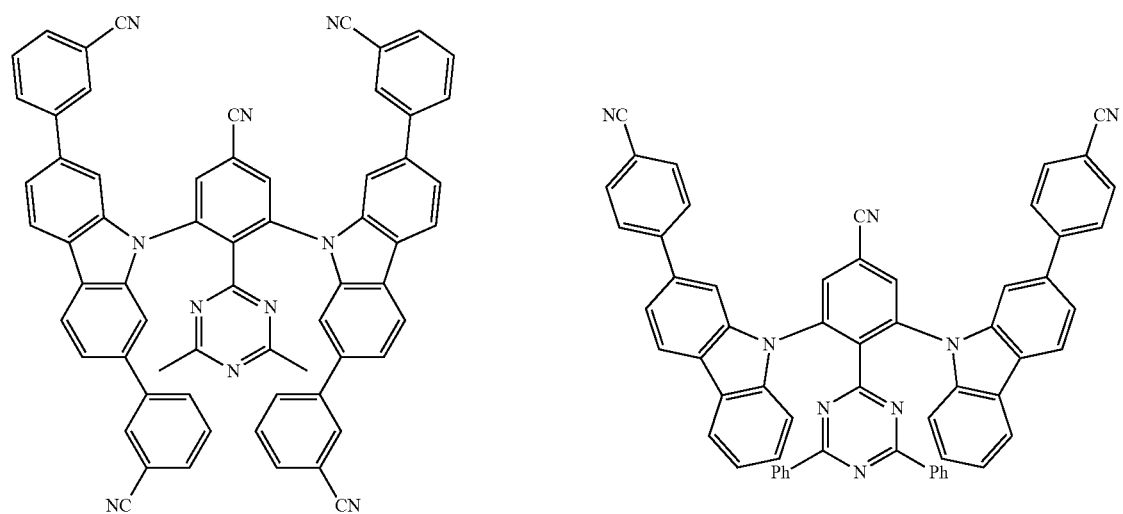
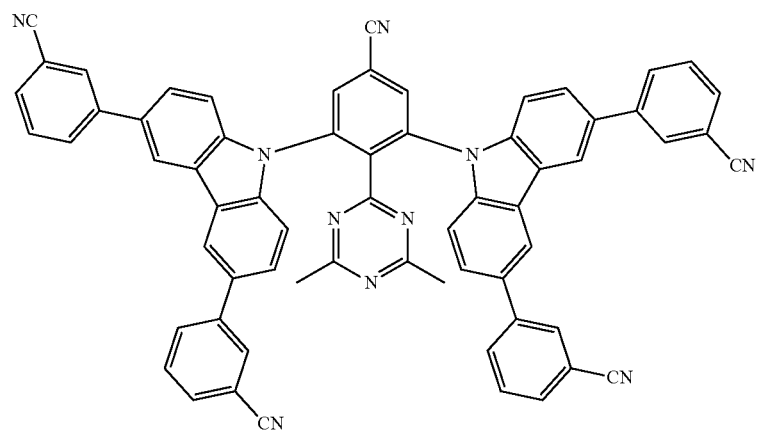

-continued
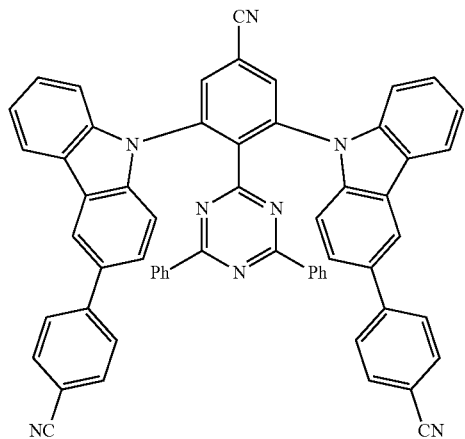
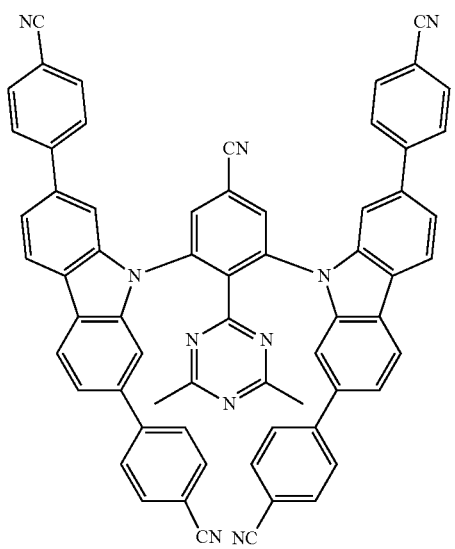
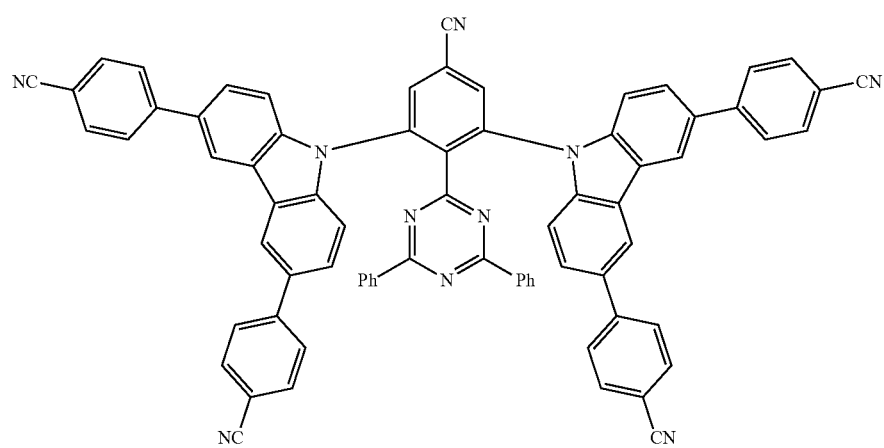
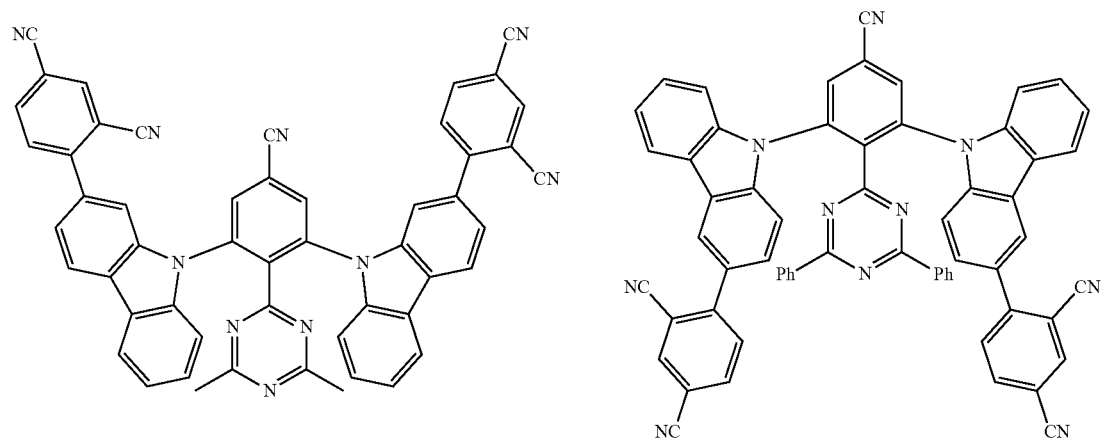

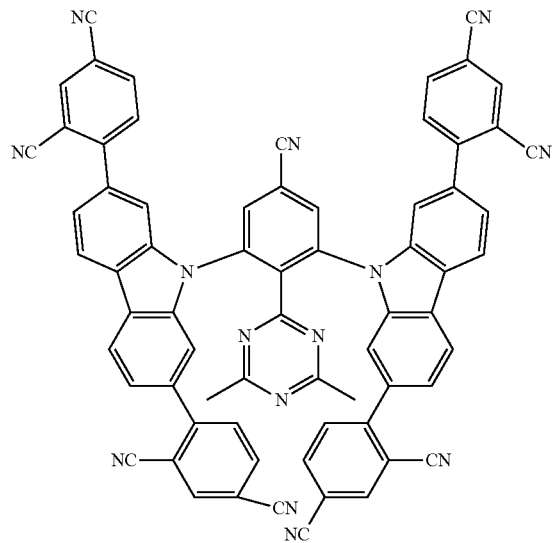
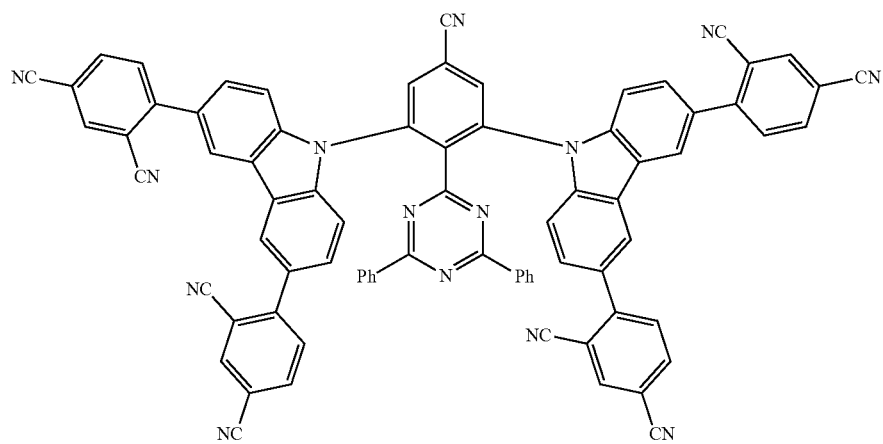
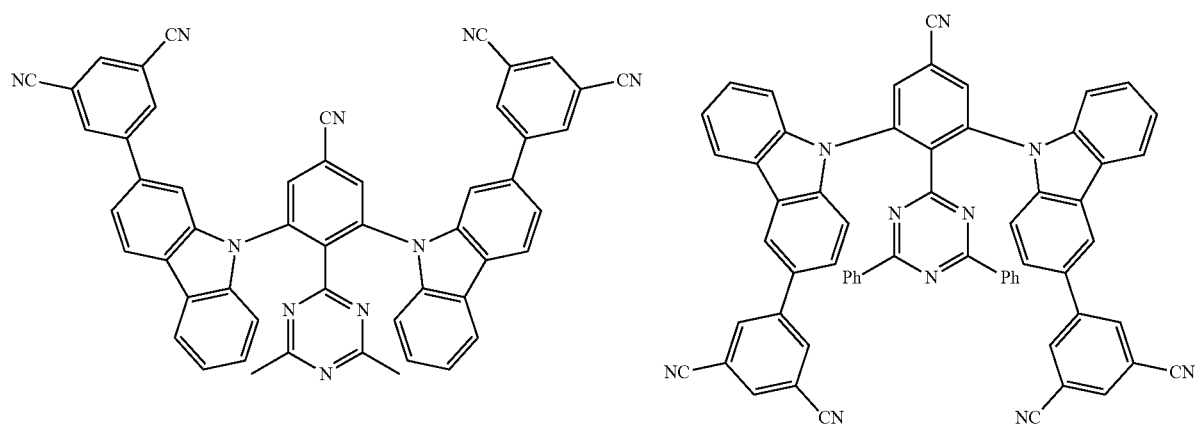

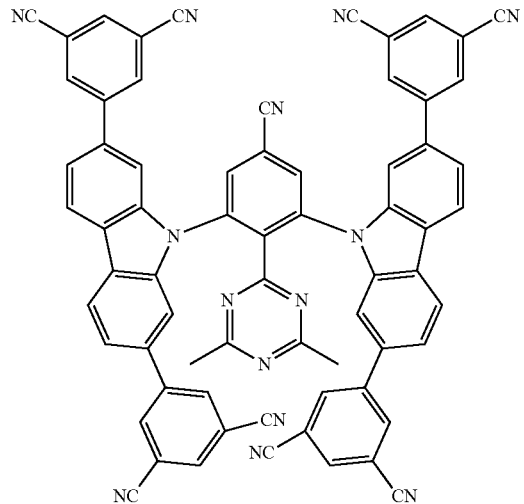
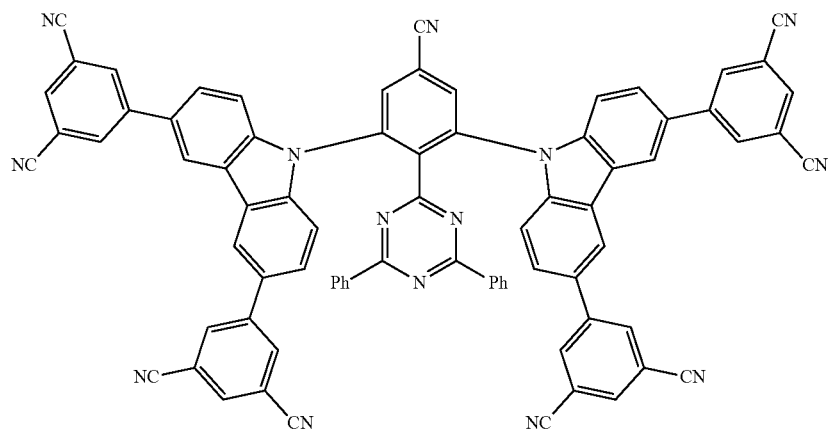
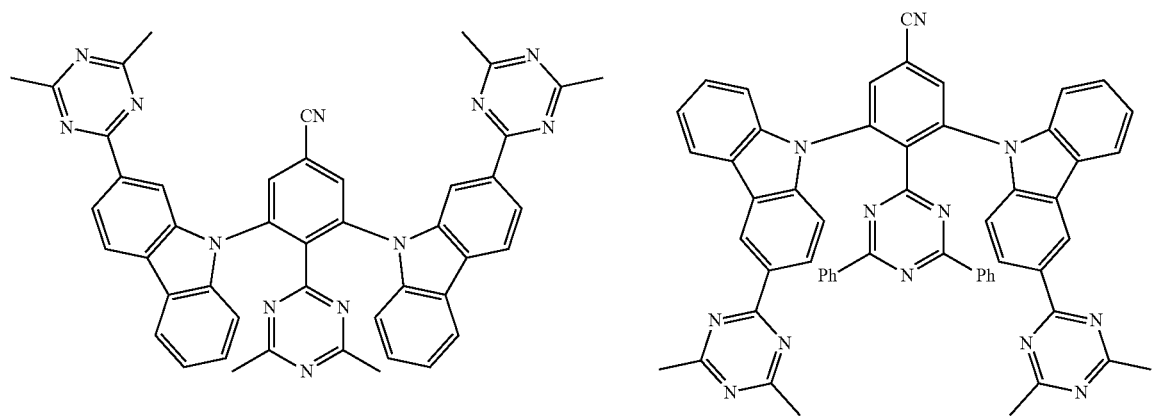

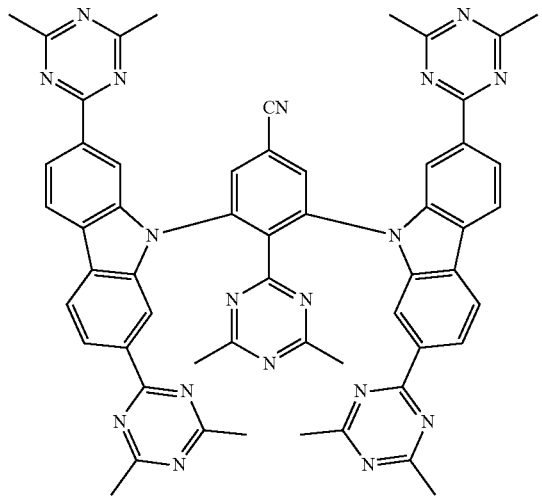
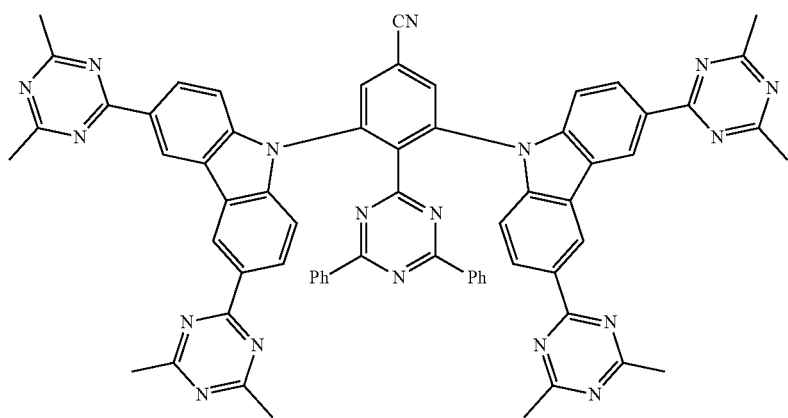
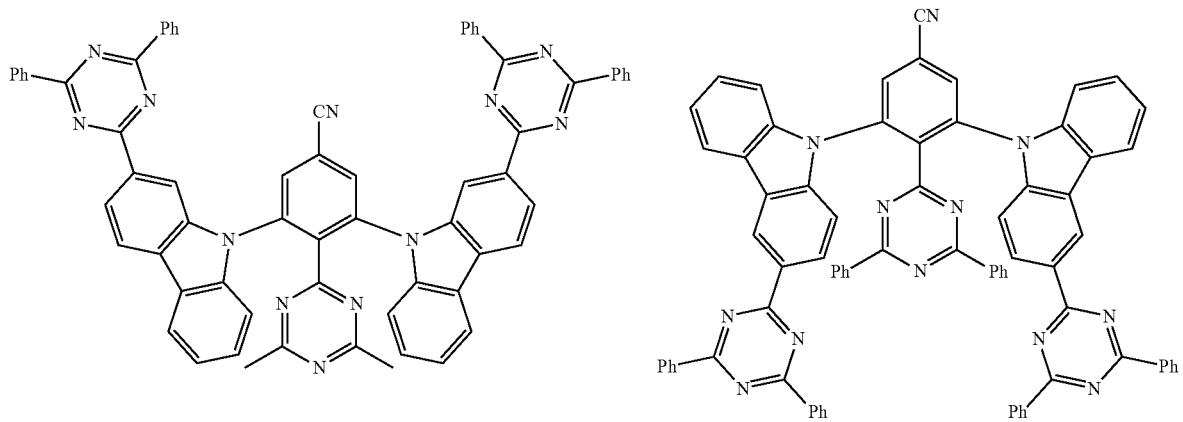

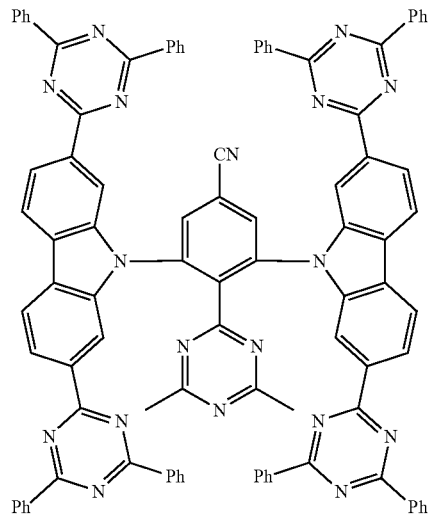
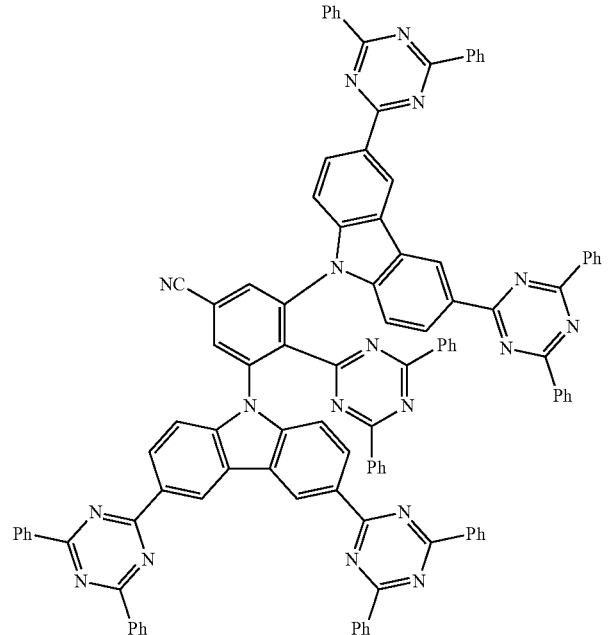
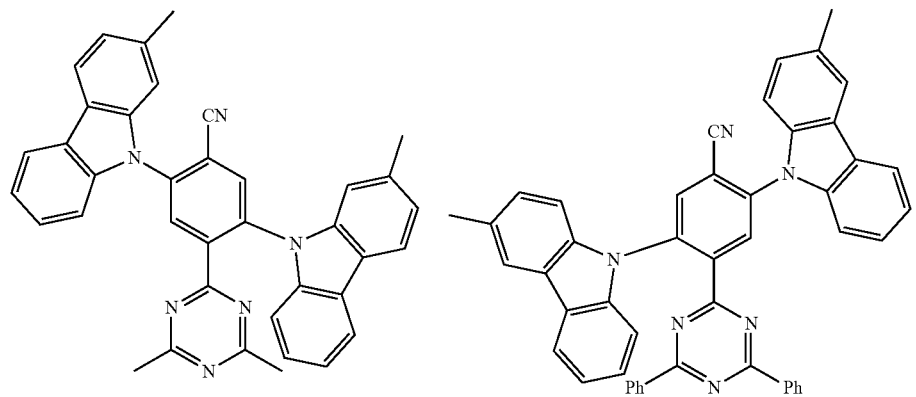
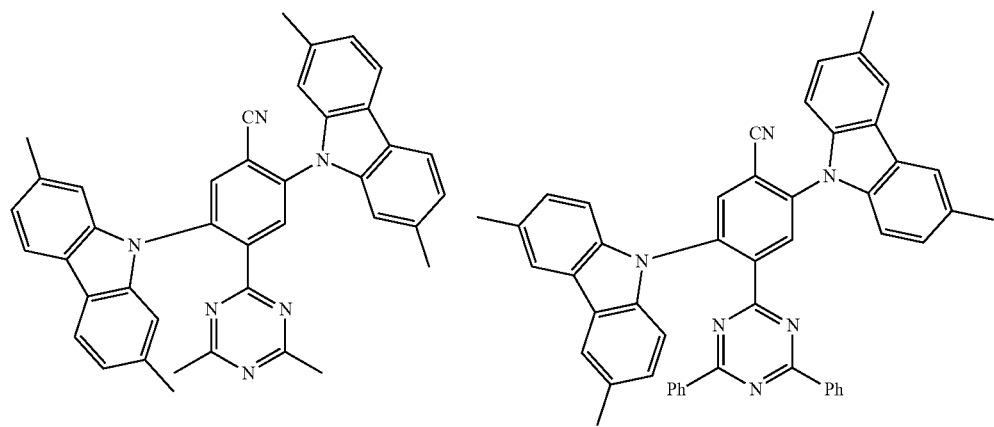

-continued
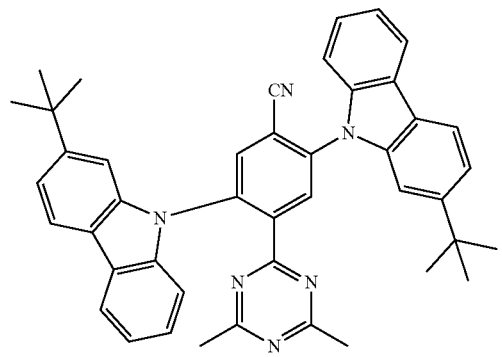
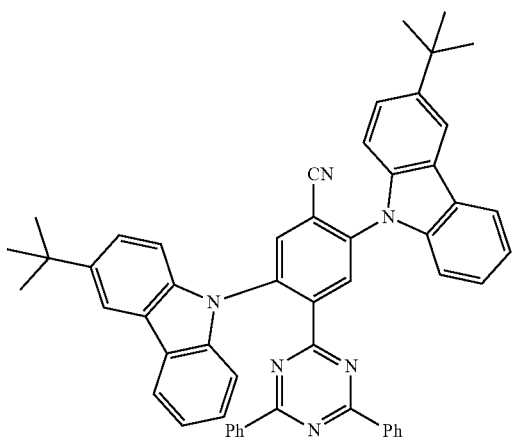
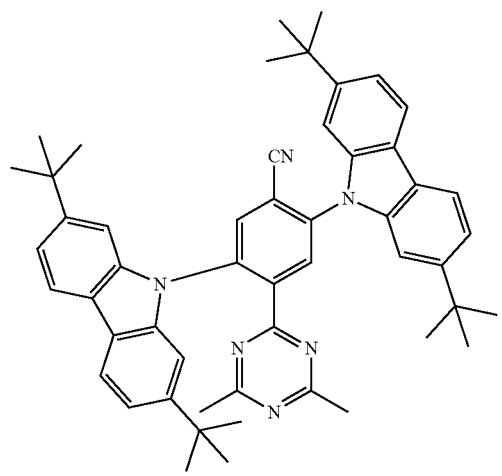
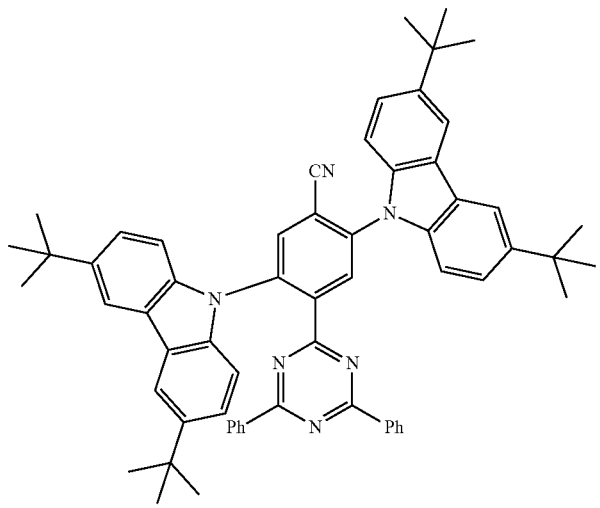
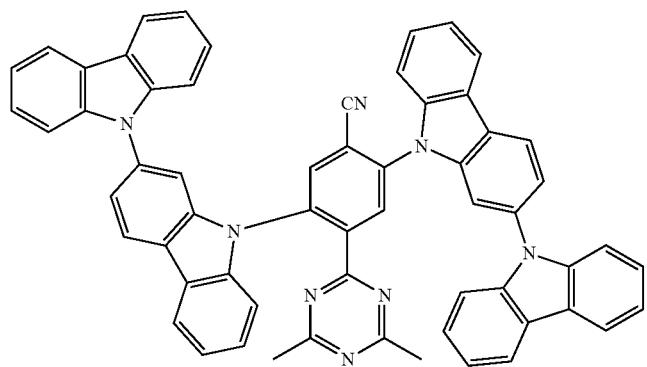

-continued
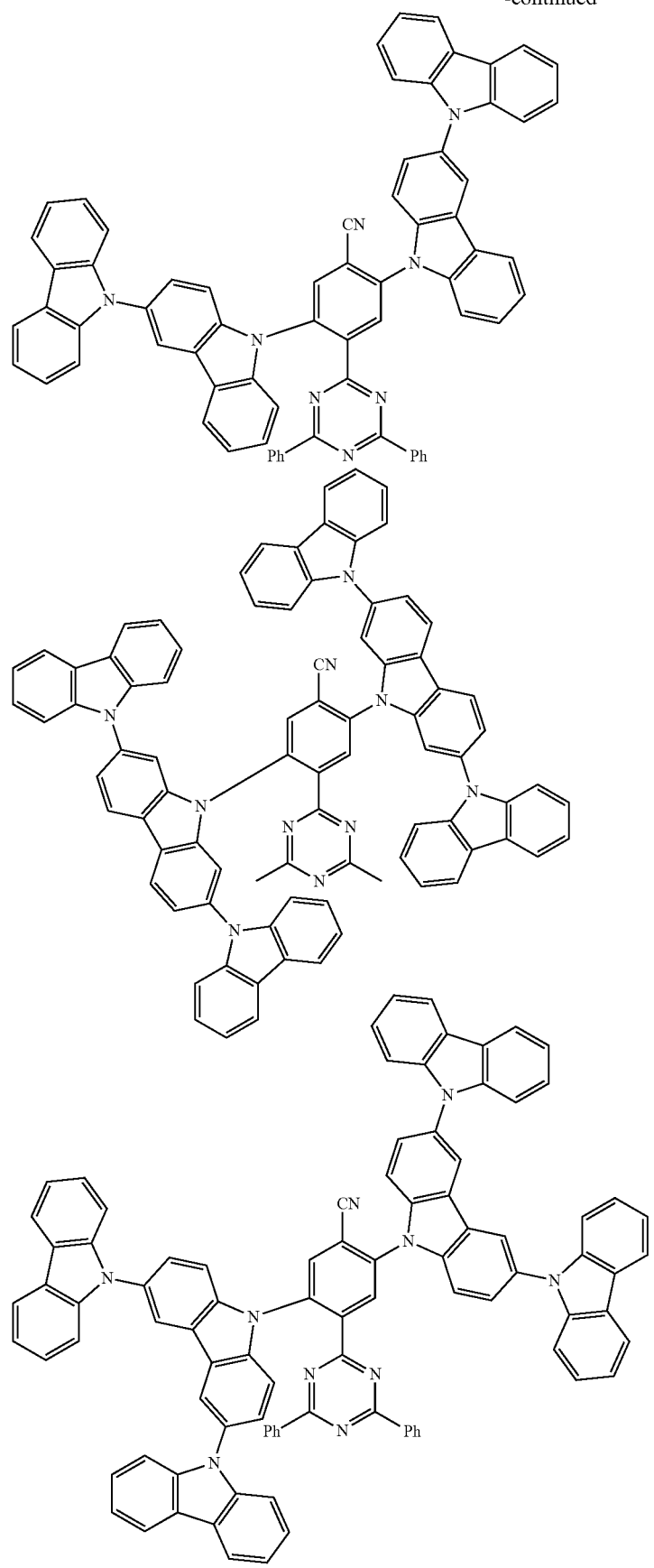

123
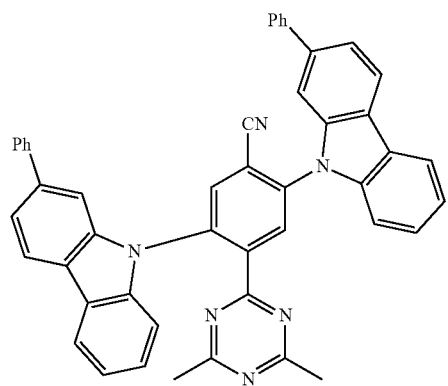
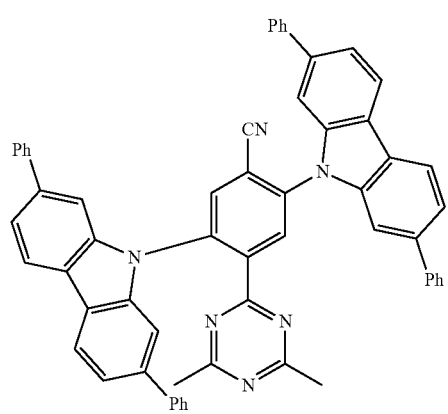
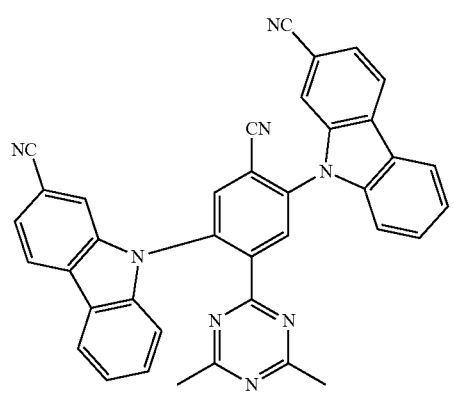
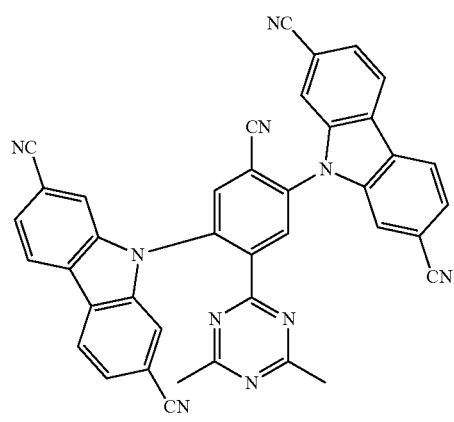
-continued
124
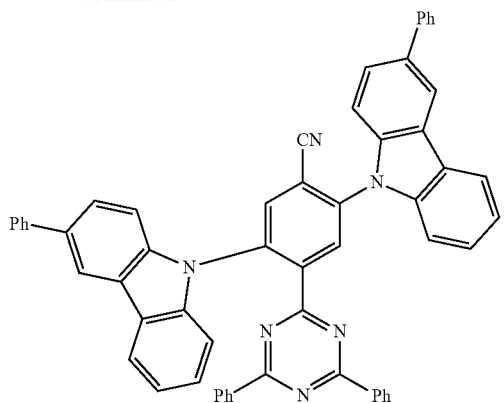
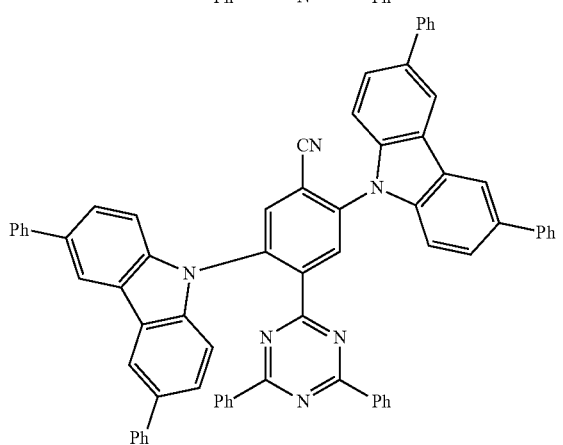
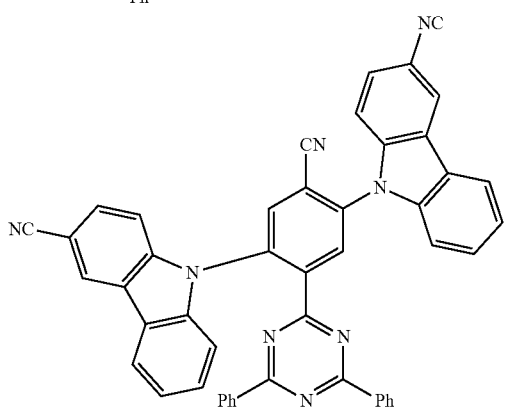
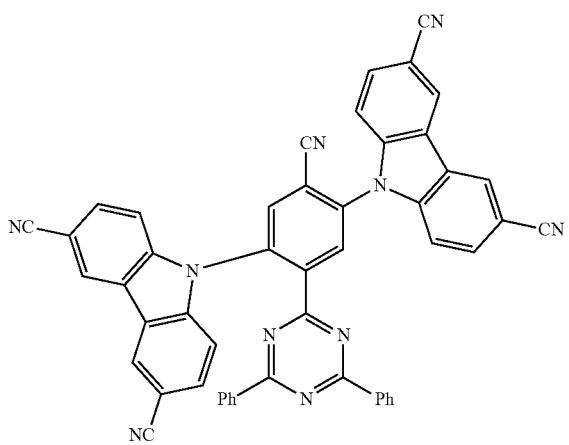

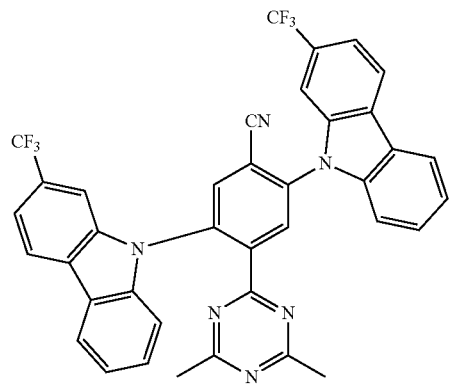
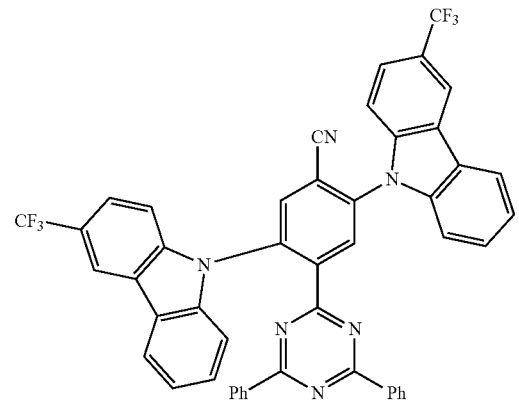
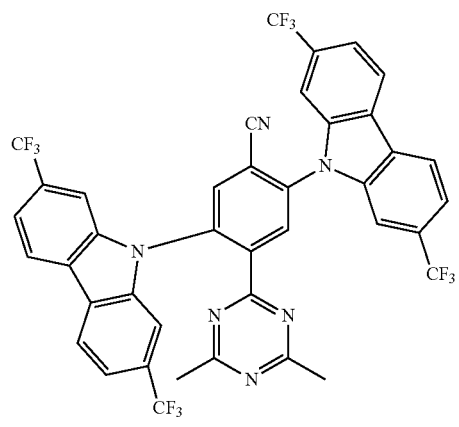
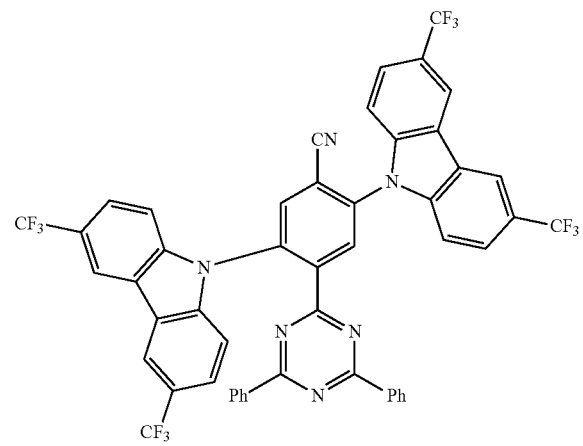
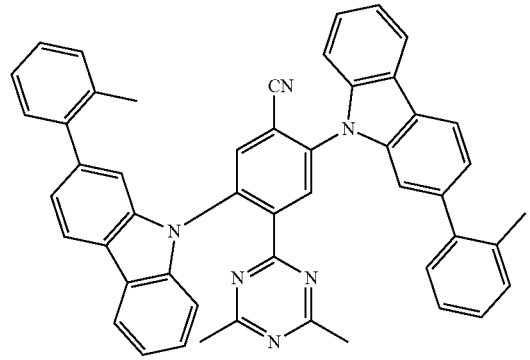
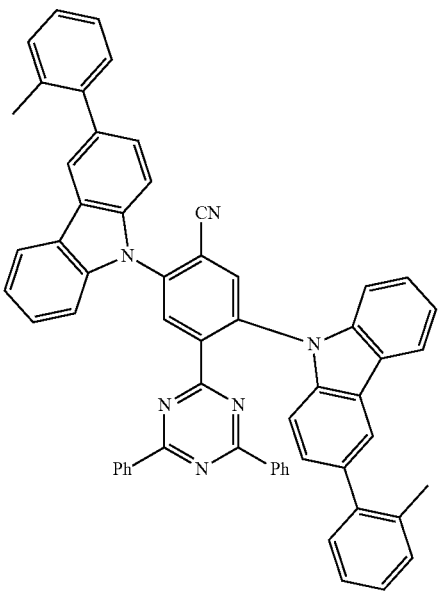

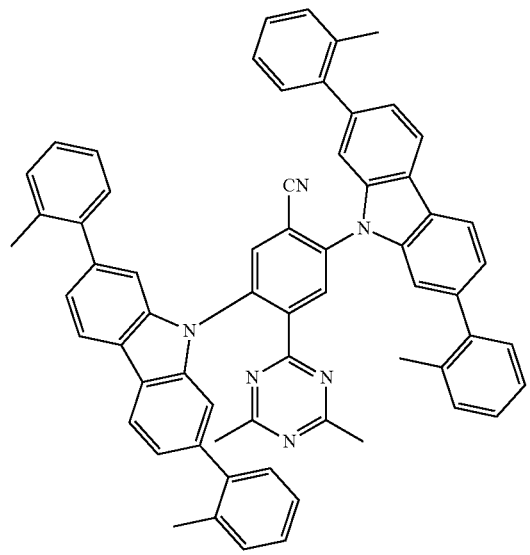
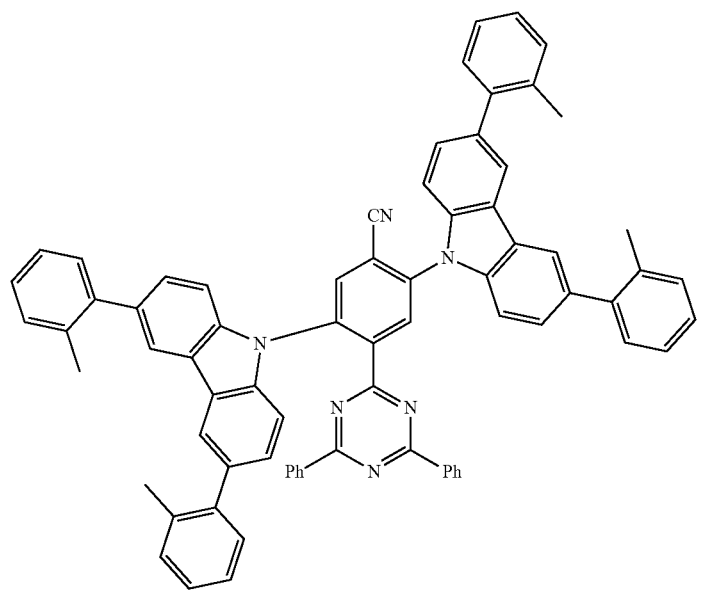
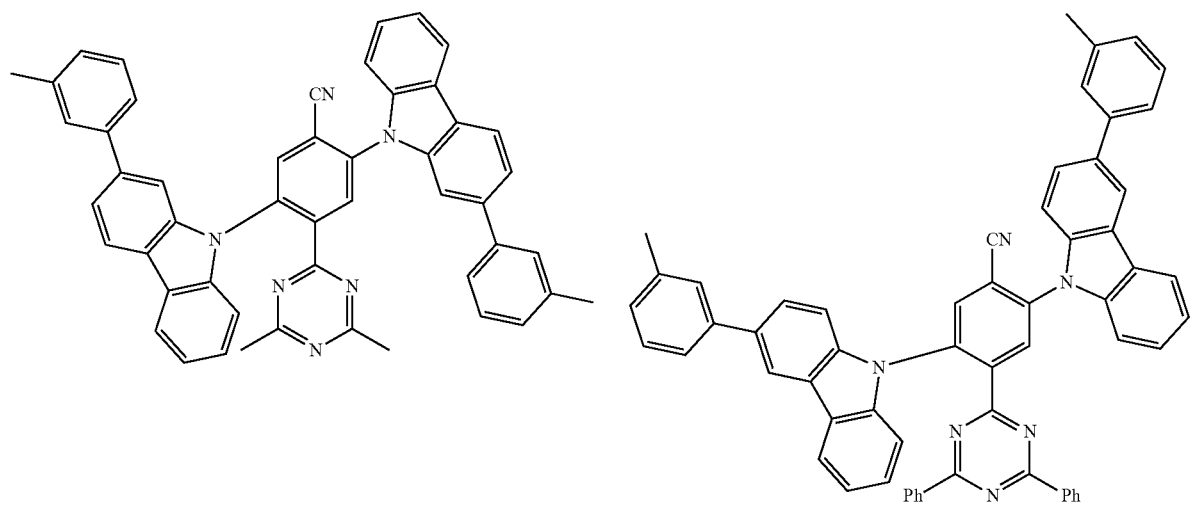

-continued
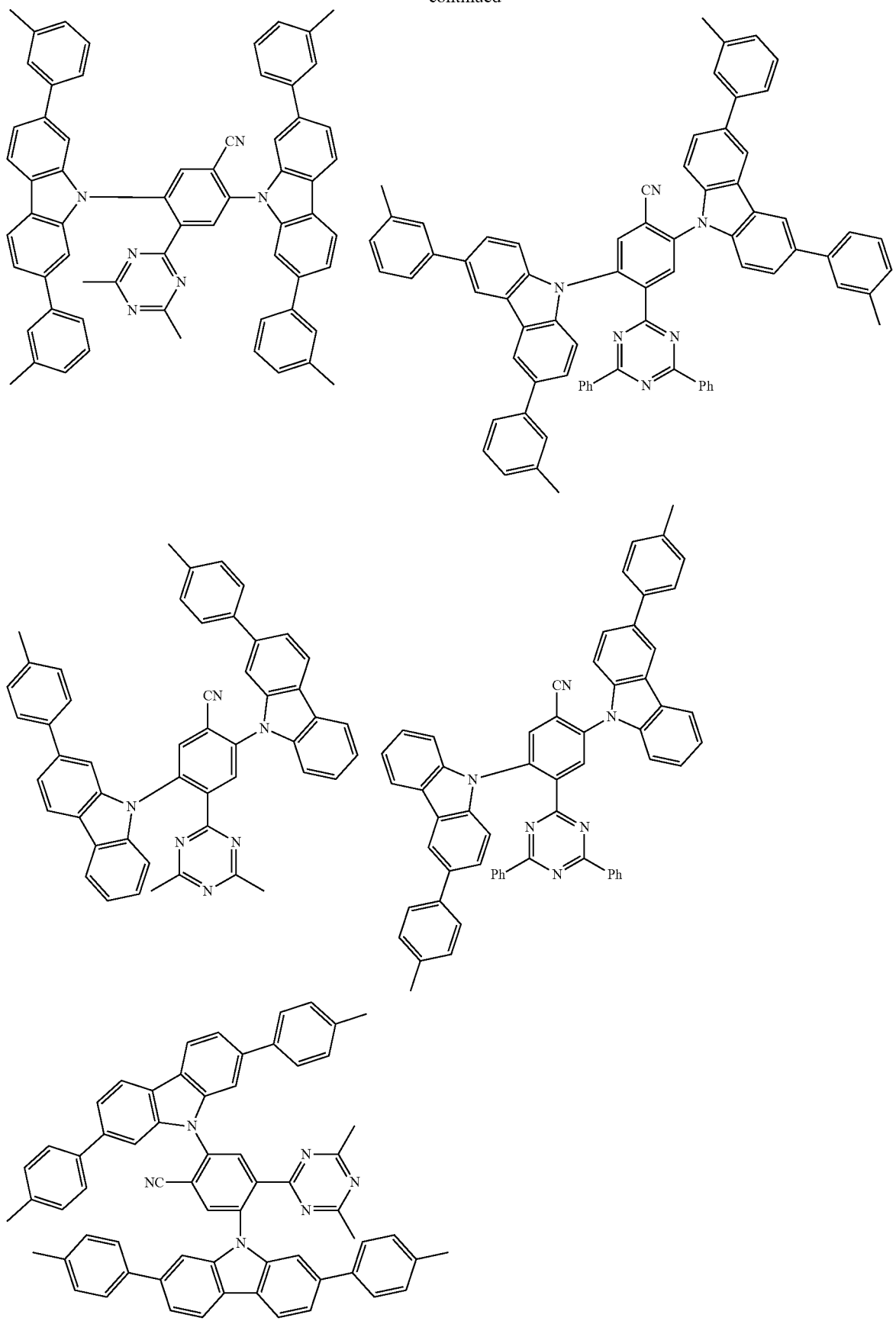

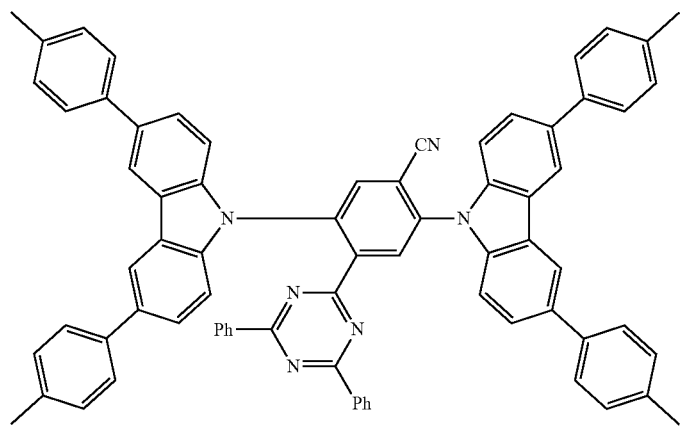
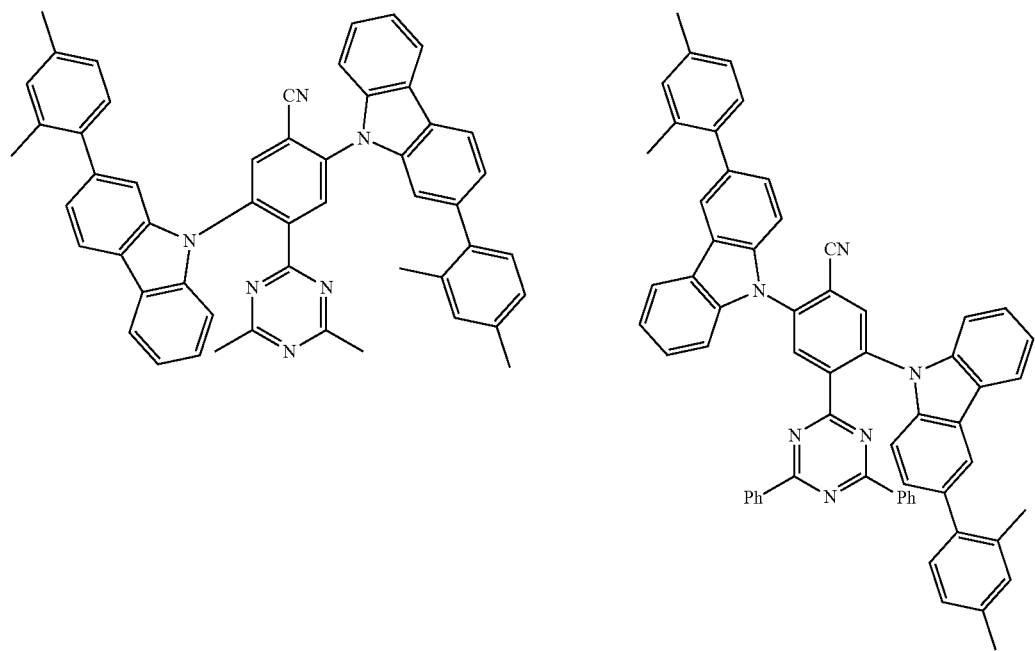
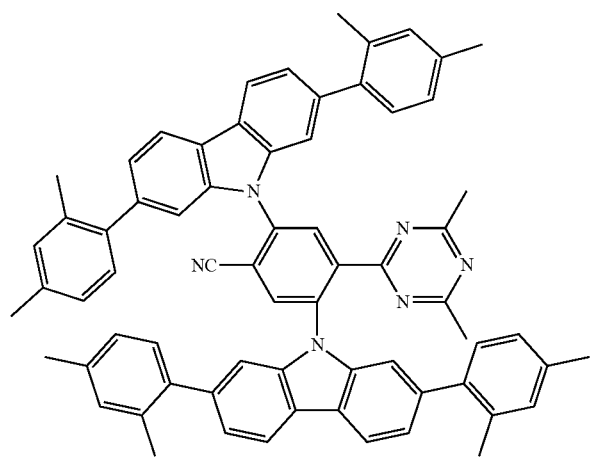

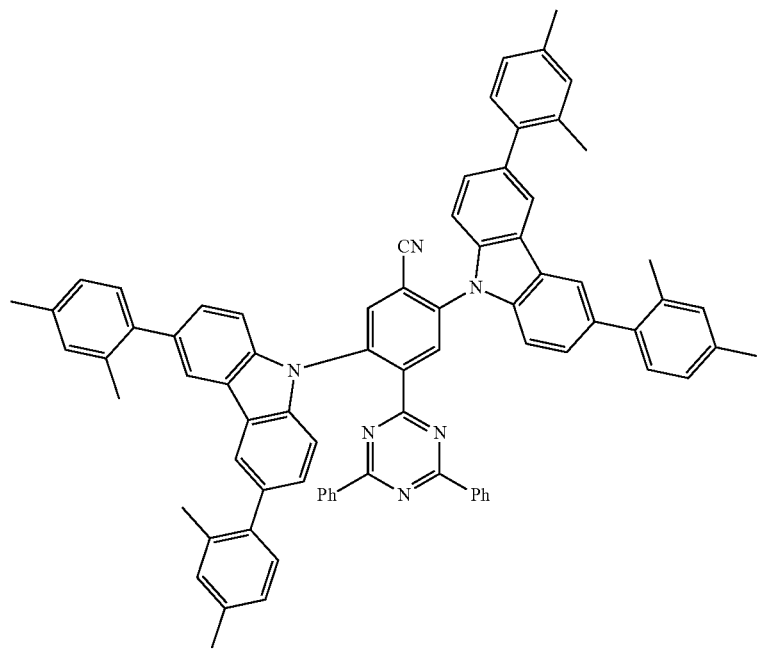
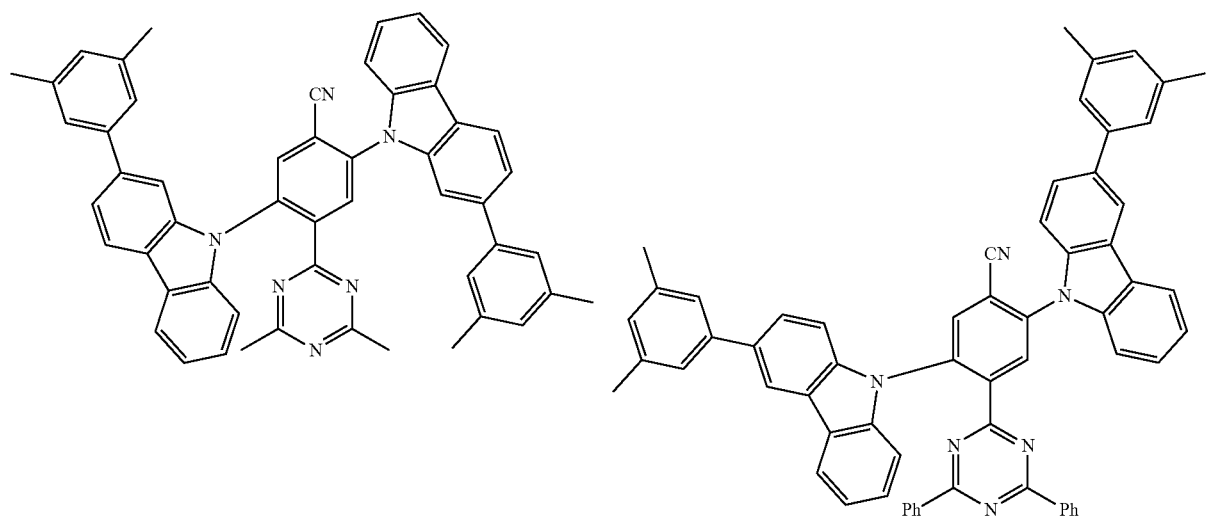
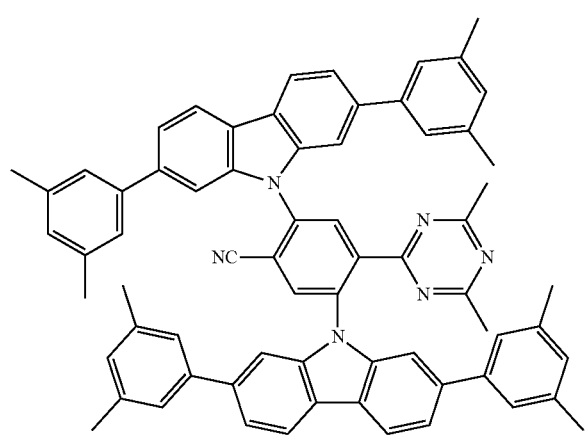

-continued
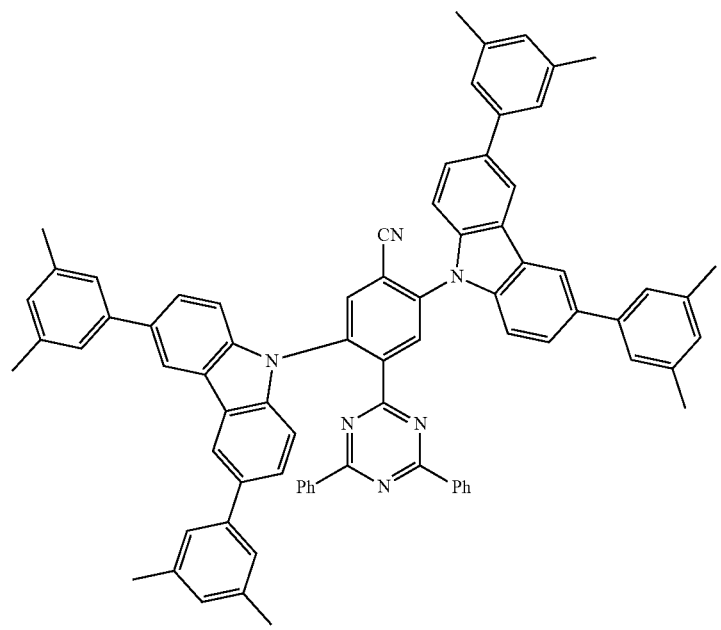
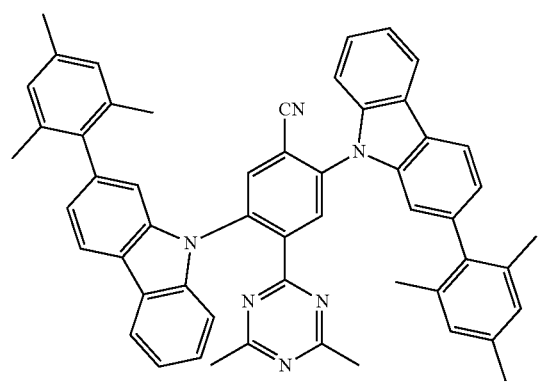
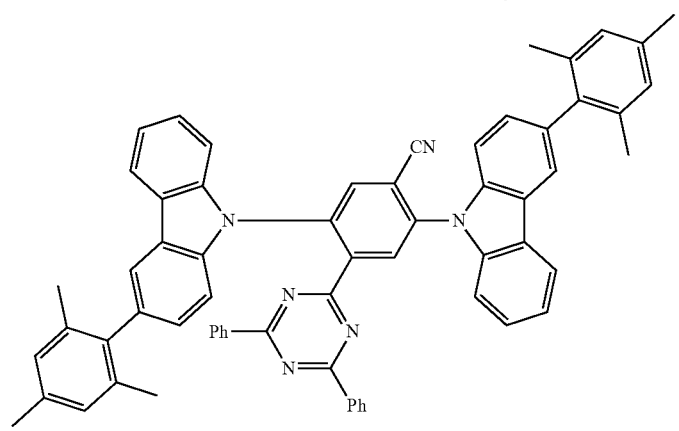
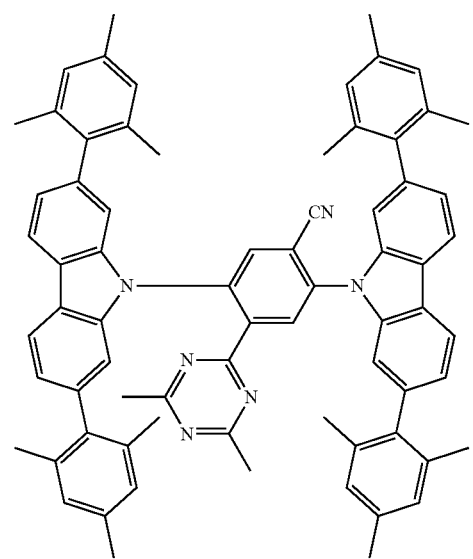

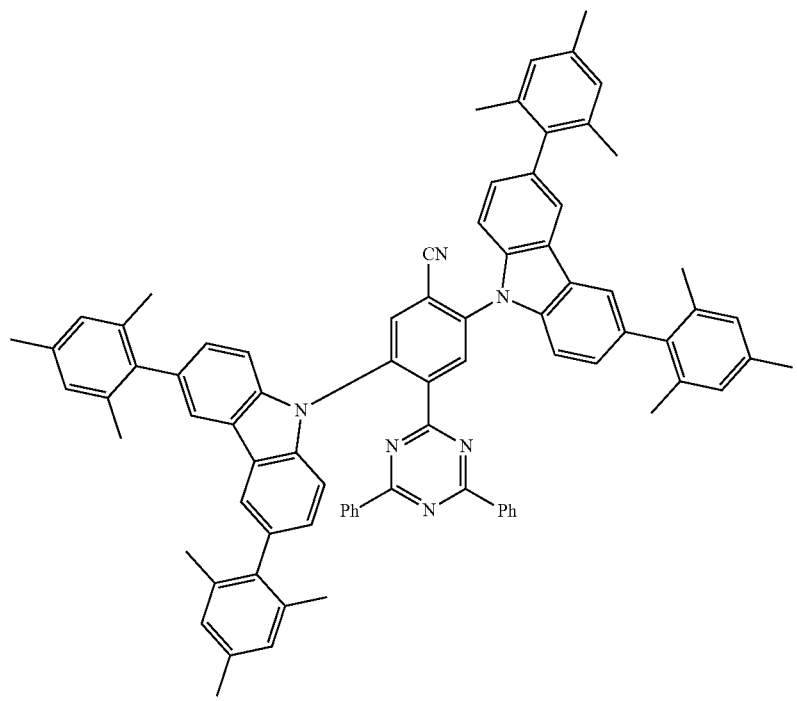
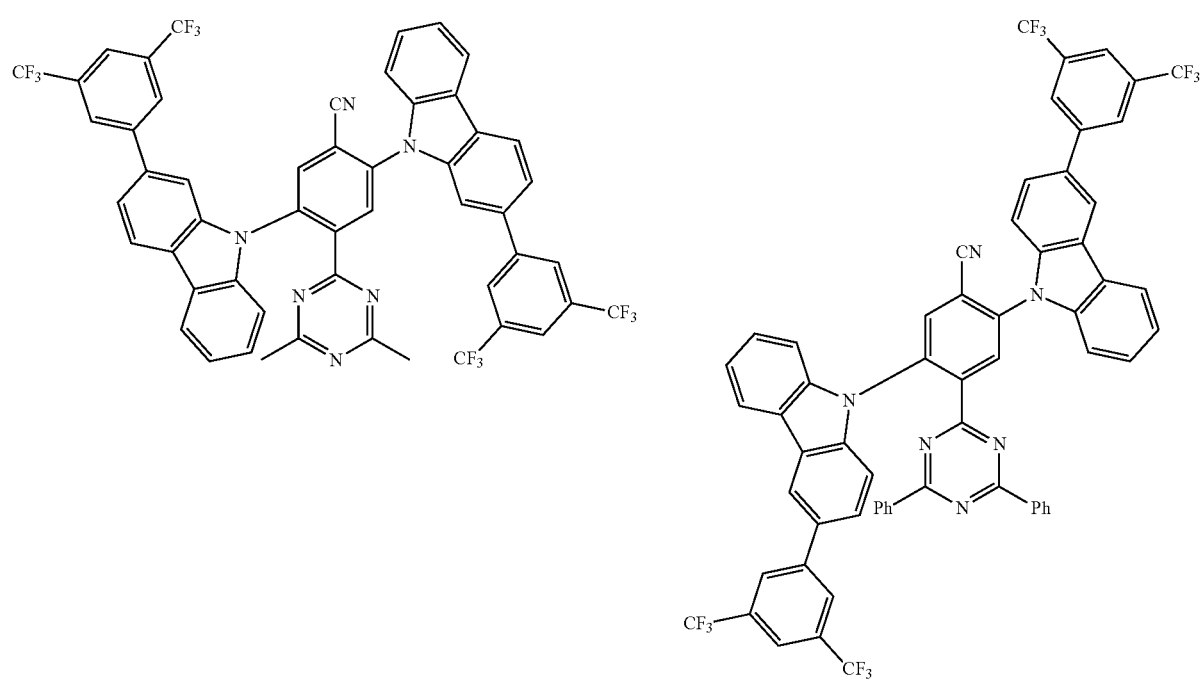

-continued
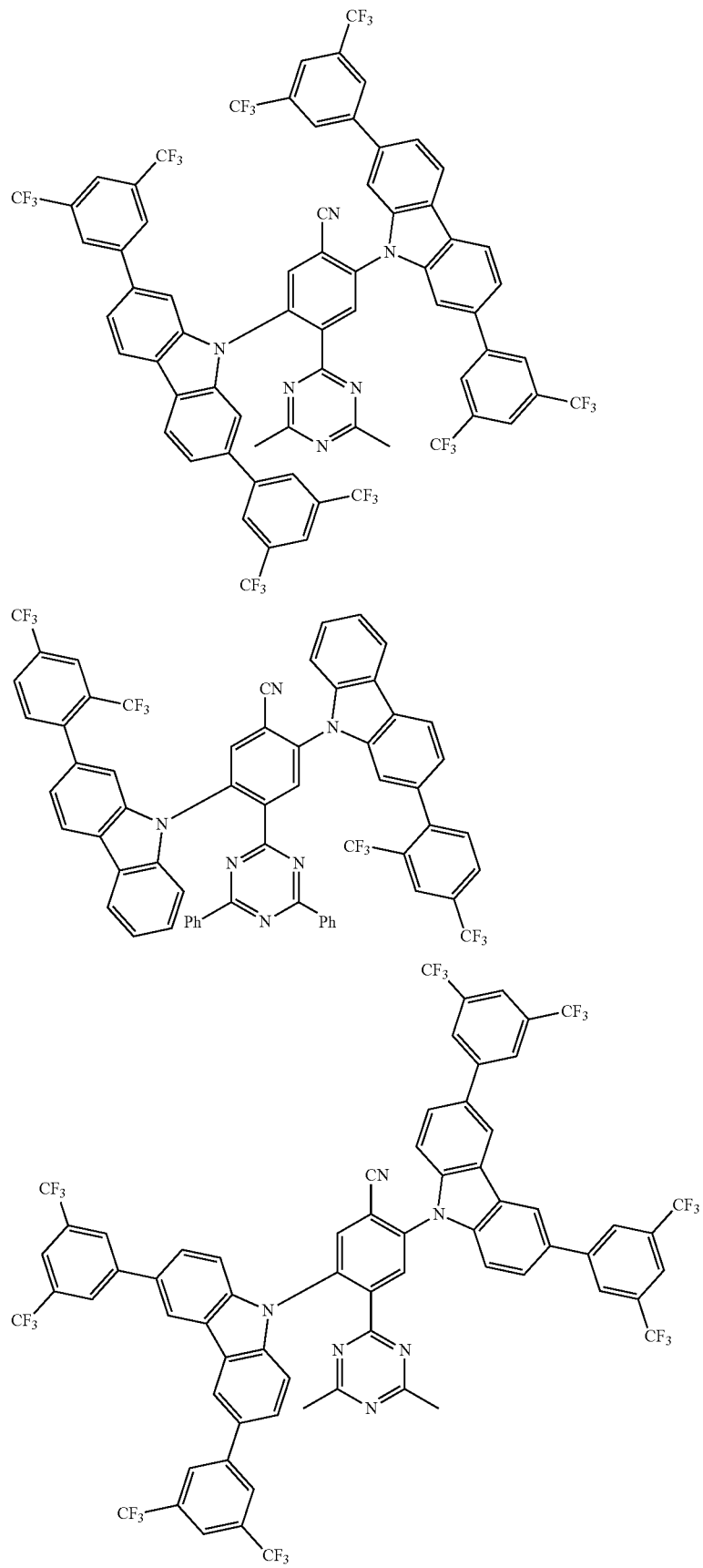

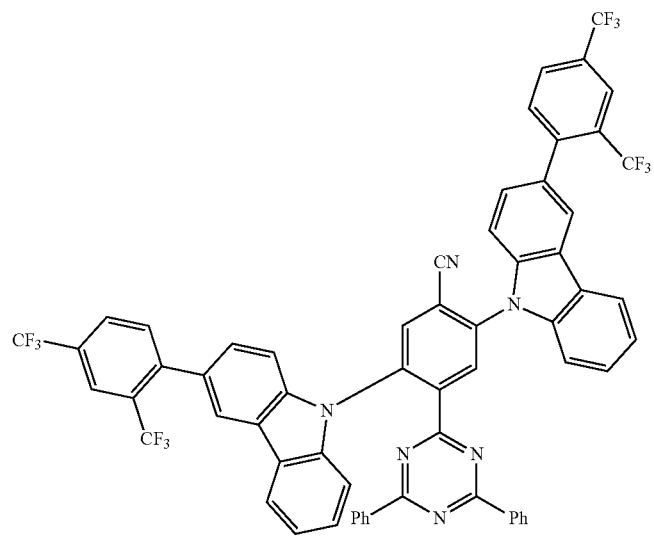
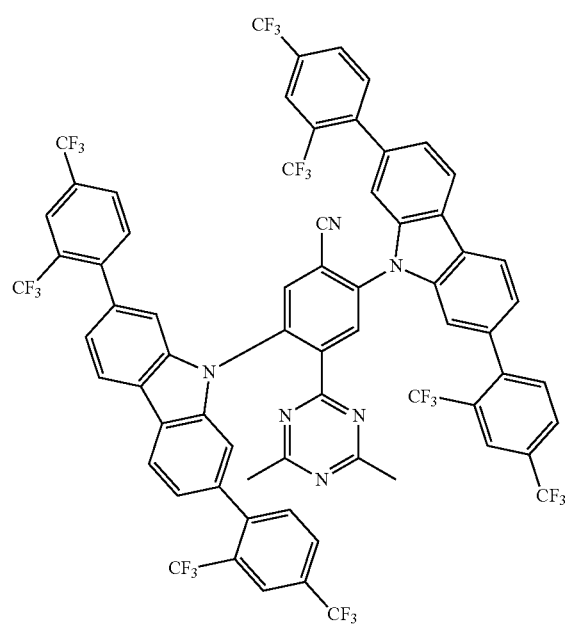
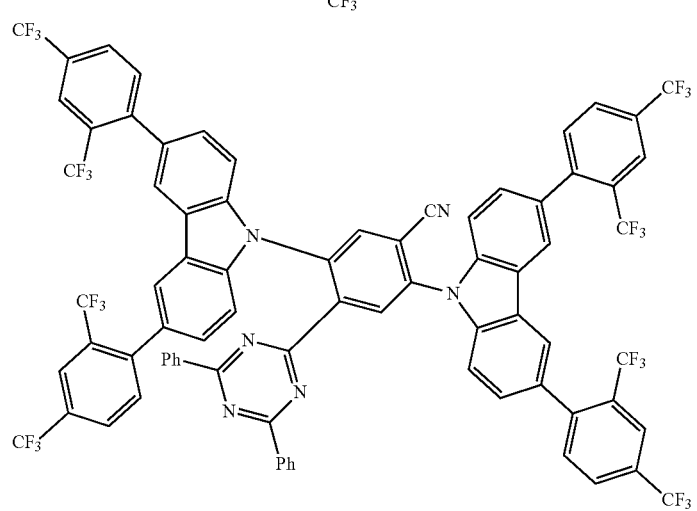

-continued
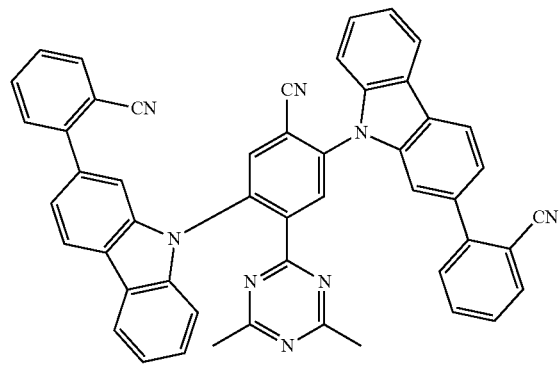
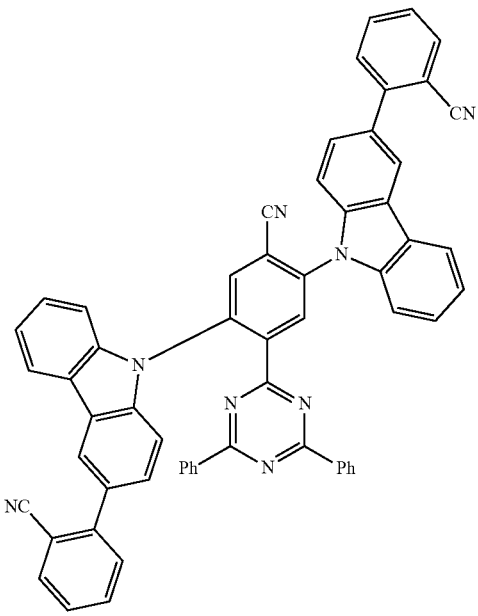
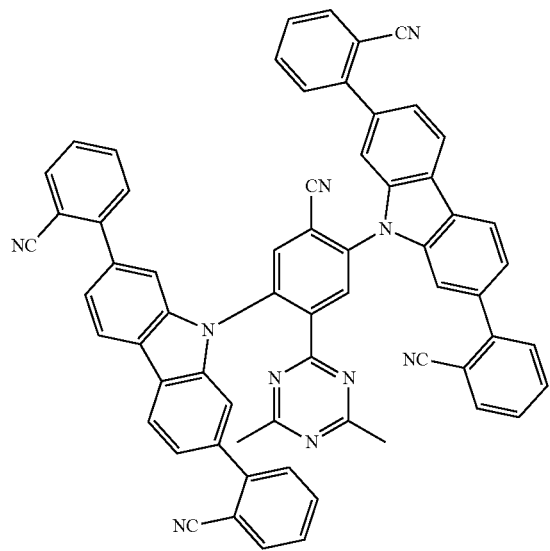
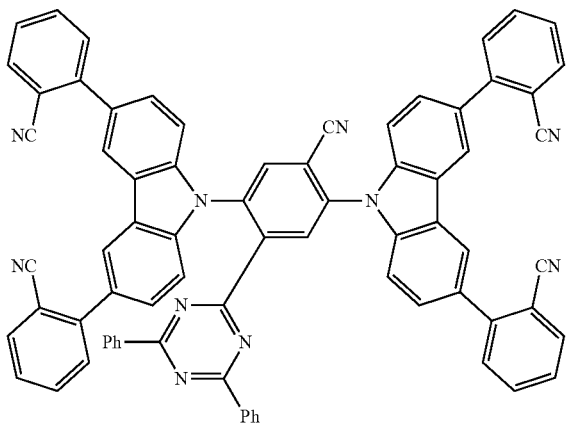

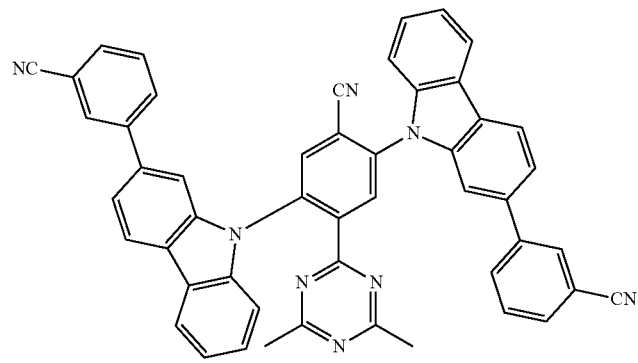
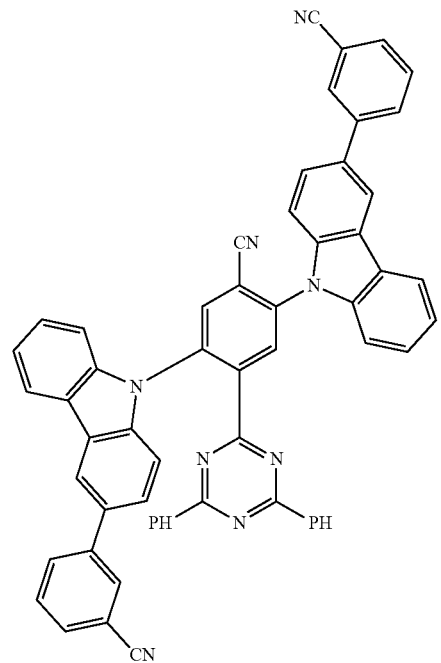
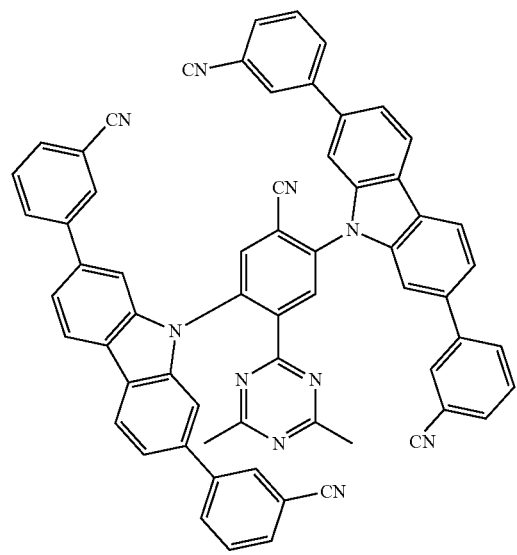
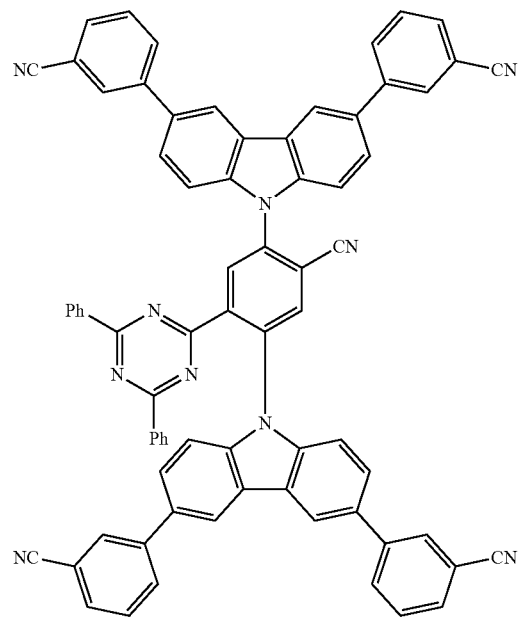

147
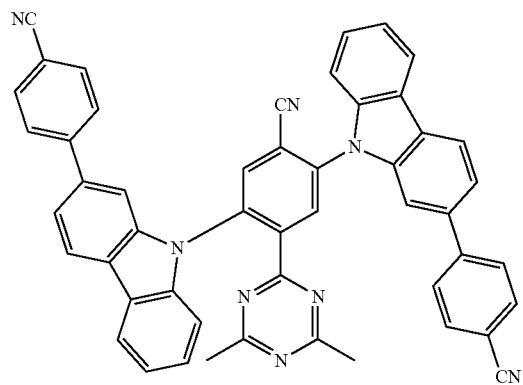
148
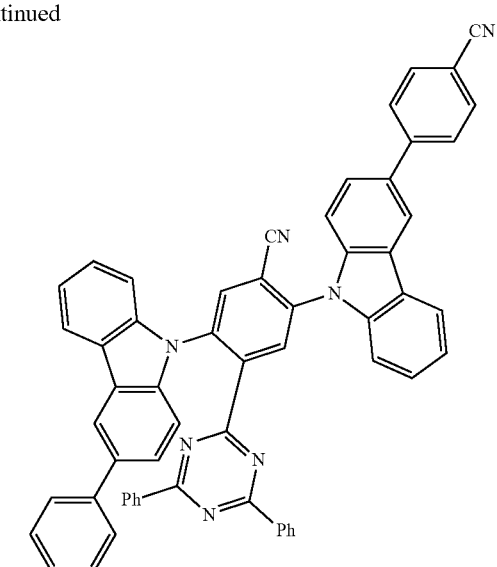
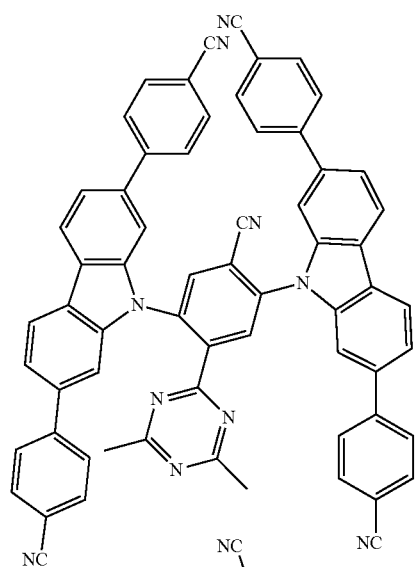
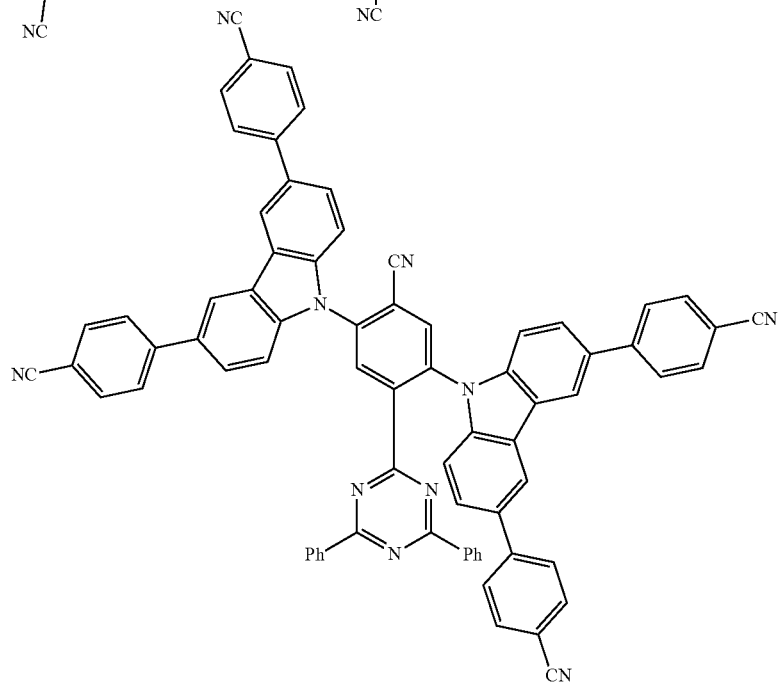

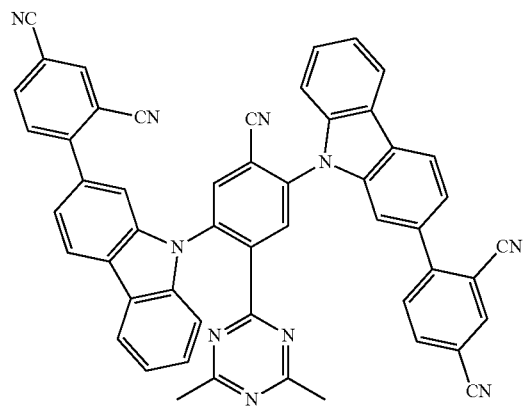
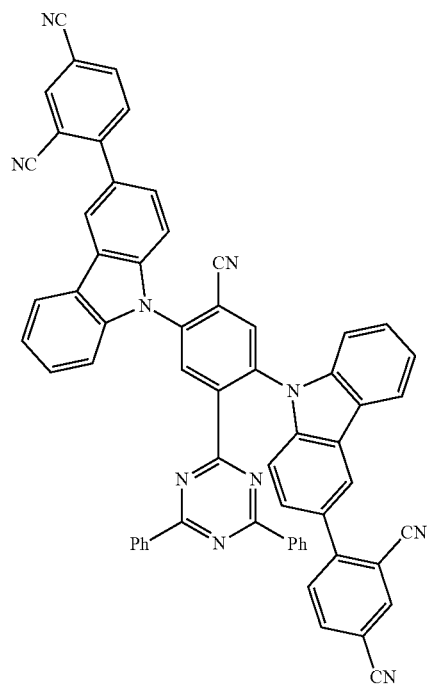
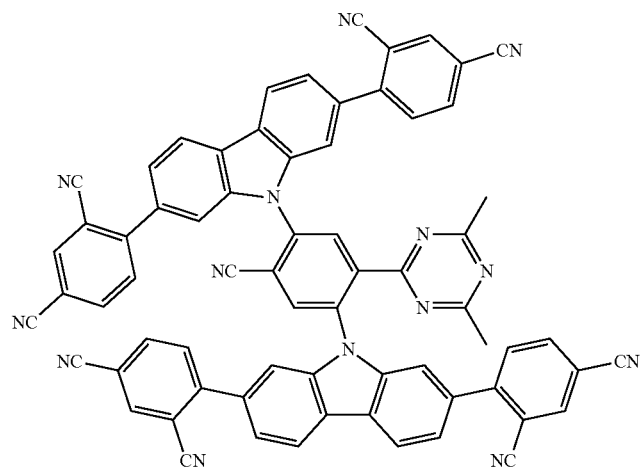
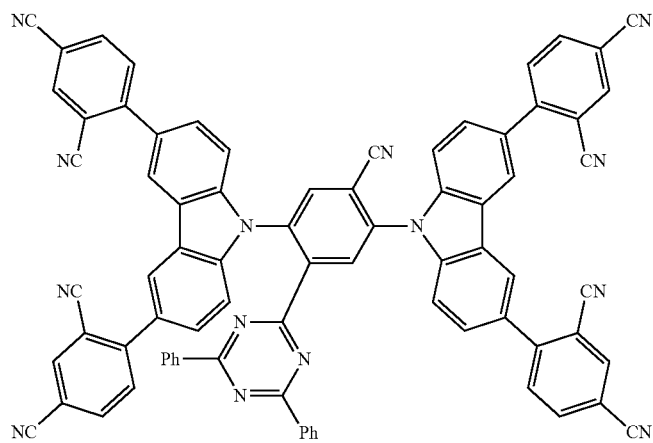

-continued
151
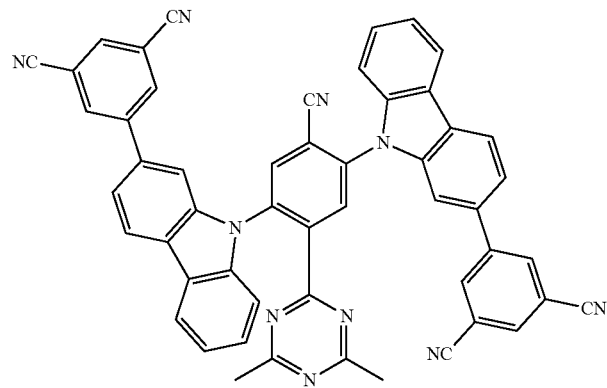
152
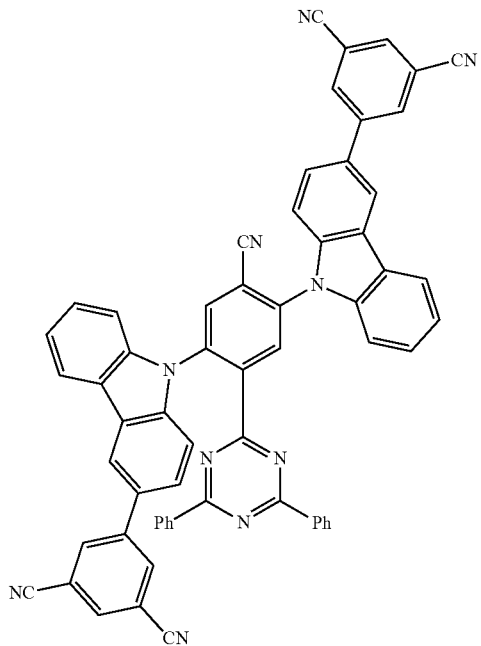
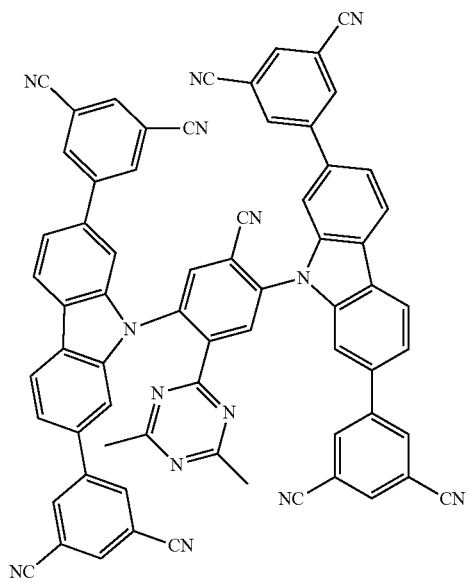
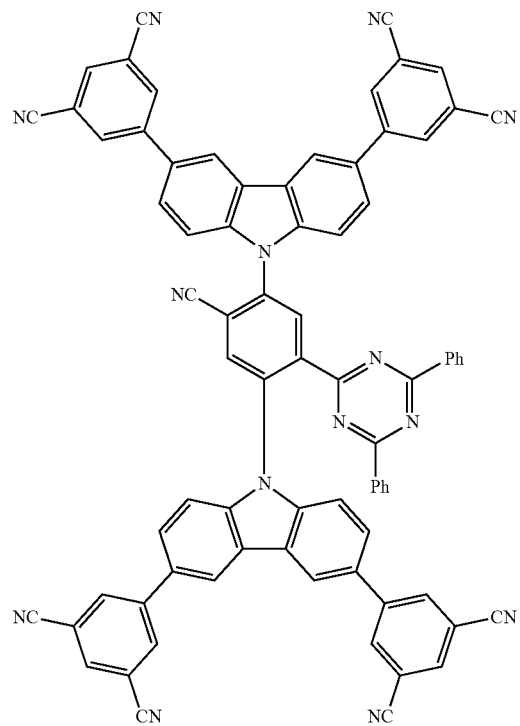

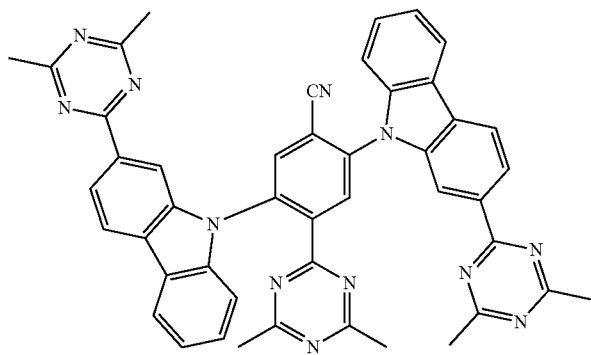
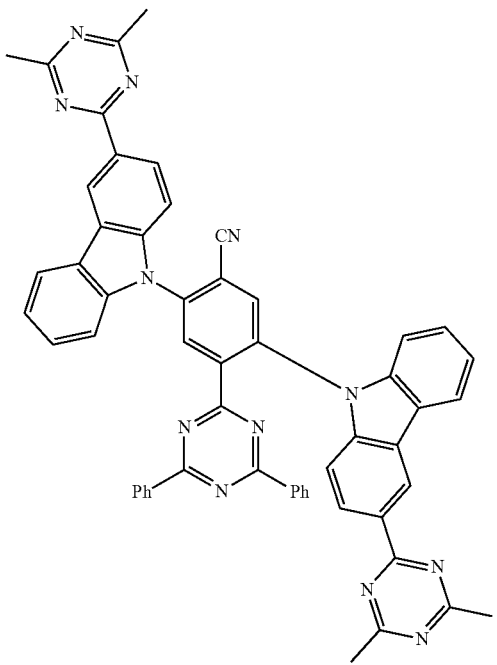
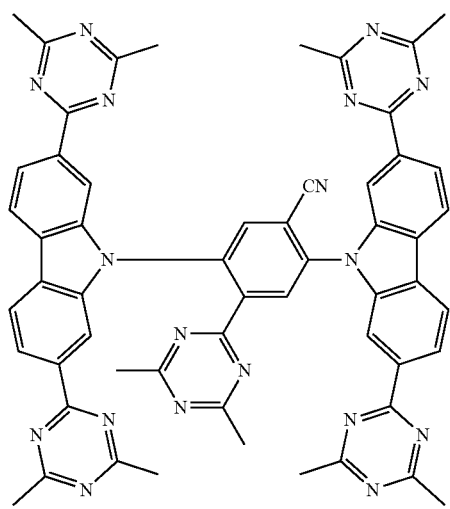
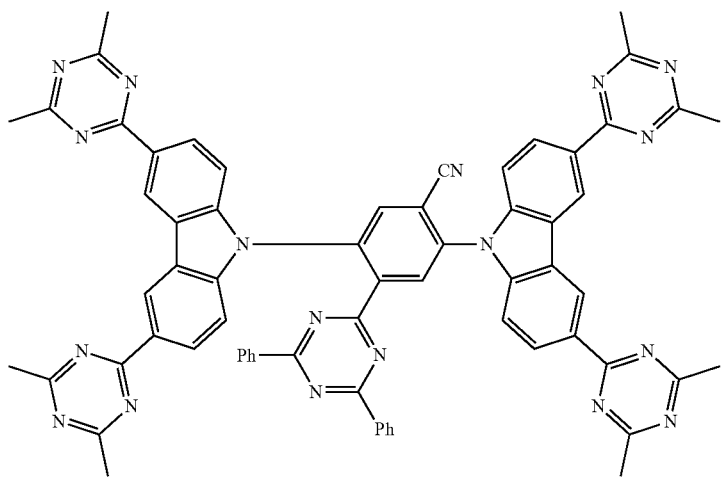

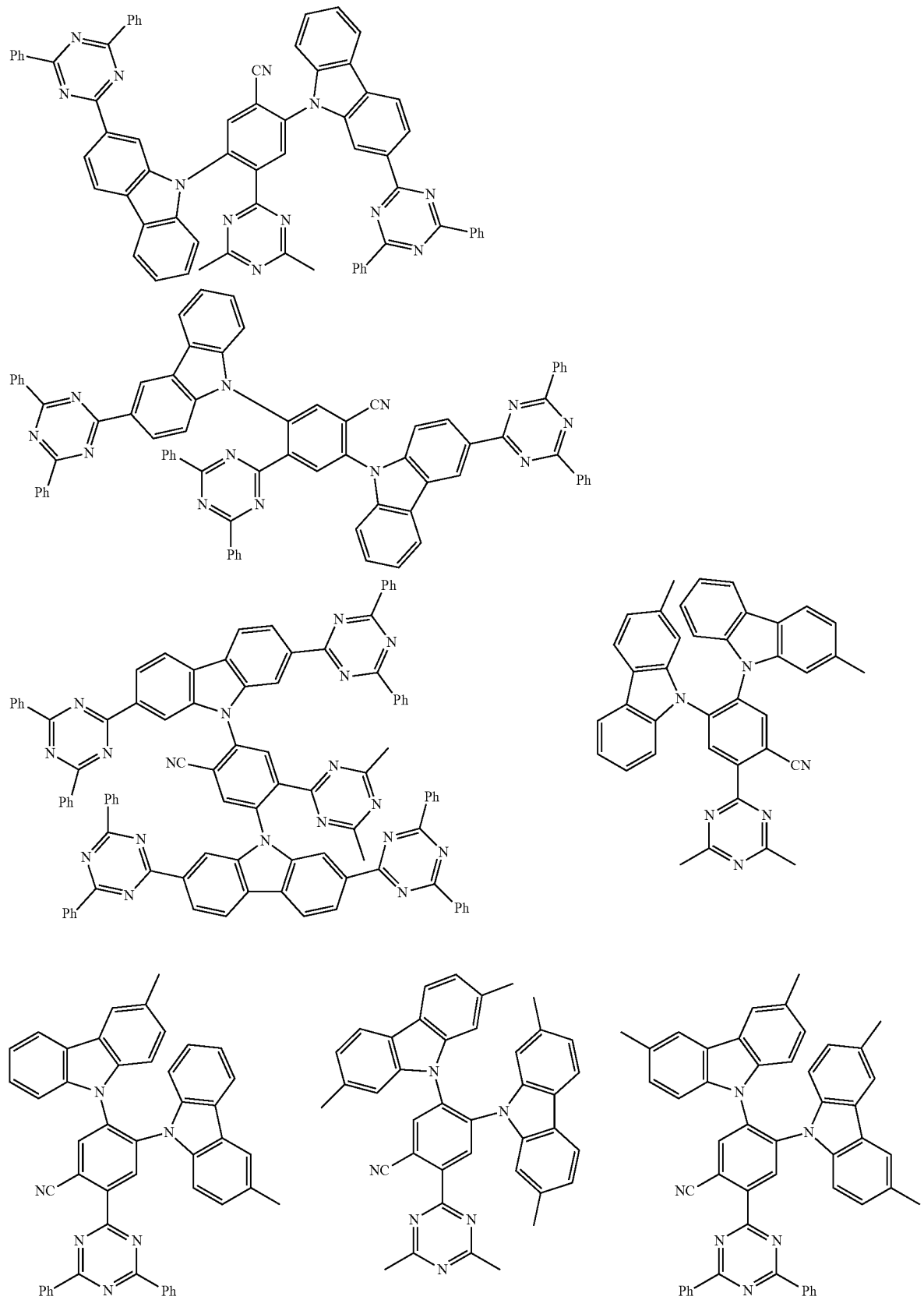

-continued
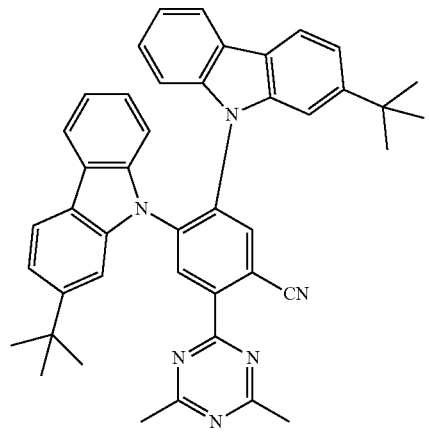
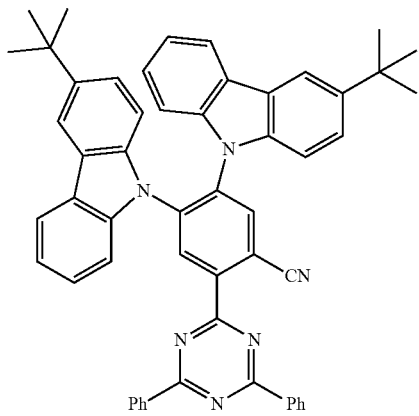
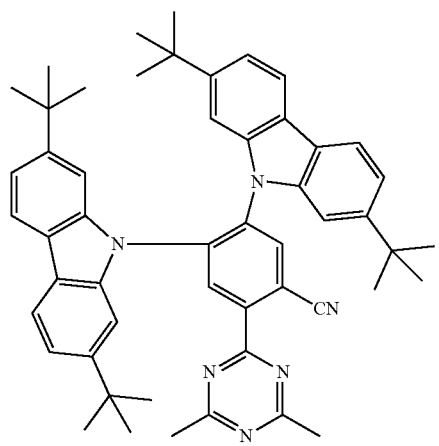
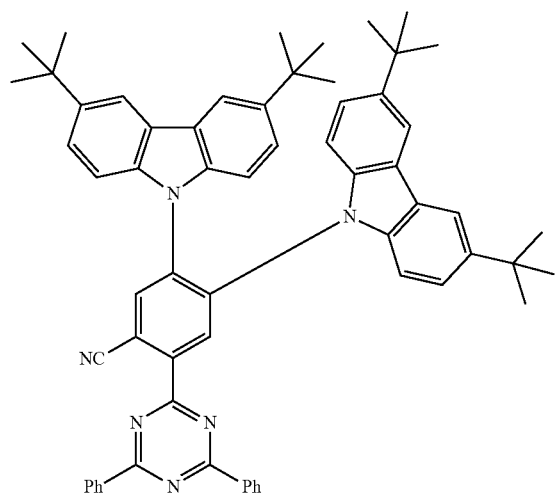
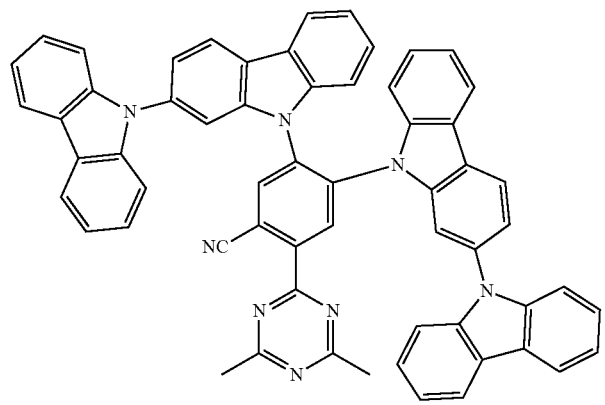
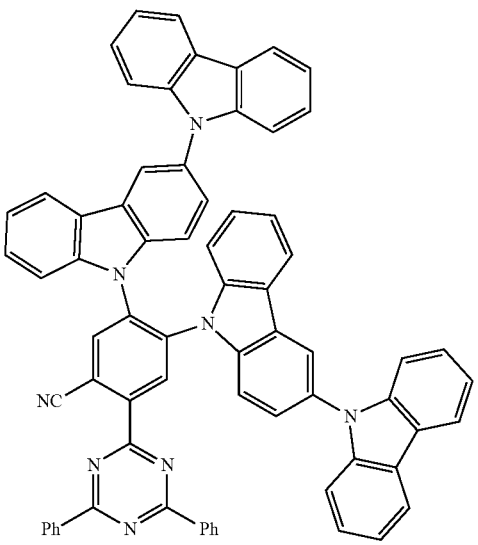

-continued
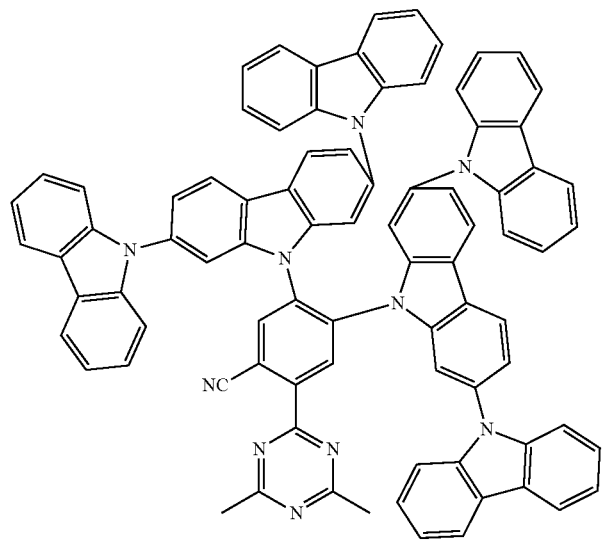
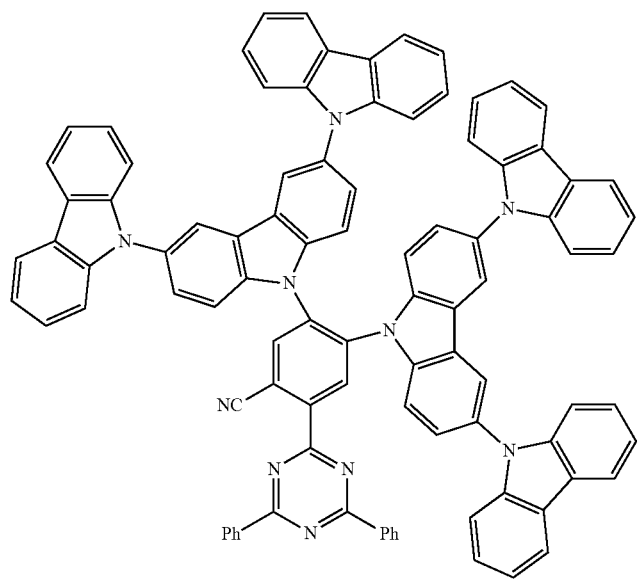
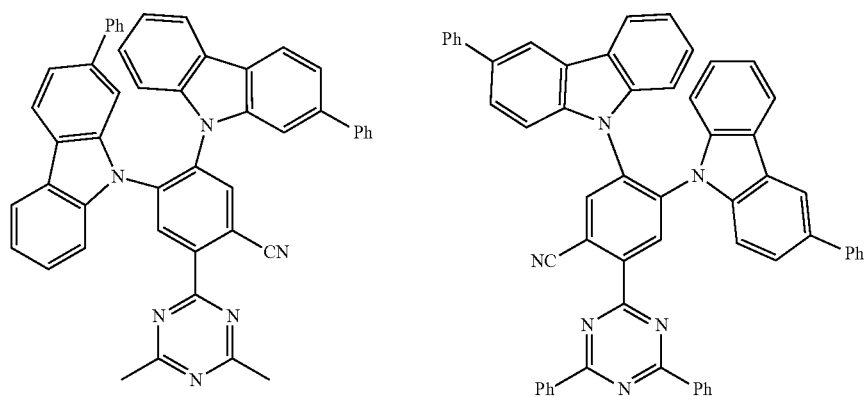

-continued
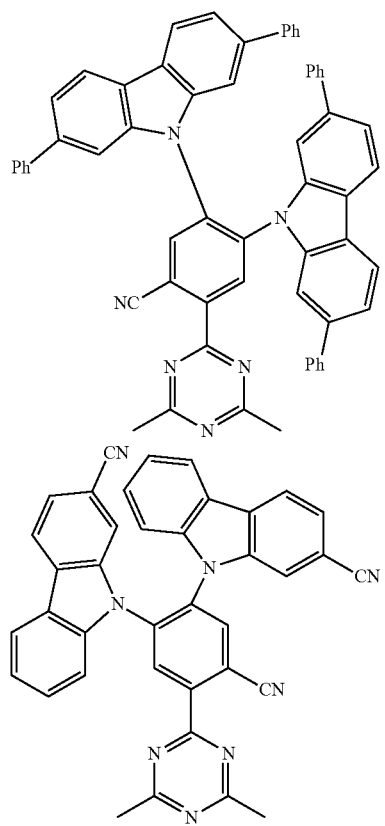
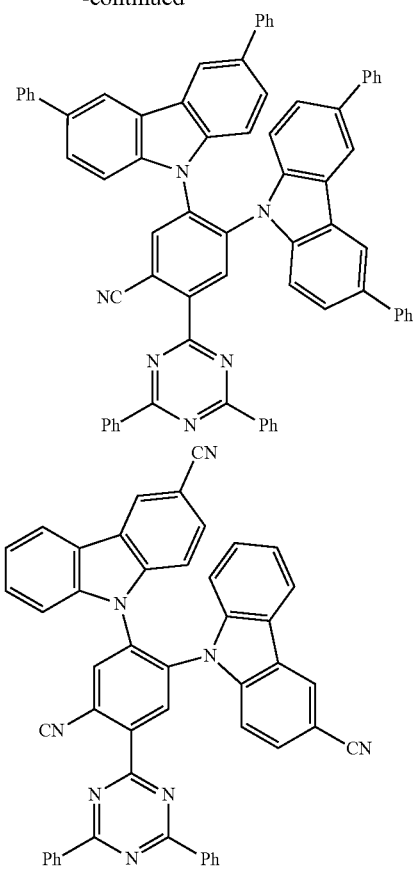
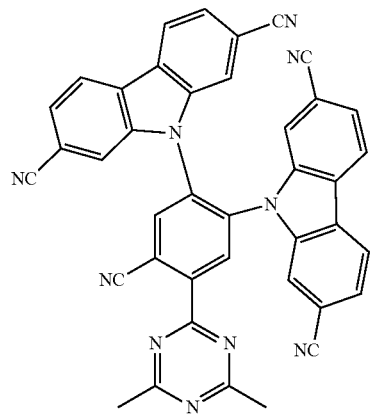
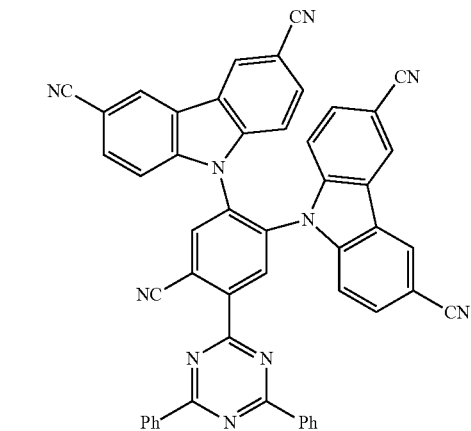
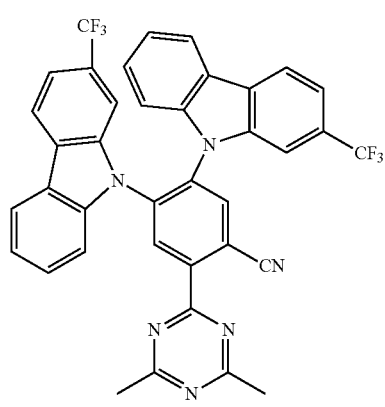
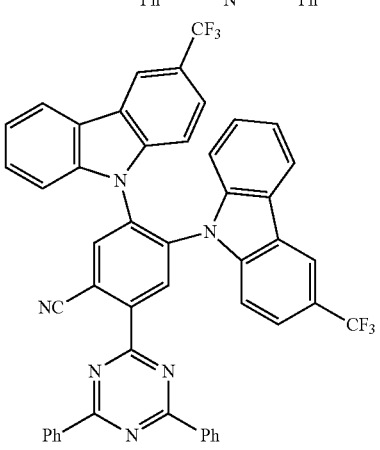

-continued
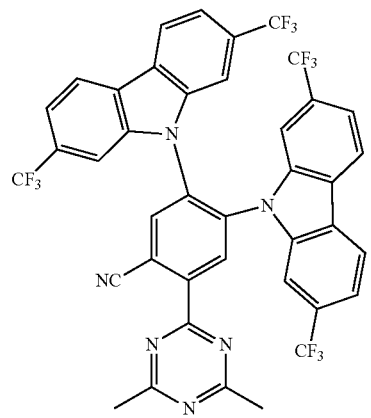
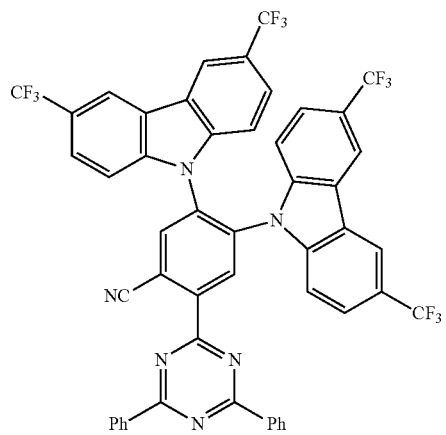
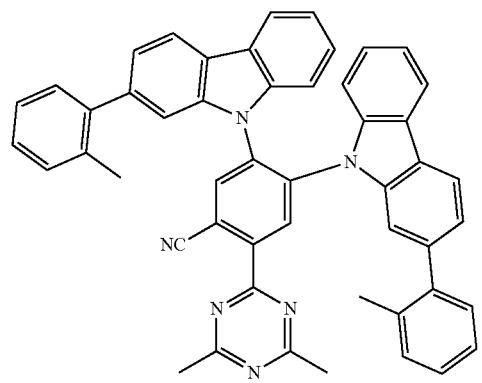
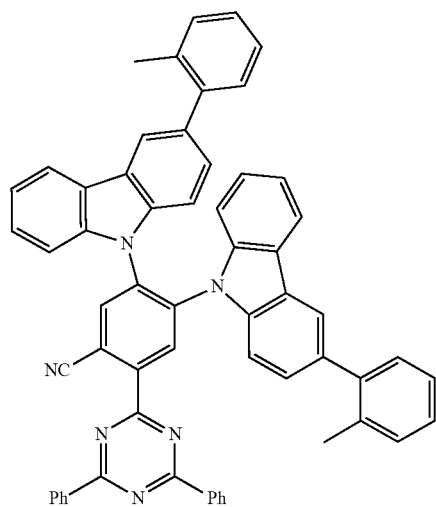
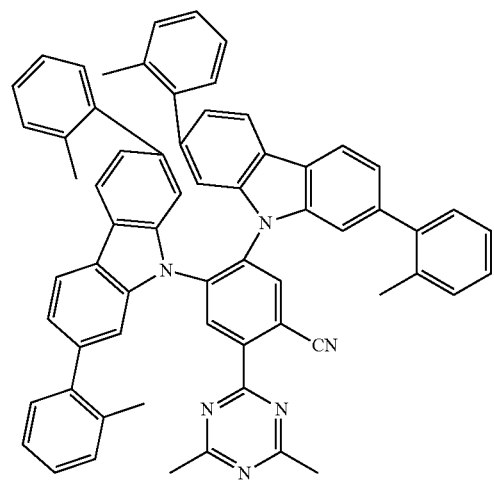
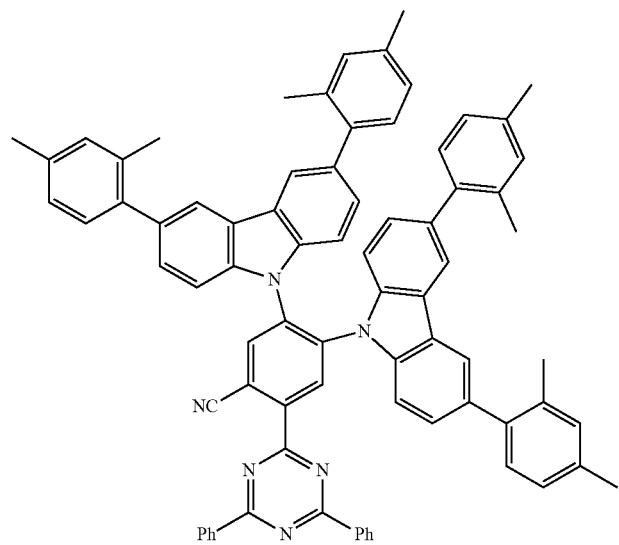

-continued
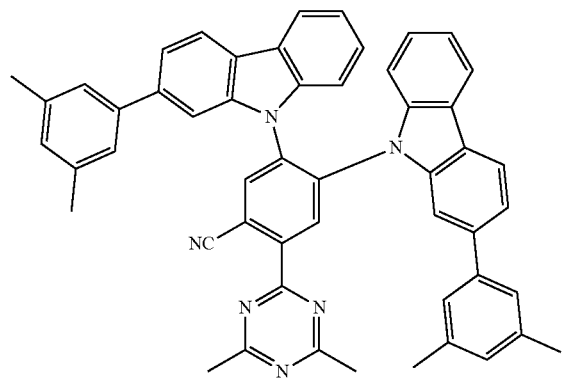
165
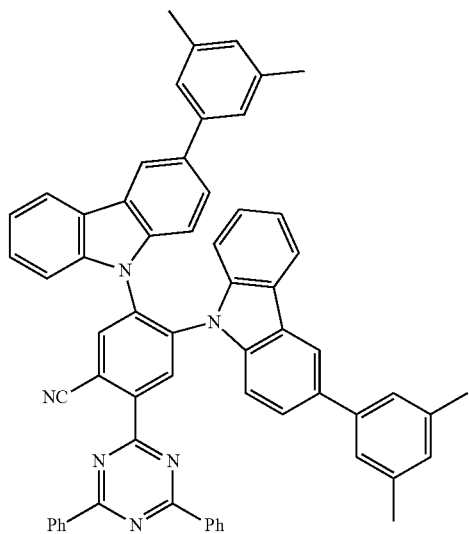
166
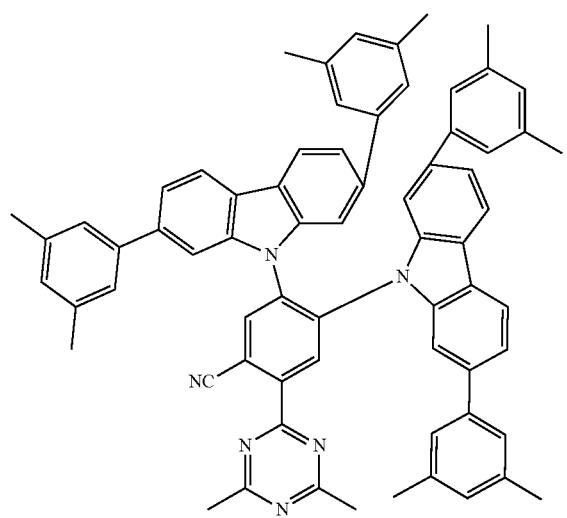
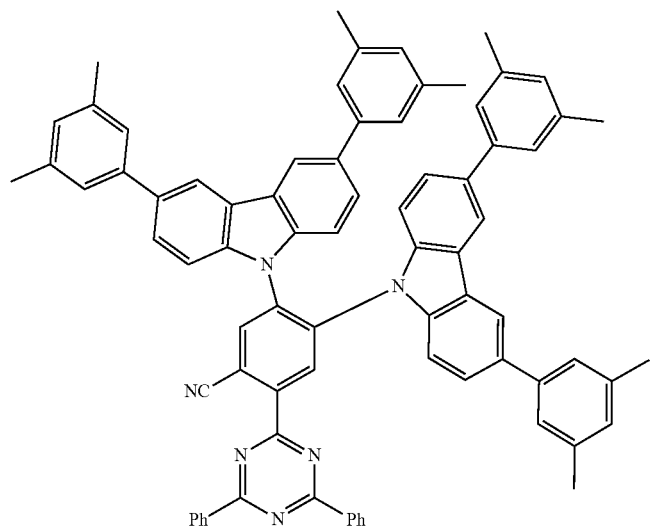

167
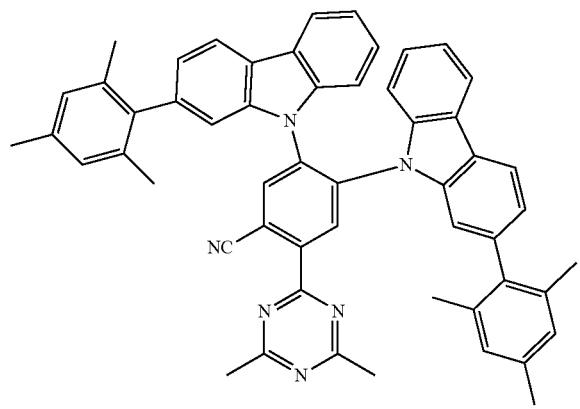
168
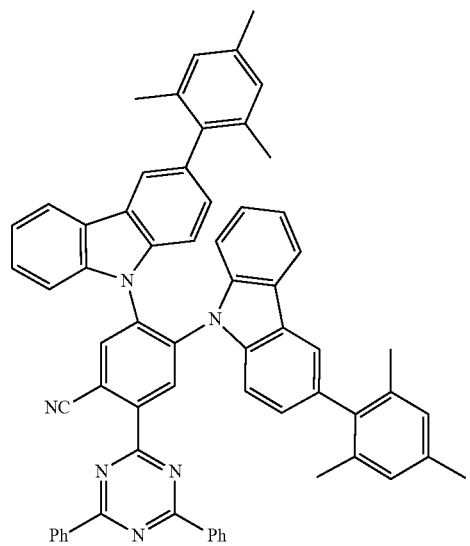
-continued
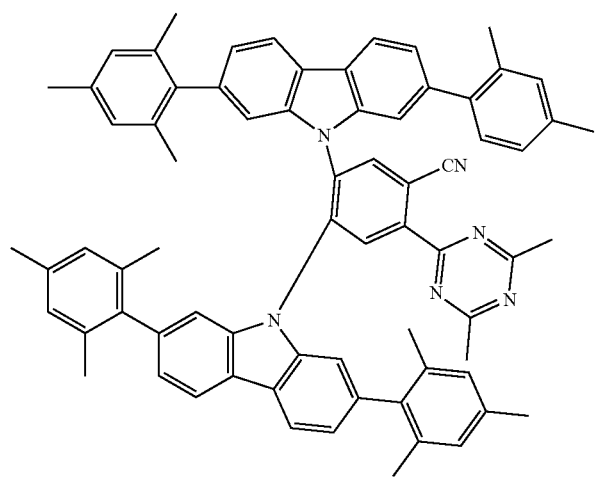
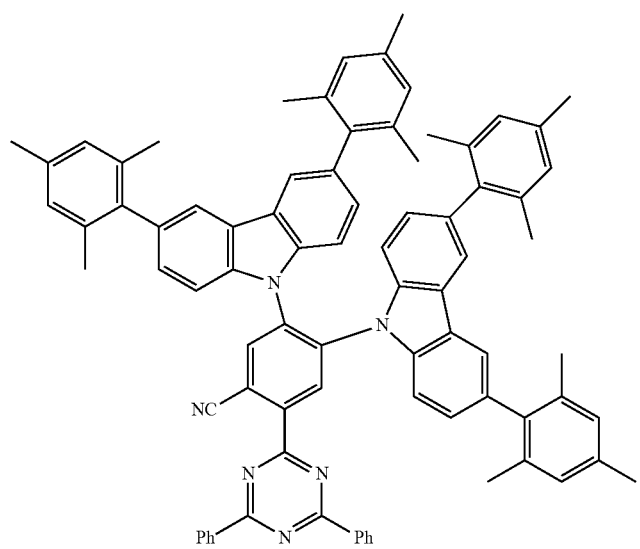

-continued
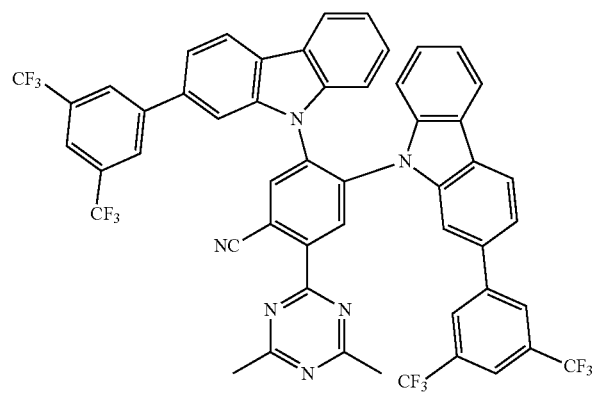
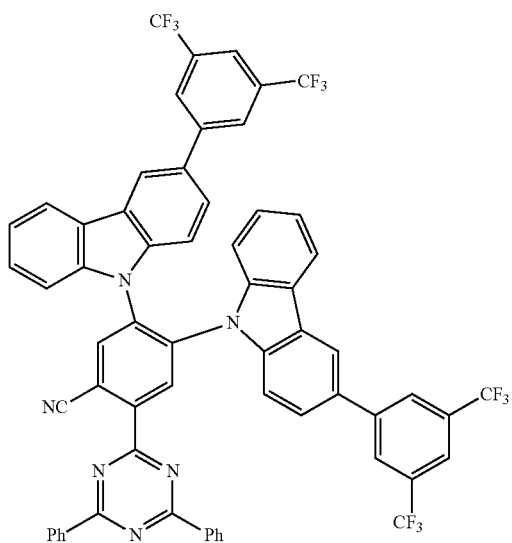
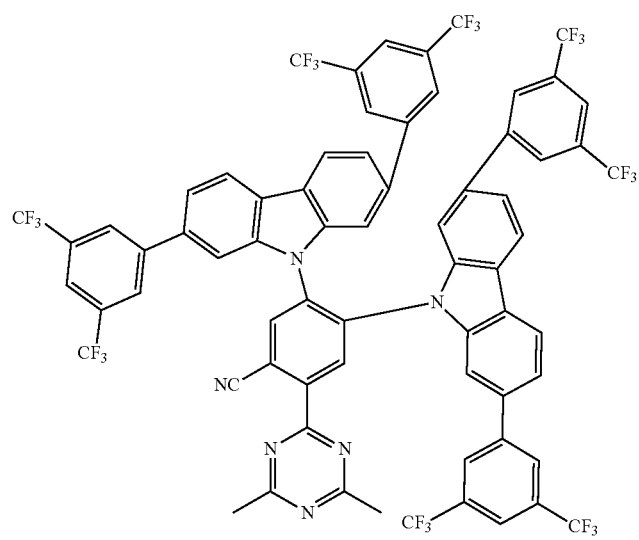
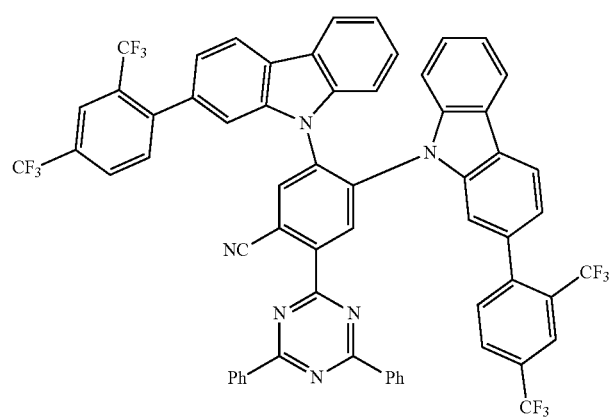

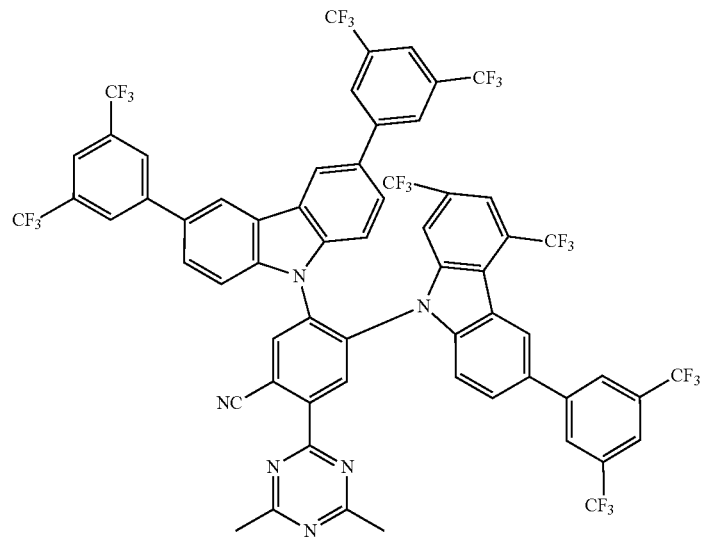
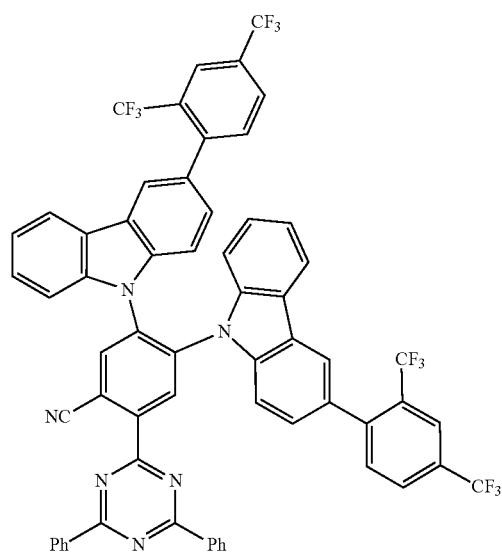
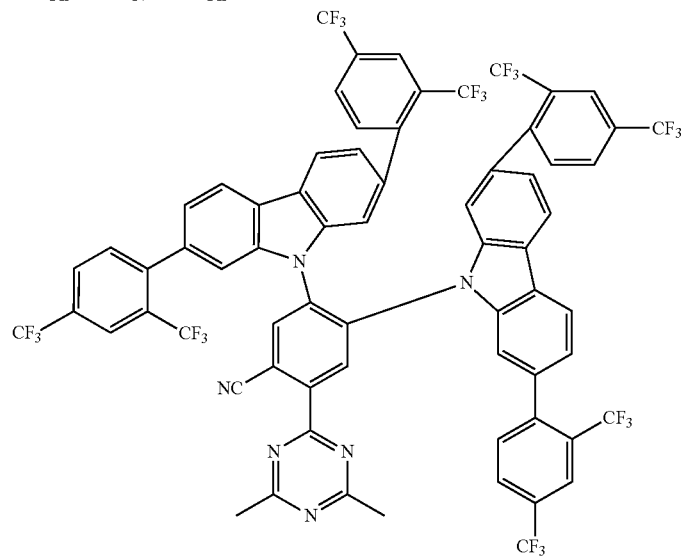

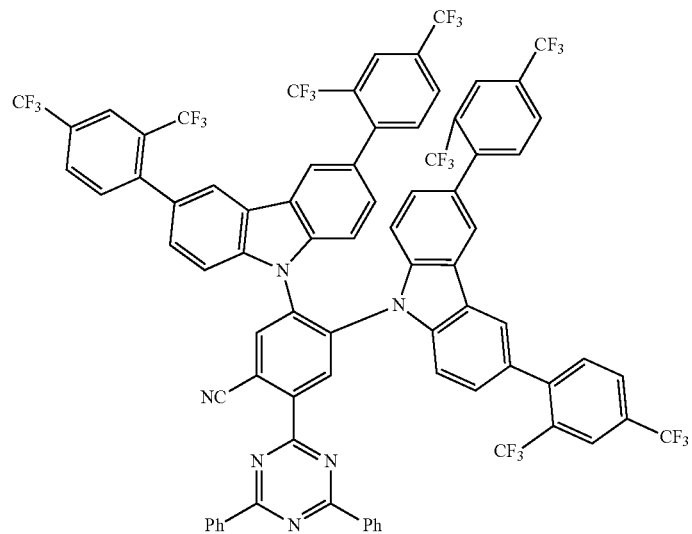
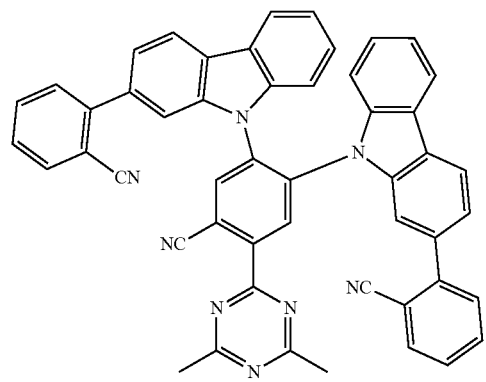
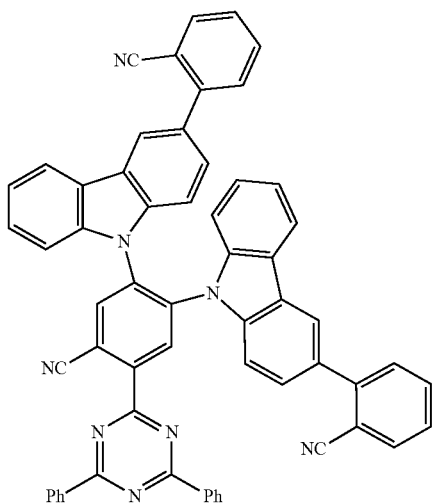
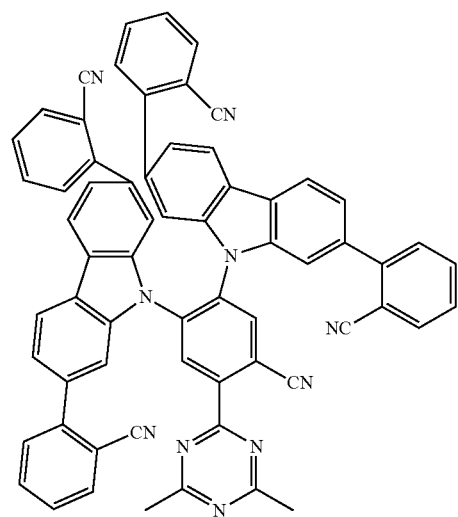
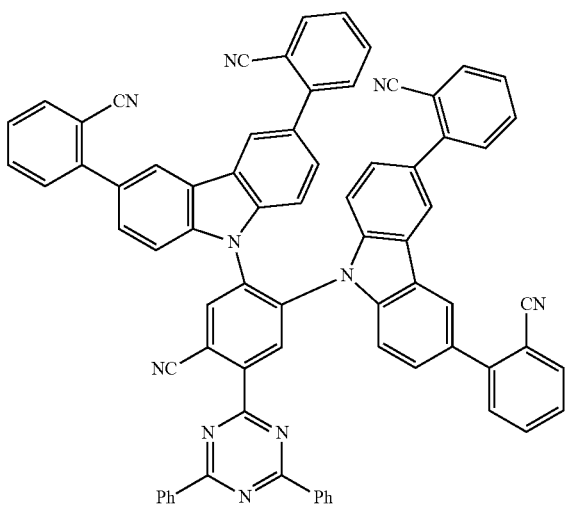

175
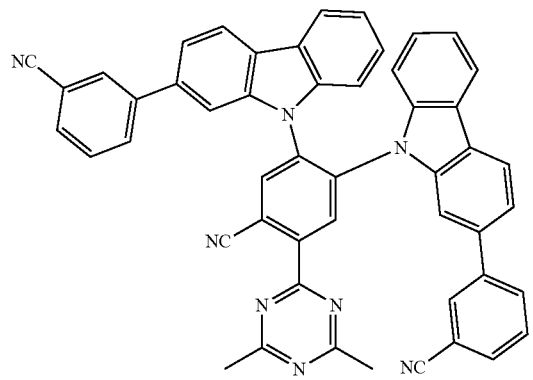
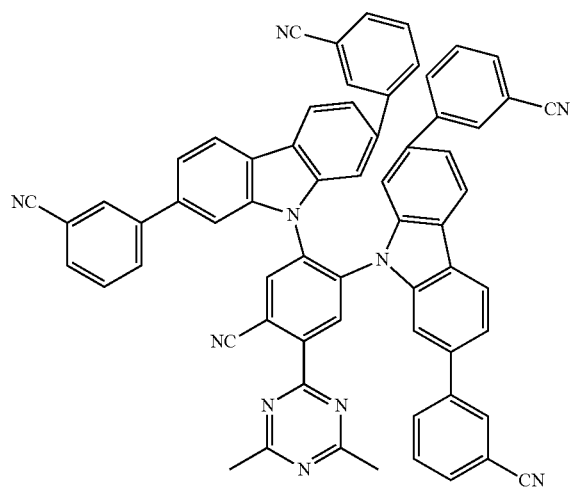
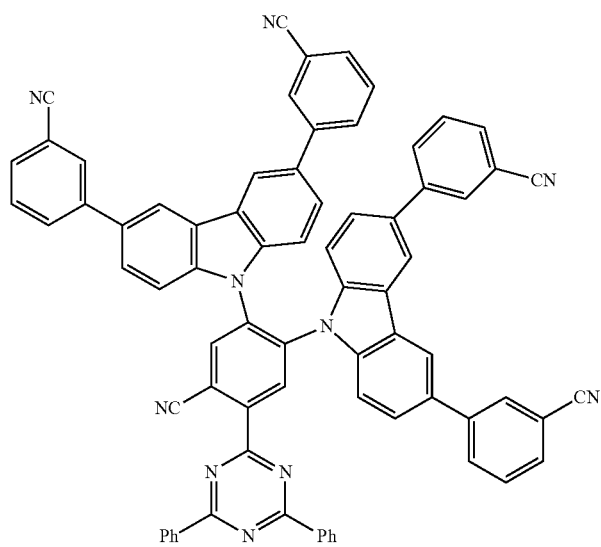
176
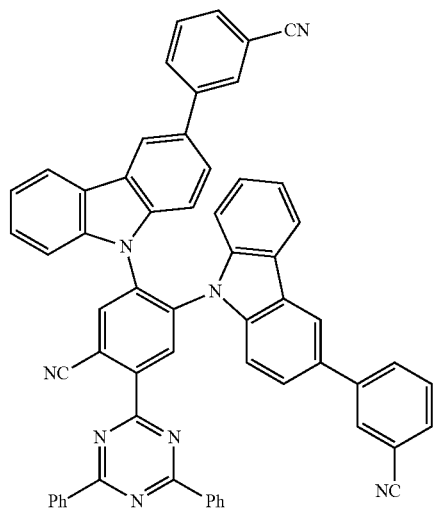
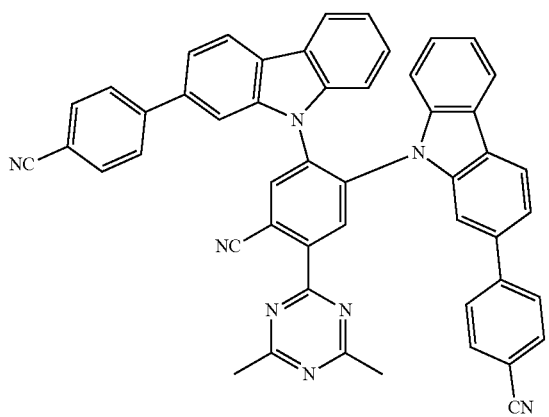

177
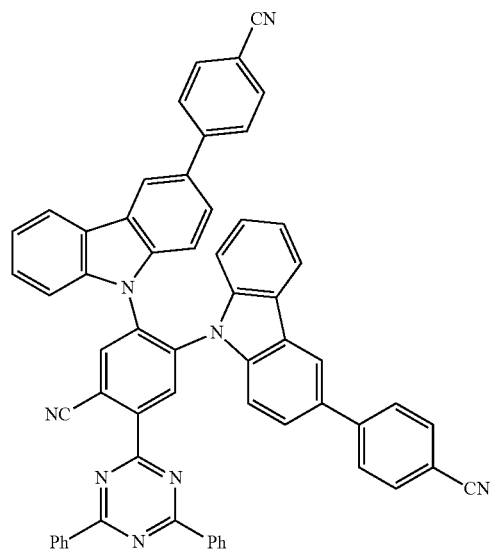
178
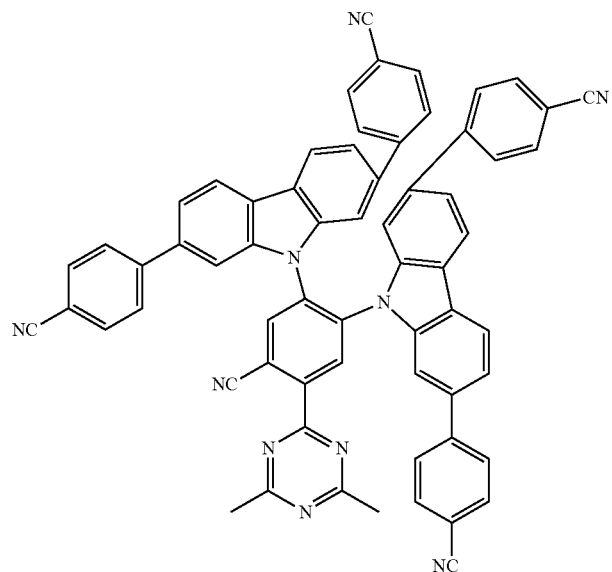
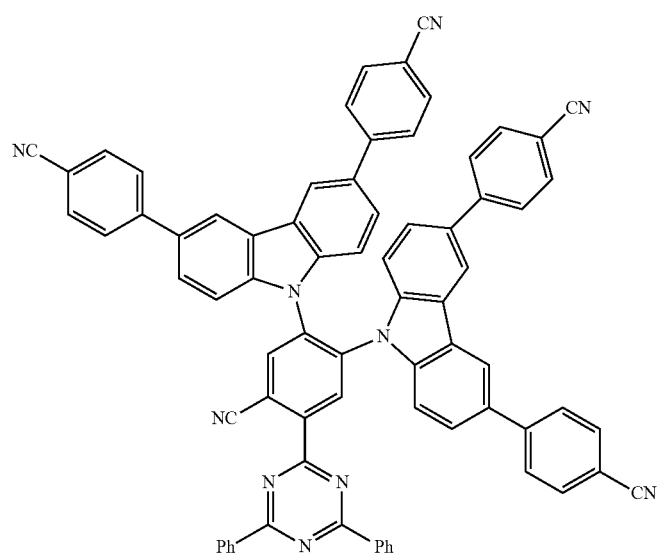
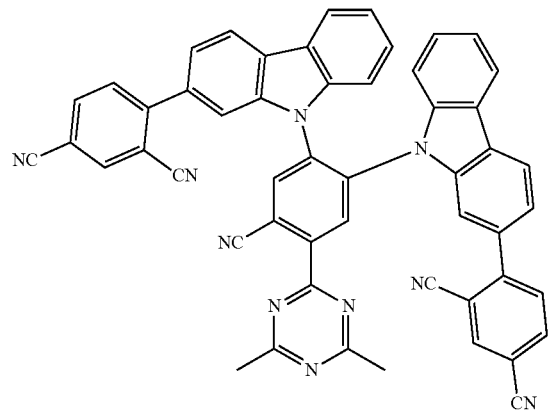
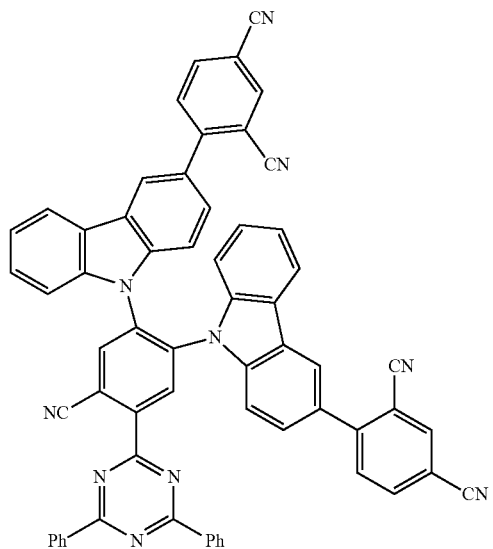

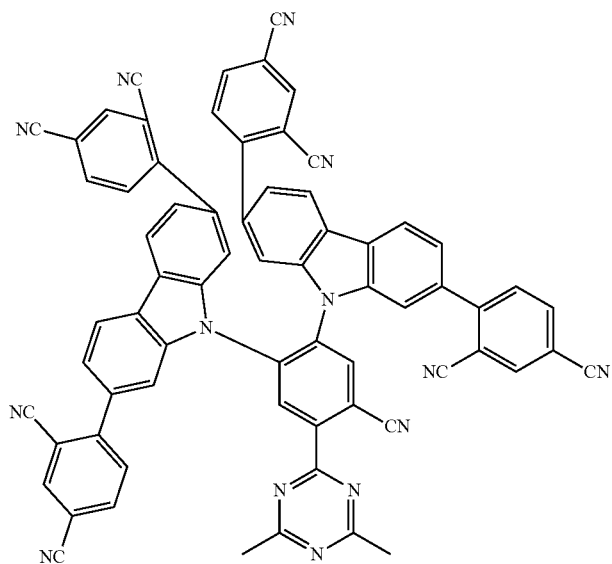
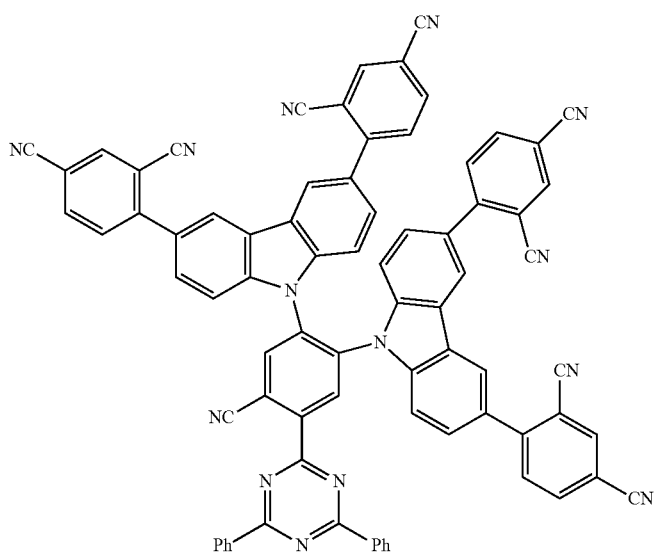
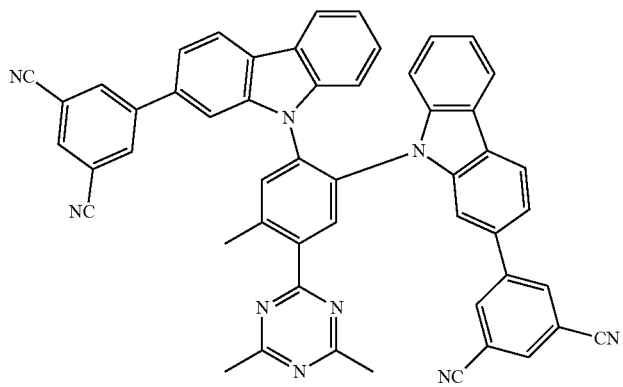
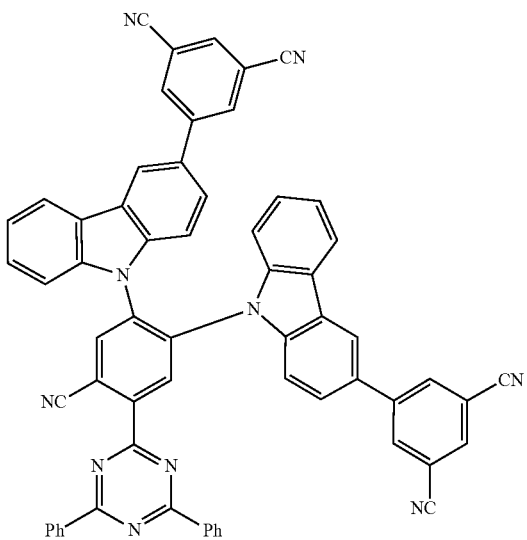

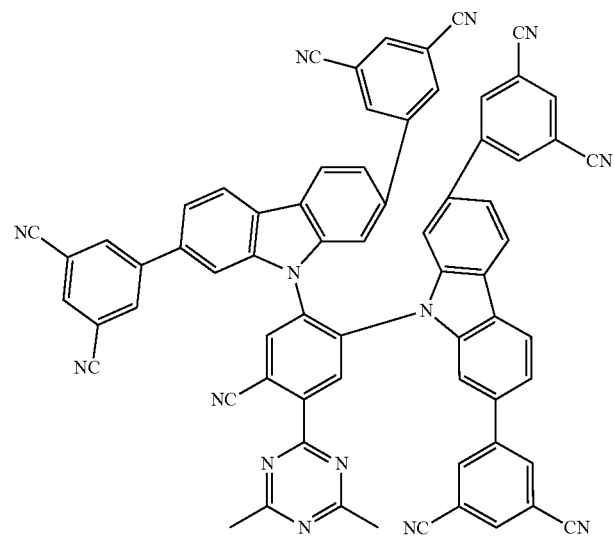
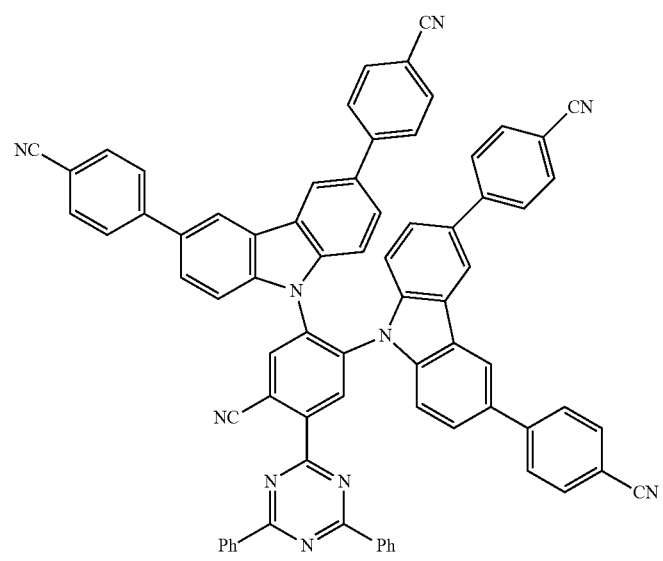
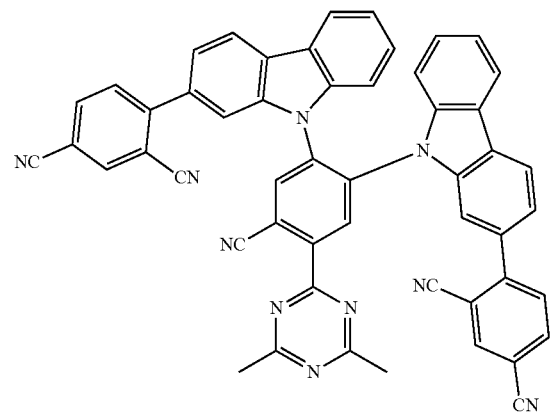
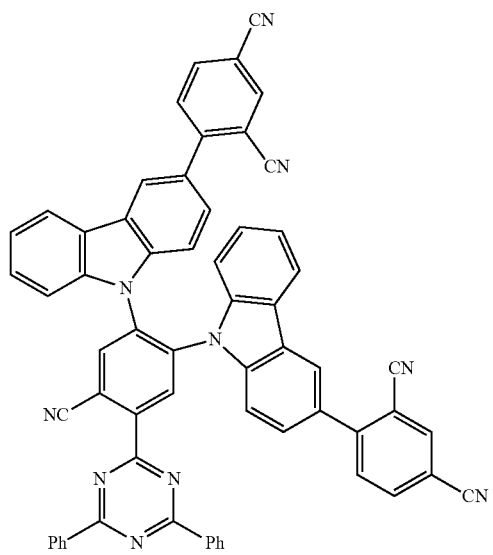

-continued
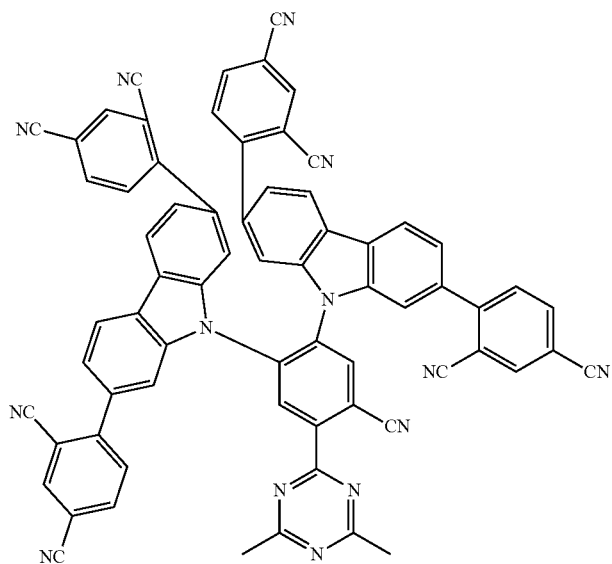
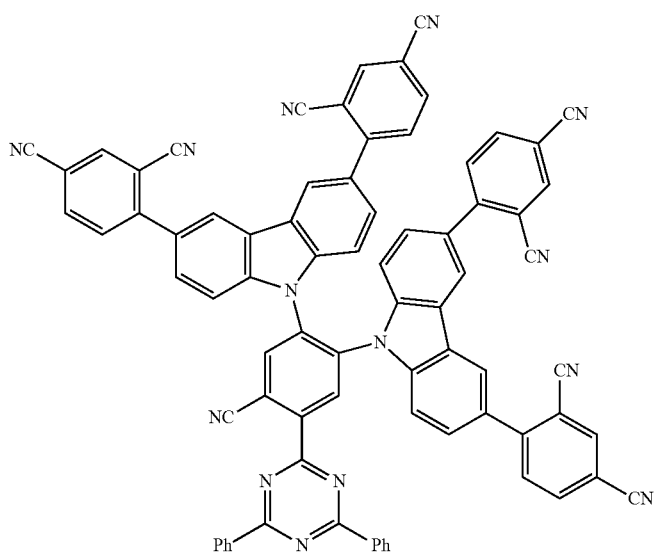
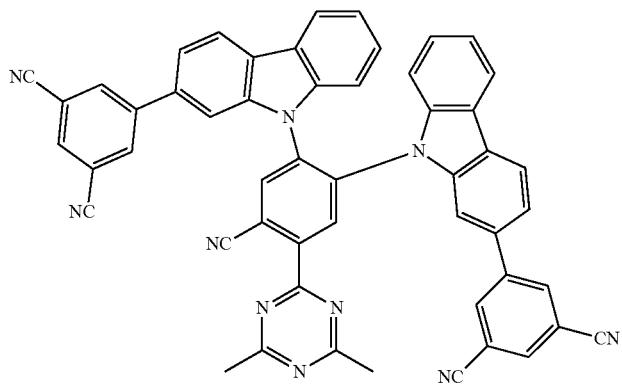
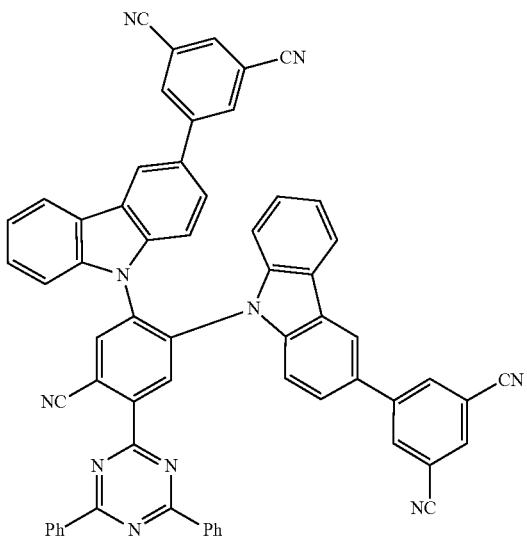

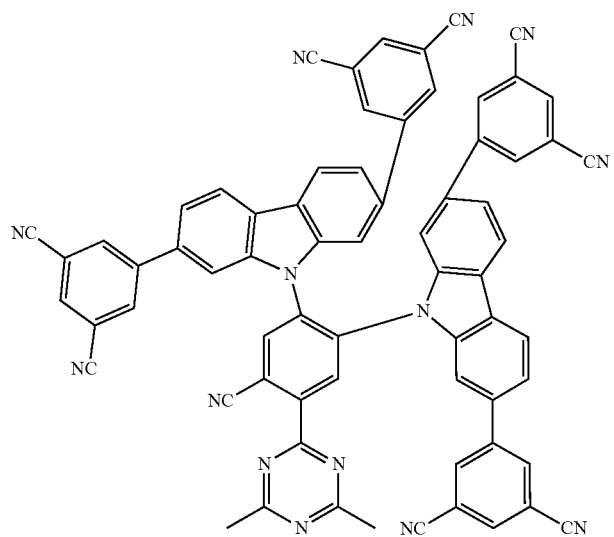
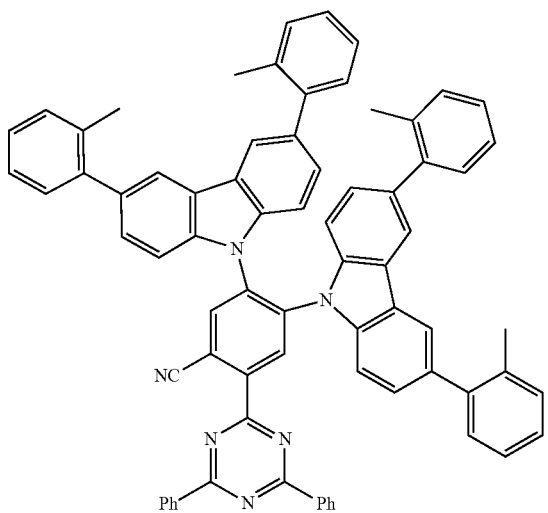
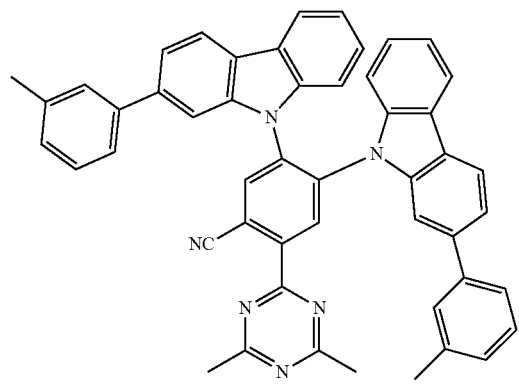
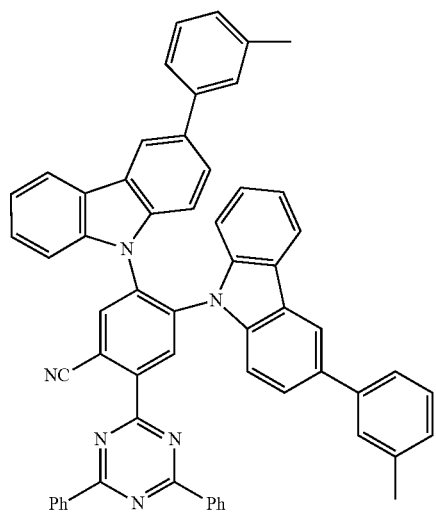
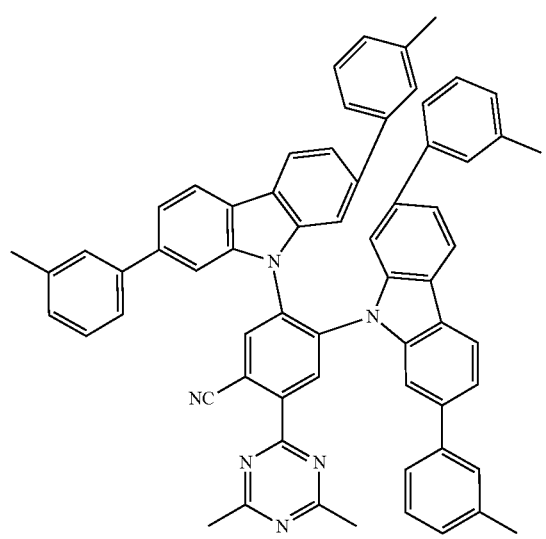

-continued
187
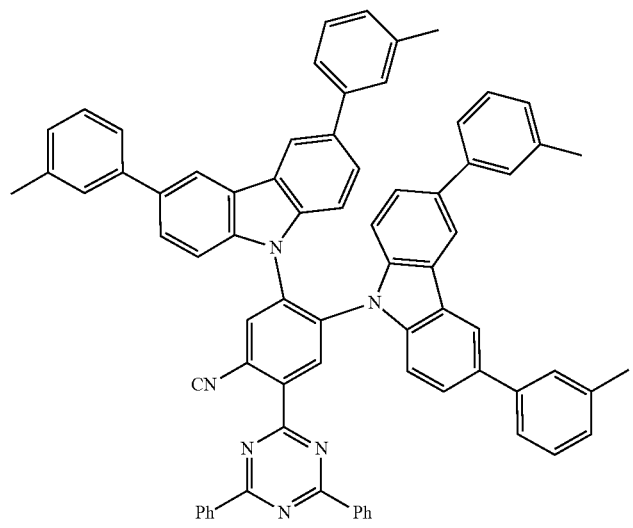
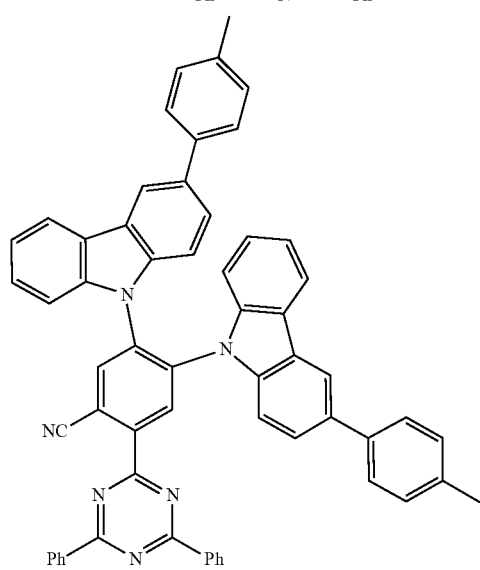
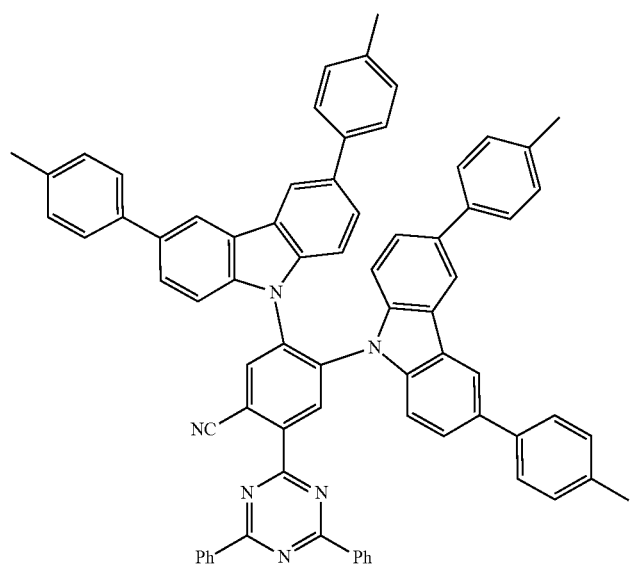
188
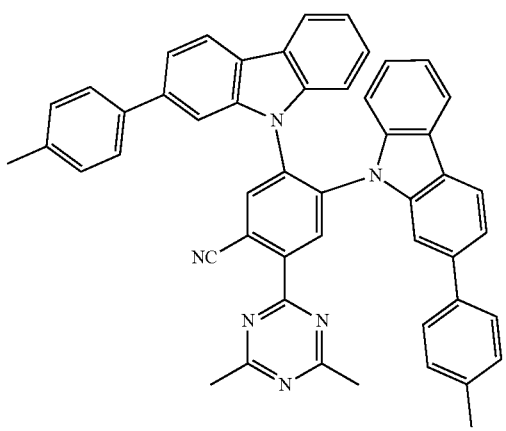
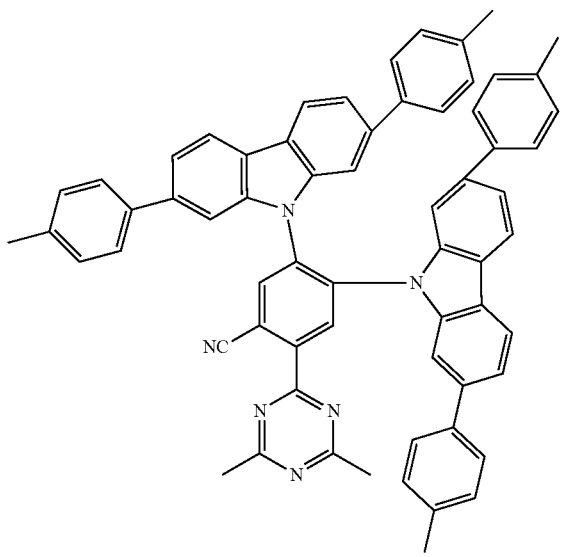

189
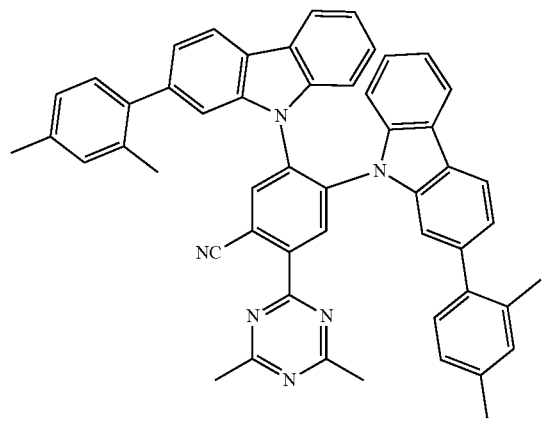
190
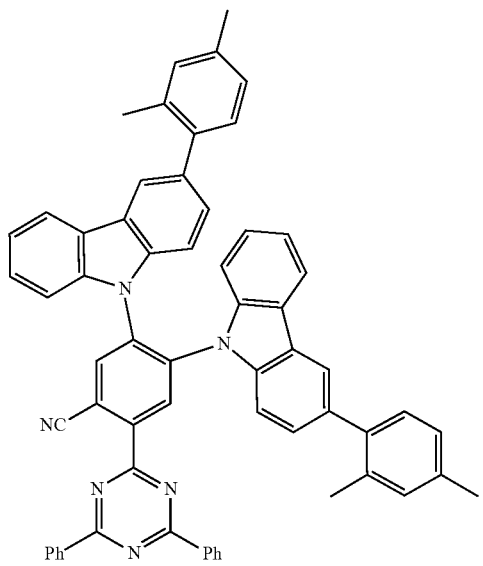
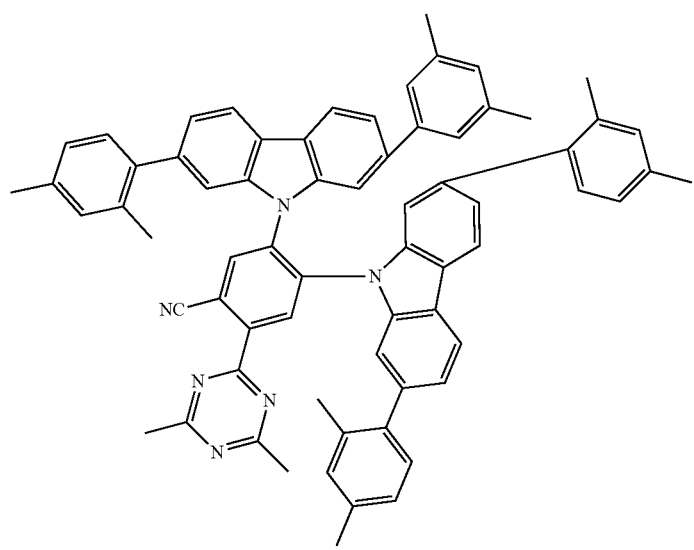
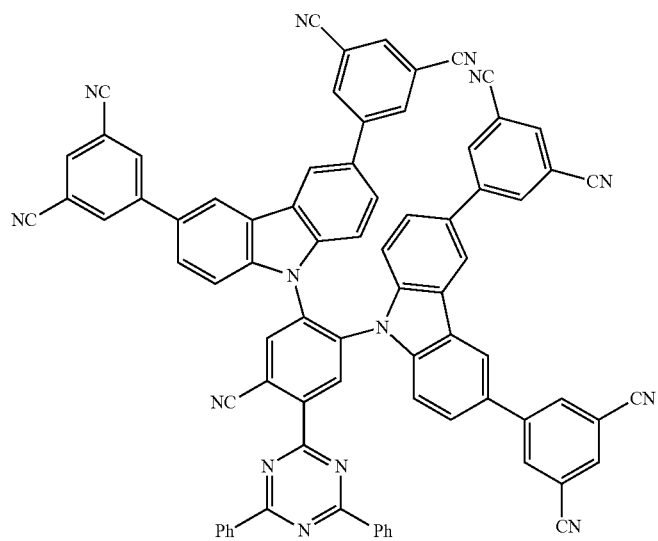

191 192
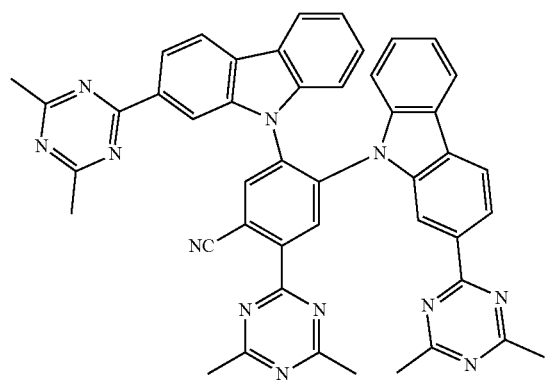
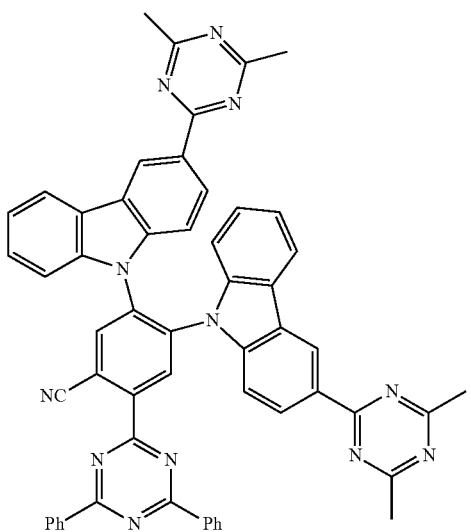
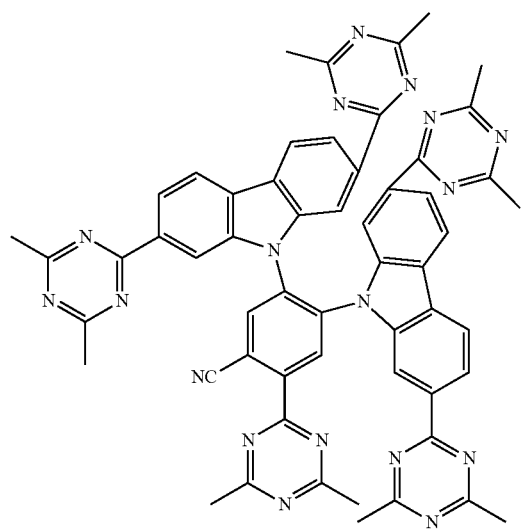
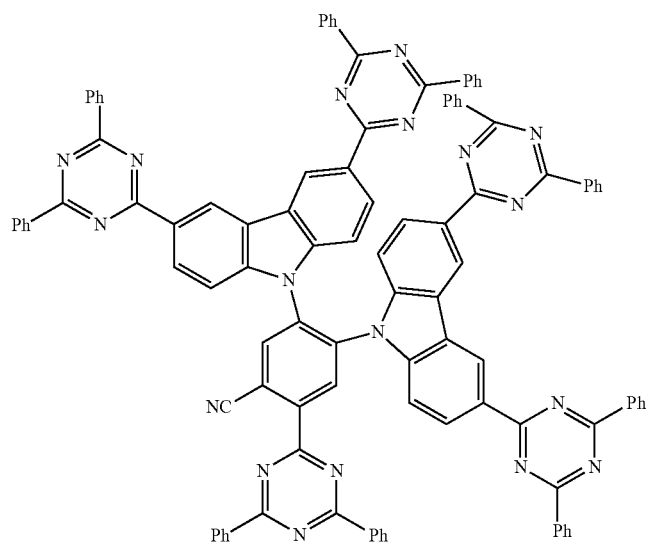

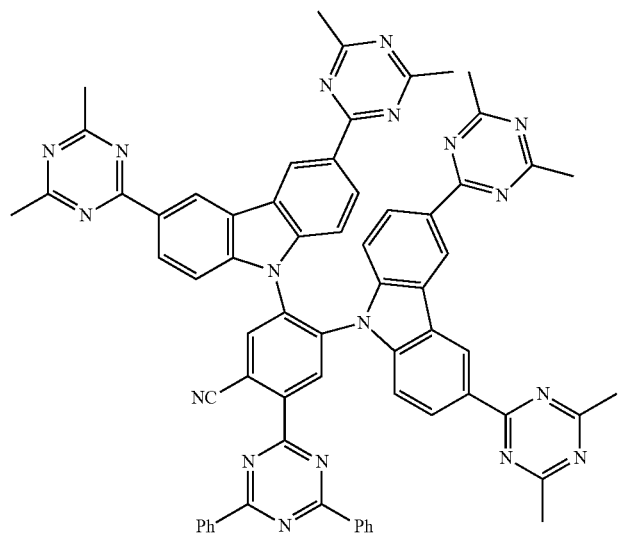
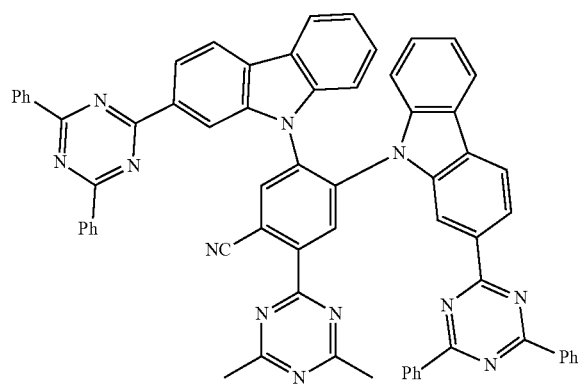
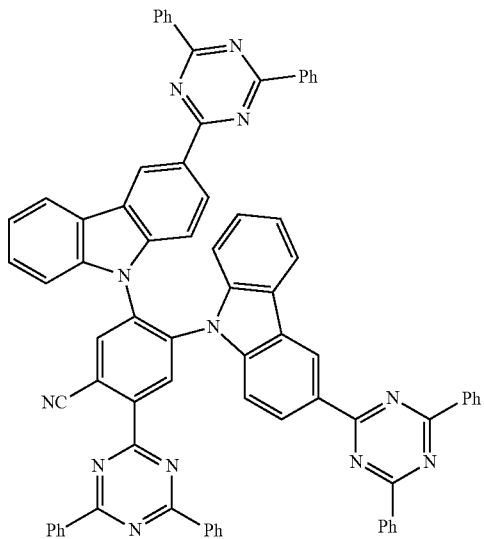
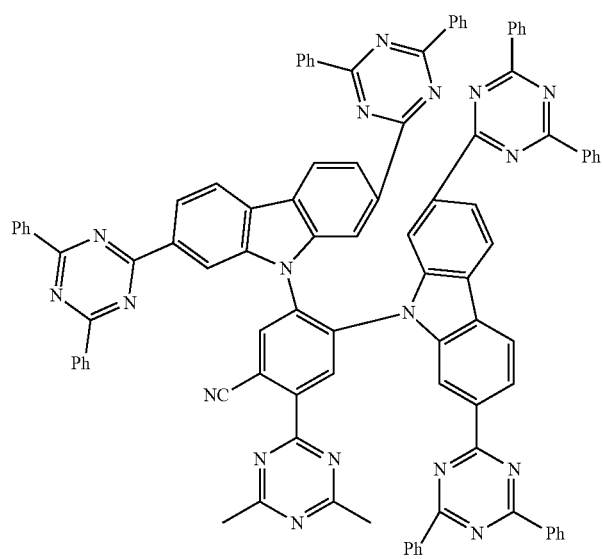
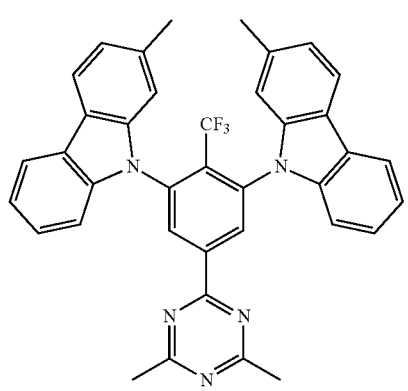

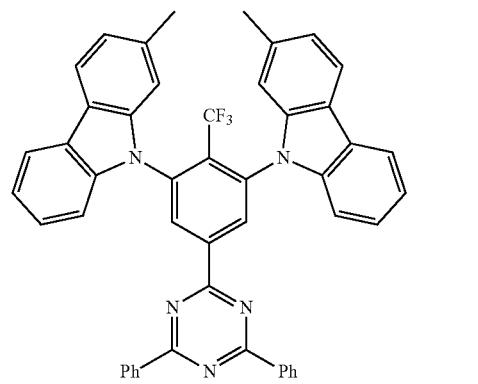
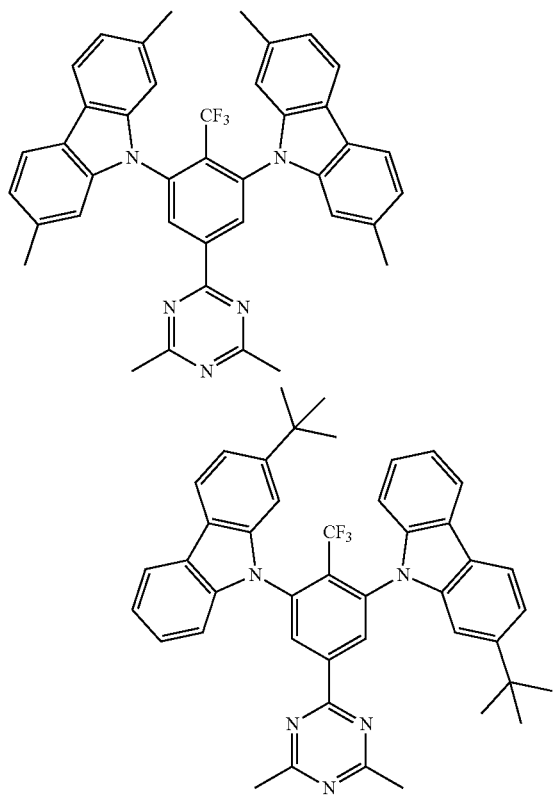
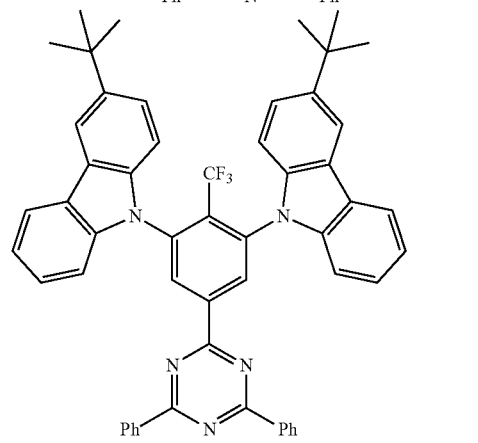
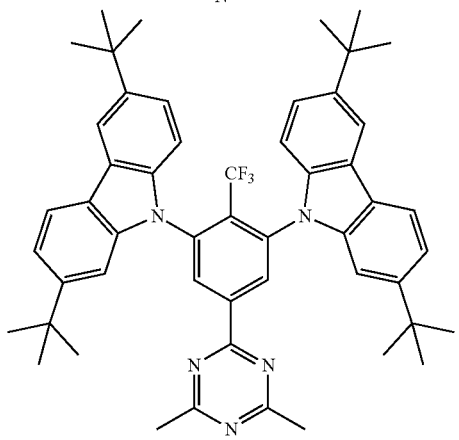
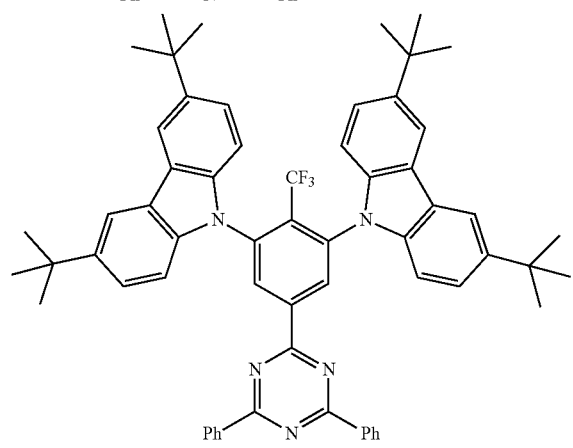

197 198
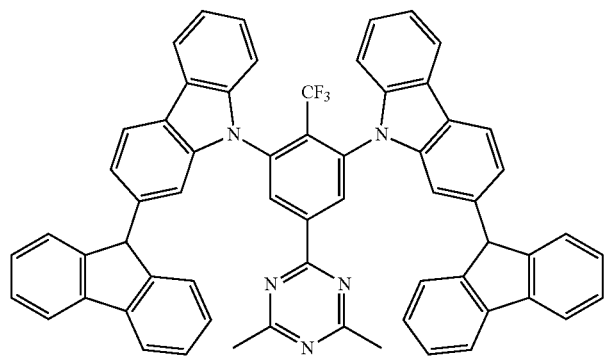
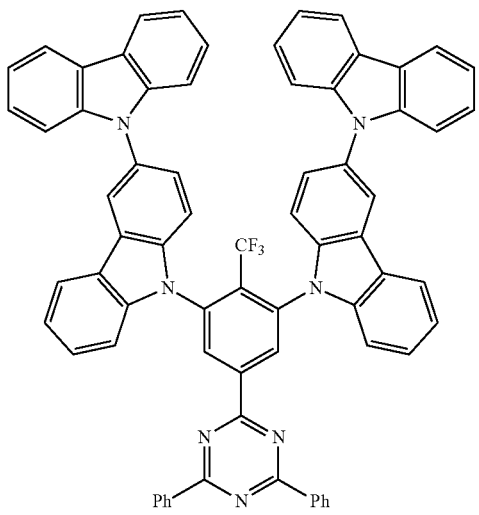
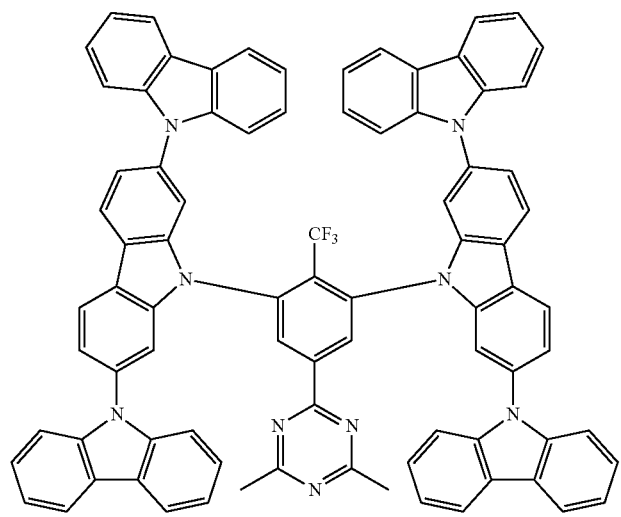
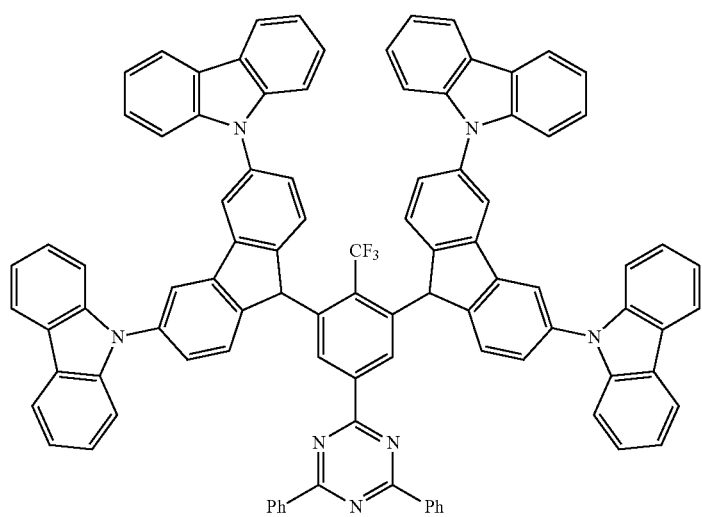
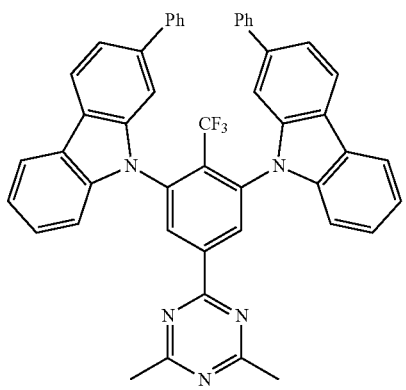

199 200
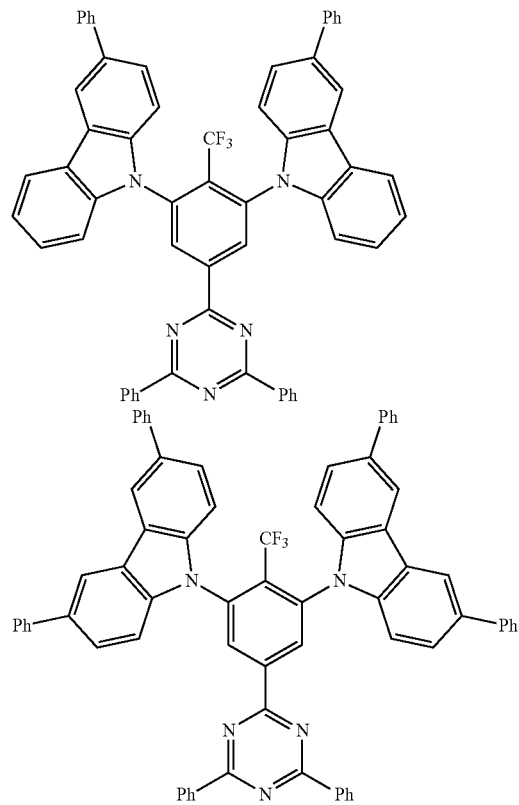
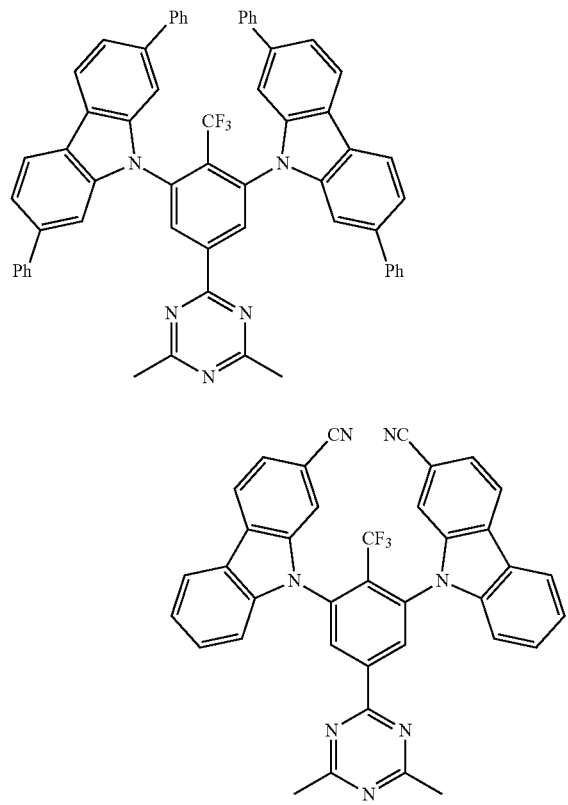
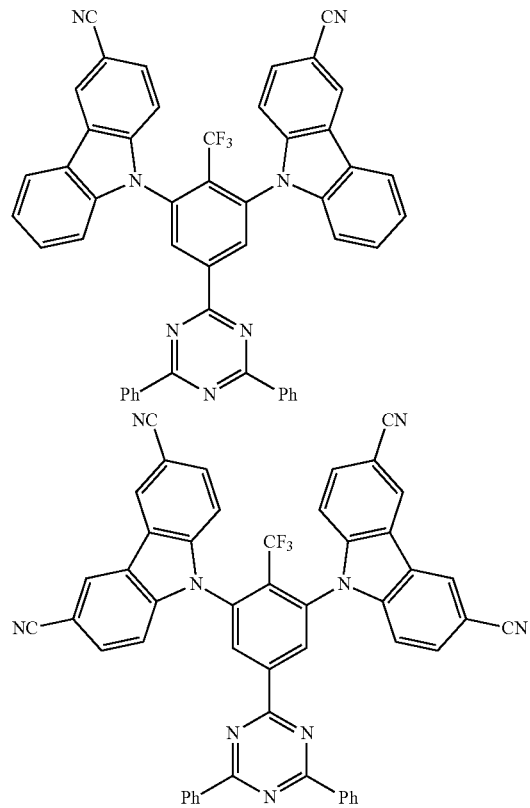
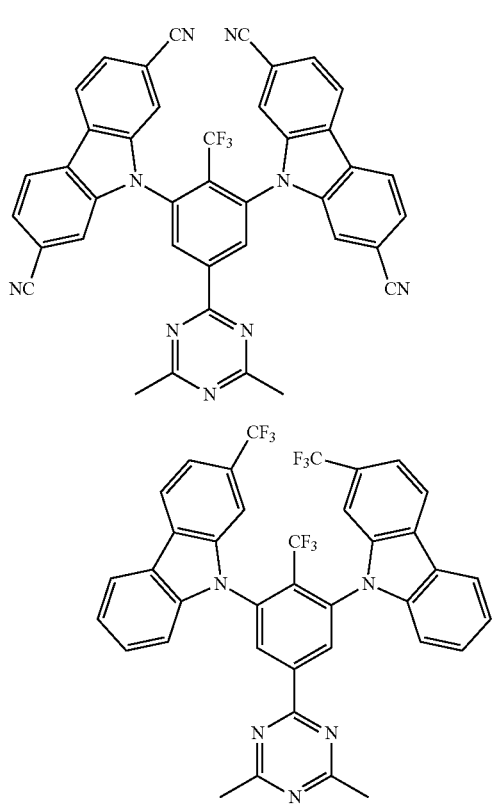

-continued
| 201 | 202 |
|---|---|
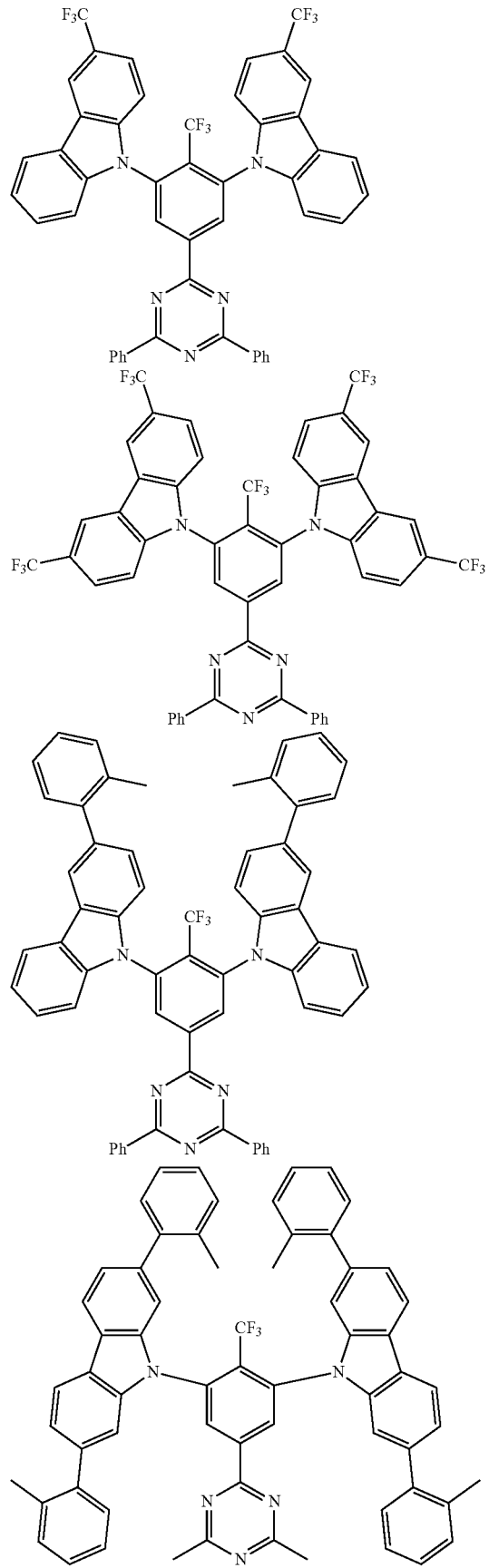
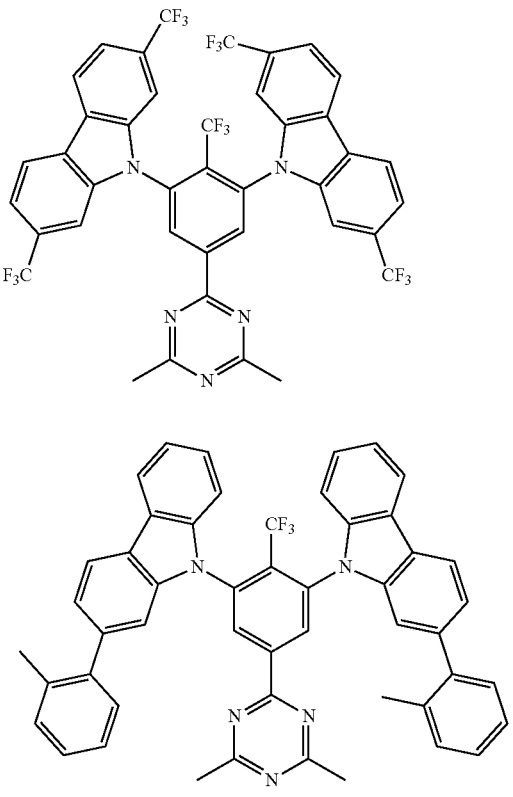

203
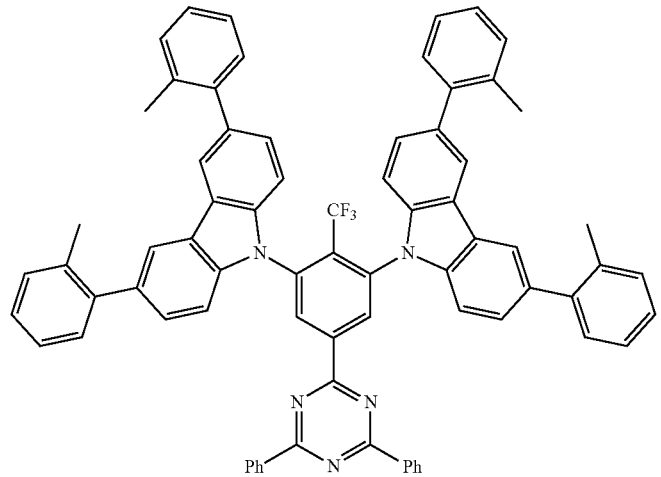
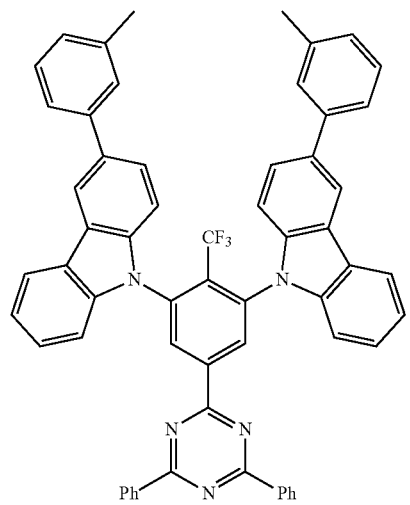
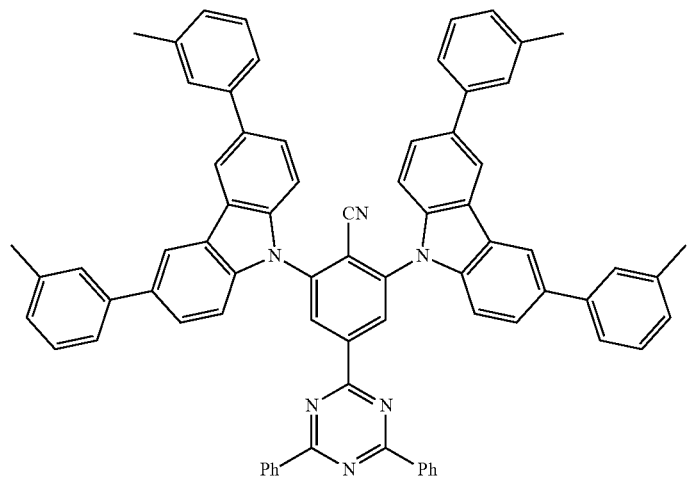
204
-continued
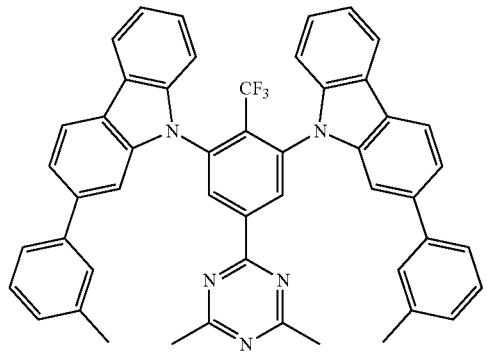
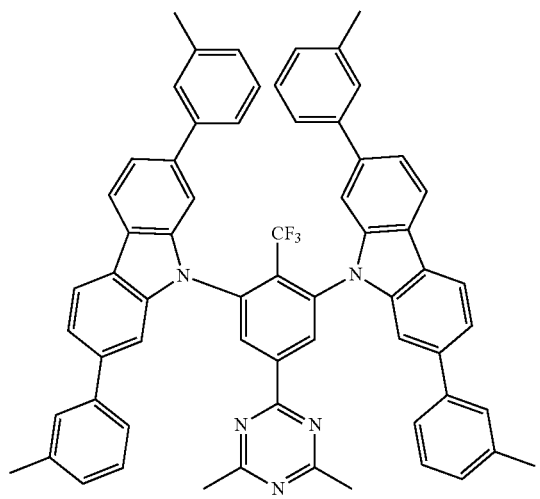
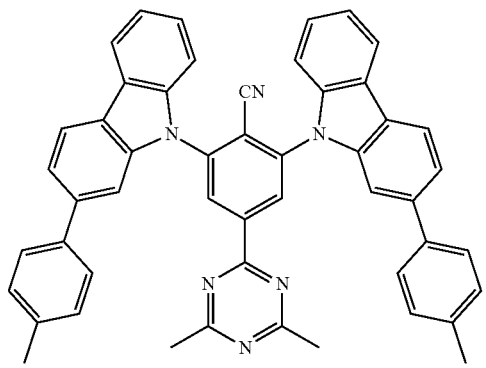

-continued
205
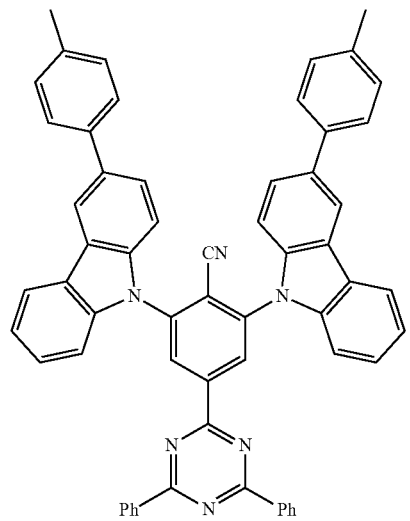
206
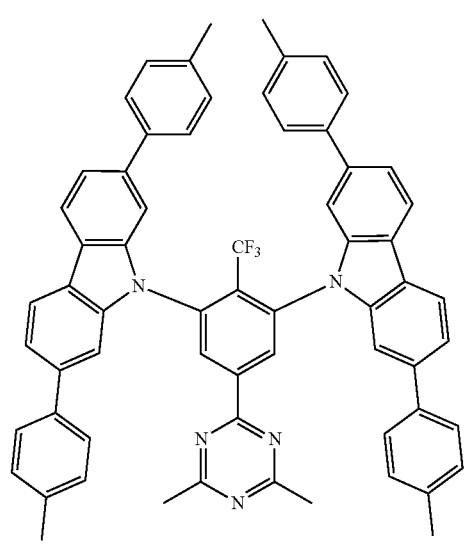
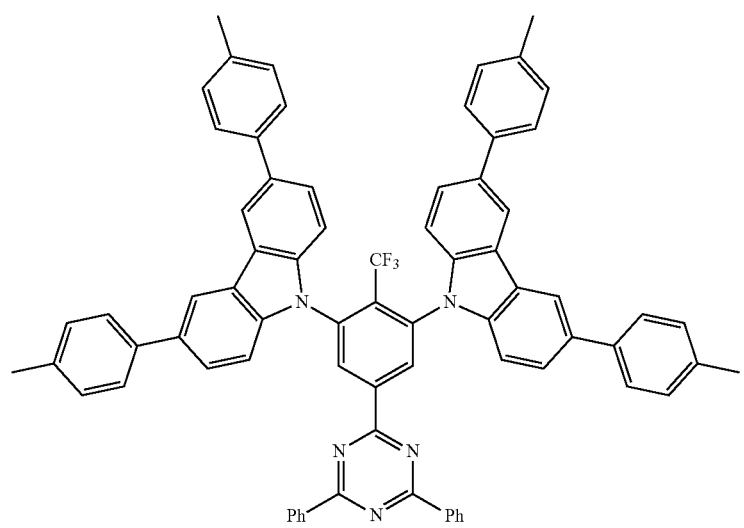
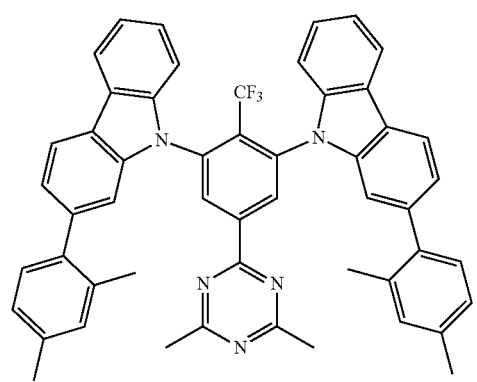
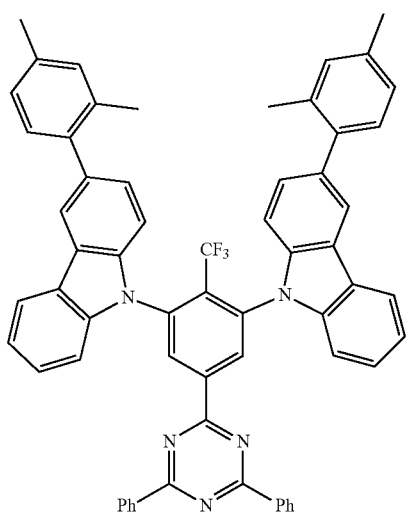

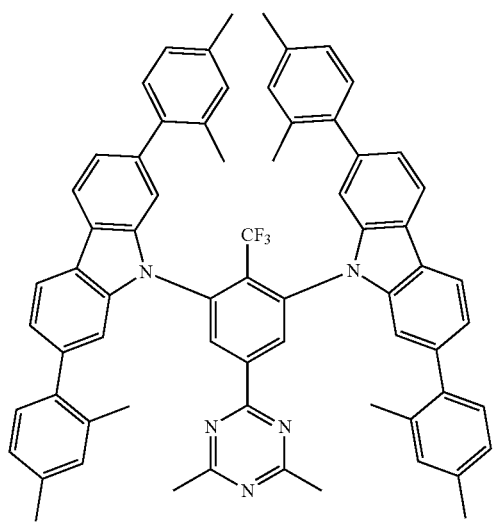
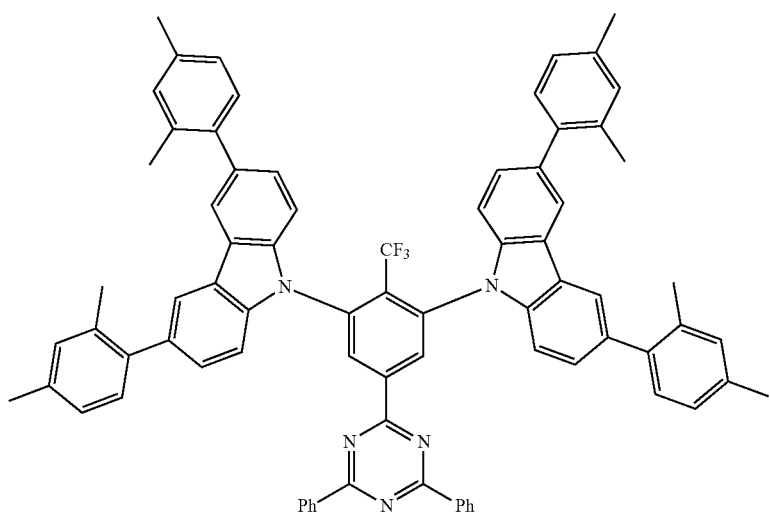
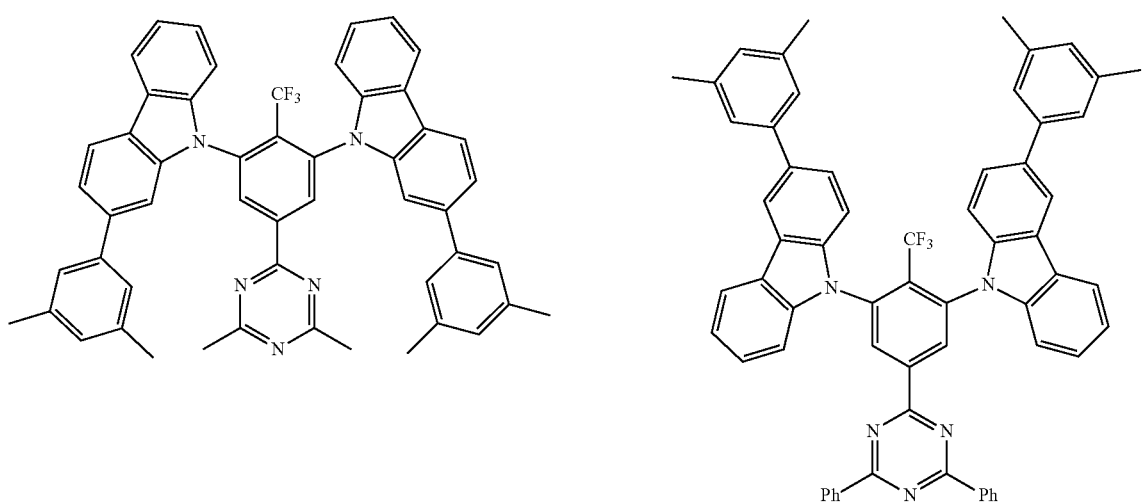

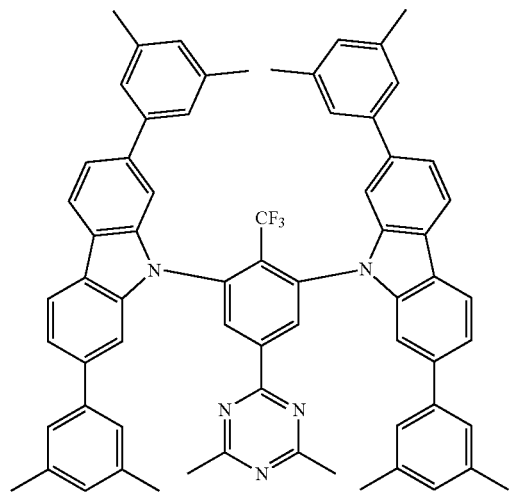
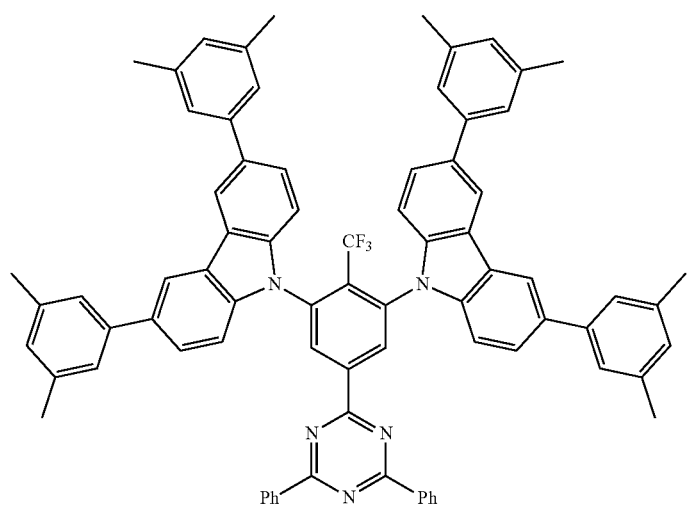
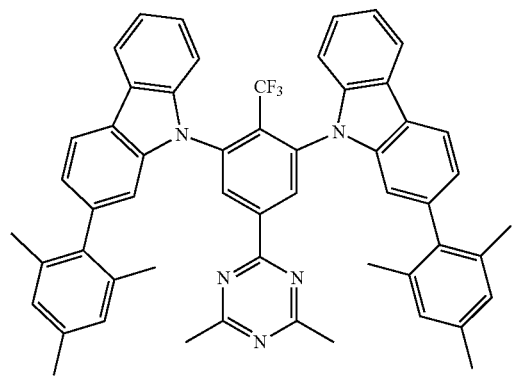
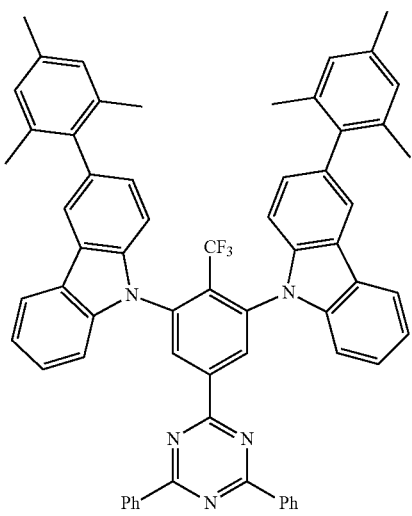

211
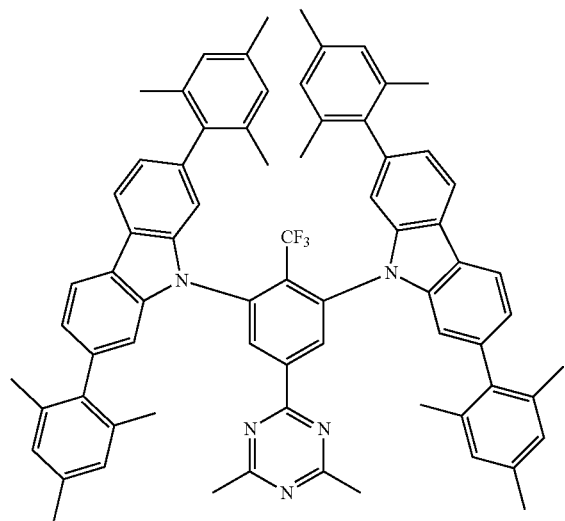
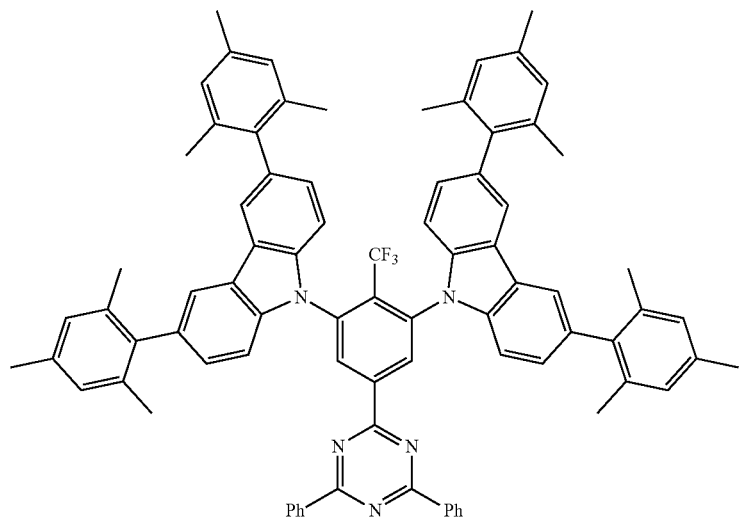
212
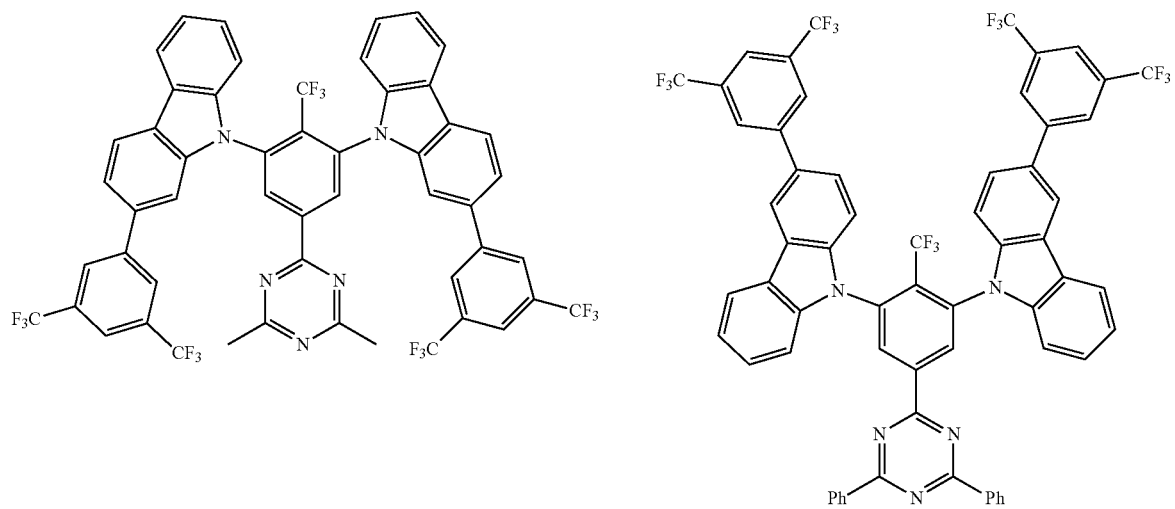

213 214
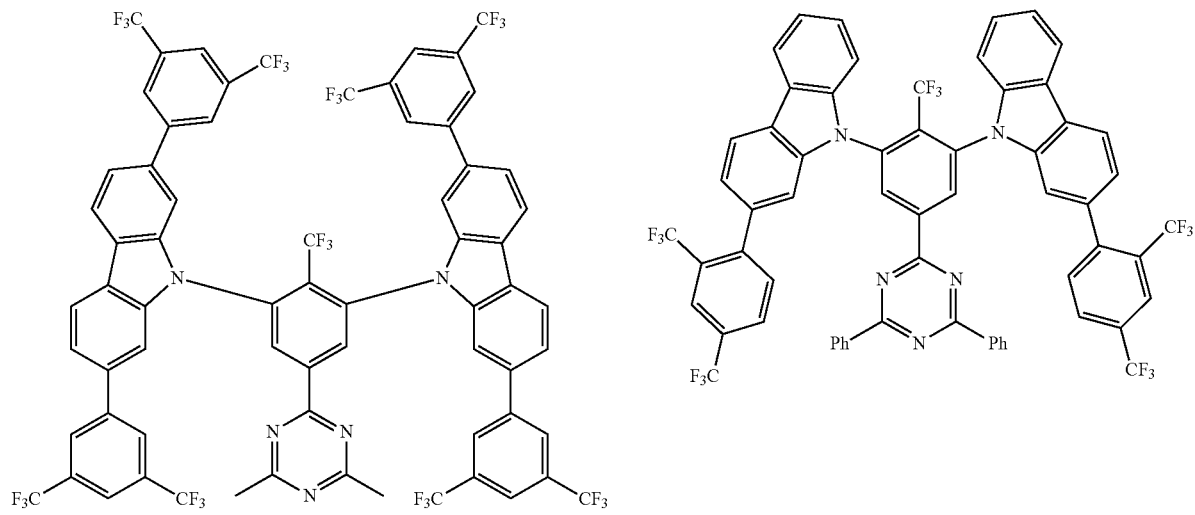
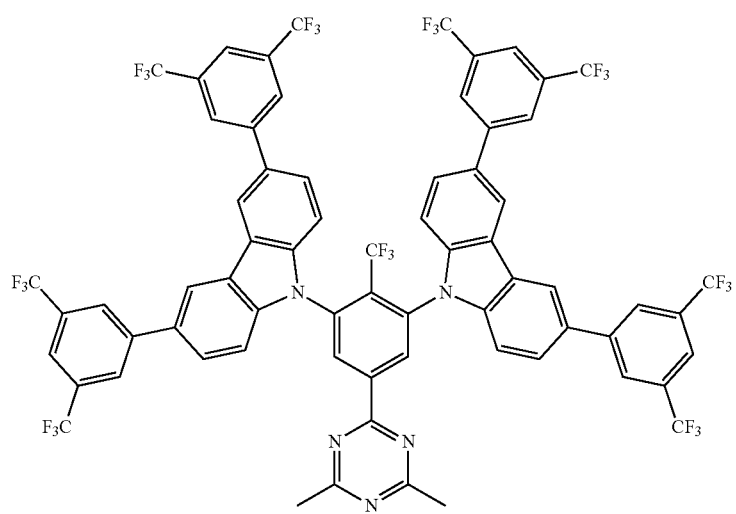
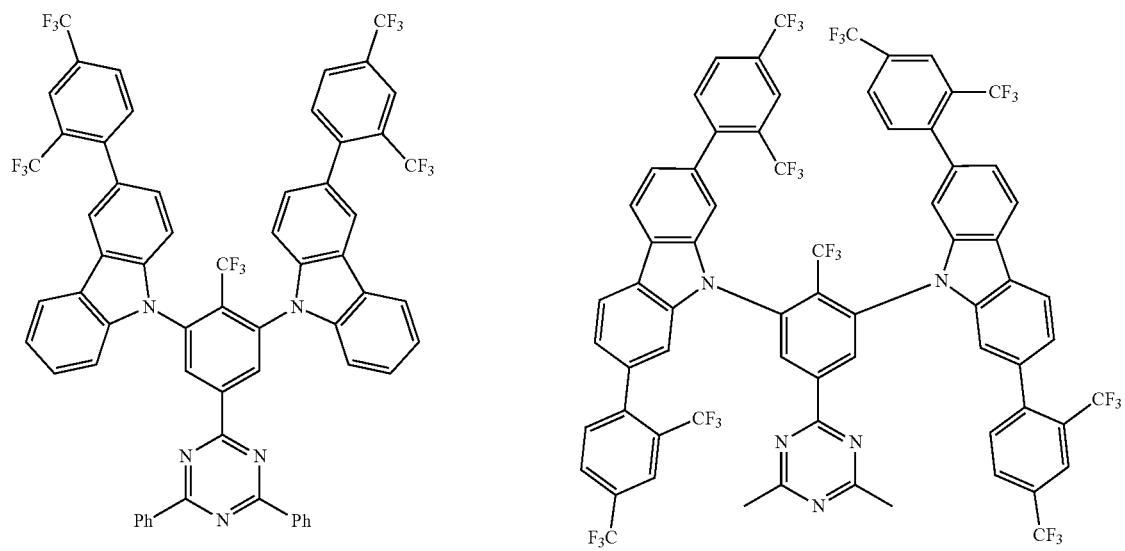

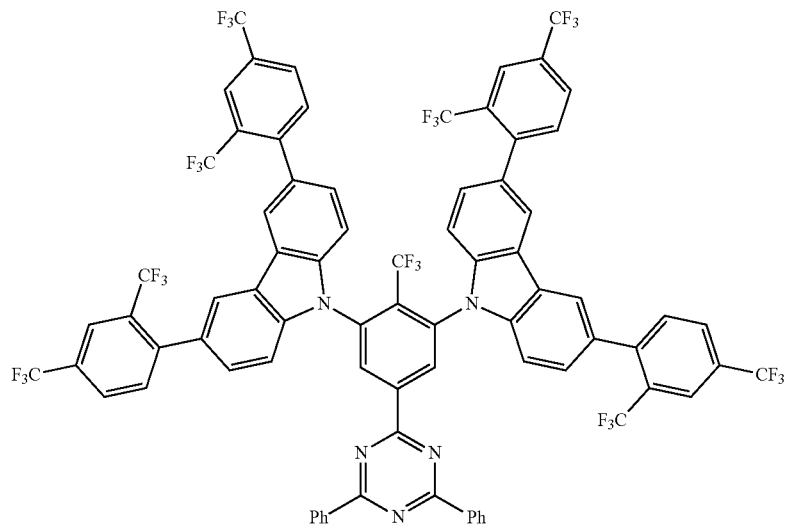
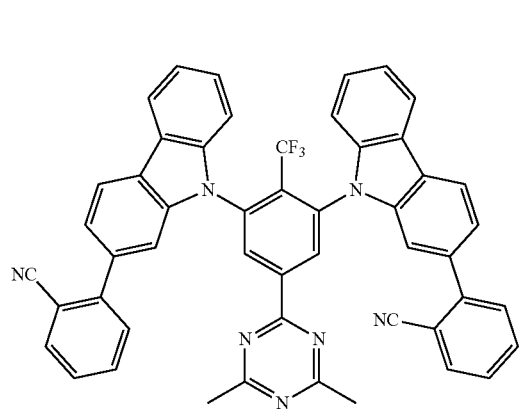
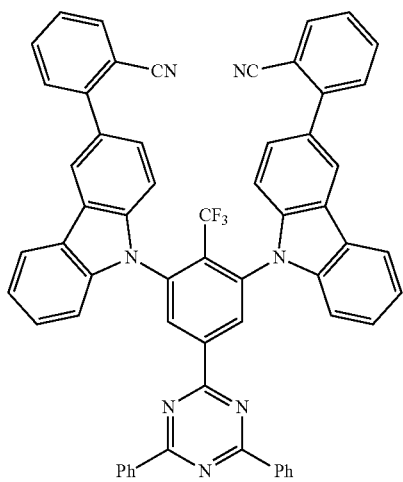
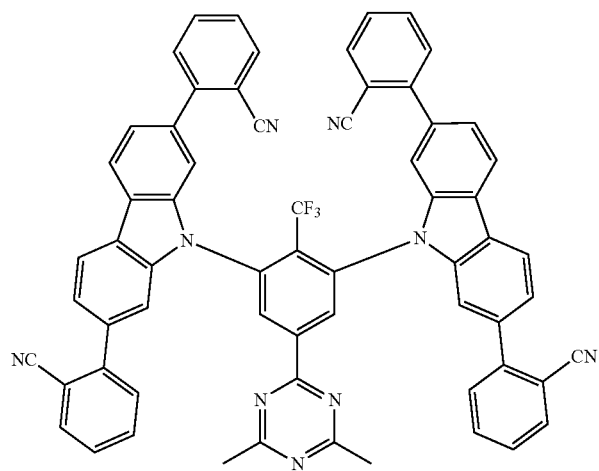

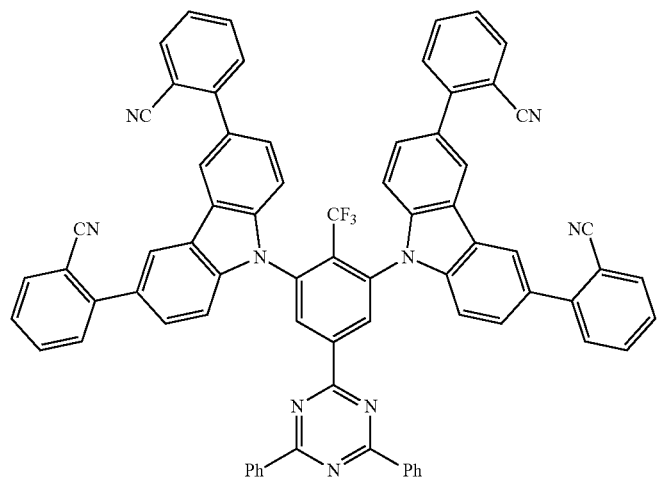
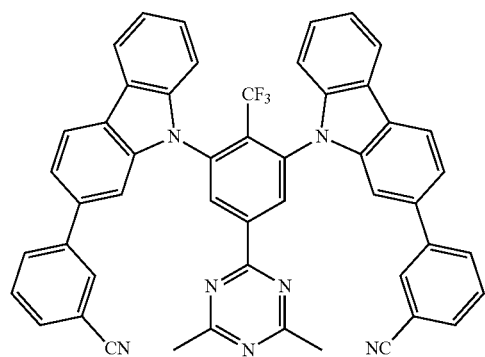
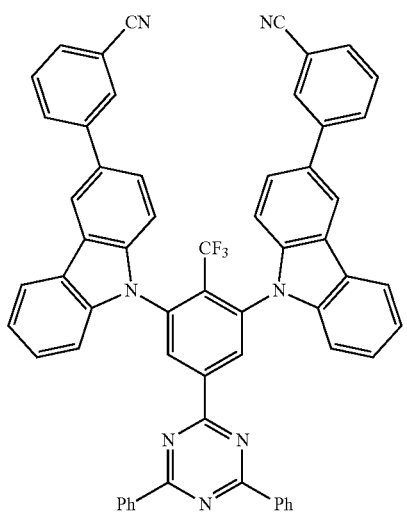
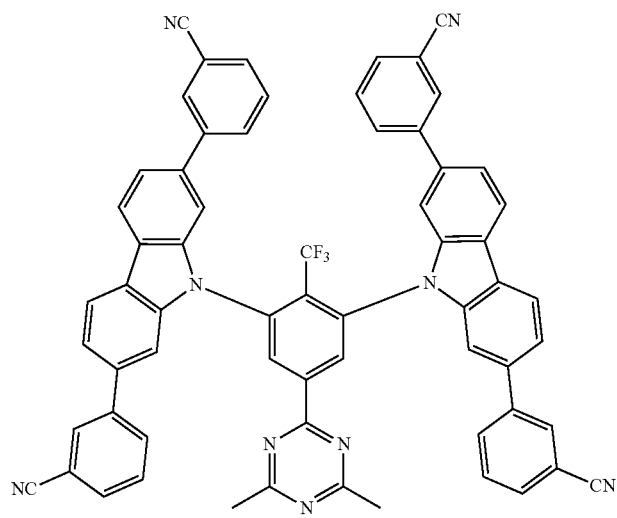

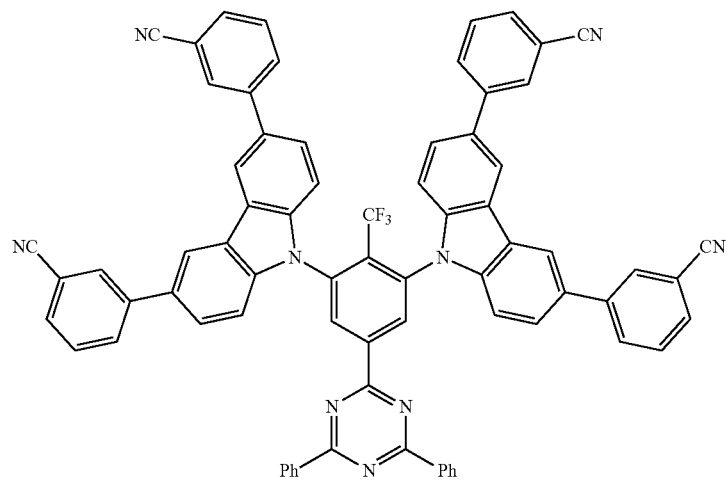
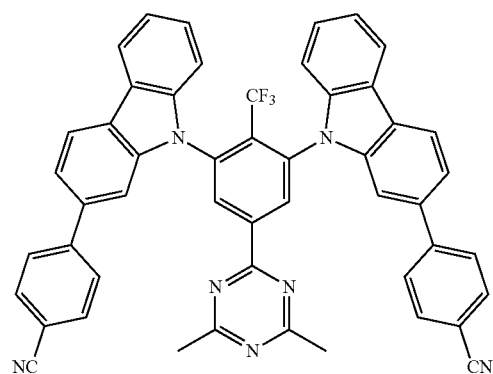
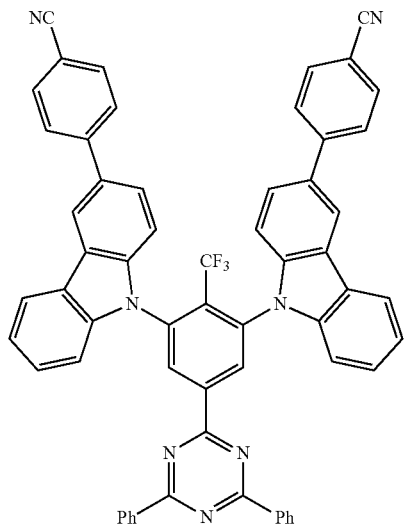
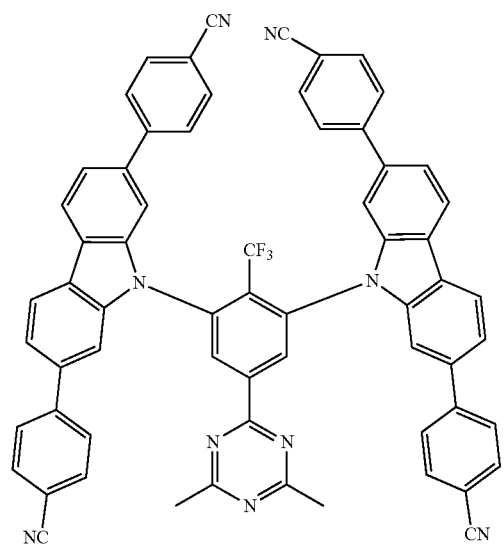

-continued
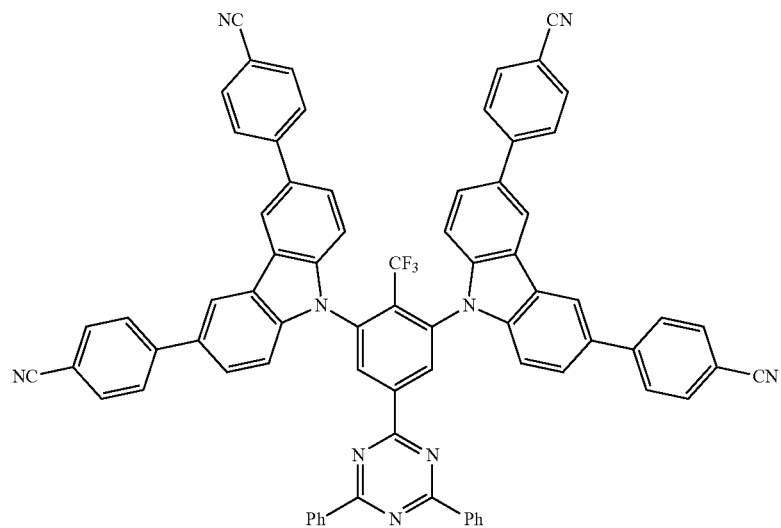
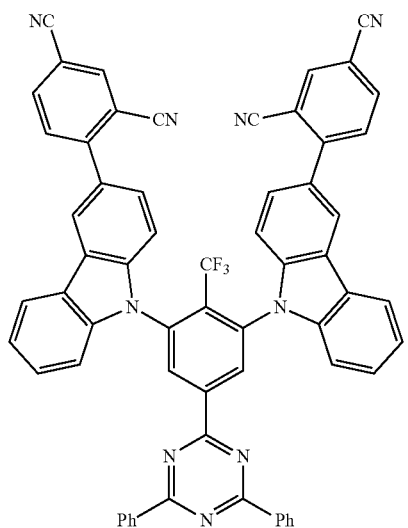
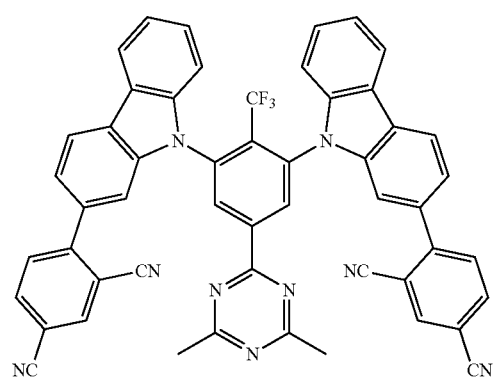
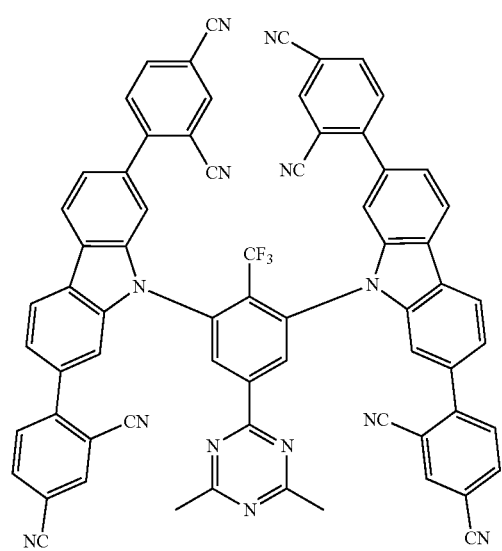

-continued
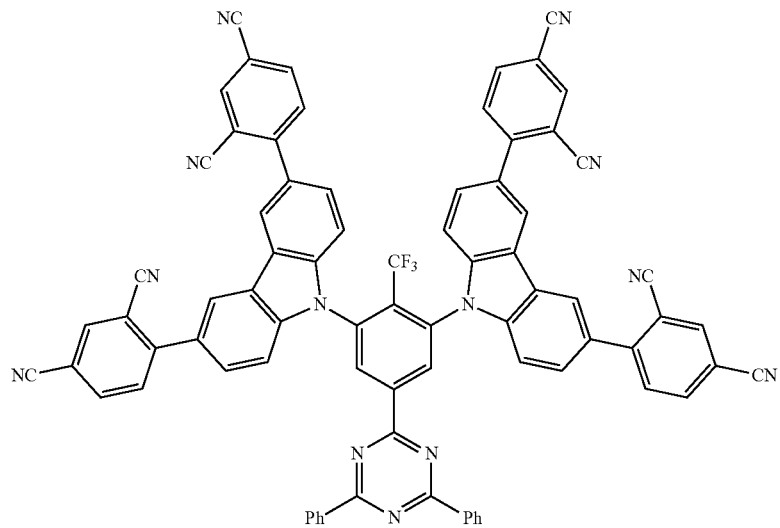
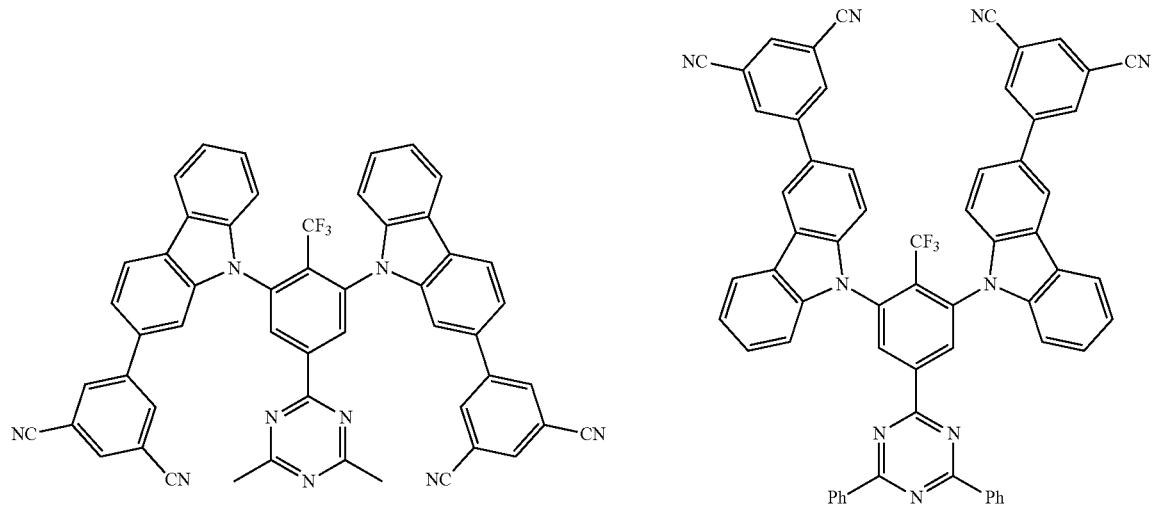
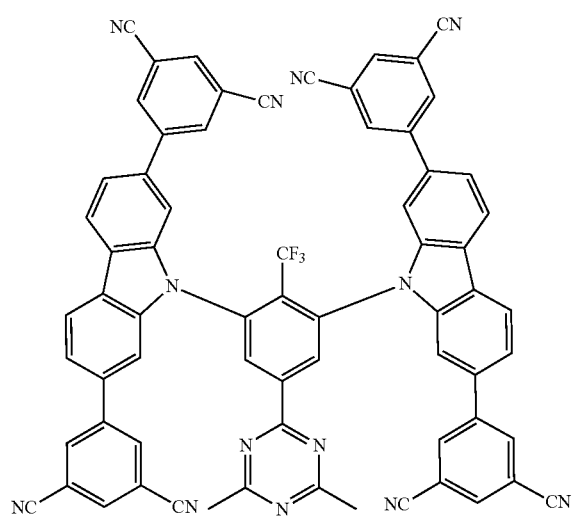

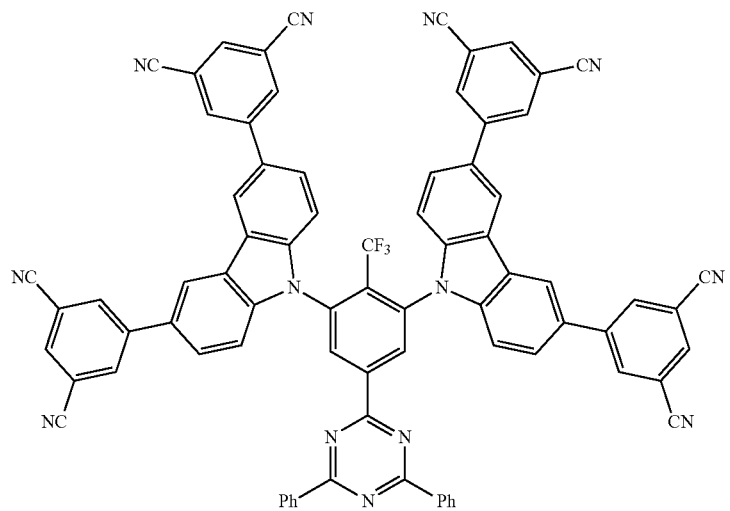
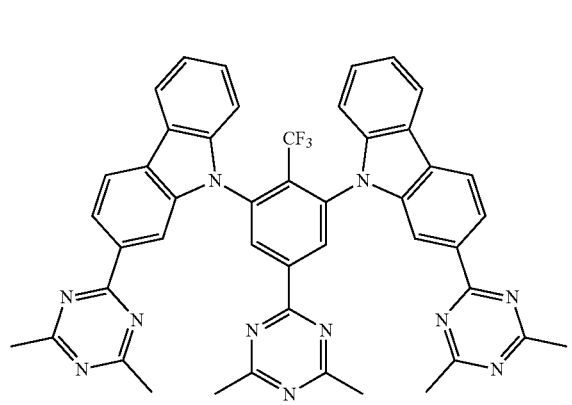
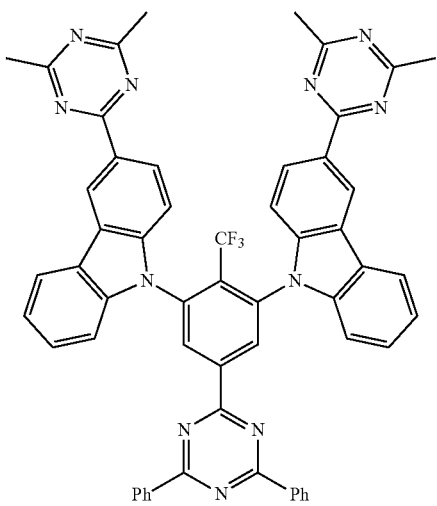
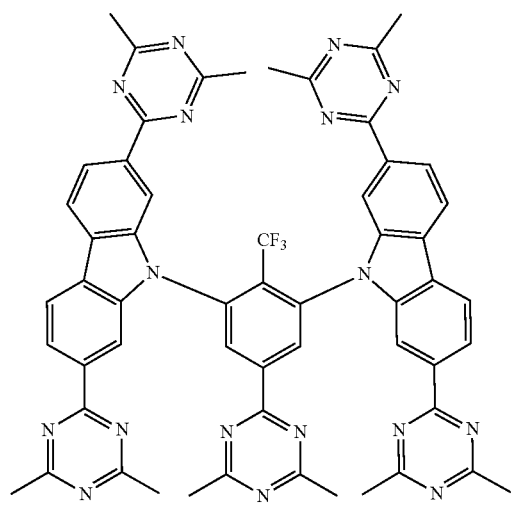

-continued

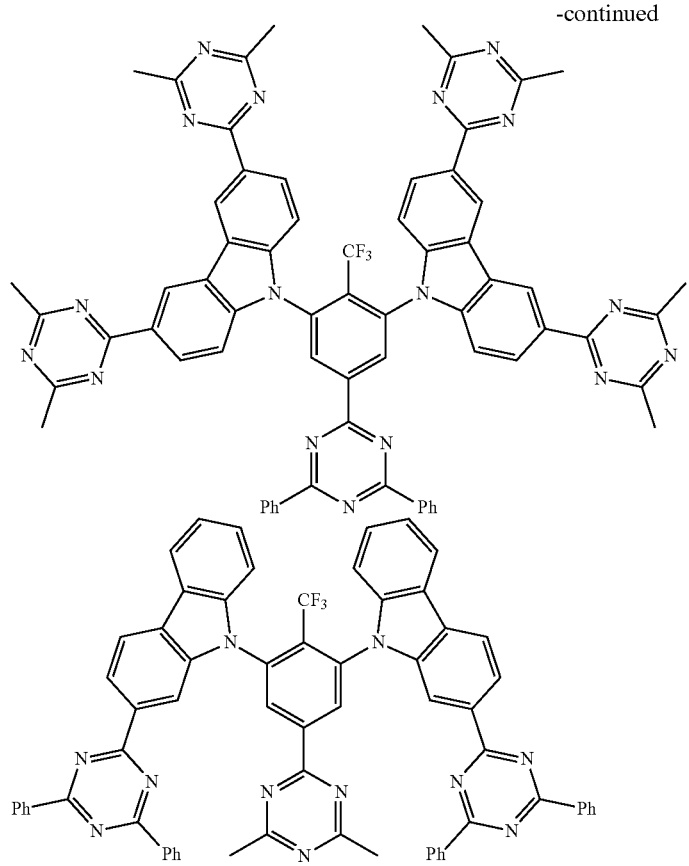

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

The invention claimed is:

1. An organic molecule comprising a first chemical unit comprising a structure according to Formula I,

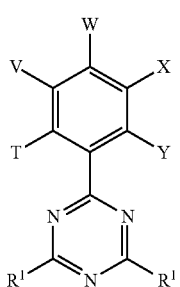

Formula I and two second chemical units D, which are respectively the same or different in each occurrence, comprising a structure according to Formula IIa,

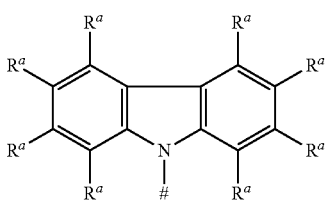

Formula IIa wherein, in each case, the first chemical unit is connected to the two second chemical units D via a single bond;

wherein

T is the point of attachment of the single bond between the first chemical unit and a second chemical unit D or is H;

V is the point of attachment of the single bond between the first chemical unit and a second chemical unit D or is H;

W is the point of attachment of the single bond between the first chemical unit and a second chemical unit D or is selected from the group consisting of H, CN and $CF_3$;

X is the point of attachment of the single bond between the first chemical unit and a second chemical unit D or is selected from the group consisting of H, CN and $CF_3$;

Y is the point of attachment of the single bond between the first chemical unit and a second chemical unit D or is selected from the group consisting of H, CN and $CF_3$;

identifies the point of attachment of the single bond between a second chemical unit D and the first chemical unit;

in each occurrence $R^a$ is the same or different and is selected from the group consisting of:

H, deuterium, $N(R^5)_2$, OH, $Si(R^5)_3$, $B(OR^5)_2$, $OSO_2R^5$, $CF_3$, CN, F, Br, I;

a linear alkyl, alkoxy or thioalkoxy group having 1 to 40 C atoms, which can in each case be substituted with one or more radicals $R^5$, wherein one or more non-adjacent $CH_2$ groups can be replaced by $R^5C=CR^5$, C≡C, $Si(R^5)_2$, $Ge(R^5)_2$, $Sn(R^5)_2$, C=O, C=S, C=Se, C=NR^5, P(=O)(R^5), SO, SO_2, NR^5, O, S or CONR^5 and wherein one or more H atoms can be replaced by deuterium, CN, $CF_3$ or $NO_2$;

a linear alkenyl or alkinyl group having 2 to 40 C atoms, which can in each case be substituted with one or more radicals $R^5$, wherein one or more non-adjacent $CH_2$ groups can be replaced by $R^5C=CR^5$, C≡C, $Si(R^5)_2$, $Ge(R^5)_2$, $Sn(R^5)_2$, C=O, C=S, C=Se, C=NR^5, P(=O)(R^5), SO, SO_2, NR^5, O, S or CONR^5 and wherein one or more H atoms can be replaced by deuterium, CN, $CF_3$ or $NO_2$;

a branched or cyclic alkyl, alkenyl, alkinyl, alkoxy or thioalkoxy group having 3 to 40 C atoms, which can in each case be substituted with one or more radicals $R^5$, wherein one or more non-adjacent $CH_2$ groups can be replaced by $R^5C=CR^5$, C≡C, $Si(R^5)_2$, $Ge(R^5)_2$, $Sn(R^5)_2$, C=O, C=S, C=Se, C=NR^5, P(=O)(R^5), SO, SO_2, NR^5, O, S or CONR^5 and wherein one or more H atoms can be replaced by deuterium, CN, $CF_3$ or $NO_2$;

an aromatic or heteroaromatic ring system having 5 to 60 aromatic ring atoms, which can in each case be substituted with one or more radicals $R^5$;

an aryloxy or heteroaryloxy group having 5 to 60 aromatic ring atoms, which can in each case be substituted with one or more radicals $R^5$; and a diarylamino group, diheteroarylamino group or arylheteroarylamino group having 10 to 40 aromatic ring atoms, which can in each case be substituted with one or more radicals $R^5$;

in each occurrence $R^5$ is the same or different and is selected from the group consisting of:

H, deuterium, $N(R^6)_2$, OH, $Si(R^6)_3$, $B(OR^6)_2$, $OSO_2R^6$, $CF_3$, CN, F, Br, I;

a linear alkyl, alkoxy or thioalkoxy group having 1 to 40 C atoms, which can in each case be substituted with one or more radicals $R^6$, wherein one or more non-adjacent $CH_2$ groups can be replaced by $R^6C=CR^6$, C≡C, $Si(R^6)_2$, $Ge(R^6)_2$, $Sn(R^6)_2$, C=O, C=S, C=Se, C=NR^6, P(=O)(R^6), SO, SO_2, NR^6, O, S or CONR^6 and wherein one or more H atoms can be replaced by deuterium, CN, $CF_3$ or $NO_2$;

a linear alkenyl or alkinyl group having 2 to 40 C atoms, which can in each case be substituted with one or more radicals $R^6$, wherein one or more non-adjacent $CH_2$ groups can be replaced by $R^6C=CR^6$, C≡C, $Si(R^6)_2$, $Ge(R^6)_2$, $Sn(R^6)_2$, C=O, C=S, C=Se, C=NR^6, P(=O)(R^6), SO, SO_2, NR^6, O, S or CONR^6 and wherein one or more H atoms can be replaced by deuterium, CN, $CF_3$ or $NO_2$;

a branched or cyclic alkyl, alkenyl, alkinyl, alkoxy or thioalkoxy group having 3 to 40 C atoms, which can in each case be substituted with one or more radicals $R^6$, wherein one or more non-adjacent $CH_2$ groups can be replaced by $R^6C=CR^6$, C≡C, $Si(R^6)_2$, $Ge(R^6)_2$, $Sn(R^6)_2$, C=O, C=S, C=Se, C=NR^6, P(=O)(R^6), SO, SO_2, NR^6, O, S or CONR^6 and wherein one or more H atoms can be replaced by deuterium, CN, $CF_3$ or $NO_2$;

an aromatic or heteroaromatic ring system having 5 to 60 aromatic ring atoms, which can in each case be substituted with one or more radicals $R^6$;

an aryloxy or heteroaryloxy group having 5 to 60 aromatic ring atoms, which can in each case be substituted with one or more radicals $R^6$; and a diarylamino group, diheteroarylamino group or arylheteroarylamino group having 10 to 40 aromatic ring atoms, which can in each case be substituted with one or more radicals $R^6$;

in each occurrence $R^6$ is the same or different and is selected from the group consisting of:

H, deuterium, OH, $CF_3$, CN, F;

a linear alkyl, alkoxy or thioalkoxy group having 1 to 5 C atoms, wherein one or more H atoms can be replaced by deuterium, CN, $CF_3$ or $NO_2$;

a linear alkenyl or alkinyl group having 2 to 5 C atoms, wherein one or more H atoms can be replaced by deuterium, CN, $CF_3$ or $NO_2$;

a branched or cyclic alkyl, alkenyl, alkinyl, alkoxy or thioalkoxy group having 3 to 5 C atoms, wherein one or more H atoms can be replaced by deuterium, CN, $CF_3$ or $NO_2$;

an aromatic or heteroaromatic ring system having 5 to 60 aromatic ring atoms;

an aryloxy or heteroaryloxy group having 5 to 60 aromatic ring atoms; and a diarylamino group, diheteroarylamino group or arylheteroarylamino group having 10 to 40 aromatic ring atoms;

wherein each of the radicals $R^a$ or $R^5$ can also form a mono- or polycyclic, aliphatic, aromatic and/or benzo-annelated ring system with one or more further radicals $R^a$ or $R^5$;

wherein exactly one radical selected from the group consisting of W, X and Y is CN or $CF_3$ and exactly two radicals selected from the group consisting of T, V, W, X and Y are a point of attachment of the single bond between the first chemical unit and a second chemical unit D; and wherein the exactly one radical that is CN or $CF_3$ is attached to the first chemical unit at a position between the exactly two radicals that are the point of attachment of the single bond between the first chemical unit and the second chemical unit D.

2. The organic molecule according to claim 1, wherein, in each occurrence, $R^1$ is the same or different and is methyl or phenyl.

3. The organic molecule according to claim 1, wherein W is CN.

4. The organic molecule according to claim 1, wherein, in each case, the second chemical unit D has a structure of Formula IIb:

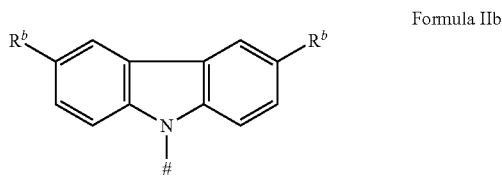

Formula IIb wherein in each occurrence $R^b$ is the same or different and is selected from the group consisting of:

N(R$^5$)$_2$, OH, Si(R$^5$)$_3$, B(OR$^5$)$_2$, OSO$_2$R$^5$, CF$_3$, CN, F, Br, I;

a linear alkyl, alkoxy or thioalkoxy group having 1 to 40 C atoms, wherein one or more non-adjacent CH$_2$ groups can be replaced by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$ and wherein one or more H atoms can be replaced by deuterium, CN, CF$_3$ or NO$_2$;

a linear alkenyl or alkinyl group having 2 to 40 C atoms, wherein one or more non-adjacent CH$_2$ groups can be replaced by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$ and wherein one or more H atoms can be replaced by deuterium, CN, CF$_3$ or NO$_2$;

a branched or cyclic alkyl, alkenyl, alkinyl, alkoxy or thioalkoxy group having 3 to 40 C atoms, which can in each case be substituted with one or more radicals R$^5$, wherein one or more non-adjacent CH$_2$ groups can be replaced by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$ and wherein one or more H atoms can be replaced by deuterium, CN, CF$_3$ or NO$_2$;

an aromatic or heteroaromatic ring system having 5 to 60 aromatic ring atoms, which can in each case be substituted with one or more radicals R$^5$;

an aryloxy or heteroaryloxy group having 5 to 60 aromatic ring atoms, which can in each case be substituted with one or more radicals R$^5$; and a diarylamino group, diheteroarylamino group or arylheteroarylamino group having 10 to 40 aromatic ring atoms, which can in each case be substituted with one or more radicals R$^5$; and and R$^5$ have the aforestated meanings.

5. The organic molecule according to claim 1, wherein, in each case, the second chemical unit D has a structure of Formula IIc:

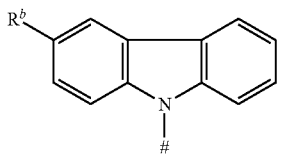

Formula IIc wherein in each occurrence R$^b$ is the same or different and is selected from the group consisting of:

N(R$^5$)$_2$, OH, Si(R$^5$)$_3$, B(OR$^5$)$_2$, OSO$_2$R$^5$, CF$_3$, CN, F, Br, I;

a linear alkyl, alkoxy or thioalkoxy group having 1 to 40 C atoms, wherein one or more non-adjacent CH$_2$ groups can be replaced by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NRS, O, S or CONR$^5$ and wherein one or more H atoms can be replaced by deuterium, CN, CF$_3$ or NO$_2$;

a linear alkenyl or alkinyl group having 2 to 40 C atoms, wherein one or more non-adjacent CH$_2$ groups can be replaced by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$ and wherein one or more H atoms can be replaced by deuterium, CN, CF$_3$ or NO$_2$;

a branched or cyclic alkyl, alkenyl, alkinyl, alkoxy or thioalkoxy group having 3 to 40 C atoms, which can in each case be substituted with one or more radicals R$^5$, wherein one or more non-adjacent CH$_2$-groups can be replaced by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$ and wherein one or more H atoms can be replaced by deuterium, CN, CF$_3$ or NO$_2$;

an aromatic or heteroaromatic ring system having 5 to 60 aromatic ring atoms, which can in each case be substituted with one or more radicals R$^5$;

an aryloxy or heteroaryloxy group having 5 to 60 aromatic ring atoms, which can in each case be substituted with one or more radicals R$^5$; and a diarylamino group, diheteroarylamino group or arylheteroarylamino group having 10 to 40 aromatic ring atoms, which can in each case be substituted with one or more radicals R$^5$; and R$^5$ has the fore stated meaning.

6. The organic molecule according to claim 4, wherein in each occurrence R$^b$ is the same or different and is Me, $^i$Pr, $^t$Bu, CN, CF$_3$ or Ph, which can in each case be substituted with one or more radicals selected from the group consisting of Me, iPr, tBu, CN, CF$_3$ and Ph, pyridinyl, which can in each case be substituted with one or more radicals selected from the group consisting of Me, iPr, tBu, CN, CF$_3$ and Ph, pyrimidinyl which can in each case be substituted with one or more radicals selected from Me, $^i$Pr, $^t$Bu, CN, CF$_3$ and Ph, triazinyl, which can in each case be substituted with one or more radicals selected from the group consisting of Me, iPr, tBu, CN, CF$_3$ and Ph, carbazolyl which can in each case be substituted with one or more radicals selected from the group consisting of Me, iPr, tBu, CN, CF$_3$ and Ph, or N(Ph)$_2$.

7. A composition comprising:
(a) at least one organic molecule according to claim 1 as an emitter and/or host;
(b) one or more emitter and/or host materials different from the at least one organic molecule according to claim 1; and
(c) optionally one or more dyes and/or one or more solvents.

8. An optoelectronic device comprising the organic molecule according to claim 1.

9. The optoelectronic device according to claim 8, wherein the optoelectronic device is an organic light-emitting diode, a light-emitting electrochemical cell, an organic light-emitting sensor, an organic diode, an organic solar cell, an organic transistor, an organic field-effect transistor, an organic laser or a down-conversion element.

10. The optoelectronic device according to claim 8, wherein the organic molecule is one of an emitter and a host in the optoelectronic device.

11. The optoelectronic device according to claim 10, wherein a proportion of the organic molecule in the emitter or the host is in the range of 1% to 80%.

12. The optoelectronic device according to claim 8, comprising:
a substrate;
an anode;
a cathode, wherein the anode or the cathode is applied to the substrate; and
at least one light-emitting layer disposed between the anode and the cathode and which comprises the organic molecule.

13. An optoelectronic device comprising the organic molecule according to claim 2.

14. The optoelectronic device according to claim 13, wherein the organic molecule is one of an emitter and a host in the optoelectronic device.

15. An optoelectronic device comprising the composition according to claim 7.

16. The optoelectronic device according to claim 15, comprising:
   a substrate;
   an anode;
   a cathode, wherein the anode or the cathode are disposed on the substrate; and
   at least one light-emitting layer disposed between the anode and the cathode and which comprises the composition.

17. The optoelectronic device according to claim 15, wherein the composition is one of an emitter and a host in the optoelectronic device.

18. A process for producing an optoelectronic component, comprising processing of the organic molecule according to claim 1 by an evaporation process or from a solution.

19. The organic molecule according to claim 1, wherein the exactly two radicals that are the point of attachment of the single bond between the first chemical unit and the second chemical unit D are each in an ortho position relative to the position of the exactly one radical that is CN or $CF_3$ and each $R^a$ is H.

* * * * *